US010947218B2

(12) United States Patent
Arista et al.

(10) Patent No.: US 10,947,218 B2
(45) Date of Patent: *Mar. 16, 2021

(54) AMINOPYRIDINE DERIVATIVES AND THEIR USE AS SELECTIVE ALK-2 INHIBITORS

(71) Applicant: NOVARTIS AG, Basel (CH)

(72) Inventors: Luca Arista, Riehen (CH); Sreehari Babu, Hyderabad (IN); Jianwei Bian, Changshu (CN); Kai Cui, Changshu (CN); Michael Patrick Dillon, Castro Valley, CA (US); Rene Lattmann, Oberwil (CH); Jialiang Li, Changshu (CN); Lv Liao, Shanghai (CN); Dimitrios Lizos, Basel (CH); Rita Ramos, Allschwil (CH); Nikolaus Johannes Stiefl, Lörrach (DE); Thomas Ullrich, Bottmingen (CH); Peggy Usselmann, Wahlbach (FR); Xiaoyang Wang, Shanghai (CN); Liladhar Murlidhar Waykole, Succasunna, PA (US); Sven Weiler, Lörrach (DE); Yubo Zhang, Shanghai (CN); Yizong Zhou, Shanghai (CN); Tingying Zhu, Shanghai (CN)

(73) Assignee: NOVARTIS AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 16/884,666

(22) Filed: May 27, 2020

(65) Prior Publication Data

US 2020/0299265 A1 Sep. 24, 2020

Related U.S. Application Data

(63) Continuation of application No. 16/318,250, filed as application No. PCT/CN2017/093385 on Jul. 18, 2017, now Pat. No. 10,710,980.

(Continued)

(51) Int. Cl.
| | | |
|---|---|---|
| A61K 31/4427 | (2006.01) | |
| C07D 405/14 | (2006.01) | |
| C07D 401/14 | (2006.01) | |
| C07D 401/10 | (2006.01) | |
| C07D 401/12 | (2006.01) | |
| C07D 409/14 | (2006.01) | |
| C07D 213/82 | (2006.01) | |
| C07D 411/14 | (2006.01) | |
| C07D 491/107 | (2006.01) | |
| A61P 19/00 | (2006.01) | |
| C07D 417/00 | (2006.01) | |
| C07D 413/00 | (2006.01) | |
| C07D 419/00 | (2006.01) | |
| A61P 19/08 | (2006.01) | |
| C07D 413/10 | (2006.01) | |
| C07D 413/12 | (2006.01) | |
| C07D 413/14 | (2006.01) | |
| C07D 491/20 | (2006.01) | |

(52) U.S. Cl.
CPC .......... *C07D 401/14* (2013.01); *A61P 19/00* (2018.01); *A61P 19/08* (2018.01); *C07D 213/82* (2013.01); *C07D 401/10* (2013.01); *C07D 401/12* (2013.01); *C07D 405/14* (2013.01); *C07D 409/14* (2013.01); *C07D 411/14* (2013.01); *C07D 413/00* (2013.01); *C07D 413/10* (2013.01); *C07D 413/12* (2013.01); *C07D 413/14* (2013.01); *C07D 417/00* (2013.01); *C07D 419/00* (2013.01); *C07D 491/107* (2013.01); *C07D 491/20* (2013.01)

(58) Field of Classification Search
CPC .................................................. A61K 31/4427
USPC ......................................................... 514/337
See application file for complete search history.

(56) References Cited

U.S. PATENT DOCUMENTS

| 5,077,290 A | 12/1991 | Fisher et al. |
| 6,090,812 A | 7/2000 | Feenstra et al. |
| 2004/0067985 A1 | 4/2004 | Haviv et al. |

FOREIGN PATENT DOCUMENTS

| EP | 1875912 A1 | 1/2008 |
| WO | WO 2003/004472 A1 | 1/2003 |

(Continued)

OTHER PUBLICATIONS

Hopkins C.R.; Inhibitors of the bone morphogenetic protein (BMP) signaling pathway: a patent review. Expert opinion on therapeutic patents. 2006;26 (10):1115-1128.

(Continued)

*Primary Examiner* — Patricia L Morris
(74) *Attorney, Agent, or Firm* — Brian C Trinque; Lathrop GPM LLP

(57) ABSTRACT

The invention relates to a compound of formula (I) in free form or in pharmaceutically acceptable salt form

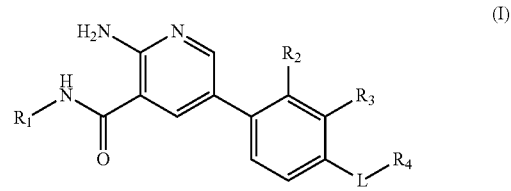

to pharmaceutical compositions comprising said compound and to the use of said compound in the treatment of heterotopic ossification and fibrodysplasia ossificans progressiva.

13 Claims, 18 Drawing Sheets

Related U.S. Application Data

(60) Provisional application No. 62/364,620, filed on Jul. 20, 2016.

(56) References Cited

FOREIGN PATENT DOCUMENTS

| WO | WO 2003/093297 | A2 | 11/2003 | | |
|----|----------------|----|---------|---|---|
| WO | WO 2004/000318 | A2 | 12/2003 | | |
| WO | WO 2004/055009 | A1 | 7/2004 | | |
| WO | WO 2004/092727 | A2 | 10/2004 | | |
| WO | WO 2005/115985 | A1 | 12/2005 | | |
| WO | WO 2006/025783 | A1 | 3/2006 | | |
| WO | WO 2007/011760 | A2 | 1/2007 | | |
| WO | WO 2007/084455 | A1 | 7/2007 | | |
| WO | WO 2008/002671 | A2 | 1/2008 | | |
| WO | WO 2010/008739 | A2 | 1/2010 | | |
| WO | WO 2012/088438 | A1 | 6/2012 | | |
| WO | WO 2012/161877 | A1 | 11/2012 | | |
| WO | WO 2013/036869 | A2 | 3/2013 | | |
| WO | WO 2014/138088 | A1 | 9/2014 | | |
| WO | WO 2014/151871 | A2 | 9/2014 | | |
| WO | WO-2014151871 | A2 | * 9/2014 | ............... | A61P 9/00 |
| WO | WO 2015/061247 | A2 | 4/2015 | | |
| WO | WO 2016/118638 | A1 | 7/2016 | | |
| WO | WO 2018/014829 | A1 | 1/2018 | | |
| WO | WO 2018106820 | A1 | 6/2018 | | |

OTHER PUBLICATIONS

Kim et al., "Identification of novel ALK2 inhibitors and their effect on cancer cells", Biochemical and Biophysical Research Communications 492 (2017) pp. 121-127.

Notification of Transmittal of The International Search Report and the Written Opinion of The International Searching Authority, or the Declaration, dated Oct. 24, 2017 in International Application No. PCT/CN2017/093385, International Filing Date: Jul. 18, 2017.

* cited by examiner

AMINOPYRIDINE DERIVATIVES AND THEIR USE AS SELECTIVE ALK-2 INHIBITORS

RELATED APPLICATIONS

This application is a continuation of U.S. patent application Ser. No. 16/318,250, filed Jan. 16, 2019, which is a 35 U.S.C. § 371 filing of International Patent Application No. PCT/CN2017/093385, filed Jul. 18, 2017, which claims priority to U.S. Provisional Patent Application Ser. No. 62/364,620, filed Jul. 20, 2016. The contents of these applications are incorporated herein by reference in their entireties.

BACKGROUND OF THE INVENTION

ALK-2, also known as activin A receptor, type I (ACVR1) or as serine threonine protein kinase receptor R1 (SKR1) is a protein kinase which in humans is encoded by the ACVR1 gene.

ALK-2 is a type I BMP receptor which is widely expressed. It comprises an extracellular ligand binding domain and a regulated intracellular serine/threonine kinase domain, both required for signal transduction.

Bone morphogenic proteins (BMPs) are multi-functional growth factors that are members of the transforming growth factor β (TGFβ) superfamily. BMP signaling plays a role in heart, neural, and cartilage development as well as in postnatal bone formation. BMPs ectopically induce endochondral bone formation and play a critical role in skeletal and joint morphogenesis (Urist, Science 110:893-899 (1965); Olsen et al, Annu. Rev. Cell Dev. Biol. 16:191-220 (2000); Kronenberg, Nature 423:332-336 (2003); Thomas et al, Nat. Genet. 12:315-317 (1996); Thomas et al, Nat. Genet. 17:58-64 (1997); Polinkowsky et al, Nat. Genet. 17:18-19 (1997); Storm et al., Nature 368:639-643 (1994); and Wozney, Prog. Growth Factor Res. 1:267-280 (1989)).

BMP signaling is controlled at many levels, including via extracellular antagonists such as noggin (Massague, Nat. Rev. Mol. Cell. Biol. 1:169-178 (2000)). It has been suggested that untimely or unwanted activation of signaling pathways fundamental for normal development may promote disease processes such as spondyloarthropathies. The effects of BMP signaling on initiation and progression of arthritis by gene transfer of noggin have also been described (Lories et al, J. Clin. Invest., 115, 1571-1579 (2005)). The physiological roles of BMPs and BMP receptor signaling in normal bone formation, including skeletal and limb development, have been studied and reviewed in Zhao, Genetics 35:43-56 (2003).

Experiments with BMP antagonists demonstrate that regulation of BMP signaling proteins is central to bone formation in vivo (Devlin et al., Endocrinology 144:1972-1978 (2003) and Wu et al., J. Clin. Invest., 112: 924 (2003)).

Fibrodysplasia ossificans progressiva (FOP) is a rare and disabling genetic disorder characterized by congenital malformations of the great toes and by progressive heterotopic endonchodral ossification in predictable anatomical patterns. Ectopic expression of BMP4 has been found in FOP patients (Gannon et al., Hum. Pathol. 28:339-343 (1997) and Xu et al, Clin. Genet. 58:291-298 (2000)). It has been shown that patients with FOP have activating mutations in ALK-2 (Shore et al., Nat. Genet., 38(5):525-7 (2006)).

It has been established that excessive BMP signaling leads to a number of conditions described above. WO2008033408 and WO2009114180 describe inhibitors of the BMP signaling pathway. There is still however a constant need to find alternative ways in which BMP signaling can be regulated.

Such a need can be met by designing selective ALK-2 inhibitors.

Specific ALK-2 antibodies are described for instance in WO1994011502 and WO2008030611. Osteogenic proteins that bind to ALK-2 are described in WO2012023113 and WO2012077031.

WO2007123896 describes a method of treating a pathology associated with heterotopic ossification by administering siRNA specific against a nucleic acid encoding a mutated ALK-2.

WO2014160203 and WO2014138088 describe inhibitors of the BMP pathway. WO 2015152183 describes ALK-2 inhibitors for the treatment of FOP. Inhibitors of ALK-2 are also described in WO2014151871.

SUMMARY OF THE INVENTION

There is a continuing need to develop new ALK-2 inhibitors that are good drug candidates. Such candidates would find applications inter alia in the treatment of fibrodysplasia ossificans progressiva (FOP) or non-hereditary heterotopic ossification (HO).

The invention provides compounds, pharmaceutically acceptable salts thereof, pharmaceutical compositions thereof, which compounds are ALK-2 inhibitors. The invention further provides methods of treating, preventing, or ameliorating fibrodysplasia ossificans progressiva (FOP) or non-hereditary heterotopic ossification (HO) comprising administering to a subject in need thereof an effective amount of an ALK-2 inhibitor.

Various embodiments of the invention are described herein.

Within certain aspects, provided herein is a compound of formula (I) in free form or in pharmaceutically acceptable salt form

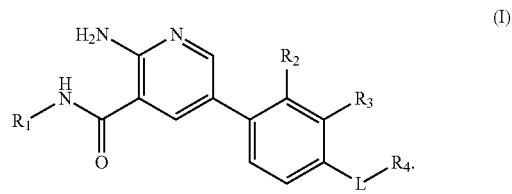

In another embodiment, the invention the invention provides a pharmaceutical composition comprising a therapeutically effective amount of a compound of formula (I) as defined herein in free form or in pharmaceutically acceptable salt form, or subformulae thereof (Ia), (II), (IIa), (IIb), and one or more pharmaceutically acceptable carriers.

In a further aspect, the invention relates to a method of inhibiting ALK-2 receptor activity in a subject, wherein the method comprises administering to the subject a therapeutically effective amount of the compound of formula (I) as defined herein in free form or in pharmaceutically acceptable salt form, or subformulae thereof (Ia), (II), (IIa), (IIb).

In yet another aspect, the invention relates to a method of treating a disorder or disease selected from heterotopic ossification or fibrodysplasia ossificans progressiva, comprising administering to the subject a therapeutically effective amount of the compound of formula (I) as defined herein in free form or in pharmaceutically acceptable salt form, or subformulae thereof (Ia), (II), (IIa), (IIb).

The compounds of the invention demonstrate favourable pharmacokinetic properties, are non-toxic and demonstrate few side-effects. In particular, the compounds of the invention are selective inhibitors of ALK-2 over other receptors. Furthermore, the ideal drug candidate will be in a form that is stable, non-hygroscopic and easily formulated.

FIGURES

FIG. 1 shows μCT quantification of heterotopic bone formed in the right hind leg of mice 6 weeks past FOP flare-up induction with adenovirus/CTX and shows the effect of compound A treatment for 6 weeks on HO formation. Mean+/−SEM. *: p<0.05, : p<0.01, *: p<0.01 versus vehicle-treated; 1 way ANOVA with Dunnett's post-hoc test.

FIG. 2 shows μCT quantification of heterotopic bone formed in the right hind leg of mice 8 weeks past FOP flare-up induction with adenovirus/CTX and shows the effect of compound A treatment for 6 weeks on HO formation. Mean+/−SEM. *: p<0.05, : p<0.01, *: p<0.01 versus vehicle-treated; T-test FIG. 3 shows the X-ray powder diffraction pattern of crystalline free form Modification $H_A$ crystals of compound A.

DETAILED DESCRIPTION OF THE INVENTION

Figure 1:
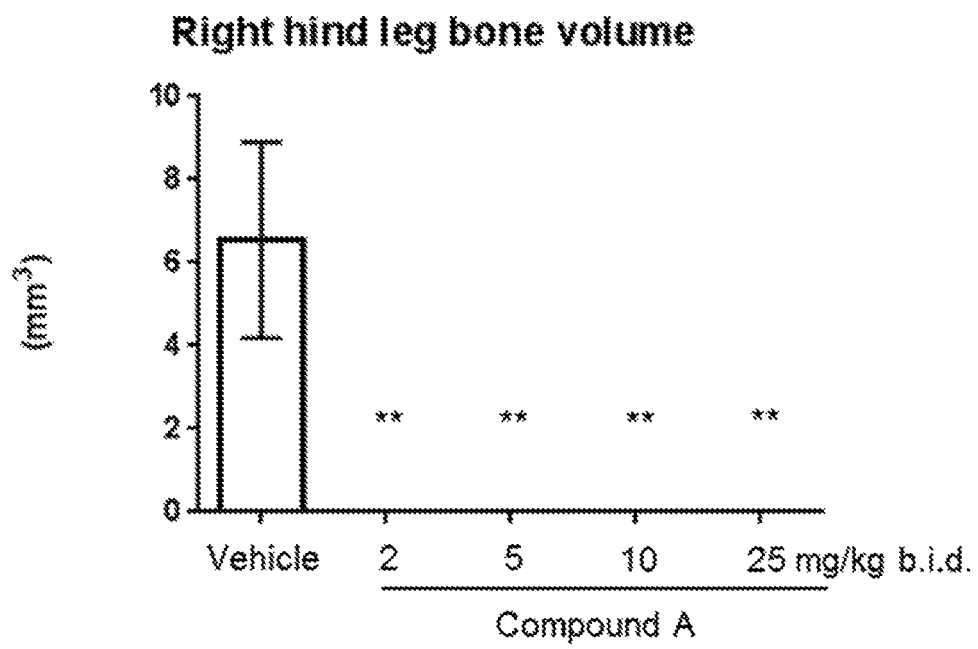

In particular, the invention relates to a compound of formula (I) in free form or in acceptable salt form,

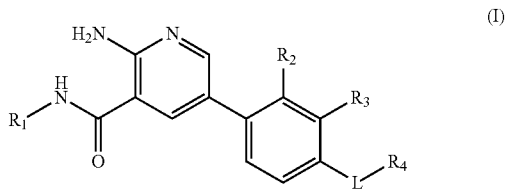

wherein
L is bond, $(CH_2)_n$, $-CH(CH_3)-$, $-O-(CH_2)_n-$, $-C(O)-$, $-C(O)-NH-(CH_2)_n-$;
n is 1, 2, 3;
$R_1$ is selected from $C_3$-$C_7$cycloalkyl optionally substituted once or more than once with a substituent independently selected from hydroxyl, halogen, $C_1$-$C_3$alkyl; bridged $C_5$-$C_{10}$cycloalkyl optionally substituted once or more than once with a substituent independently selected from hydroxyl, hydroxy$C_1$-$C_3$alkyl;
$R_2$ and $R_3$ are independently selected from H, halogen, $C_1$-$C_3$alkyl;
$R_4$ is a N-containing heterocylic non-aromatic ring optionally comprising one or more additional heteroatom(s) selected from N, O or S, wherein said ring is optionally substituted once or more than once with $R_7$;
$R_7$ is independently selected from $C_1$-$C_3$alkyl, hydroxy$C_1$-$C_3$alkyl, halo$C_1$-$C_3$alkyl, $C_1$-$C_3$alkoxy$C_1$-$C_3$alkyl, halo$C_1$-$C_3$alkoxy$C_1$-$C_3$alkyl, $C_2$-$C_4$alkynyl, cyano$C_1$-$C_3$alkyl, $(CH_2)$ m-R8;
m is 0, 1, 2 or 3;
$R_8$ is selected from
  a 4-, 5-, or 6-membered saturated or unsaturated non-aromatic heterocyclic ring comprising one or more heteroatom(s) selected from N, O or S, said ring being optionally substituted once or more than once with a substituent independently selected from oxo, $SO_2C_1$-$C_3$alkyl, halo$C_1$-$C_3$alkyl; or
  a $C_3$-$C_6$cycloalkyl optionally substituted once or more than once with halo.

Unless specified otherwise, the term "compounds of the present invention" or "compounds of the invention" refers to compounds of formula (I), (Ia), (II), (IIa), (IIb) and salts thereof, as well as all stereoisomers (including diastereoisomers and enantiomers), rotamers, tautomers and isotopically labeled compounds (including deuterium substitutions), as well as inherently formed moieties.

As used herein, the term "$C_1$-$C_3$alkyl" refers to a straight or branched hydrocarbon chain radical consisting solely of carbon and hydrogen atoms, containing no unsaturation, having from one to three carbon atoms, and which is attached to the rest of the molecule by a single bond. Examples of $C_1$-$C_3$alkyl include methyl, ethyl, n-propyl, 1-methylethyl (iso-propyl).

As used herein, the term "hydroxy$C_1$-$C_3$alkyl" refers to a radical of formula $-R_a-OH$, wherein $R_a$ is $C_1$-$C_3$alkyl as defined above.

As used herein, the term "$C_3$-$C_7$cycloalkyl" refers to saturated monocyclic hydrocarbon groups of 3-7 carbon atoms. Examples of $C_3$-$C_7$cycloalkyl include cyclopropyl, cyclobutyl, cyclopentyl, cyclohexyl, cycloheptyl.

As used herein, the term "$C_1$-$C_3$alkoxy" refers to a radical of the formula —$OR_a$ where $R_a$ is a $C_1$-$C_3$alkyl radical as generally defined above. Examples of $C_1$-$C_3$alkoxy include, but are not limited to, methoxy, ethoxy, propoxy, isopropoxy, butoxy, isobutoxy, pentoxy, and hexoxy.

As used herein, the term "$C_1$-$C_3$alkoxy$C_1$-$C_3$alkyl" refers to a radical of the formula —$R_b$—O—$R_a$ where $R_a$ is a $C_1$-$C_3$alkyl radical and $R_b$ is a $C_1$-$C_3$alkyl radical as defined above. The oxygen atom may be bonded to any carbon atom in either alkyl radical. Examples of $C_1$-$C_3$alkoxy$C_1$-$C_3$alkyl include, for example, methoxy-methyl, methoxy-ethyl, ethoxy-ethyl.

"Halogen" or "halo" refers to bromo, chloro, fluoro or iodo.

As used herein, the term "halogen$C_1$-$C_3$alkyl" or "halo$C_1$-$C_3$alkyl" refers to $C_1$-$C_3$alkyl radical, as defined above, substituted by one or more halo radicals, as defined above. Examples of halogen$C_1$-$C_3$alkyl include, for example, trifluoromethyl, difluoromethyl, fluoromethyl, trichloromethyl, 2,2,2-trifluoroethyl, 1-fluoromethyl-2-fluoroethyl, 3-bromo-2-fluoropropyl and 1-bromomethyl-2-bromoethyl.

As used herein, the term "halo$C_1$-$C_3$alkoxy$C_1$-$C_3$alkyl" refers to a radical of the formula —$R_b$—O—$R_a$ where $R_a$ is a $C_1$-$C_3$alkyl radical and $R_b$ is a halo$C_1$-$C_3$alkyl radical as defined above.

As used herein, the term "a N-containing heterocylic non-aromatic ring optionally comprising one or more additional heteroatom(s) selected from N, O or S" in relation to $R_4$ refers to a saturated or unsaturated non-aromatic ring or ring system, which is a 4-, 5-, 6-, or 7-membered monocyclic ring containing 1, 2 or 3 heteroatom(s) selected from O, S and N wherein at least one heteroatom is N, a 6-, 7-, 8-, 9-, 10-, 11-, or 12-membered bicyclic ring system containing 1, 2, 3, 4 or 5 heteroatom(s) selected from O, S and N wherein at least one heteroatom is N, or a 10-, 11-, 12-, 13-, 14- or 15-membered tricyclic ring system containing 1, 2, 3, 4, 5, 6 or 7 heteroatom(s) selected from O, S and N wherein at least one heteroatom is N, where the N and S can also optionally be oxidized to various oxidation states. The N-containing heterocylic non-aromatic ring can be attached via a heteroatom or a carbon atom. The N-containing heterocylic non-aromatic ring can include fused or bridged rings as well as spirocyclic rings. In a preferred embodiment, the "N-containing heterocyclic non-aromatic ring optionally comprising one or more additional heteroatom(s) selected from N, O or S" is a N-containing 5-membered saturated monocyclic ring, a N-containing 6-membered saturated monocyclic or bicyclic ring, a N-containing 7-membered saturated spirocyclic ring. Examples of a N-containing heterocyclic non-aromatic ring include morpholine, piperazine, piperidine, imidazolidine, imidazoline, pyrroline, pyrrolidine, thiomorpholine, 3-azabicyclo[3.1.0]hexane.

As used herein, the term "a N-containing 5-membered heterocylic non-aromatic ring optionally comprising one or more additional heteroatom(s) selected from N, O or S" in relation to $R_4$ includes, as examples, pyrrolidine, 2,3-dihydropyrrole, oxazolidine, imidazolidine. In a preferred embodiment, it refers to pyrrolidine. The ring is attached to the rest of the molecule via a ring carbon atom.

As used herein, the term "a N-containing 6-membered heterocylic non-aromatic monocyclic or bicyclic ring optionally comprising one or more additional heteroatom(s) selected from N, O or S" in relation to $R_4$ includes, as examples, morpholine, thiomorpholine, piperidine, piperazine, 3-azabicyclo[3.1.0]hexane. In a preferred embodiment, it refers to 3-azabicyclo[3.1.0]hexane. The ring is attached to the rest of the molecule via a ring carbon atom.

As used herein, the term "a 5-membered ring optionally comprising one additional heteroatom selected from N, O or S" in relation to embodiments where $R_5$ and $R_6$ together with the N atom to which they are attached form said ring, includes as examples, pyrrolidine, 2,3-dihydropyrrole, oxazolidine, imidazolidine. In a preferred embodiment, it refers to pyrrolidine.

As used herein, the term "a 6-membered ring optionally comprising one additional heteroatom selected from N, O or S" in relation to the embodiments where $R_5$ and $R_6$ together with the N atom to which they are attached form said ring, includes as examples, piperidinyl, morpholinyl, piperazinyl.

As used herein, the term "a 7-membered spirocycle optionally comprising one additional heteroatom selected from N, O or S" in relation to the embodiments where $R_5$ and $R_6$ together with the N atom to which they are attached form said ring, includes as examples, 2-azaspiro[3.3]heptane, 2-oxa-6-azaspiro[3.3]heptane.

As used herein, the term "a bridged $C_5$-$C_{10}$cycloalkyl" refers to a saturated bicyclic or tricyclic ring system comprising at least one bridge. Examples of bridged $C_5$-$C_{10}$cycloalkyl include, for example, bicyclo[1.1.1]pentane, bicyclo[2.2.2]octane, bicyclo[2.2.1]heptane, tricyclo-[3.3.1.1$^{3,7}$] decane.

As used herein, the term "$C_2$-$C_4$alkynyl" refers to a straight chain radical group consisting solely of carbon and hydrogen atoms, containing at least one triple bond, having from two to four carbon atoms, and which is attached to the rest of the molecule by a single bond. Examples of $C_2$-$C_4$alkynyl include, for example, ethynyl, prop-1-ynyl, but-1-ynyl.

As used herein, the term "cyano$C_1$-$C_3$alkyl" refers to a radical of formula —$R_a$—CN, wherein $R_a$ is $C_1$-$C_3$alkyl as defined above.

As used herein, the term "a 4-, 5-, or 6-membered saturated or unsaturated non-aromatic heterocyclic ring comprising one or more heteroatom(s) selected from N, O or S" includes, as examples, tetrahydropyran, morpholine, piperidine, oxetane. In a preferred embodiment, it is tetrahydropyran.

As used herein, the term "ALK-2" refers to activin A receptor, type I (ACVRI), also known as ACVRLK2; SKR1; ACVR1A; Activin receptor type I; Activin receptor-like kinase 2; Serine/threonine-protein kinase receptor R1; TGF-B superfamily receptor type I; ACTRI; TSRI; activin A receptor, type II-like kinase 2; activin receptor type-1; hydroxyalkyl-protein kinase; ACTR-I; TSR-I.

Various embodiments of the invention are described herein. It will be recognized that features specified in each embodiment may be combined with other specified features to provide further embodiments of the present invention.

Embodiment 1

A compound of the formula (I) in free form or in pharmaceutically acceptable salt form,

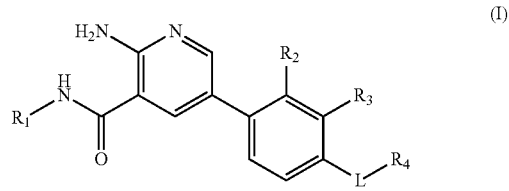

wherein
L is bond, (CH$_2$)$_n$, —CH(CH$_3$)—, —O—(CH$_2$)$_n$—, —C(O)—, —C(O)—NH—(CH$_2$)$_n$—;
n is 1, 2, 3;
R$_1$ is selected from C$_3$-C$_7$cycloalkyl optionally substituted once or more than once with a substituent independently selected from hydroxyl, halogen, C$_1$-C$_3$alkyl; bridged C$_5$-C$_{10}$ cycloalkyl optionally substituted once or more than once with a substituent independently selected from hydroxyl, hydroxyC$_1$-C$_3$alkyl;
R$_2$ and R$_3$ are independently selected from H, halogen, C$_1$-C$_3$alkyl;
R$_4$ is a N-containing heterocylic non-aromatic ring optionally comprising one or more additional heteroatom(s) selected from N, O or S, wherein said ring is optionally substituted once or more than once with R$_7$;
R$_7$ is independently selected from C$_1$-C$_3$alkyl, hydroxyC$_1$-C$_3$alkyl, haloC$_1$-C$_3$alkyl, C$_1$-C$_3$alkoxyC$_1$-C$_3$alkyl, haloC$_1$-C$_3$alkoxyC$_1$-C$_3$alkyl, C$_2$-C$_4$alkynyl, cyanoC$_1$-C$_3$alkyl, (CH$_2$)$_m$—R$_8$;
m is 0, 1, 2 or 3;
R$_8$ is selected from
a 4-, 5-, or 6-membered saturated or unsaturated non-aromatic heterocyclic ring comprising one or more heteroatom(s) selected from N, O or S, said ring being optionally substituted once or more than once with a substituent independently selected from oxo, SO$_2$C$_1$-C$_3$alkyl, haloC$_1$-C$_3$alkyl; or
a C$_3$-C$_6$cycloalkyl optionally substituted once or more than once with halo.

Embodiment 2

A compound according to embodiment 1 of formula (Ia) in free form or in pharmaceutically acceptable salt form

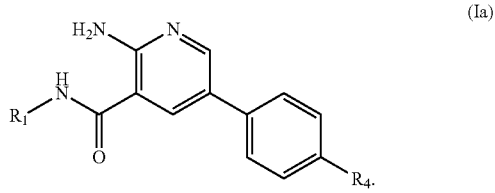

(Ia)

Embodiment 3

A compound according to any of embodiments 1 or 2, in free form or in pharmaceutically acceptable salt form, wherein R$_4$ is NR$_5$R$_6$ wherein R$_5$ and R$_6$ together with the N atom to which they are attached form a 5-membered ring optionally comprising one additional heteroatom selected from N, O or S, optionally substituted once or more than once with R$_7$.

Embodiment 4

A compound according to any of embodiments 1 or 2, in free form or in pharmaceutically acceptable salt form, wherein R$_4$ is NR$_5$R$_6$ wherein R$_5$ and R$_6$ together with the N atom to which they are attached form a 6-membered ring optionally comprising one additional heteroatom selected from N, O or S, optionally substituted once or more than once with R$_7$.

Embodiment 5

A compound according to any of embodiments 1 or 2, in free form or in pharmaceutically acceptable salt form, wherein R$_4$ is NR$_5$R$_6$ wherein R$_5$ and R$_6$ together with the N atom to which they are attached form a 7-membered spirocycle optionally comprising one additional heteroatom selected from N, O or S, optionally substituted once or more than once with R$_7$.

Embodiment 6

A compound according to any of embodiments 1 or 2 in free form or in pharmaceutically acceptable salt form, wherein R$_4$ is a N-containing 5-membered heterocyclic non-aromatic ring optionally comprising one or more additional heteroatom(s) selected from N, O, or S wherein said ring is optionally substituted once or more than once with R$_7$ and wherein said ring is attached to the rest of the molecule via a ring carbon atom.

Embodiment 7

A compound according to any of embodiments 1 or 2 in free form or in pharmaceutically acceptable salt form, wherein R$_4$ is a N-containing 6-membered heterocyclic non-aromatic monocyclic or bicyclic ring optionally comprising one or more additional heteroatom(s) selected from N, O, or S, wherein said ring is optionally substituted once or more than once with R$_7$ and wherein said ring is attached to the rest of the molecule via a ring carbon atom.

Embodiment 8

A compound according to any of embodiments 1, 2 or 7 of formula (II) in free form or in pharmaceutically acceptable salt form,

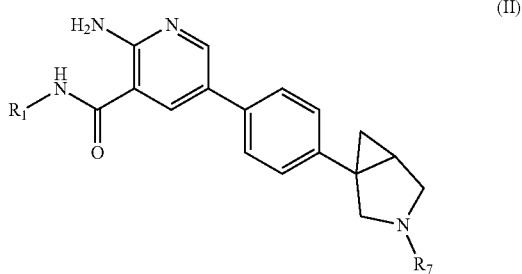

(II)

wherein R$_7$ is independently selected from C$_1$-C$_3$alkyl, hydroxyC$_1$-C$_3$alkyl, haloC$_1$-C$_3$alkyl, C$_1$-C$_3$alkoxyC$_1$-C$_3$alkyl, haloC$_1$-C$_3$alkoxyC$_1$-C$_3$alkyl, C$_2$-C$_4$alkynyl, cyanoC$_1$-C$_3$alkyl, (CH$_2$)$_m$—R$_8$;
m is 0, 1, 2 or 3.

Embodiment 9

A compound according to embodiment 8 of formula (IIa) in free form or in pharmaceutically acceptable salt form

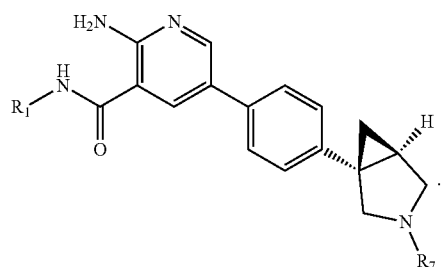

(IIa)

Embodiment 10

A compound according to embodiment 8 of formula (IIIb) in free form or in pharmaceutically acceptable salt form

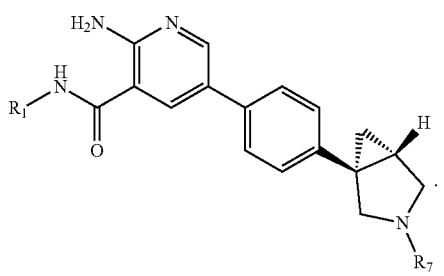

(IIb)

Embodiment 11

A compound according to any of the preceding embodiments in free form or in pharmaceutically acceptable salt form, wherein $R_7$ is $(CH_2)_m$—$R_8$;

$R_8$ is a 6-membered heterocyclic ring comprising one or more heteroatom(s) selected from N, O or S, said ring being optionally substituted once or more than once with a substituent independently selected from oxo, $SO_2C_1$-$C_3$alkyl, halo$C_1$-$C_3$alkyl;

m is 0, 1, 2 or 3.

Embodiment 12

A compound according to embodiment 11 in free form or in pharmaceutically acceptable salt form, wherein $R_8$ is unsubstituted tetrahydropyran and m is 0.

Embodiment 13

A compound according to embodiment 11 in free form or in pharmaceutically acceptable salt form, wherein $R_8$ is unsubstituted morpholine and m is 2 or 3.

Embodiment 14

A compound according to any of the preceding embodiments in free form or in pharmaceutically acceptable salt form, wherein $R_1$ is cyclohexyl optionally substituted once or more than once with a substituent independently selected from hydroxyl, halogen, $C_1$-$C_3$alkyl.

Embodiment 15

A compound according to any of the preceding embodiments in free form or in pharmaceutically acceptable salt form, wherein $R_1$ is

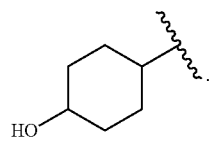

Embodiment 16

A compound according to any of the preceding embodiments in free form or in pharmaceutically acceptable salt form, wherein $R_1$ is

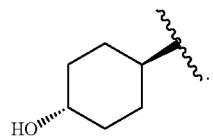 [SMILES: *[C@H]1CC[C@H](O)CC1]

Embodiment 17

A compound according to any of embodiments 1 to 13 in free form or in pharmaceutically acceptable salt form, wherein $R_1$ is bicyclo[2.2.2]octanyl substituted once with hydroxyl.

Embodiment 18

A compound according to embodiment 17 in free form or in pharmaceutically acceptable salt form, wherein $R_1$ is

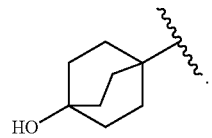

Embodiment 19

A compound according to embodiment any of embodiments 1 to 13 in free form or in pharmaceutically acceptable salt form, wherein $R_1$ is bicyclo[1.1.1]pentanyl substituted with hydroxymethyl.

Embodiment 20

A compound according to embodiment 19 in free form or in pharmaceutically acceptable salt form, wherein $R_1$ is

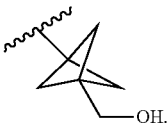 [SMILES: *C12CC(CO)(C1)C2]

Embodiment 21

A compound according to embodiment 1, in free form or in pharmaceutically acceptable salt form which is selected from
2-amino-N-(-4-hydroxycyclohexyl)-5-(4-(-3-(1-(methylsulfonyl)piperidin-4-yl)-3-azabicyclo[3.1.0]hexan-1-yl)phenyl)nicotinamide;
2-amino-N-(-4-hydroxycyclohexyl)-5-(4-(-3-isopropyl-3-azabicyclo[3.1.0]hexan-1-yl)phenyl)nicotinamide;
5-(4-(-1-(2-oxa-6-azaspiro[3.3]heptan-6-yl)ethyl)phenyl)-2-amino-N-(-4-hydroxycyclohexyl)nicotinamide;
2-amino-N-(-4-hydroxycyclohexyl)-5-(4-(-3-(3-morpholinopropyl)-3-azabicyclo[3.1.0]hexan-1-yl)phenyl)nicotinamide;
2-amino-5-(4-(-3-(1,3-difluoropropan-2-yl)-3-azabicyclo[3.1.0]hexan-1-yl)phenyl)-N-(-4-hydroxycyclohexyl)nicotinamide;
2-amino-N-(4-hydroxybicyclo[2.2.2]octan-1-yl)-5-(4-(-3-(2-methoxyethyl)-3-azabicyclo[3.1.0]hexan-1-yl)phenyl)nicotinamide;
2-amino-5-(2-fluoro-4-(4-isopropylpiperazin-1-yl)phenyl)-N-(-4-hydroxycyclohexyl)nicotinamide;
2-amino-N-(-4-hydroxycyclohexyl)-5-(4-(-3-(2-morpholinoethyl)-3-azabicyclo[3.1.0]hexan-1-yl)phenyl)nicotinamide;
2-amino-5-(4-(-3-(2-fluoroethyl)-3-azabicyclo[3.1.0]hexan-1-yl)phenyl)-N-(-4-hydroxycyclohexyl)nicotinamide;
2-amino-N-(-4-hydroxycyclohexyl)-5-(4-(1-isopropylpyrrolidin-3-yl)phenyl)nicotinamide;
2-amino-N-(-4-hydroxy-4-methylcyclohexyl)-5-(4-(-3-(tetrahydro-2H-pyran-4-yl)-3-azabicyclo[3.1.0]hexan-1-yl)phenyl)nicotinamide;
2-amino-N-(4-hydroxybicyclo[2.2.2]octan-1-yl)-5-(4-(-3-(2-morpholinoethyl)-3-azabicyclo[3.1.0]hexan-1-yl)phenyl)nicotinamide;
2-amino-N-(3-(hydroxymethyl)bicyclo[1.1.1]pentan-1-yl)-5-(4-(-3-isopropyl-3-azabicyclo[3.1.0]hexan-1-yl)phenyl)nicotinamide;
2-amino-N-(-4-hydroxycyclohexyl)-5-(4-(-3-(3,3,3-trifluoropropyl)-3-azabicyclo[3.1.0]hexan-1-yl)phenyl)nicotinamide;
2-amino-N-(-4-hydroxycyclohexyl)-5-(4-(pyrrolidin-3-yl)phenyl)nicotinamide;
2-amino-N-(-4-hydroxycyclohexyl)-5-(4-(-3-(tetrahydro-2H-pyran-4-yl)-3-azabicyclo[3.1.0]hexan-1-yl)phenyl)nicotinamide;
2-amino-N-(-4-hydroxycyclohexyl)-5-(4-(-3-(2-methoxyethyl)-3-azabicyclo[3.1.0]hexan-1-yl)phenyl)nicotinamide;
2-amino-N-(3-fluoro-4-hydroxycyclohexyl)-5-(4-(-3-(tetrahydro-2H-pyran-4-yl)-3-azabicyclo[3.1.0]hexan-1-yl)phenyl)nicotinamide;
5-(4-(2-azaspiro[3.3]heptan-2-ylmethyl)phenyl)-2-amino-N-(-4-hydroxycyclohexyl)nicotinamide;
2-amino-N-(-4-hydroxy-4-methylcyclohexyl)-5-(4-(-3-isopropyl-3-azabicyclo[3.1.0]hexan-1-yl)phenyl)nicotinamide;
2-amino-5-(4-(-3-(4,4-difluorocyclohexyl)-3-azabicyclo[3.1.0]hexan-1-yl)phenyl)-N-(-4-hydroxycyclohexyl)nicotinamide;
2-amino-N-(-4-hydroxycyclohexyl)-5-(4-(-3-(oxetan-3-yl)-3-azabicyclo[3.1.0]hexan-1-yl)phenyl)nicotinamide;
2-amino-N-(3-(hydroxymethyl)bicyclo[1.1.1]pentan-1-yl)-5-(4-(-3-(tetrahydro-2H-pyran-4-yl)-3-azabicyclo[3.1.0]hexan-1-yl)phenyl)nicotinamide;
2-amino-5-(2-fluoro-4-(piperazin-1-yl)phenyl)-N-(-4-hydroxycyclohexyl)nicotinamide;
2-amino-N-(-4-hydroxycyclohexyl)-5-(4-((2-methylpyrrolidin-1-yl)methyl)phenyl)nicotinamide;
2-amino-N-(4-hydroxycyclohexyl)-5-(4-(-3-(tetrahydro-2H-pyran-4-yl)-3-azabicyclo[3.1.0]hexan-1-yl)phenyl)nicotinamide;
2-amino-N-(4-hydroxybicyclo[2.2.2]octan-1-yl)-5-(4-(-3-(tetrahydro-2H-pyran-4-yl)-3-azabicyclo[3.1.0]hexan-1-yl)phenyl)nicotinamide;
2-amino-5-(4-(-3-(4,4-difluorocyclohexyl)-3-azabicyclo[3.1.0]hexan-1-yl)phenyl)-N-(4-hydroxybicyclo[2.2.2]octan-1-yl)nicotinamide;
2-amino-5-(4-(-3-(but-2-yn-1-yl)-3-azabicyclo[3.1.0]hexan-1-yl)phenyl)-N-(-4-hydroxycyclohexyl)nicotinamide;
2-amino-N-(-4-hydroxycyclohexyl)-5-(4-(-3-(oxetan-3-ylmethyl)-3-azabicyclo[3.1.0]hexan-1-yl)phenyl)nicotinamide;
2-amino-N-(-4-hydroxycyclohexyl)-5-(4-(-3-(1-(2,2,2-trifluoroethyl)piperidin-4-yl)-3-azabicyclo[3.1.0]hexan-1-yl)phenyl)nicotinamide;
2-amino-N-(-4-hydroxycyclohexyl)-5-(4-(-3-(2-(2,2,2-trifluoroethoxy)ethyl)-3-azabicyclo[3.1.0]hexan-1-yl)phenyl)nicotinamide;
2-amino-N-cyclohexyl-5-(4-(3-(piperidin-1-yl)propoxy)phenyl)nicotinamide;
2-amino-5-(4-(-3-(1,1-dioxidotetrahydro-2H-thiopyran-4-yl)-3-azabicyclo[3.1.0]hexan-1-yl)phenyl)-N-(-4-hydroxycyclohexyl)nicotinamide;
2-amino-N-cyclohexyl-5-(4-(4-methylpiperazine-1-carbonyl)phenyl)nicotinamide
2-amino-5-(3-fluoro-4-(2-methylpyrrolidin-1-yl)methyl)phenyl)-N-(-4-hydroxy-4-methylcyclohexyl) nicotinamide;
2-amino-N-cyclohexyl-5-(4-morpholinophenyl)nicotinamide;
2-amino-5-(4-(-3-(2,2-difluoropropyl)-3-azabicyclo[3.1.0]hexan-1-yl)phenyl)-N-(-4-hydroxycyclohexyl)nicotinamide;
2-amino-5-(4-(-3-(2-cyanoethyl)-3-azabicyclo[3.1.0]hexan-1-yl)phenyl)-N-(-4-hydroxycyclohexyl)nicotinamide;
2-amino-N-cyclohexyl-5-(4-(3-morpholinopropoxy)phenyl)nicotinamide;
2-amino-N-(4-hydroxycyclohexyl)-5-(4-(3-(prop-2-yn-1-yl)-3-azabicyclo[3.1.0]hexan-1-yl)phenyl)nicotinamide;
5-(4-(-1-(2-oxa-6-azaspiro[3.3]heptan-6-yl)ethyl)-2-chlorophenyl)-2-amino-N-(-4-hydroxycyclohexyl)nicotinamide;
2-amino-5-(2-fluoro-4-((2-methylpyrrolidin-1-yl)methyl)phenyl)-N-(-4-hydroxy-4-methylcyclohexyl)nicotinamide;

2-amino-5-(4-(-3-(2-fluoroethyl)-3-azabicyclo[3.1.0]hexan-1-yl)phenyl)-N-(4-hydroxybicyclo[2.2.2]octan-1-yl)nicotinamide;

2-amino-5-(4-(-3-(4,4-difluorocyclohexyl)-3-azabicyclo[3.1.0]hexan-1-yl)phenyl)-N-(-4-hydroxy-4-methylcyclohexyl)nicotinamide;

5-(4-(-1-(2-oxa-6-azaspiro[3.3]heptan-6-yl)ethyl)phenyl)-2-amino-N-(-4-hydroxy-4-methylcyclohexyl) nicotinamide;

2-amino-N-cyclohexyl-5-(4-(piperidin-1-yl)phenyl)nicotinamide;

2-amino-N-(4-hydroxy-4-methylcyclohexyl)-5-(4-(3-(tetrahydro-2H-pyran-4-yl)-3-azabicyclo[3.1.0]hexan-1-yl)phenyl)nicotinamide;

2-amino-N-(4-hydroxybicyclo[2.2.2]octan-1-yl)-5-(4-(-3-(oxetan-3-yl)-3-azabicyclo[3.1.0]hexan-1-yl)phenyl)nicotinamide;

2-amino-N-cyclohexyl-5-(4-((2-(4-methyl piperazin-1-yl)ethyl)carbamoyl)phenyl)nicotinamide;

2-amino-N-(-4-hydroxycyclohexyl)-5-(4-(-3-(2,2,2-trifluoroethyl)-3-azabicyclo[3.1.0]hexan-1-yl)phenyl)nicotinamide;

5-(4-(-1-(2-oxa-6-azaspiro[3.3]heptan-6-yl)ethyl)phenyl)-2-amino-N-(-3-hydroxyadamantan-1-yl)nicotinamide;

2-amino-N-cyclohexyl-5-(4-(morpholine-4-carbonyl)phenyl)nicotinamide;

2-amino-N-(-4-hydroxy-4-methylcyclohexyl)-5-(4-((2-methylpyrrolidin-1-yl)methyl)phenyl)nicotinamide;

2-amino-5-(2,3-difluoro-4-((2-methylpyrrolidin-1-yl)methyl)phenyl)-N-(-4-hydroxy-4-methylcyclohexyl)nicotinamide;

2-amino-N-(-4-hydroxycyclohexyl-4-d)-5-(4-(-3-isopropyl-3-azabicyclo[3.1.0]hexan-1-yl)phenyl)nicotinamide;

2-amino-N-(-4-hydroxycyclohexyl)-5-(4-(4-methylpiperazine-1-carbonyl)phenyl)nicotinamide;

2-amino-5-(2-chloro-4-((2-methylpyrrolidin-1-yl)methyl)phenyl)-N-(-4-hydroxy-4-methylcyclohexyl) nicotinamide;

2-amino-N-(3-(2-hydroxypropan-2-yl)bicyclo[1.1.1]pentan-1-yl)-5-(4-(-3-(tetrahydro-2H-pyran-4-yl)-3-azabicyclo[3.1.0]hexan-1-yl)phenyl)nicotinamide;

2-amino-N-cyclohexyl-5-(3-(morpholine-4-carbonyl)phenyl)nicotinamide;

2-amino-5-(3-chloro-4-((2-methylpyrrolidin-1-yl)methyl)phenyl)-N-(-4-hydroxy-4-methylcyclohexyl) nicotinamide;

5-(4-(-1-(2-oxa-6-azaspiro[3.3]heptan-6-yl)ethyl)phenyl)-2-amino-N-(-4-hydroxy-1-methylcyclohexyl) nicotinamide;

2-amino-N-(-4-hydroxy-4-methylcyclohexyl)-5-(2-methyl-4-((2-methylpyrrolidin-1-yl)methyl)phenyl)nicotinamide; and 2-amino-N-cyclohexyl-5-(3-(4-(2-hydroxyethyl) piperazine-1-carbonyl)phenyl)nicotinamide.

Embodiment 22

A compound according to embodiment 21 in free form or in pharmaceutically acceptable salt form, which is selected from 2-amino-N-((1r,4R)-4-hydroxycyclohexyl)-5-(4-((1R,5S)-3-(1-(methylsulfonyl)piperidin-4-yl)-3-azabicyclo[3.1.0]hexan-1-yl)phenyl)nicotinamide;

2-amino-N-((1r,4R)-4-hydroxycyclohexyl)-5-(4-((1R,5S)-3-isopropyl-3-azabicyclo[3.1.0]hexan-1-yl)phenyl)nicotinamide;

5-(4-((R)-1-(2-oxa-6-azaspiro[3.3]heptan-6-yl)ethyl)phenyl)-2-amino-N-((1r,4R)-4-hydroxycyclohexyl)nicotinamide;

5-(4-((S)-1-(2-oxa-6-azaspiro[3.3]heptan-6-yl)ethyl)phenyl)-2-amino-N-((1r,4R)-4-hydroxycyclohexyl)nicotinamide;

2-amino-N-((1r,4S)-4-hydroxycyclohexyl)-5-(4-((1S,5R)-3-(3-morpholinopropyl)-3-azabicyclo[3.1.0]hexan-1-yl)phenyl)nicotinamide;

2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide;

2-amino-N-(4-hydroxybicyclo[2.2.2]octan-1-yl)-5-(4-((1S,5R)-3-(2-methoxyethyl)-3-azabicyclo[3.1.0]hexan-1-yl)phenyl)nicotinamide;

2-amino-5-(2-fluoro-4-(4-isopropylpiperazin-1-yl)phenyl)-N-((1r,4r)-4-hydroxycyclohexyl)nicotinamide;

2-amino-N-((1r,4S)-4-hydroxycyclohexyl)-5-(4-((1S,5R)-3-isopropyl-3-azabicyclo[3.1.0]hexan-1-yl)phenyl)nicotinamide;

2-amino-N-((1r,4R)-4-hydroxycyclohexyl)-5-(4-((1R,5S)-3-(2-morpholinoethyl)-3-azabicyclo[3.1.0]hexan-1-yl)phenyl)nicotinamide;

2-amino-5-(4-((1S,5R)-3-(2-fluoroethyl)-3-azabicyclo[3.1.0]hexan-1-yl)phenyl)-N-((1r,4S)-4-hydroxycyclohexyl)nicotinamide;

2-amino-N-((1r,4r)-4-hydroxycyclohexyl)-5-(4-(1-isopropylpyrrolidin-3-yl)phenyl)nicotinamide;

2-amino-N-((1r,4S)-4-hydroxycyclohexyl)-5-(4-((1S,5R)-3-(2-morpholinoethyl)-3-azabicyclo[3.1.0]hexan-1-yl)phenyl)nicotinamide;

2-amino-N-((1r,4R)-4-hydroxy-4-methylcyclohexyl)-5-(4-((1R,5S)-3-(tetrahydro-2H-pyran-4-yl)-3-azabicyclo[3.1.0]hexan-1-yl)phenyl)nicotinamide;

2-amino-N-(4-hydroxybicyclo[2.2.2]octan-1-yl)-5-(4-((1R,5S)-3-(2-morpholinoethyl)-3-azabicyclo[3.1.0]hexan-1-yl)phenyl)nicotinamide;

2-amino-N-(3-(hydroxymethyl)bicyclo[1.1.1]pentan-1-yl)-5-(4-((1S,5R)-3-isopropyl-3-azabicyclo[3.1.0]hexan-1-yl)phenyl)nicotinamide;

2-amino-N-((1r,4S)-4-hydroxycyclohexyl)-5-(4-((1S,5R)-3-(3,3,3-trifluoropropyl)-3-azabicyclo[3.1.0]hexan-1-yl)phenyl)nicotinamide;

2-amino-N-((1r,4r)-4-hydroxycyclohexyl)-5-(4-(pyrrolidin-3-yl)phenyl)nicotinamide;

2-amino-N-((1r,4R)-4-hydroxycyclohexyl)-5-(4-((1R,5S)-3-(tetrahydro-2H-pyran-4-yl)-3-azabicyclo[3.1.0]hexan-1-yl)phenyl)nicotinamide;

2-amino-N-((1r,4S)-4-hydroxycyclohexyl)-5-(4-((1S,5R)-3-(2-methoxyethyl)-3-azabicyclo[3.1.0]hexan-1-yl)phenyl)nicotinamide;

2-amino-N-((1R,3S,4R)-3-fluoro-4-hydroxycyclohexyl)-5-(4-((1R,5S)-3-(tetrahydro-2H-pyran-4-yl)-3-azabicyclo[3.1.0]hexan-1-yl)phenyl)nicotinamide;

2-amino-N-((1s,4S)-4-hydroxycyclohexyl)-5-(4-((1R,5S)-3-(tetrahydro-2H-pyran-4-yl)-3-azabicyclo[3.1.0]hexan-1-yl)phenyl)nicotinamide;

5-(4-(2-azaspiro[3.3]heptan-2-ylmethyl)phenyl)-2-amino-N-((1r,4r)-4-hydroxycyclohexyl)nicotinamide;

2-amino-N-((1r,4R)-4-hydroxy-4-methylcyclohexyl)-5-(4-((1R,5S)-3-isopropyl-3-azabicyclo[3.1.0]hexan-1-yl)phenyl)nicotinamide;

2-amino-5-(4-((1R,5S)-3-(4,4-difluorocyclohexyl)-3-azabicyclo[3.1.0]hexan-1-yl)phenyl)-N-((1r,4R)-4-hydroxycyclohexyl)nicotinamide;

2-amino-N-((1r,4S)-4-hydroxycyclohexyl)-5-(4-((1S,5R)-3-(oxetan-3-yl)-3-azabicyclo[3.1.0]hexan-1-yl)phenyl)nicotinamide;

2-amino-5-(4-((1S,5R)-3-(4,4-difluorocyclohexyl)-3-azabicyclo[3.1.0]hexan-1-yl)phenyl)-N-((1r,4S)-4-hydroxycyclohexyl)nicotinamide;

2-amino-N-(3-(hydroxymethyl)bicyclo[1.1.1]pentan-1-yl)-5-(4-((1S,5R)-3-(tetrahydro-2H-pyran-4-yl)-3-azabicyclo[3.1.0]hexan-1-yl)phenyl)nicotinamide;

2-amino-5-(2-fluoro-4-(piperazin-1-yl)phenyl)-N-((1r,4r)-4-hydroxycyclohexyl)nicotinamide 2-amino-N-(3-(hydroxymethyl)bicyclo[1.1.1]pentan-1-yl)-5-(4-((1R,5S)-3-(tetrahydro-2H-pyran-4-yl)-3-azabicyclo[3.1.0]hexan-1-yl)phenyl)nicotinamide;

2-amino-N-((1r,4R)-4-hydroxycyclohexyl)-5-(4-(((R)-2-methylpyrrolidin-1-yl)methyl)phenyl)nicotinamide;

2-amino-N-((1r,4S)-4-hydroxy-4-methylcyclohexyl)-5-(4-((1S,5R)-3-isopropyl-3-azabicyclo[3.1.0]hexan-1-yl)phenyl)nicotinamide;

2-amino-N-((1r,4S)-4-hydroxycyclohexyl)-5-(4-((1S,5R)-3-(tetrahydro-2H-pyran-4-yl)-3-azabicyclo[3.1.0]hexan-1-yl)phenyl)nicotinamide;

2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide;

2-amino-5-(4-((1S,5R)-3-(4,4-difluorocyclohexyl)-3-azabicyclo[3.1.0]hexan-1-yl)phenyl)-N-(4-hydroxybicyclo[2.2.2]octan-1-yl)nicotinamide;

2-amino-N-(3-(hydroxymethyl)bicyclo[1.1.1]pentan-1-yl)-5-(4-((1R,5S)-3-isopropyl-3-azabicyclo[3.1.0]hexan-1-yl)phenyl)nicotinamide;

2-amino-5-(4-((1S,5R)-3-(but-2-yn-1-yl)-3-azabicyclo[3.1.0]hexan-1-yl)phenyl)-N-((1r,4S)-4-hydroxycyclohexyl)nicotinamide;

2-amino-N-((1r,4S)-4-hydroxycyclohexyl)-5-(4-((1S,5R)-3-(oxetan-3-ylmethyl)-3-azabicyclo[3.1.0]hexan-1-yl)phenyl)nicotinamide;

2-amino-N-((1r,4R)-4-hydroxycyclohexyl)-5-(4-((1R,5S)-3-(1-(2,2,2-trifluoroethyl)piperidin-4-yl)-3-azabicyclo[3.1.0]hexan-1-yl)phenyl)nicotinamide;

2-amino-N-(4-hydroxybicyclo[2.2.2]octan-1-yl)-5-(4-((1S,5R)-3-(2-morpholinoethyl)-3-azabicyclo[3.1.0]hexan-1-yl)phenyl)nicotinamide;

2-amino-N-((1r,4R)-4-hydroxycyclohexyl)-5-(4-((1R,5S)-3-(2-(2,2,2-trifluoroethoxy)ethyl)-3-azabicyclo[3.1.0]hexan-1-yl)phenyl)nicotinamide;

2-amino-N-(4-hydroxybicyclo[2.2.2]octan-1-yl)-5-(4-((1S,5R)-3-(tetrahydro-2H-pyran-4-yl)-3-azabicyclo[3.1.0]hexan-1-yl)phenyl)nicotinamide;

2-amino-5-(4-((1R,5S)-3-(1,1-dioxidotetrahydro-2H-thiopyran-4-yl)-3-azabicyclo[3.1.0]hexan-1-yl)phenyl)-N-((1r,4R)-4-hydroxycyclohexyl)nicotinamide;

2-amino-5-(3-fluoro-4-(((R)-2-methylpyrrolidin-1-yl)methyl)phenyl)-N-((1r,4R)-4-hydroxy-4-methylcyclohexyl) nicotinamide;

2-amino-N-((1r,4R)-4-hydroxycyclohexyl)-5-(4-((1R,5S)-3-(3,3,3-trifluoropropyl)-3-azabicyclo[3.1.0]hexan-1-yl)phenyl)nicotinamide;

2-amino-5-(4-((1R,5S)-3-(2-fluoroethyl)-3-azabicyclo[3.1.0]hexan-1-yl)phenyl)-N-((1r,4R)-4-hydroxycyclohexyl)nicotinamide;

2-amino-5-(4-((1R,5S)-3-(2,2-difluoropropyl)-3-azabicyclo[3.1.0]hexan-1-yl)phenyl)-N-((1r,4R)-4-hydroxycyclohexyl)nicotinamide;

2-amino-5-(4-((1S,5R)-3-(2-cyanoethyl)-3-azabicyclo[3.1.0]hexan-1-yl)phenyl)-N-((1r,4S)-4-hydroxycyclohexyl)nicotinamide;

2-amino-N-((1r,4S)-4-hydroxycyclohexyl)-5-(4-((1S,5R)-3-(prop-2-yn-1-yl)-3-azabicyclo[3.1.0]hexan-1-yl)phenyl)nicotinamide;

2-amino-N-((1r,4R)-4-hydroxycyclohexyl)-5-(4-((1R,5S)-3-(prop-2-yn-1-yl)-3-azabicyclo[3.1.0]hexan-1-yl)phenyl)nicotinamide;

5-(4-((R)-1-(2-oxa-6-azaspiro[3.3]heptan-6-yl)ethyl)-2-chlorophenyl)-2-amino-N-((1r,4R)-4-hydroxycyclohexyl)nicotinamide;

2-amino-5-(2-fluoro-4-(((R)-2-methylpyrrolidin-1-yl)methyl)phenyl)-N-((1r,4R)-4-hydroxy-4-methylcyclohexyl) nicotinamide;

2-amino-5-(4-((1R,5S)-3-(2-fluoroethyl)-3-azabicyclo[3.1.0]hexan-1-yl)phenyl)-N-(4-hydroxybicyclo[2.2.2]octan-1-yl)nicotinamide;

2-amino-5-(4-((1S,5R)-3-(4,4-difluorocyclohexyl)-3-azabicyclo[3.1.0]hexan-1-yl)phenyl)-N-((1r,4S)-4-hydroxy-4-methylcyclohexyl)nicotinamide;

5-(4-((R)-1-(2-oxa-6-azaspiro[3.3]heptan-6-yl)ethyl)phenyl)-2-amino-N-((1r,4R)-4-hydroxy-4-methylcyclohexyl) nicotinamide;

2-amino-5-(4-((1R,5S)-3-(but-2-yn-1-yl)-3-azabicyclo[3.1.0]hexan-1-yl)phenyl)-N-((1r,4R)-4-hydroxycyclohexyl)nicotinamide;

2-amino-N-((1r,4S)-4-hydroxy-4-methylcyclohexyl)-5-(4-((1S,5R)-3-(tetrahydro-2H-pyran-4-yl)-3-azabicyclo[3.1.0]hexan-1-yl)phenyl)nicotinamide;

2-amino-N-(4-hydroxybicyclo[2.2.2]octan-1-yl)-5-(4-((1S,5R)-3-(oxetan-3-yl)-3-azabicyclo[3.1.0]hexan-1-yl)phenyl)nicotinamide;

2-amino-N-(4-hydroxybicyclo[2.2.2]octan-1-yl)-5-(4-((1R,5S)-3-(oxetan-3-yl)-3-azabicyclo[3.1.0]hexan-1-yl)phenyl)nicotinamide;

2-amino-N-cyclohexyl-5-(4-((2-(4-methyl piperazin-1-yl)ethyl)carbamoyl)phenyl)nicotinamide;

2-amino-5-(4-((1S,5R)-3-(1,3-difluoropropan-2-yl)-3-azabicyclo[3.1.0]hexan-1-yl)phenyl)-N-((1r,4S)-4-hydroxycyclohexyl)nicotinamide;

2-amino-N-((1r,4S)-4-hydroxycyclohexyl)-5-(4-((1S,5R)-3-(2,2,2-trifluoroethyl)-3-azabicyclo[3.1.0]hexan-1-yl)phenyl)nicotinamide;

5-(4-((R)-1-(2-oxa-6-azaspiro[3.3]heptan-6-yl)ethyl)phenyl)-2-amino-N-((1R,3R)-3-hydroxyadamantan-1-yl)nicotinamide;

2-amino-N-((1r,4R)-4-hydroxycyclohexyl)-5-(4-((1R,5S)-3-(oxetan-3-ylmethyl)-3-azabicyclo[3.1.0]hexan-1-yl)phenyl)nicotinamide;

2-amino-N-((1s,4R)-4-hydroxycyclohexyl)-5-(4-((1S,5R)-3-isopropyl-3-azabicyclo[3.1.0]hexan-1-yl)phenyl)nicotinamide;

2-amino-N-((1r,4R)-4-hydroxy-4-methylcyclohexyl)-5-(4-(((R)-2-methylpyrrolidin-1-yl)methyl)phenyl)nicotinamide;

2-amino-5-(4-((1S,5R)-3-(2-fluoroethyl)-3-azabicyclo[3.1.0]hexan-1-yl)phenyl)-N-(4-hydroxybicyclo[2.2.2]octan-1-yl)nicotinamide;

2-amino-5-(2,3-difluoro-4-(((R)-2-methylpyrrolidin-1-yl)methyl)phenyl)-N-((1r,4R)-4-hydroxy-4-methylcyclohexyl) nicotinamide;

2-amino-N-((1r,4R)-4-hydroxycyclohexyl)-5-(4-((1R,5S)-3-(2-methoxyethyl)-3-azabicyclo[3.1.0]hexan-1-yl)phenyl)nicotinamide;

2-amino-5-(4-((1S,5R)-3-(2,2-difluoropropyl)-3-azabicyclo[3.1.0]hexan-1-yl)phenyl)-N-((1r,4S)-4-hydroxycyclohexyl)nicotinamide;

2-amino-N-((1r,4R)-4-hydroxycyclohexyl)-5-(4-((1R,5S)-3-(2,2,2-trifluoroethyl)-3-azabicyclo[3.1.0]hexan-1-yl)phenyl)nicotinamide;

2-amino-N-((1r,4S)-4-hydroxycyclohexyl-4-d)-5-(4-((1S,5R)-3-isopropyl-3-azabicyclo[3.1.0]hexan-1-yl)phenyl)nicotinamide;

2-amino-N-((1s,4s)-4-hydroxycyclohexyl)-5-(4-(4-methylpiperazine-1-carbonyl)phenyl)nicotinamide;

2-amino-5-(4-((1R,5S)-3-(4,4-difluorocyclohexyl)-3-azabicyclo[3.1.0]hexan-1-yl)phenyl)-N-(4-hydroxybicyclo[2.2.2]octan-1-yl)nicotinamide;

2-amino-5-(2-chloro-4-(((R)-2-methylpyrrolidin-1-yl)methyl)phenyl)-N-((1r,4R)-4-hydroxy-4-methylcyclohexyl) nicotinamide;

2-amino-5-(4-((1R,5S)-3-(4,4-difluorocyclohexyl)-3-azabicyclo[3.1.0]hexan-1-yl)phenyl)-N-((1r,4R)-4-hydroxy-4-methylcyclohexyl)nicotinamide;

2-amino-N-(3-(2-hydroxypropan-2-yl)bicyclo[1.1.1]pentan-1-yl)-5-(4-((1R,5S)-3-(tetrahydro-2H-pyran-4-yl)-3-azabicyclo[3.1.0]hexan-1-yl)phenyl)nicotinamide;

2-amino-5-(3-chloro-4-(((R)-2-methylpyrrolidin-1-yl)methyl)phenyl)-N-((1r,4R)-4-hydroxy-4-methylcyclohexyl) nicotinamide;

5-(4-((R)-1-(2-oxa-6-azaspiro[3.3]heptan-6-yl)ethyl)phenyl)-2-amino-N-((1r,4R)-4-hydroxy-1-methylcyclohexyl)nicotinamide; and 2-amino-N-((1r,4R)-4-hydroxy-4-methylcyclohexyl)-5-(2-methyl-4-(((R)-2-methylpyrrolidin-1-yl)methyl)phenyl) nicotinamide.

Embodiment 23

A pharmaceutical composition comprising a therapeutically effective amount of a compound according to any of the preceding embodiments in free form or in pharmaceutically acceptable salt form and one or more pharmaceutically acceptable carriers.

Embodiment 24

A combination comprising a therapeutically effective amount of a compound according to any of embodiments 1 to 22 in free form or in pharmaceutically acceptable salt form and one or more therapeutically active agents.

Embodiment 25

A compound according to any of embodiments 1 to 22 in free form or in pharmaceutically acceptable salt form, for use as a medicament.

Embodiment 26

A compound according to any of the embodiments 1 to 22 in free form or in pharmaceutically acceptable salt form, for use in the treatment of a disorder or disease selected from heterotopic ossification or fibrodysplasia ossificans progressiva.

Embodiment 27

Figure 3:
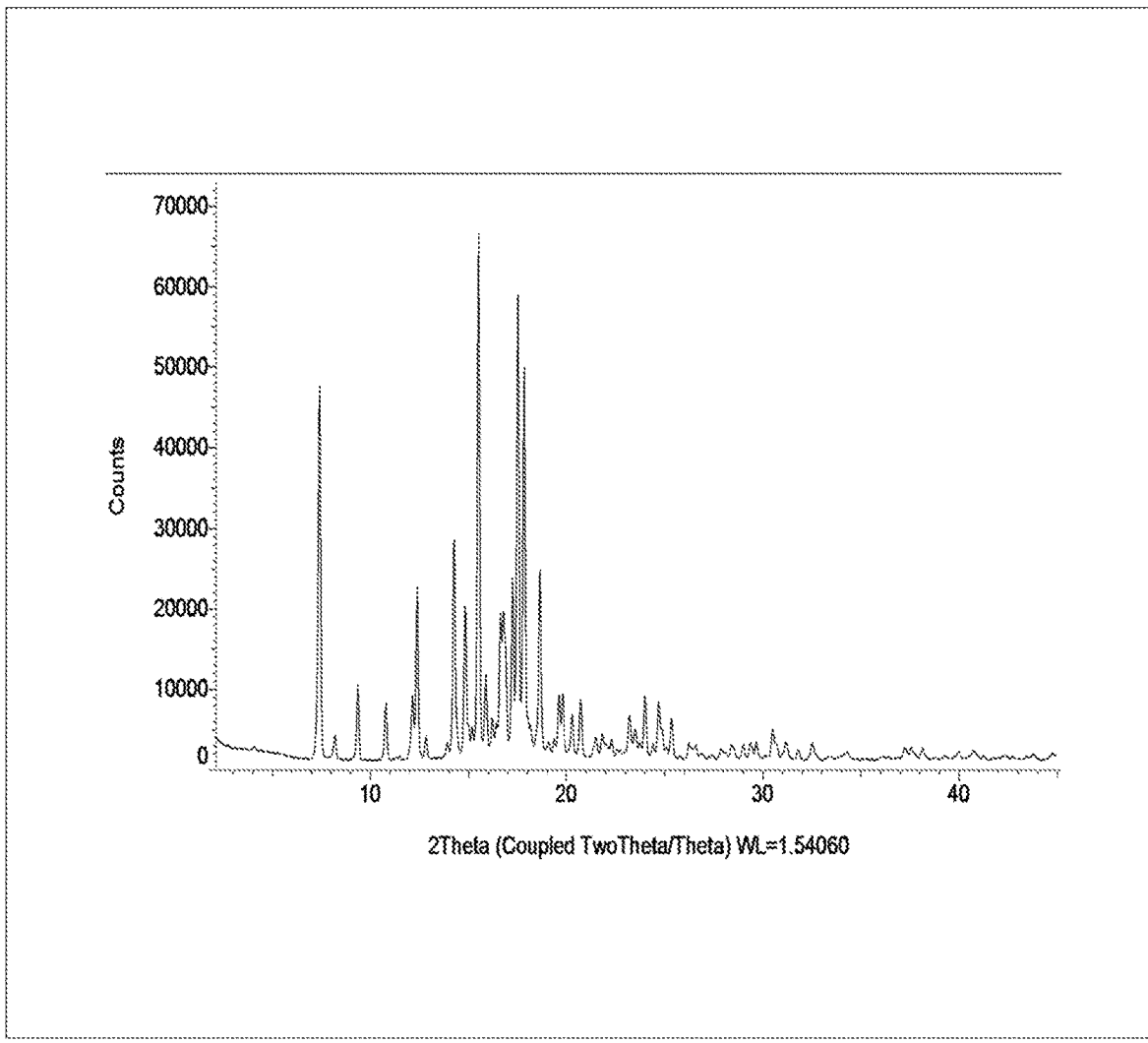
Figure 4:
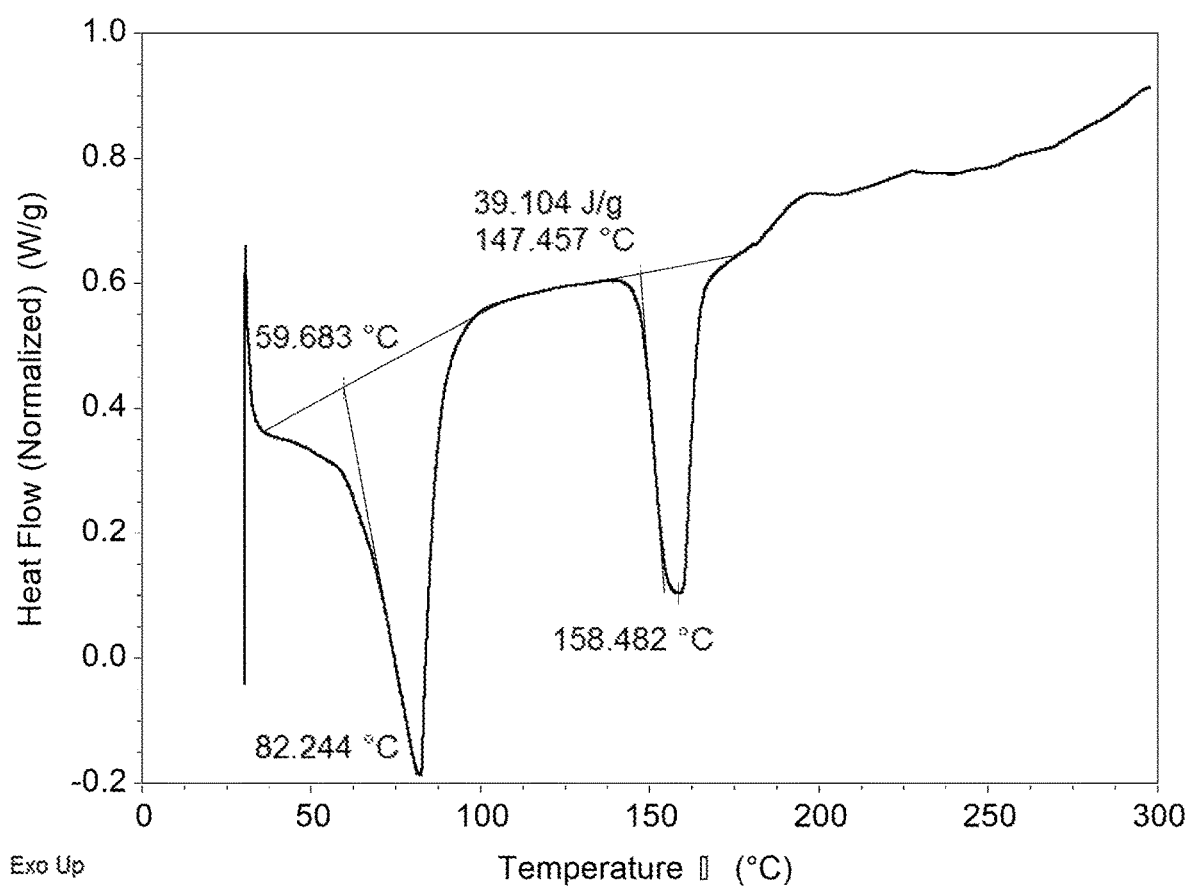
FIG. 4 shows the Differential Scanning Diagram of crystalline free form Modification $H_A$ crystals of compound A.
Figure 5:
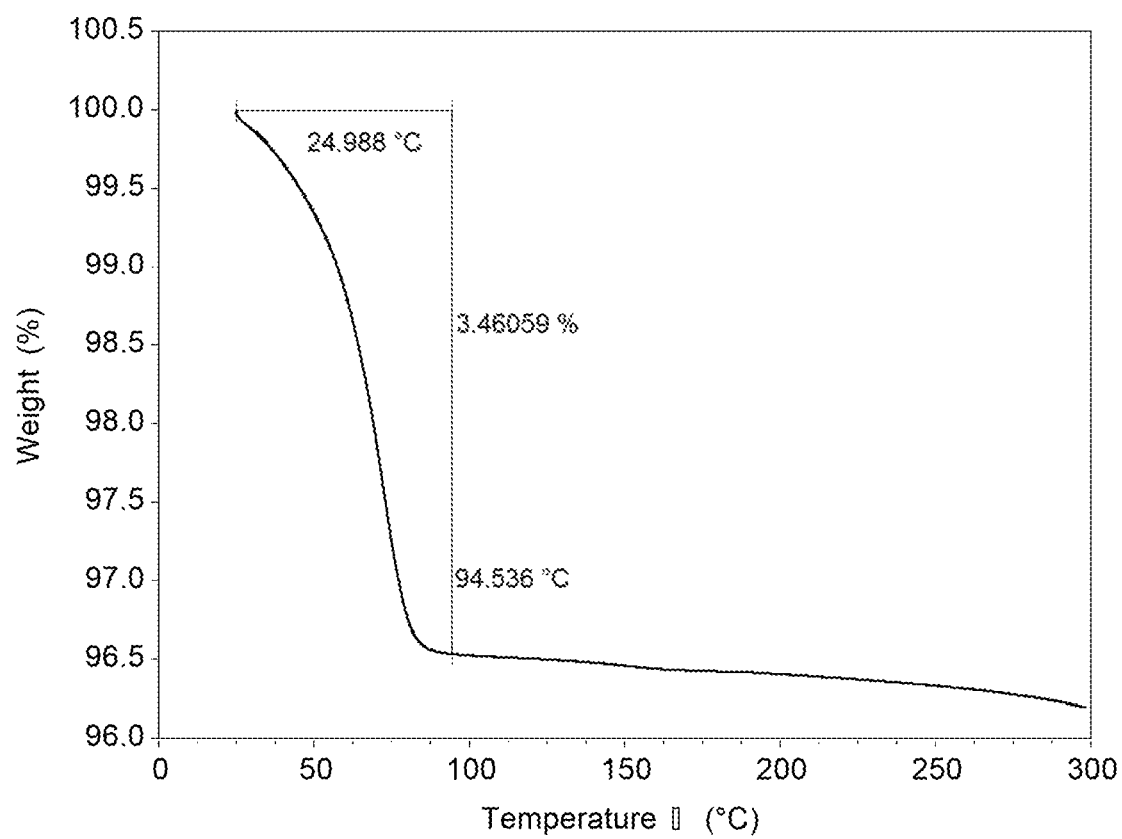
FIG. 5 shows the Thermogravimetric Analysis diagram of crystalline free form Modification $H_A$ of compound A.
Figure 6:
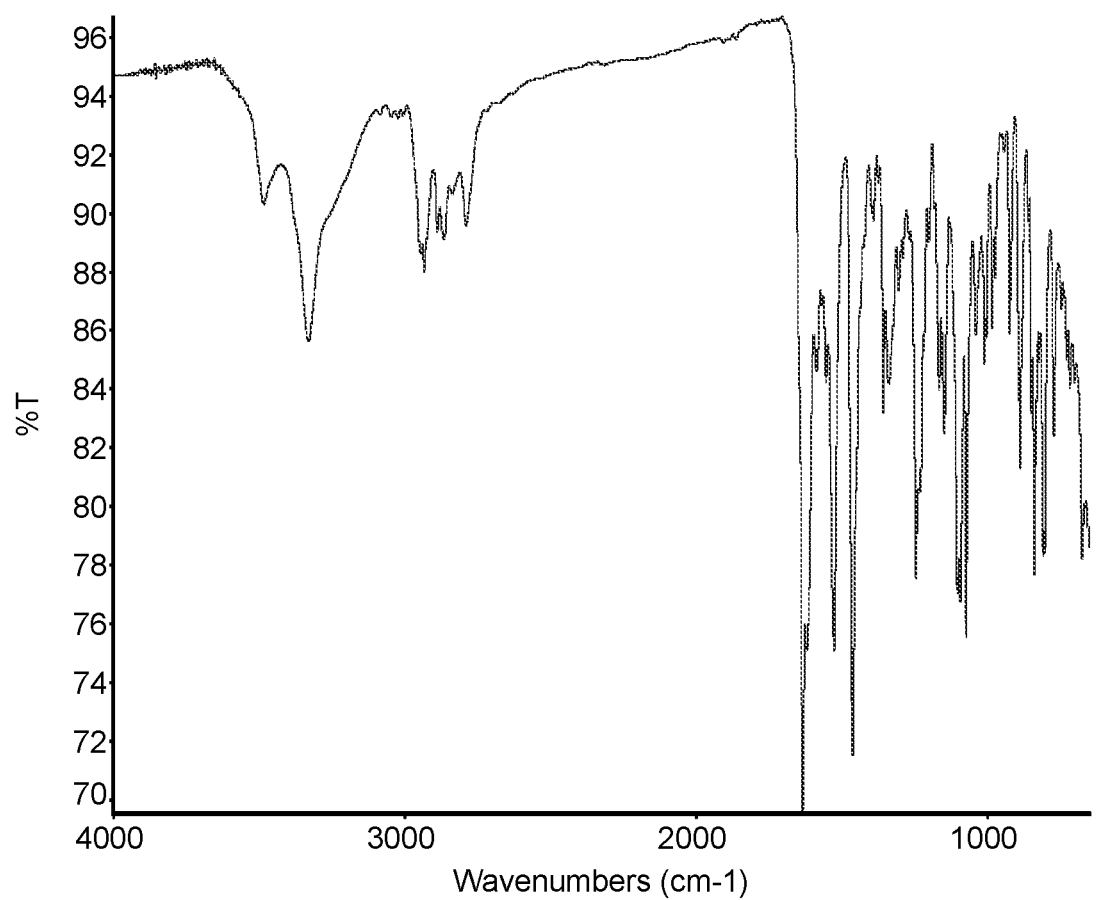
FIG. 6 shows the Fourier-Transform Infrared diagram of crystalline free form Modification $H_A$ of compound A.

2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide in free form, especially in free form Modification $H_A$, especially (i) having 2Theta values in reflection XRPD of the first 2, first 3, first 4, first 5, first 6, first 8, especially the first ten or in particular all of the 2Theta values given in Table A below; or (ii) showing a DSC diagram as shown in FIG. 4; or (iii) having a TGA diagram as shown in FIG. 5; or (iv) having an FT-IR diagram as shown in FIG. 6; or having two or three or especially all of the propterties (i) to (iv) just mentioned; or in particular having an XRPD diagram as shown in FIG. 3.

Embodiment 28

Figure 7:
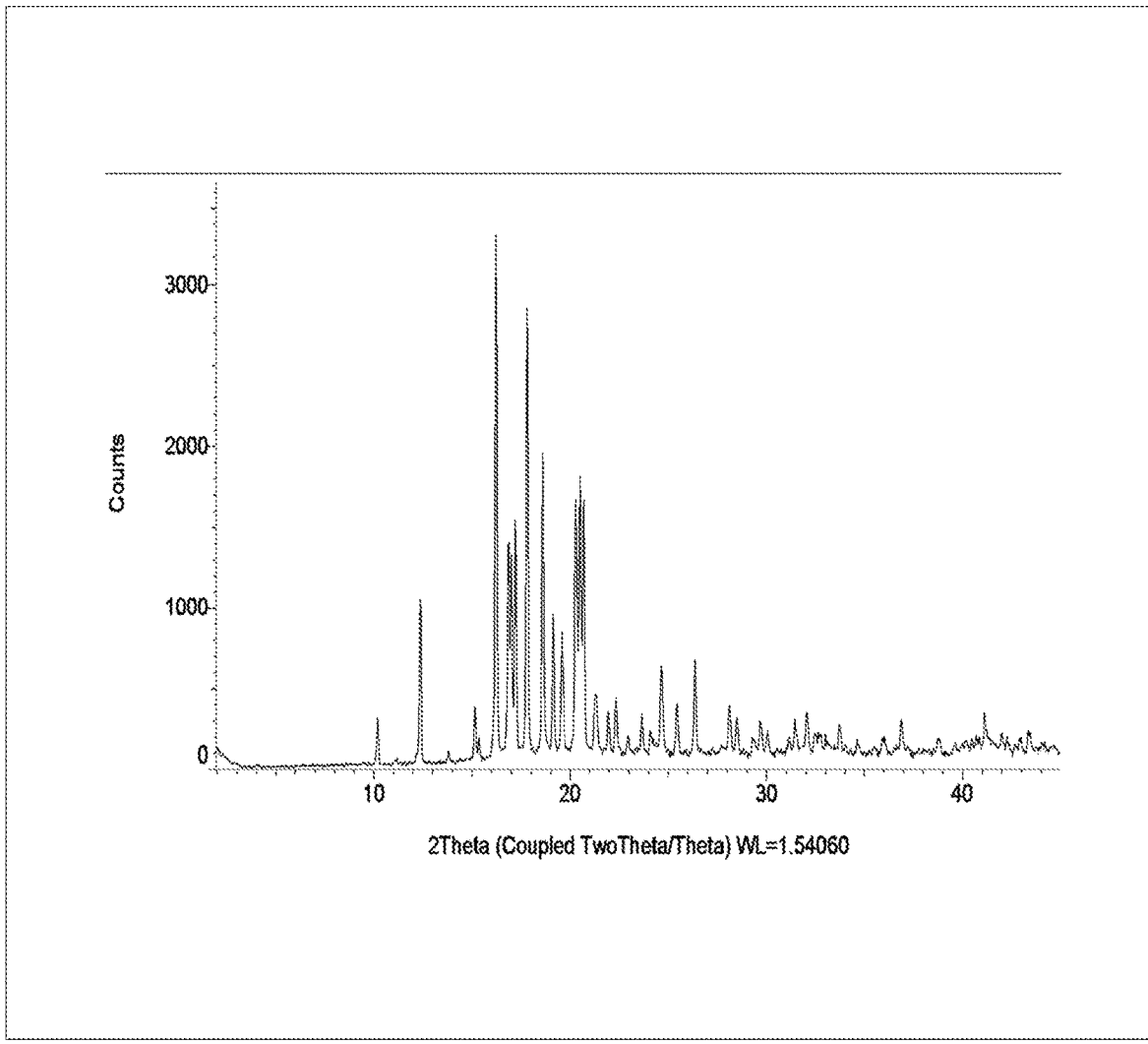
FIG. 7 shows the X-ray powder diffraction pattern of crystalline free form Modification A of compound A.
Figure 8:
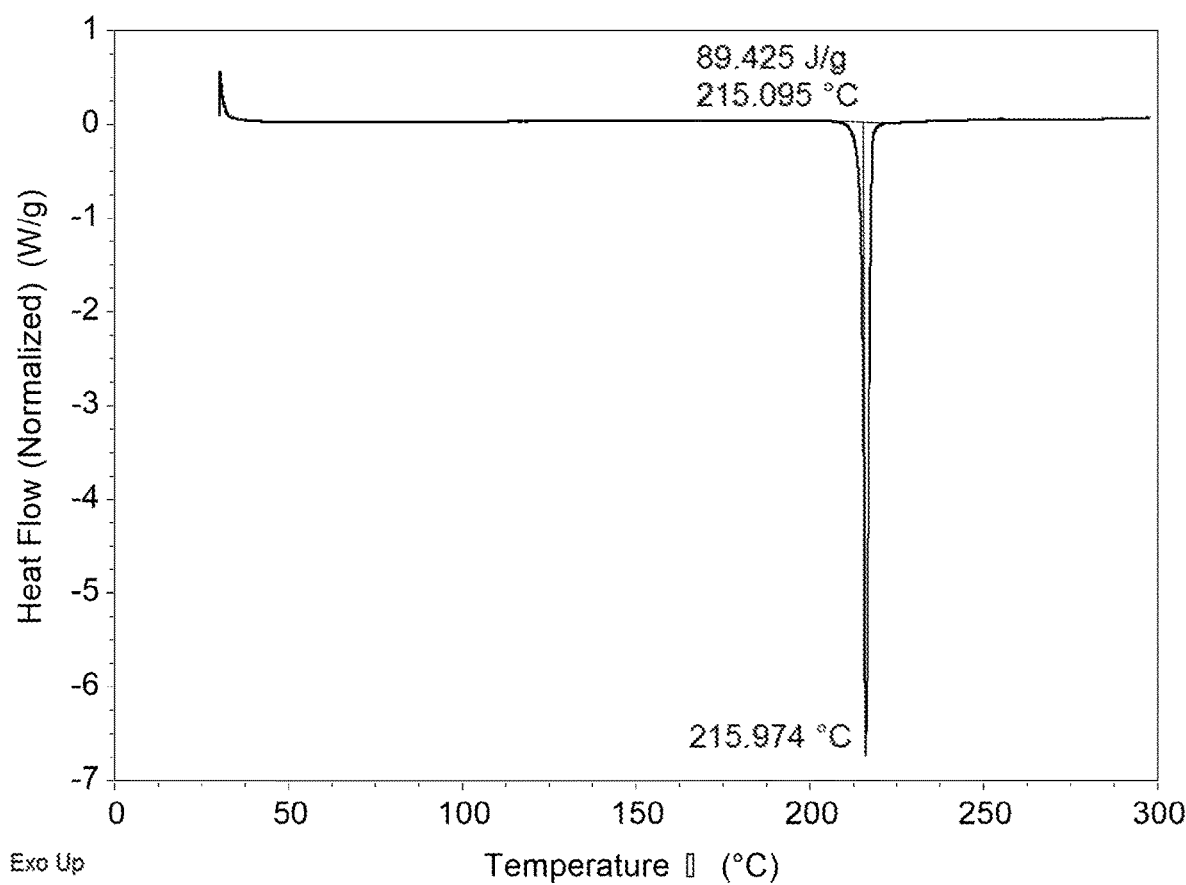
FIG. 8 shows the Differential Scanning Diagram of crystalline free form Modification A of compound A.
Figure 9:
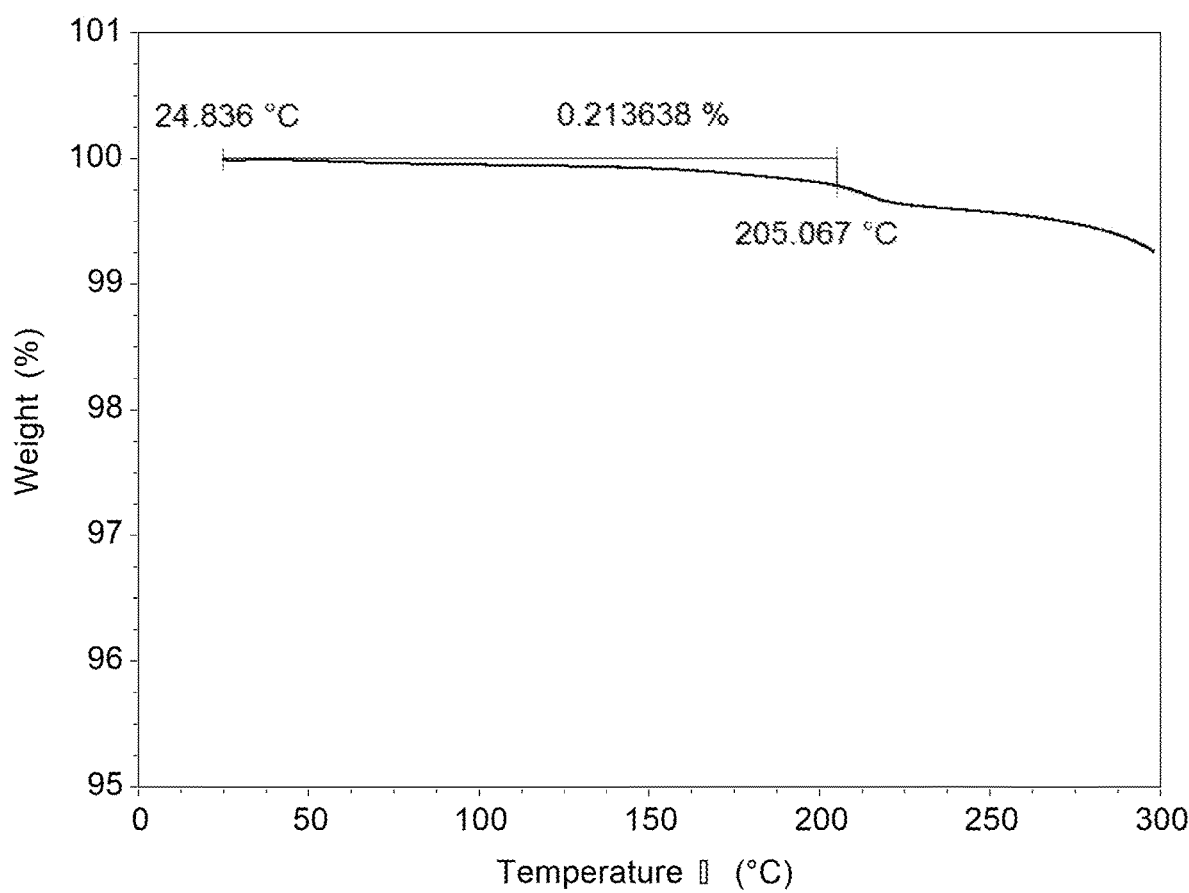
FIG. 9 shows the Thermogravimetric Analysis diagram of crystalline free form Modification A of compound A.
Figure 10:
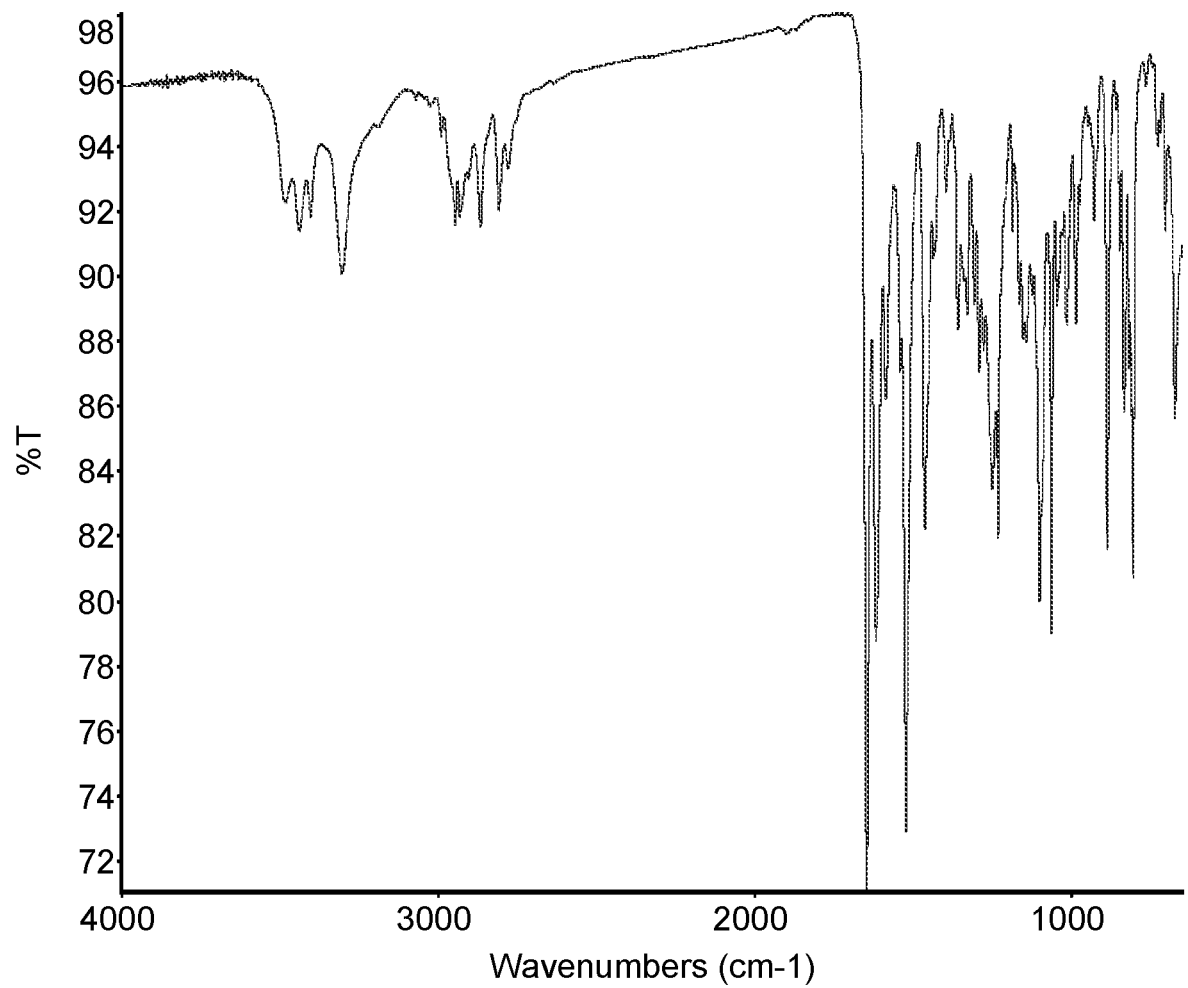
FIG. 10 shows the Fourier-Transform Infrared diagram of crystalline free form Modification A of compound A.

2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide in free form, especially in the form of Modification A, especially (i) having 2Theta values in reflection XRPD of the first 2, first 3, first 4, first 5, first 6, first 8, especially the first ten or all of the 2Theta values given in Table B below; or (ii) showing a DSC diagram as shown in FIG. 8; or (iii) having a TGA diagram as shown in FIG. 9; or (iv) having an FT-IR diagram as shown in FIG. 10; or having two or three or especially all of the propterties (i) to (iv) just mentioned; or in particular having an XRPD diagram as shown in FIG. 7.

Embodiment 29

Figure 18:
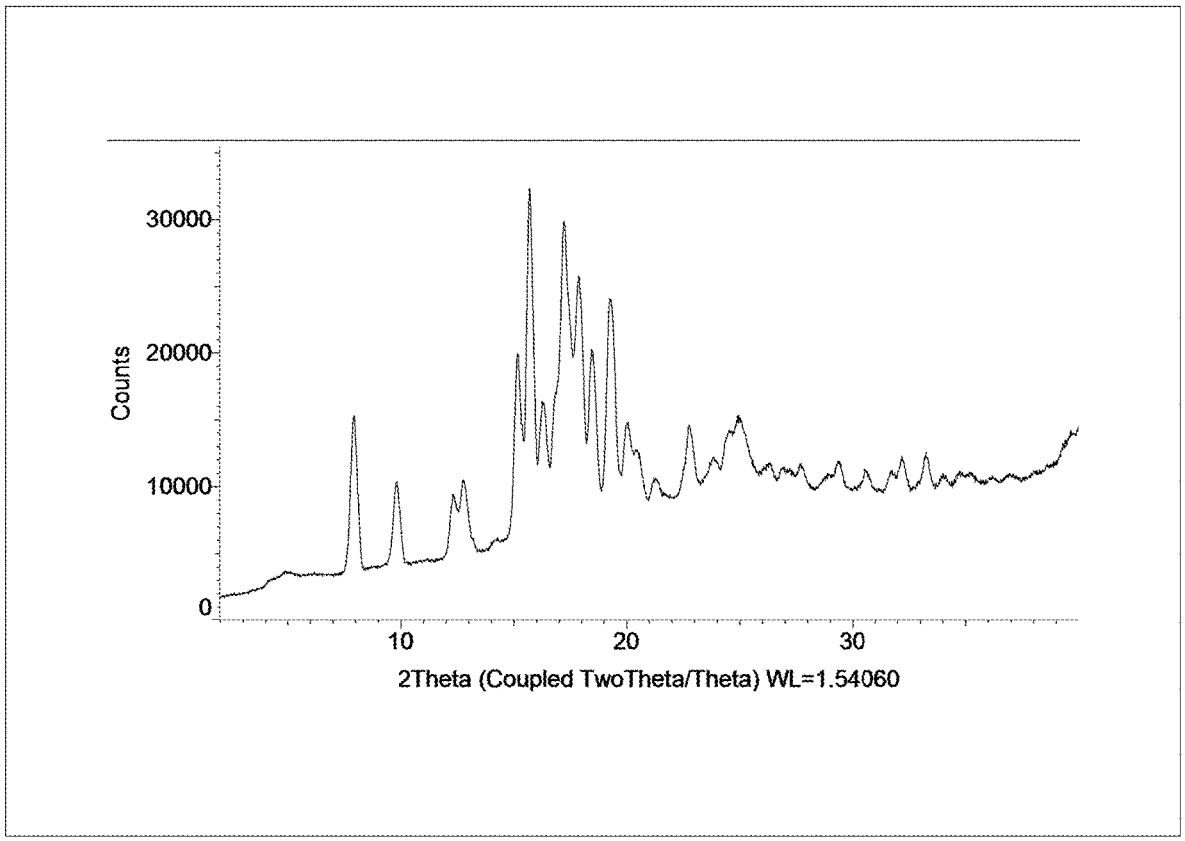
FIG. 18 shows the X-ray powder diffraction pattern of crystalline free form anhydrate (Example 89 C)).

2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide as free form anhydrate, in particular having an XRPD diagram as shown in FIG. 18.

Embodiment 30

Figure 19:
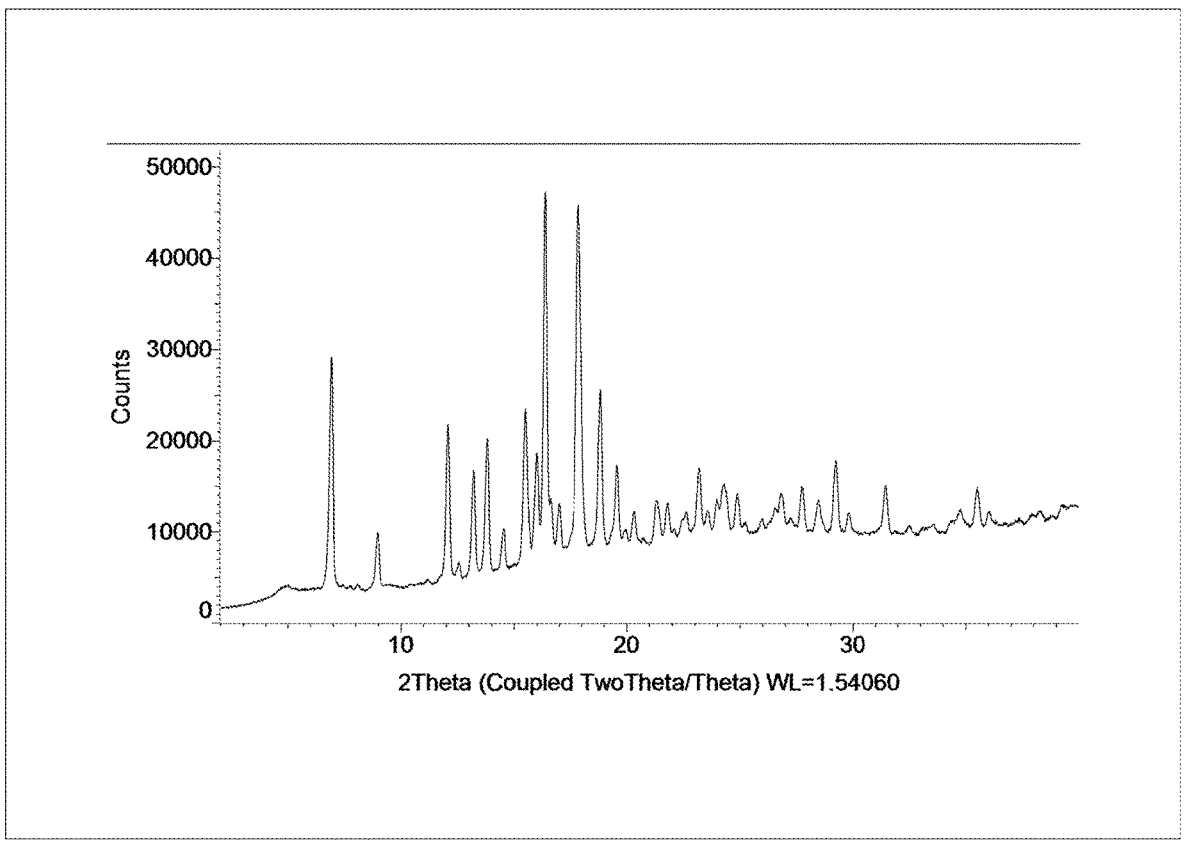
FIG. 19 shows the X-ray powder diffraction pattern of crystalline free form trihydrate (Example 89 D)).

2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide as free form trihydrate, in particular having an XRPD diagram as shown in FIG. 19.

Embodiment 31

Figure 11:
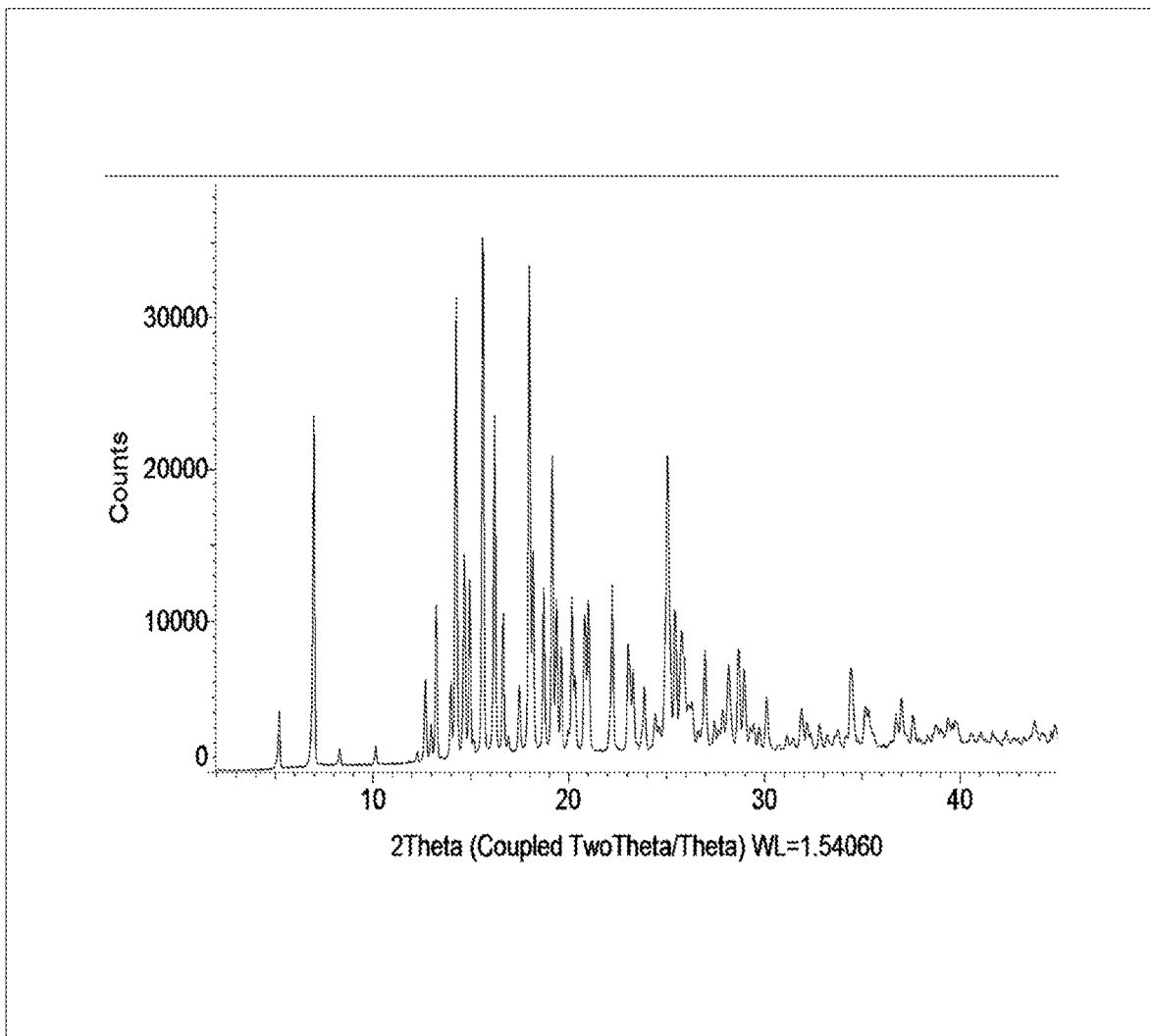
FIG. 11 shows the X-ray powder diffraction pattern of crystalline fumarate salt Modification $H_A$ of compound A.
Figure 12:
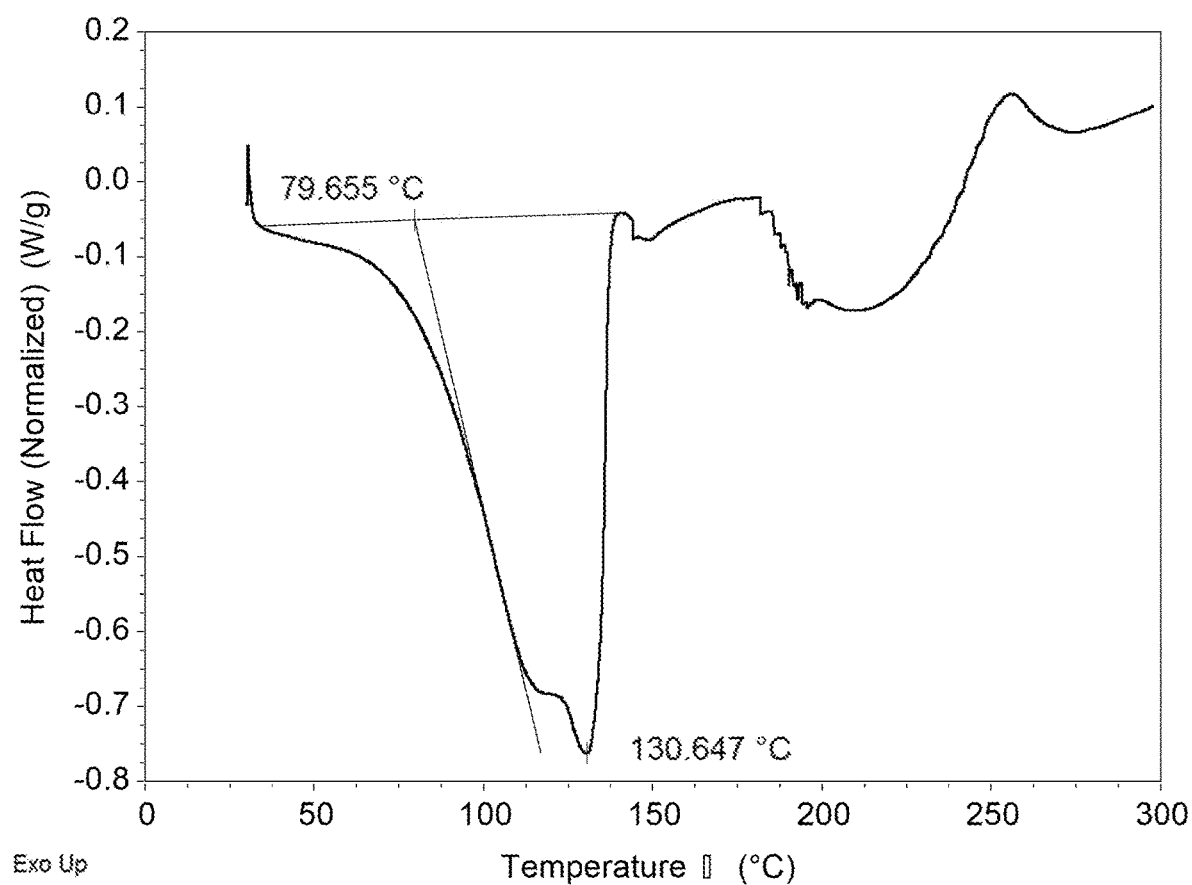
FIG. 12 shows the Differential Scanning Diagram of crystalline fumarate salt Modification $H_A$ Of compound A.
Figure 13:
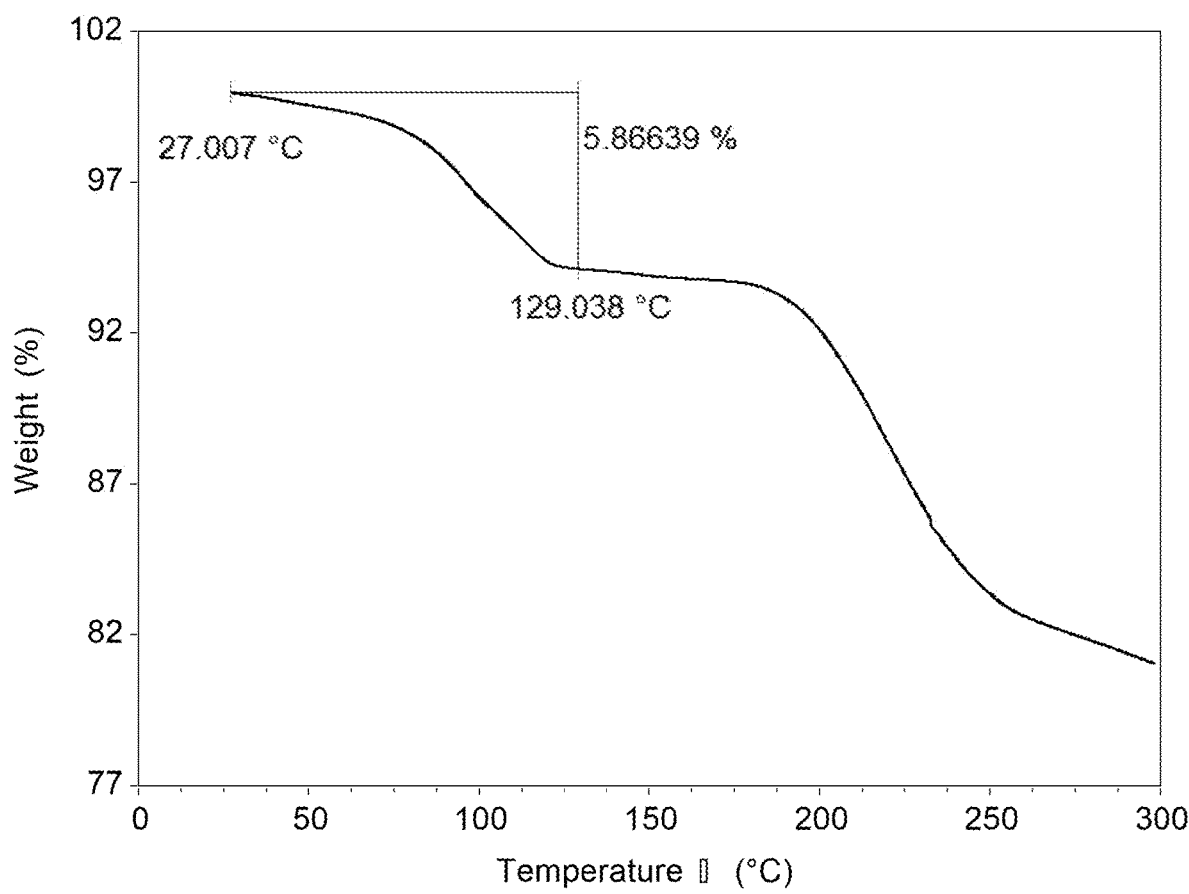
FIG. 13 shows the Thermogravimetric Analysis diagram of crystalline fumarate salt Modification $H_A$ of compound A.
Figure 14:
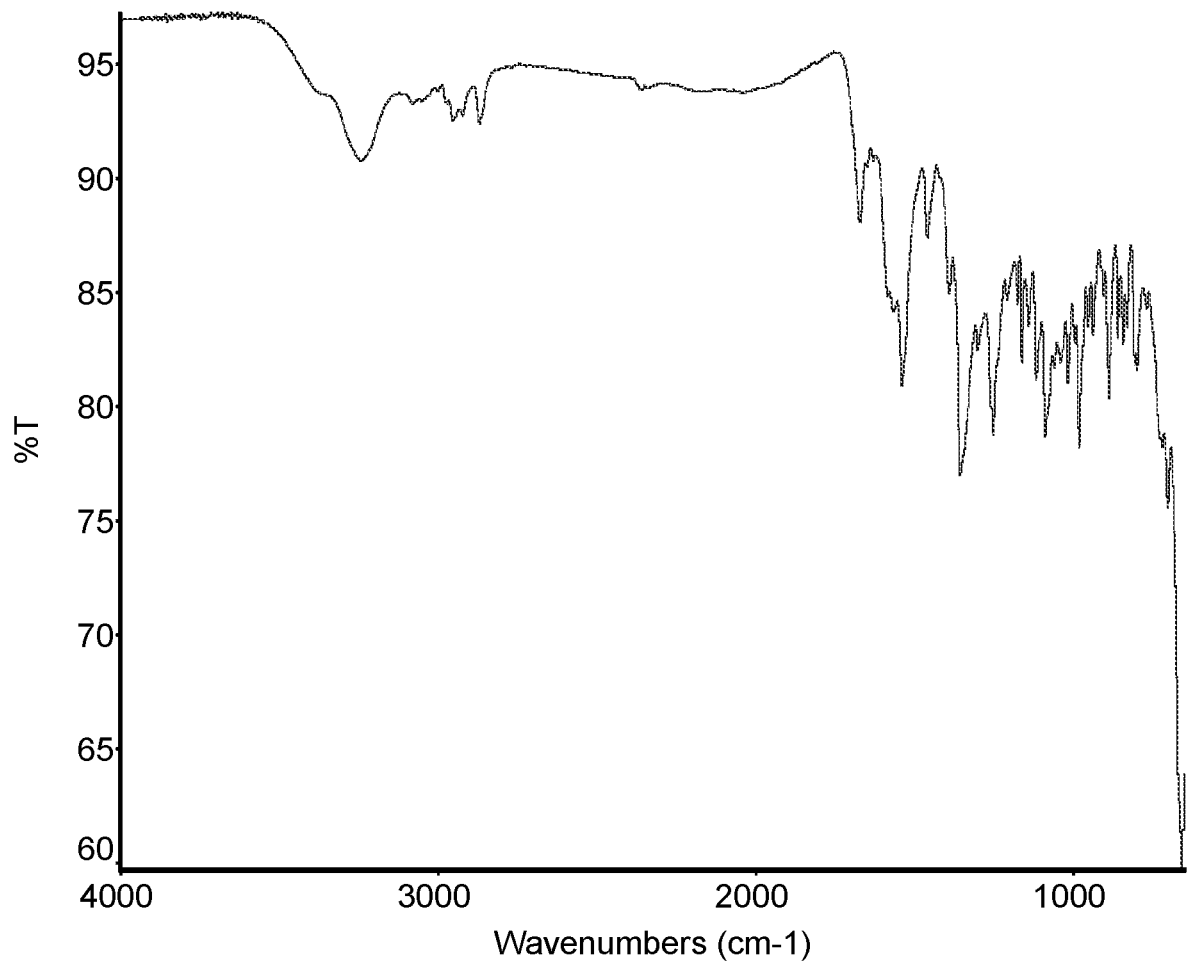
FIG. 14 shows the Fourier-Transform Infrared diagram of crystalline fumarate salt Modification $H_A$ of compound A.
Figure 15:
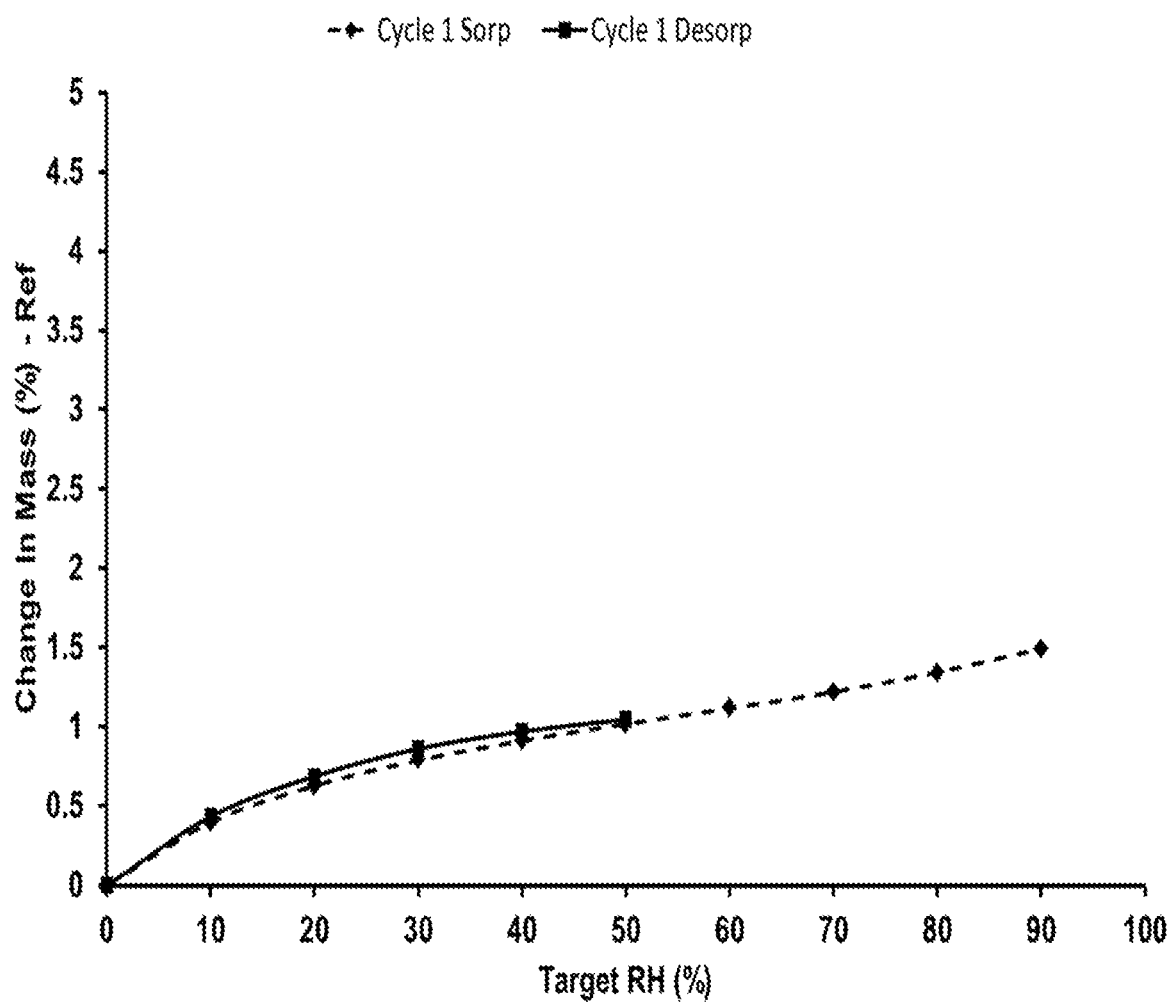
FIG. 15 shows the Dynamic Vapor Sorption Diagram of crystalline fumarate salt Modification $H_A$ of compound A at 25 degree C., method 50%-0%-90% Relative Humidity (RH).
Figure 16:
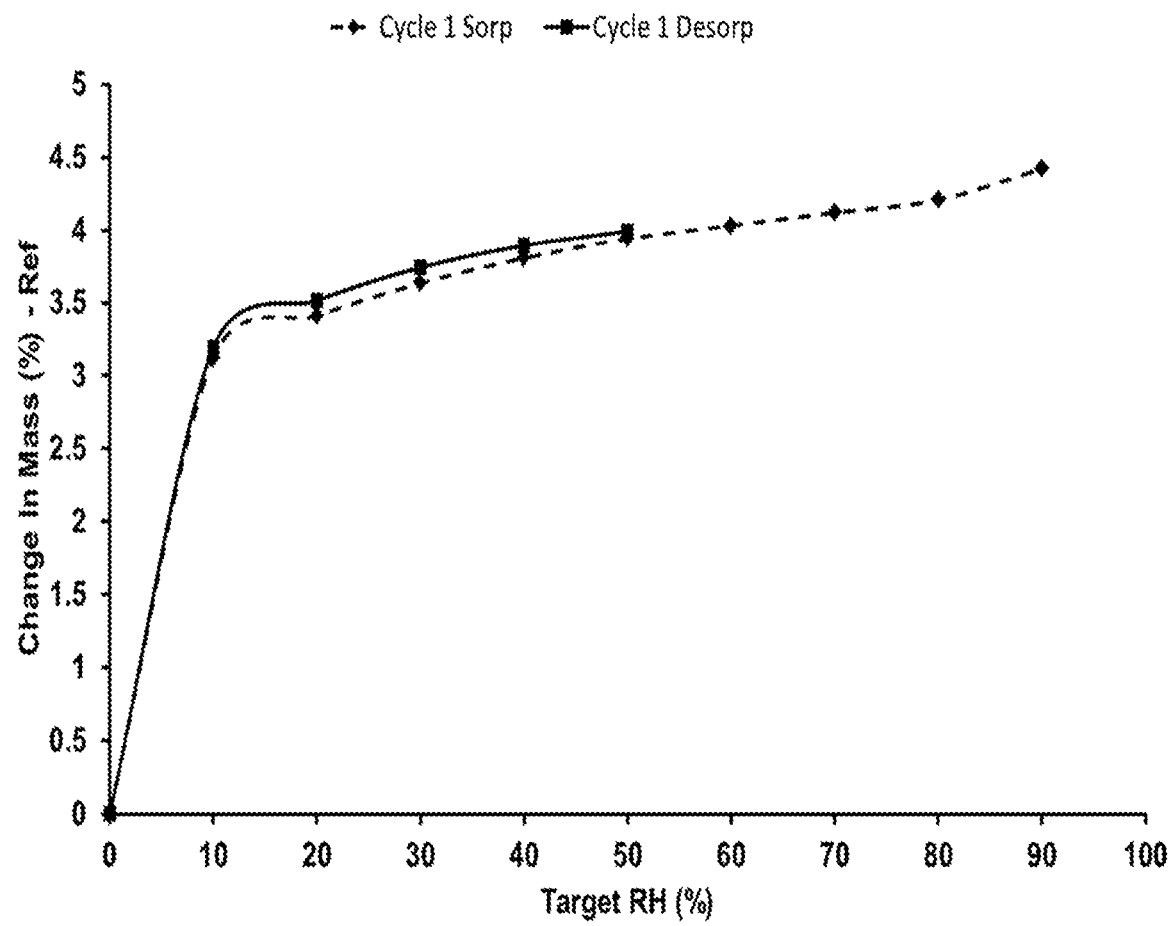
FIG. 16 shows the Dynamic Vapor Sorption Diagram of crystalline fumarate salt Modification $H_A$ of compound A, at 40 degree C., method 50%-0%-90% RH.

2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide in fumarate salt form, in particular having a molar ratio of 1:1 of compound A to fumaric acid, especially in form of Fumarate salt Modification $H_A$, especially (i) having 2Theta values in reflection XRPD of the first 2, first 3, first 4, first 5, first 6, first 8, especially the first ten or in particular all of the 2Theta values given in Table C below; or (ii) showing a DSC diagram as shown in FIG. 12; or (iii) having a TGA diagram as shown in FIG. 13; or (iv) having an FT-IR diagram as shown in FIG. 14; or (v) having a DVS diagram at 25° C. as shown in FIG. 15; or (vi) having a DVS diagram at 40° C. as shown in FIG. 16; or having two or three or four or five or especially all of the propterties (i) to (iv) just mentioned; or in particular having an XRPD diagram as shown in FIG. 11.

Embodiment 32

2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide in Fumarate salt amorphous form variant 1, in particular having a molar ratio of 1:1 of compound A to fumaric acid, especially showing a glass transition at about 143° C., when analyzed by modulated DSC at a heating rate of 1 K/min, amplitude temperature of 1 K, period 60 seconds.

Embodiment 33

2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide in Fumarate amorphous form variant 2, in particular having a molar ratio of 1:1 of compound A to fumaric acid, especially showing a glass transition at about 78° C. when analyzed by DSC at a heating rate of 10K/min.

Embodiment 34

Figure 17:
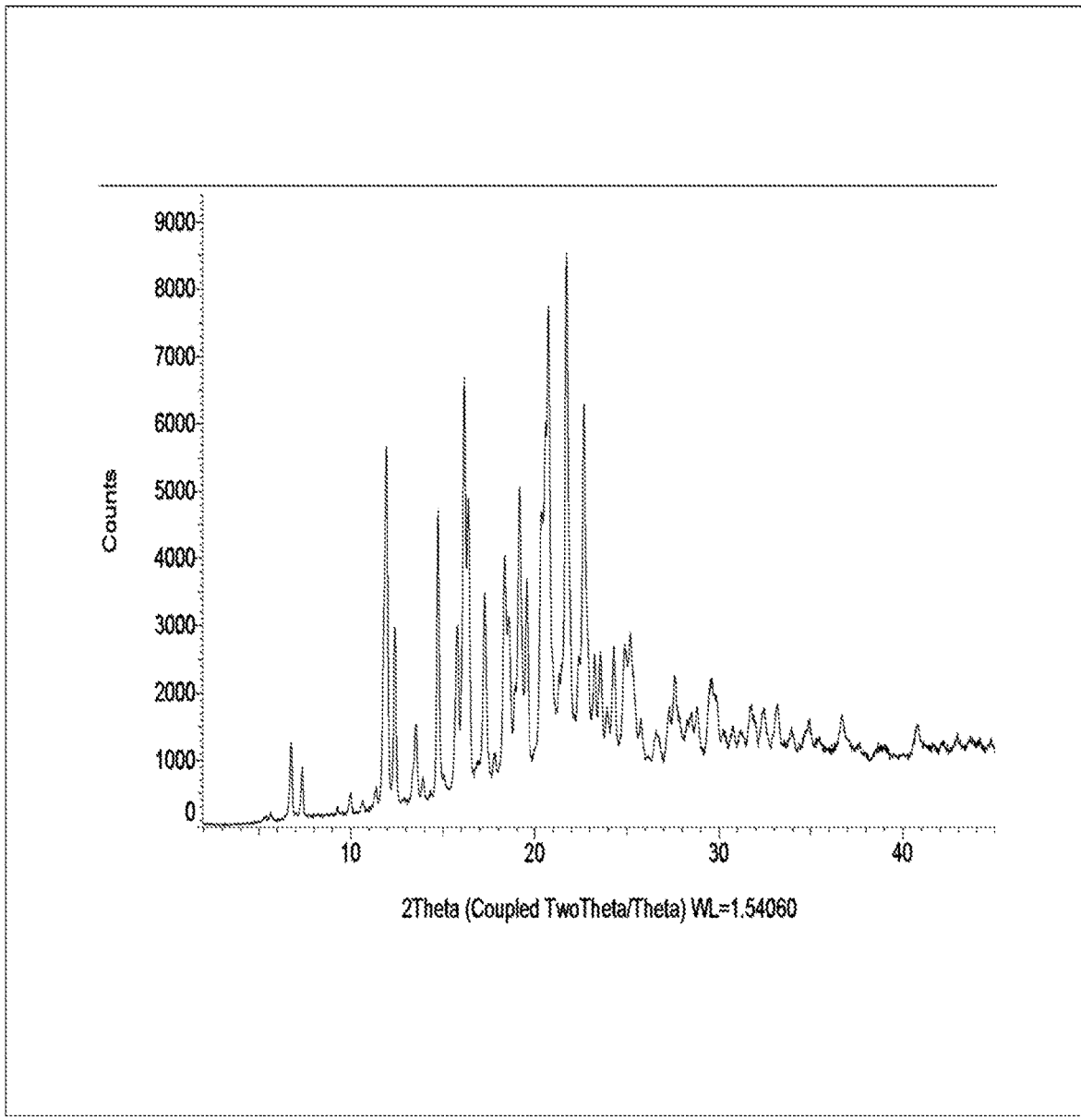
FIG. 17 shows the X-ray powder diffraction pattern of crystalline phosphate salt of compound A.

2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide in phosphate salt form, in particular having a molar ratio of 1:1.5 of compound A to phosphoric acid, especially (i) having 2Theta values in reflection XRPD of the first 2, first 3, first 4, first 5, first 6, first 8, especially the first ten or in particular all of the 2Theta values given in Table D below; or in particular having an XRPD diagram as shown in FIG. 17.

Embodiment 35

A compound in a form according to any one of embodiments 27 to 34 for use as a medicament.

Embodiment 36

A compound in a form according to any one of embodiments 27 to 34 for use in the treatment of a disorder or disease selected from heterotopic ossification or fibrodysplasia ossificans progressiva.

Where a 2Theta value (or in the tables below "Angle") is given in this disclosure, this means the respective value±0.2, or especially the value itself.

Where the term "Modification" is used, this relates to amorphous forms or especially to crystalline polymorphs (that is, forms of crystal structures), also including pseudopolymorphs, such as solvates or especially hydrates, of free forms or of salts, respectively.

Depending on the choice of the starting materials and procedures, the compounds can be present in the form of pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid salts by virtue of the presence of a basic aminopyridine moiety. Where "free form" is mentioned, this refers to the form without additional acids and/or bases, that is the compound as such (which may however form internal salts if the compound comprises basic and acidic groups).

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

In another aspect, the present invention provides compounds of formula (I) in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}$H, $^{3}$H, $^{11}$C, $^{13}$C, $^{14}$C, $^{15}$N, $^{18}$F, $^{31}$P, $^{32}$P, $^{35}$S, $^{36}$Cl, $^{123}$I, $^{124}$I, $^{125}$I respectively. The invention includes various isotopically labeled compounds as defined herein, for example those into which radioactive isotopes, such as $^{3}$H and $^{14}$C, or those into which non-radioactive isotopes, such as $^{2}$H and $^{13}$C are present. Such isotopically labelled compounds are useful in metabolic studies (with $^{14}$C), reaction kinetic studies (with, for example $^{2}$H or $^{3}$H), detection or imaging techniques, such as positron emission tomography (PET) or single-photon emission computed tomography (SPECT) including drug or substrate tissue distribution assays, or in radioactive treatment of patients. In particular, an $^{18}$F labeled compound may be particularly desirable for PET or SPECT studies. Isotopically-labeled compounds of formula (I) can generally be prepared by conventional techniques known to those skilled in the art or by processes analogous to those described in the accompanying Examples using an appropriate isotopically-labeled reagents in place of the non-labeled reagent previously employed.

Further, substitution with heavier isotopes, particularly deuterium (i.e., $^{2}$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated. The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by ALK-2, or (ii) associated with ALK-2 activity, or (iii) characterized by activity (normal or abnormal) of ALK-2; or (2) reduce or inhibit the activity of ALK-2; or (3) reduce or inhibit the expression of ALK-2. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of ALK-2; or at least partially reducing or inhibiting the expression of ALK-2.

As used herein, the term "subject" refers to a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis- (Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Typically, the compounds of formula (I) can be prepared according to the Schemes provided infra.

Step 1: A compound of formula (III) wherein $R_2$, $R_3$, $R_4$ and L are as defined herein in relation to a compound of formula (I) can be prepared by coupling a compound of formula (IV) wherein the $B(OR)_2$ moiety forms a boronic acid derivative (for example wherein R is hydrogen or pinacol) with a compound of formula (V) wherein $R_2$, $R_3$, $R_4$ and L are as defined herein in relation to a compound of formula (I) in the presence of a suitable solvent, such as e.g. dioxane or 2-methyl-2-butanol, a base such as potassium carbonate and a suitable catalyst, preferably a palladium-based catalyst such as e.g. [1,1'-bis(diphenylphosphino)ferrocene]dichloropalladium(II). Compounds of the formulae IV, V, III and II may be used in the free form or in the form of salts thereof.

Step 2: A compound of formula (II) wherein $R_2$, $R_3$, $R_4$ and L are as defined herein in relation to a compound of formula (I) can be prepared by treating a compound of formula (III) wherein $R_2$, $R_3$, $R_4$ and L are as defined herein in relation to a compound of formula (I) with a suitable base such as e.g. lithium hydroxide or sodium hydroxide in the presence of a suitable solvent such as e.g. tetrahydrofuran or an alkanol, such as methanol, Addition of an acid, such as HCl, leads to the corresponding salt, e.g. the hydrochloride salt, of the compound of formula II.

Step 3: A compound of formula (I) wherein $R_1$, $R_2$, $R_3$, $R_4$ and L are as defined herein can be prepared by coupling a compound of formula (II) wherein $R_2$, $R_3$, $R_4$ and L are as defined herein in relation to a compound of formula (I) with a suitable amine having the formula $R_1$—$NH_2$ wherein $R_1$ is as defined herein in relation to a compound of formula (I), such as e.g. trans-4-aminocyclohexanol, a suitable amide coupling reagent such as e.g. O-(7-azabenzotriazol-1-yl)-N,N,N',N'-tetramethyluronium-hexafluorphosphate, and a base such as e.g. N-methylmorpholine or triethylamine in the presence of a suitable solvent such as e.g. N,N-dimethylformamide or acetonitrile.

Compounds of formula (IV) and (V) can be obtained as described in the examples further below.

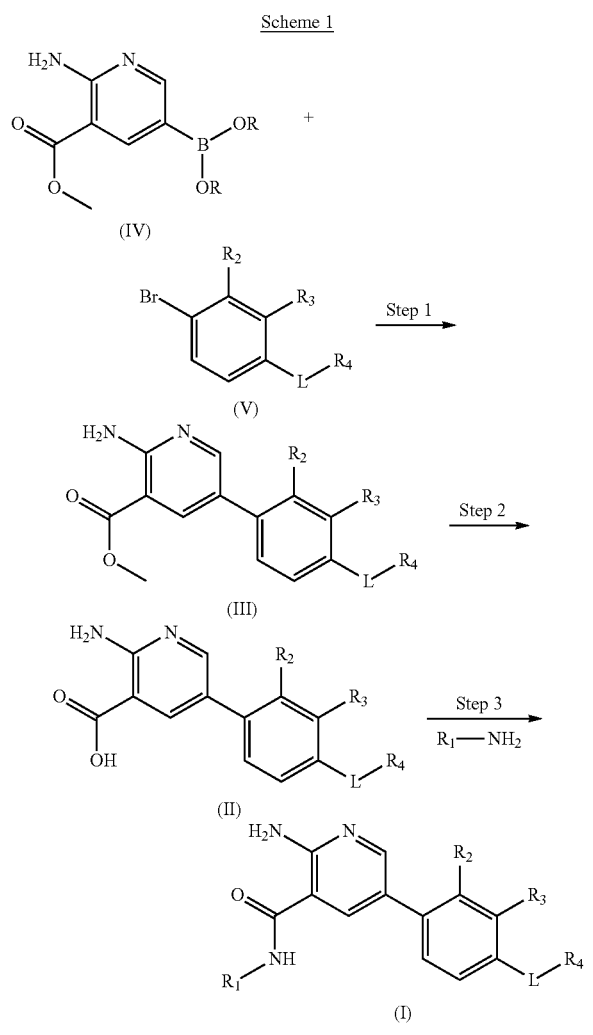

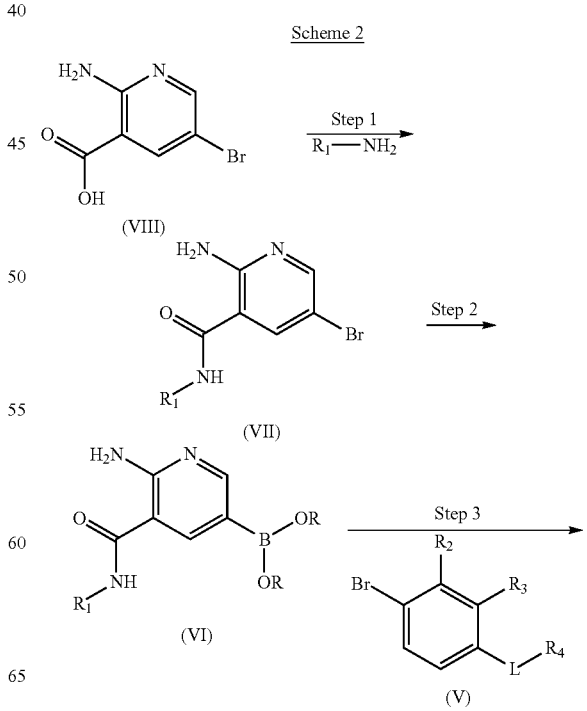

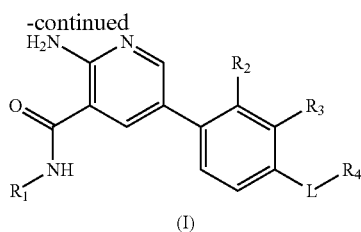

(I)

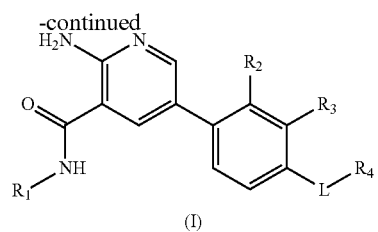

(I)

Step 1: A compound of formula (VII) wherein $R_1$ is as defined herein in relation to a compound of formula (I) can be obtained by treating a compound of formula (VIII) with a suitable amine of formula $R_1$—$NH_2$, such as e.g. trans-4-aminocyclohexanol, a suitable amide coupling reagent such as e.g. O-(7-azabenzotriazol-1-yl)-N,N,N',N'-tetramethyl-uronium-hexafluorphosphate, and a base such as e.g. N-methylmorpholine in the presence of a suitable solvent such as e.g. N,N-dimethylformamide.

Step 2: A compound of formula (VI) wherein R, is as defined herein in relation to a compound of formula (I) and the $B(OR)_2$ moiety forms a boronic acid derivative (for example wherein R is hydrogen or pinacole) can be obtained by coupling a compound of formula (VII) wherein R, is as defined herein in relation to a compound of formula (I) with a boron compound such as e.g. bis(pinacolato)diboron in the presence of a suitable solvent, such as e.g. dioxane, a salt such as potassium acetate and a suitable catalyst, preferably a palladium-based catalyst such as e.g. [1,1'-bis(diphenylphosphino)ferrocene]dichloropalladium(II).

Step 3: A compound of formula (I) wherein $R_1$, $R_2$, $R_3$, $R_4$ and L are as defined herein can be obtained by coupling a compound of formula (VI) wherein R, is as defined herein in relation to a compound of formula (I) and the $B(OR)_2$ moiety forms a boronic acid derivative (for example wherein R is hydrogen or pinacole) with a compound of formula (V) wherein $R_2$, $R_3$, $R_4$ and L are as defined herein in relation to a compound of formula (I) in the presence of a suitable solvent, such as e.g. dioxane, a base such as sodium hydroxide and a suitable catalyst, preferably a palladium-based catalyst such as e.g. [1,1'-bis(diphenylphosphino)ferrocene]dichloropalladium(II).

Step 1: A compound of formula (VIII) wherein $R_2$, $R_3$, L, $R_4$ are as defined herein in relation to a compound of formula (I) and the $B(OR)_2$ moiety forms a boronic acid derivative (for example wherein R is hydrogen or pinacole) can be obtained by coupling a compound of formula (V) wherein $R_2$, $R_3$, L, $R_4$ are as defined herein in relation to a compound of formula (I) with a boron compound such as e.g. bis (pinacolato)diboron in the presence of a suitable solvent, such as e.g. dioxane, a salt such as potassium acetate and a suitable catalyst, preferably a palladium-based catalyst such as e.g. [1,1'-bis(diphenylphosphino)ferrocene]dichloropalladium(II), or alternatively in a suitable solvent such as tetrahydrofurane and a strong base, such as n-butyllithium or isopropylmagnesium chloride or a mixture of two with a boron compound such as trimethylboronate.

Step 2: A compound of formula (I) wherein $R_1$, $R_2$, $R_3$, $R_4$ and L are as defined herein can be obtained by coupling a compound of formula (VIII) wherein $R_2$, $R_3$, L, $R_4$ are as defined herein in relation to a compound of formula (I) and the $B(OR)_2$ moiety forms a boronic acid derivative (for example wherein R is hydrogen or pinacole) with a compound of formula (VII) wherein $R_1$ is as defined herein in relation to a compound of formula (I), in the presence of a suitable solvent such as e.g. dioxane, a base such as potassium carbonate and a suitable catalyst, preferably a palladium-based catalyst such as e.g. [1,1'-bis(diphenylphosphino)ferrocene]dichloropalladium(II).

Scheme 3

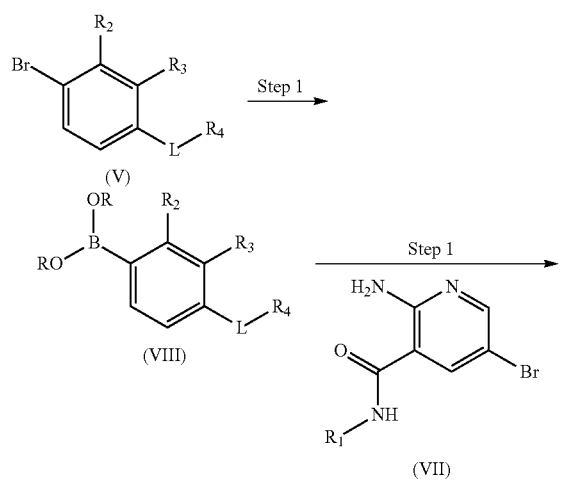

Scheme 4

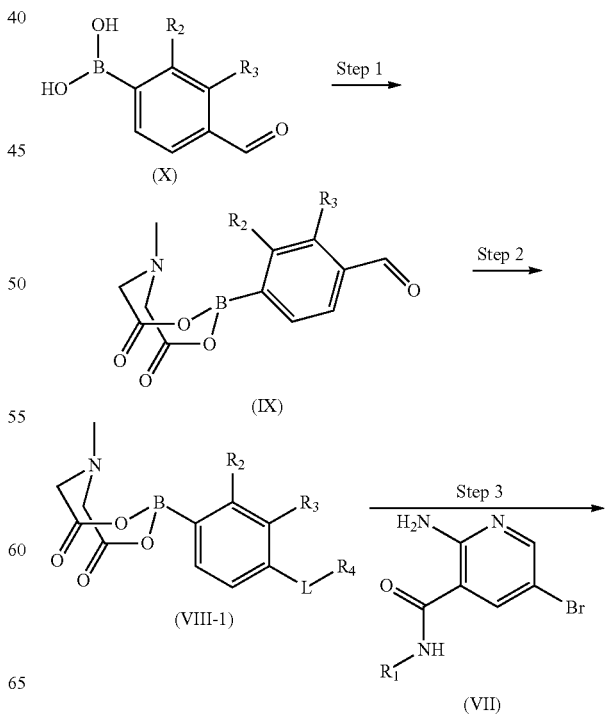

-continued

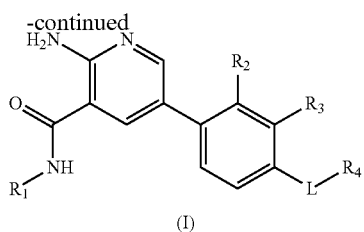

(I)

Step 1: A compound of formula (IX) wherein $R_2$ and $R_3$ are as defined herein in relation to a compound of formula (I) can be obtained by treating a compound of formula (X) wherein $R_2$ and $R_3$ are as defined herein in relation to a compound of formula (I) with N-methyl iminodiacetic acid in the presence of a suitable solvent, such as e.g. DMF.

Step 2: A compound of formula (VIII-1) wherein $R_1$, $R_2$, $R_3$, $R_4$ and L are as defined herein can be obtained by treating a compound of formula (IX) wherein $R_2$ and $R_3$ are as defined herein in relation to a compound of formula (I) with a suitable amine with a suitable reducing agent, such as e.g. sodium triacetoxyborohydride, and an acid such as acetic acid, in the presence of a suitable solvent, such as e.g. THF.

Step 3: A compound of formula (I) wherein $R_1$, $R_2$, $R_3$, $R_4$ and L are as defined herein can be obtained by coupling a compound of formula (VIII-1) wherein $R_2$, $R_3$, L, $R_4$ are as defined herein in relation to a compound of formula (I) with a compound of formula (VII) wherein $R_1$ is as defined herein in relation to a compound of formula (I), in the presence of a suitable solvent such as e.g. dioxane, a base such as potassium phosphate and a suitable catalyst, preferably a palladium-based catalyst such as e.g. (2-dicyclohexylphosphino-2',4',6'-triisopropyl-1,1'-biphenyl)[2-(2-aminoethyl)phenyl)]palladium(II) chloride.

In a further aspect, the invention relates to a process for the preparation of a compound of formula (I), in free form or in pharmaceutically acceptable salt form, comprising the steps of:
  a) coupling a compound of formula (II) as defined herein with a compound of formula $R_1$—$NH_2$ as defined herein to give a compound of formula (I);
  b) recovering the so obtainable compound of formula (I) in free form or in pharmaceutically acceptable salt form.

In a further aspect, the invention relates to a process for the preparation of a compound of formula (I), in free form or in pharmaceutically acceptable salt form, comprising the steps of:
  a) coupling a compound of formula (VI) as defined herein with a compound of formula (V) as defined herein to give a compound of formula (I);
  b) recovering the so obtainable compound of formula (I) in free form or in pharmaceutically acceptable salt form.

In a further aspect, the invention relates to a process for the preparation of a compound of formula (I), in free form or in pharmaceutically acceptable salt form, comprising the steps of:
  a) coupling a compound of formula (VIII) or a compound of formula (VIII-1) as defined herein with a compound of formula (VII) as defined herein to give a compound of formula (I);
  b) recovering the so obtainable compound of formula (I) in free form or in pharmaceutically acceptable salt form.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, rectal administration, transdermal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with one or more of:
  a) diluents, e.g., lactose, dextrose, sucrose, mannitol, sorbitol, cellulose and/or glycine;
  b) lubricants, e.g., silica, talcum, stearic acid, its magnesium or calcium salt and/or polyethyleneglycol; for tablets also
  c) binders, e.g., magnesium aluminum silicate, starch paste, gelatin, tragacanth, methylcellulose, sodium carboxymethylcellulose and/or polyvinylpyrrolidone; if desired
  d) disintegrants, e.g., starches, agar, alginic acid or its sodium salt, or effervescent mixtures; and
  e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed.

Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

The compounds of formula (I) in free form or in pharmaceutically acceptable salt form, exhibit valuable pharmacological properties, e.g. ALK-2 modulating properties, e.g. as indicated in vitro and in vivo tests as provided in the next sections, and are therefore indicated for therapy or for use as research chemicals, e.g. as tool compounds.

Compounds of the invention may be useful in the treatment of an indication selected from: heterotopic ossification or fibrodysplasia ossificans progressiva.

Without wishing to be bound by theory, it is thought that the compounds of the invention being selective ALK-2 inhibitors reduce/inhibit BMP signaling and the abnormal tissue repair associated with it.

Thus, as a further embodiment, the present invention provides the use of a compound of formula (I) or subformulae thereof (Ia), (II), (IIa), (IIb) in free form or in pharmaceutically acceptable salt form in therapy. In a further embodiment, the therapy is selected from a disease which may be treated by inhibition of ALK-2 receptor. In another embodiment, the disease is selected from heterotopic ossification or fibrodysplasia ossificans progressiva.

Thus, as a further embodiment, the present invention provides a compound of formula (I) or subformulae thereof (Ia), (II), (IIa), (IIb) in free form or in pharmaceutically acceptable salt form for use in therapy. In a further embodiment, the therapy is selected from a disease which may be treated by inhibition of ALK-2 receptor. In another embodiment, the disease is selected from heterotopic ossification or fibrodysplasia ossificans progressiva.

In another embodiment, the invention provides a method of treating a disease which is treated by inhibition of ALK-2 receptor comprising administration of a therapeutically acceptable amount of a compound of formula (I) or subformulae thereof (Ia), (II), (IIa), (IIb) in free form or in pharmaceutically acceptable salt form. In a further embodiment, the disease is selected from heterotopic ossification or fibrodysplasia ossificans progressiva.

Thus, as a further embodiment, the present invention provides the use of a compound of formula (I) or subformulae thereof (Ia), (II), (IIa), (IIb) in free form or in pharmaceutically acceptable salt form for the manufacture of a medicament. In a further embodiment, the medicament is for treatment of a disease which may be treated by inhibition of ALK-2 receptor. In another embodiment, the disease is selected from heterotopic ossification or fibrodysplasia ossificans progressiva.

In one embodiment of the present invention, there is provided 2-amino-N-(4-hydroxybicyclo[2.2.2]octan-1-yl)-5-(4-(3-(tetrahydro-2H-pyran-4-yl)-3-azabicyclo[3.1.0]hexan-1-yl)phenyl)nicotinamide in free form or a pharmaceutically acceptable salt thereof, especially in one of the Modifications mentioned herein, for use in the treatment of heterotopic ossification or fibrodysplasia ossificans progressiva.

In one embodiment, there is provided 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide in free form or a pharmaceutically acceptable salt thereof, especially in one of the Modifications mentioned herein, for use in the treatment of heterotopic ossification or fibrodysplasia ossificans progressiva.

In one embodiment, there is provided 2-amino-N-(4-hydroxybicyclo[2.2.2]octan-1-yl)-5-(4-((1S,5R)-3-(tetrahydro-2H-pyran-4-yl)-3-azabicyclo[3.1.0]hexan-1-yl)phenyl)nicotinamide in free form or a pharmaceutically acceptable salt thereof, especially in one of the Modifications mentioned herein, for use in the treatment of heterotopic ossification or fibrodysplasia ossificans progressiva The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art, or by processes as described or in analogy, respectively, to those in the Examples. Further, the compounds of the present invention can be produced by organic synthesis methods known to one of ordinary skill in the art as shown in the following examples.

EXAMPLES

Abbreviations

δ chemical shift
AcOH acetic acid
aq rr aq. aqueous
APCI-MS atmospheric-pressure chemical ionization mass spectroscopy
BH$_3$DMS borane dimethyl sulfide complex
Brine saturated sodium chloride solution
n-BuLi n-butyllithium
DCM dichloromethane
DMAP 4-(dimethylamino)pyridine
DMF N,N-dimethylformamide
DIPEA diisopropylethylamine
DMSO dimethylsulfoxide
DSC Differential Scanning Calorimetry
DVS Dynamic Vapor Sorption
eq equivalent(s)
Et ethyl
Et$_3$N triethylamine
EtOAc ethyl acetate
EtOH ethanol
ESI-MS electron-spray ionisation mass spectroscopy
FIA-MS flow injection analysis mass spectroscopy
FT-IR Fourier Transform Infrared spectroscopy
h hour
HATU O-(7-azabenzotriazol-1-yl)-N,N,N',N'-tetramethyl-uronium-hexafluorophosphate
HPLC high performance liquid chromatography
HRMS high-resolution mass spectroscopy
IPA isopropanol
IPAc isopropyl acetate i-PrOH isopropanol
IT Internal Temperature
$K_2CO_3$ potassium carbonate
$K_3PO_4$ potassium phosphate
KOAc potassium acetate
L liter
LC-MS Liquid chromatography-mass spectrometry
$LiAlH_4$ lithium aluminium hydride
LiOH lithium hydroxide
M molar
MCC microcrystalline cellulose
mg milligram
mM millimolar
MeOH methanol
min minutes
mL milliliter
$MgSO_4$ magnesium sulfate
MHz megahertz
MTBE methyl tert.-butyl ether
N normal
$Na_2SO_4$ sodium sulfate
$NaHCO_3$ sodium bicarbonate
NaHMDS sodium-bis(trimethylsilyl))amide
NaOH sodium hydroxyde
$NH_4Cl$ ammonium chloride
$NH_4OH$ ammonium hydroxide
$NH_4OAc$ ammonium acetate
NMR nuclear magnetic resonance
$PdCl_2(dppf)$
or $Pd(dppf)Cl_2$ [1,1'-bis(diphenylphosphino)ferrocene]dichloropalladium(II)
$PdCl_2(PPh_3)_2$ bis(triphenylphosphine)palladium(II) chloride
prepHPLC preparative high performance liquid chromatography
ppm parts per million
RT or r.t. room temperature (23±3° C.)
sat. saturated
SFC supercritical fluid chromatography
SPE solid-phase extraction
TEA triethylamine
TFA trifluoroacetic acid
THF tetrahydrofuran
TGA Thermogravimetric Analysis
$t_R$ retention time
UPLC-MS ultra-high performance liquid chromatography mass spectroscopy
XPhos Pd (2-dicyclohexylphosphino-2',4',6'-triisopropyl-1,1'-biphenyl)[2-(2-aminoethyl)phenyl)]palladium(II) chloride
XRPD X-ray Powder Diffraction Analytical Methods

1H-NMR

Measurements were performed on a Bruker Ultrashield™ 400 (400 MHz), Bruker Ultrashield™ 600 (600 MHz), 400 MHz DRX Bruker CryoProbe (400 MHz) or a 500 MHz DRX Bruker CryoProbe (500 MHz) spectrometer using or not trimethylsilane as an internal standard. Chemical shifts (δ-values) are reported in ppm downfield from tetramethylsilane, spectra splitting pattern are designated as singlet (s), doublet (d), triplet (t), quartet (q), multiplet, unresolved or more overlapping signals (m), broad signal (bs). Solvents are given in parentheses.

UPLC-MS

Column: Waters Acquity HSS T3, C18, 1.8 µm, 2.1×50 mm, oven at 60° C. Flow: 1.0 mL/min. Gradient: 5% to 98% B in 1.40 min, then 98% B for 0.40 min, 98% to 5% B in 0.10 min, 5% B for 0.10 min; A=water+0.05% formic acid+3.75 mM $NH_4OAc$, B=acetonitrile+0.04% formic acid. Detection UV/VIS (DAD), ESI (+/−). Mass spectrometer range: 100-1200 Da.

For Examples 46, 56, 74, 81, 85 and 87:

Column: Waters Acquity BEH, C18, 1.7 µm, 2.1×50 mm, oven at 50° C. Flow: 1.0 mL/min. Gradient: 2% to 98% B in 4.40 min, then 98% B for 0.75 min, 98% to 2% B in 0.04 min; A=water+0.1% formic acid, B=acetonitrile+0.1% formic acid. Detection UV/VIS (DAD), ESI (+/−). Mass spectrometer range: 100-1200 Da.

UPLC-HRMS:

Waters Acquity SDS, C18, 1.7 µm, 2.1×50 mm, oven at 50° C. Gradient: 5% to 98% B in 7.50 min, then 98% B for 0.40 min, 98% to 5% B in 0.15 min; A=water+5 mM $NH_4OH$, B=acetonitrile+5 mM $NH_4OH$. Detection UV/VIS (DAD), ESI (+/−). Mass spectrometer range: 100-1200 Da.

HPLC-MS

Column: Waters Symmetry C8, 3.5 µm, 2.1×50 mm, oven at 50° C. Flow: 1.0 mL/min. Gradient: 10% to 95% B in 2 min, then 95% B for 1 min, 95% to 10% B in 0.5 min, 10% B for 0.50 min; A=water+0.1% TFA, B=Acetonitrile+0.1% TFA. Detection UV/VIS (DAD), APCI (+). Mass spectrometer range: 100-1200 Da.

Optical Rotation Measurement

The optical rotation was measured using a polarimeter Perkin Elmer PE241 Series No. 5325 operating at 589 nm using chloroform as a solvent.

Purification Methods prepHPLC

Gilson GX-281, pumps 331/332.

Column: Waters Sunfire C18, 30×100 mm, 5 µm. Flow: 30 mL/min.

Mobile phase: Water (containing 0.1% TFA) and acetonitrile (Method 1a) or:

Column: X-Bridge C18, 30×50 mm, 5 µm. Flow: 75 mL/min

Mobile phase: Water (containing 5 mM $NH_4OH$) and acetonitrile (Method 1b)

Normal-Phase Flash Chromatography

Teledyne ISCO CombiFlash:

Column: Redisep Rf Silica Flash

Mobile phase: cyclohexane/EtOAc (Method 2a) or DCM/MeOH (Method 2b).

Biotage Flash-Master II:

Column: Pre-filled with silica gel 60 (40-63 µm) from Merck

Mobile phase: DCM and MeOH (containing 7.3 mM $NH_4OH$) (Method 2c).

Reversed-Phase Flash Chromatography:

Teledyne ISCO CombiFlash

Column Redisep Rf Gold C18 High Performance, 15.5 g, 50 g or 240 g pre-packed columns, 20-40 µm, 100A Mobile phase: Water and acetonitrile (containing 7.3 mM $NH_4OH$) (Method 3a) or water (containing 0.1% TFA) and acetonitrile (Method 3b).

Example 1: 2-amino-N-((1r,4R)-4-hydroxycyclohexyl)-5-(4-((1R,5S)-3-(1-(methylsulfonyl)piperidin-4-yl)-3-azabicyclo[3.1.0]hexan-1-yl)phenyl)nicotinamide

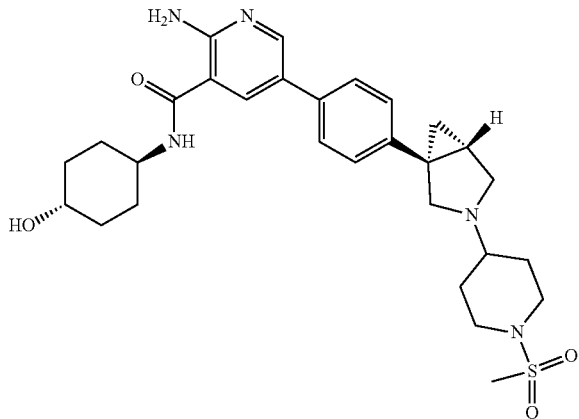 [SMILES: CS(=O)(=O)N1CCC(N2C[C@H]3C[C@@]3(c3ccc(-c4cnc(N)c(C(=O)N[C@H]5CC[C@H](O)CC5)c4)cc3)C2)CC1]

To a solution of 5-(4-((1R,5S)-3-azabicyclo[3.1.0]hexan-1-yl)phenyl)-2-amino-N-((1r,4R)-4-hydroxycyclohexyl)nicotinamide TFA salt (Intermediate 1a, 80 mg, 0.158 mmol) in DCM (4 mL) was added 1-(methylsulfonyl)piperidin-4-one (30.8 mg, 0.174 mmol) and AcOH (0.018 mL, 0.316 mmol) under a nitrogen atmosphere at RT. The reaction mixture was stirred at 45° C. for 30 min. Sodium triacetoxyborohydride (84 mg, 0.395 mmol) was added at RT and the reaction mixture was stirred at 45° C. for 1 h. The reaction mixture was then diluted with a sat. aq. solution of NaHCO$_3$ and mixed with EtOAc. After phase separation, the aq. layer was extracted again with EtOAc. The combined organic layers were washed with brine, dried over MgSO$_4$, filtered and concentrated under reduced pressure. The crude product was purified by normal-phase chromatography (Method 2b) to give the title compound as a colorless solid. 1H NMR (400 MHz, DMSO-d6) δ 8.39 (d, 1H), 8.31 (d, 1H), 8.11 (d, 1H), 7.59 (d, 2H), 7.24 (d, 2H), 7.12 (s, 2H), 4.58 (d, 1H), 3.80-3.63 (m, 1H), 3.45-3.36 (m, 4H), 3.15 (dd, 1H), 2.89-2.83 (m, 5H), 2.65 (dd, 1H), 2.35-2.29 (m, 1H), 1.98-1.81 (m, 7H), 1.57-1.18 (m, 8H), 0.83-0.70 (m, 1H). (UPLC-MS) $t_R$ 0.49 min; ESI-MS 554 [M+H]$^+$.

Intermediate 1a: 5-(4-((1R,5S)-3-azabicyclo[3.1.0]hexan-1-yl)phenyl)-2-amino-N-((1r,4R)-4-hydroxycyclohexyl)nicotinamide To a solution of (1R,5S)-tert-butyl 1-(4-(6-amino-5-(((1r,4R)-4-hydroxycyclohexyl)carbamoyl)pyridin-3-yl)phenyl)-3-azabicyclo[3.1.0]hexane-3-carboxylate (Intermediate 1b, 940 mg, 1.55 mmol) in dioxane (10 mL) was added a 4M solution of HCl in dioxane (1.55 mL, 6.20 mmol) at RT. The reaction mixture was stirred at 65° C. for 5 h and then concentrated under reduced pressure to give the title compound as a hydrochloride salt. Occasionally the title compound was further purified by prepHPLC (Method 1a) to give a TFA salt after evaporation of solvents. (UPLC-MS) $t_R$ 0.45 min; ESI-MS 393 [M+H]$^+$.

Intermediate 1b: (1R,5S)-tert-butyl 1-(4-(6-amino-5-(((1r,4R)-4-hydroxycyclohexyl)carbamoyl)pyridin-3-yl)phenyl)-3-azabicyclo[3.1.0]hexane-3-carboxylate To a solution of 2-amino-5-(4-((1R,5S)-3-(tert-butoxycarbonyl)-3-azabicyclo[3.1.0]hexan-1-yl)phenyl)nicotinic acid (Intermediate 1c, 630 mg, 1.59 mmol) in DMF (10 mL) was added trans-4-aminocyclohexanol (290 mg, 1.91 mmol), HATU (909 mg, 2.39 mmol) and N-methylmorpholine (0.53 mL, 4.78 mmol) at RT. The reaction mixture was stirred for 2 h, diluted with a sat. aq. solution of NaHCO$_3$ and extracted three times with EtOAc. The combined organic layers were washed with brine, dried over MgSO$_4$, filtered and concentrated under reduced pressure. The crude product was purified by prepHPLC (Method 1a) to give the title compound as a colorless solid. (UPLC-MS) $t_R$1.00 min; ESI-MS 493 [M+H]$^+$.

Intermediate 1c: 2-amino-5-(4-((1R,5S)-3-(tert-butoxycarbonyl)-3-azabicyclo[3.1.0]hexan-1-yl)phenyl)nicotinic acid To a solution of (1R,5S)-tert-butyl 1-(4-(6-amino-5-(methoxycarbonyl)pyridin-3-yl)phenyl)-3-azabicyclo[3.1.0]hexane-3-carboxylate (Intermediate 1d, 1.00 g, 2.44 mmol) in THF (15 mL) was added a 2M aq. solution of LiOH (3.66 mL, 7.33 mmol) at RT. The reaction mixture was stirred at 65° C. for 2 h and then concentrated under reduced pressure. The crude product was purified by prepHPLC (Method 1a) to give the title compound. (UPLC-MS) $t_R$ 0.92 min; ESI-MS 396 [M+H]$^+$.

Intermediate 1 d: (1R,5S)-tert-butyl-1-(4-(6-amino-5-(methoxycarbonyl)pyridin-3-yl)phenyl)-3-azabicyclo[3.1.0]hexane-3-carboxylate Racemic tert-butyl-1-(4-(6-amino-5-(methoxycarbonyl)pyridin-3-yl)phenyl)-3-aza-bicyclo[3.1.0]hexane-3-carboxylate (Intermediate 1e, 13.5 g, 33.0 mmol) was resolved by chiral preparative SFC (Waters SFC 200, Waters SFC 200, CHIRALPAK AD-H 5 µm 30*250 mm, mobile phase CO$_2$/i-PrOH 70:30, flow rate 120 g/min; UV detection at 278 nm). The title compound was obtained as an off-white solid after concentration under reduced pressure. Chiral analytical SFC (CHIRALPAK AD-3 3 µm 2*100 mm, mobile phase CO$_2$/MeOH+0.1% DEA 60:40, flow rate 1 mL/min; UV detection at 274 nm): $t_R$ 2.30 min, ee=98.6%, $[\alpha]_D^{20}$=+90°.

Intermediate 1e: tert-butyl 1-(4-(6-amino-5-(methoxycarbonyl)pyridin-3-yl)phenyl)-3-azabicyclo[3.1.0]hexane-3-carboxylate To a solution of tert-butyl 1-(4-bromophenyl)-3-aza-bicyclo[3.1.0]hexane-3-carboxylate (prepared analogously to a description in WO2007/022935) (3.34 g, 9.38 mmol) in dioxane (75 mL) was added methyl 2-amino-5-(4,4,5,5-tetramethyl-1,3,2-dioxaborolan-2-yl)nicotinate (prepared analogously to a description in WO2012/087938) (3.91 g, 14.1 mmol). A 2M aq. solution of K$_2$CO$_3$ (9.38 mL, 18.8 mmol) and Pd(dppf)Cl$_2$-DCM adduct (0.766 g, 0.938 mmol) were added under a nitrogen atmosphere and the mixture was heated to 80° C. under a nitrogen atmosphere for 18 h. The reaction mixture was diluted with 150 mL of water and extracted three times with EtOAc. The combined organic layers were washed with brine, dried over Na$_2$SO$_4$, filtered and concentrated under reduced pressure. The crude residue was purified by normal-phase chromatography (Method 2b)

Example 2: 2-amino-N-((1r,4R)-4-hydroxycyclohexyl)-5-(4-((1R,5S)-3-isopropyl-3-azabicyclo[3.1.0]hexan-1-yl)phenyl)nicotinamide

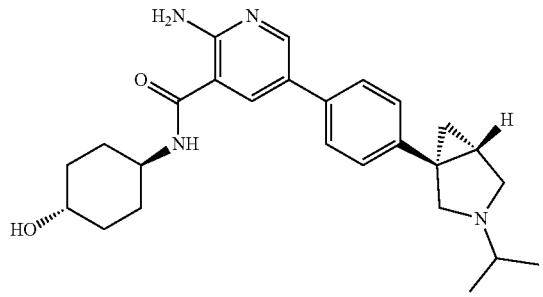 [SMILES: CC(C)N1C[C@H]2C[C@@]2(c2ccc(-c3cnc(N)c(C(=O)N[C@H]4CC[C@H](O)CC4)c3)cc2)C1]

To a solution of 2-amino-5-(4-((1R,5S)-3-isopropyl-3-azabicyclo[3.1.0]hexan-1-yl)phenyl)nicotinic acid TFA salt (Intermediate 2a, 117 mg, 0.259 mmol) in DMF (3 mL) was added trans-4-aminocyclohexanol hydrochloride (39.3 mg, 0.259 mmol), HATU (148 mg, 0.389 mmol) and N-methylmorpholine (0.085 mL, 0.778 mmol) at RT. The reaction mixture was stirred at RT for 2 h and then diluted with a sat. aq. solution of NaHCO$_3$ and mixed with EtOAc. After phase separation, the aq. layer was extracted again with EtOAc. The combined organic layers were washed with brine, dried over MgSO$_4$, filtered and concentrated under reduced pressure. The crude product was purified by prepHPLC (Method 1a) to give the title compound as a yellow solid. 1H NMR (400 MHz, DMSO-d6) δ 8.38 (d, 1H), 8.31 (d, 1H), 8.11 (d, 1H), 7.58 (d, 2H), 7.23 (d, 2H), 7.12 (s, 2H), 4.58 (d, 1H), 3.82-3.66 (m, 1H), 3.48-3.34 (m, 3H), 3.07 (d, 1H), 2.64-2.55 (m, 2H), 1.96-1.77 (m, 5H), 1.50-1.19 (m, 5H), 1.04 (dd, 6H), 0.75 (dd, 1H). (UPLC-MS) $t_R$ 0.50 min; ESI-MS 435 [M+H]$^+$.

Intermediate 2a: 2-amino-5-(4-((1R,5S)-3-isopropyl-3-azabicyclo[3.1.0]hexan-1-yl)phenyl)nicotinic acid TFA salt To a solution of methyl 2-amino-5-(4-((1R,5S)-3-isopropyl-3-azabicyclo[3.1.0]hexan-1-yl)phenyl)nicotinate (Intermediate 2b, 660 mg, 1.22 mmol) in THF (10 mL) was added a 2M aq. solution of LiOH (1.22 mL, 2.44 mmol) at RT. The reaction mixture was stirred at 65° C. for 2 h and then concentrated under reduced pressure. The crude product was purified by prepHPLC (Method 1a) to give the title compound as a TFA salt. (UPLC-MS) $t_R$ 0.37 min; ESI-MS 338 [M+H]$^+$.

Intermediate 2b: methyl 2-amino-5-(4-((1R,5S)-3-isopropyl-3-azabicyclo[3.1.0]hexan-1-yl)phenyl)nicotinate To a solution of methyl 2-amino-5-(4,4,5,5-tetramethyl-1,3,2-dioxaborolan-2-yl)nicotinate (prepared analogously to a description in WO 2012/087938) (462 mg, 1.663 mmol) in acetonitrile (7 mL) was added (1R,5S)-1-(4-bromophenyl)-3-isopropyl-3-azabicyclo[3.1.0]hexane (Intermediate 2c, 466 mg, 1.66 mmol), 2M aq. K$_2$CO$_3$ (1.66 mL, 3.33 mmol) and PdCl$_2$(dppf)-DCM adduct (67.9 mg, 0.083 mmol) at RT. The reaction mixture was sealed and irradiated in a microwave reactor at 120° C. for 10 min, then cooled, filtered over celite, diluted with a sat. aq. solution of NaHCO$_3$ and mixed with EtOAc. After phase separation, the aq. layer was extracted again with EtOAc. The combined organic layers were washed with brine, dried over MgSO$_4$, filtered and concentrated under reduced pressure. The crude product was used without further purification. (UPLC-MS) $t_R$ 0.62 min; ESI-MS 352 [M+H]$^+$.

Intermediate 2c: (1R,5S)-1-(4-bromophenyl)-3-isopropyl-3-azabicyclo[3.1.0]hexane To a solution of (1R,5S)-1-(4-bromophenyl)-3-azabicyclo[3.1.0]hexane (prepared analogously to a description in WO2007/022935) (525 mg, 2.21 mmol) in acetonitrile (10 mL) was added 2-iodopropane (0.420 mL, 2.65 mmol) and K$_2$CO$_3$ (609 mg, 4.41 mmol) at RT under a nitrogen atmosphere. The reaction mixture was stirred at 65° C. for 3 h, then diluted with EtOAc and mixed with a sat. aq. solution of NaHCO$_3$. After phase separation the aq. phase was extracted with EtOAc. The combined organic layers were washed with brine, dried over MgSO$_4$, filtered and concentrated under reduced pressure to give the title compound as an off-white solid. (UPLC-MS) $t_R$ 0.72 min; ESI-MS 280/282 [M+H]$^+$.

Example 3: 5-(4-((R)-1-(2-oxa-6-azaspiro[3.3]heptan-6-yl)ethyl)phenyl)-2-amino-N-((1r,4R)-4-hydroxycyclohexyl)nicotinamide

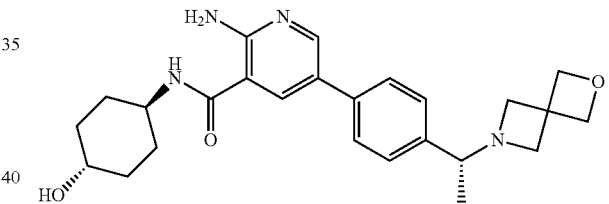

To a solution of (6-amino-5-(((1r,4r)-4-hydroxycyclohexyl)carbamoyl)pyridin-3-yl)boronic acid (Intermediate 3a, 300 mg, 0.645 mmol) in dioxane (5 mL) was added (R)-6-(1-(4-bromophenyl)ethyl)-2-oxa-6-azaspiro[3.3]heptane (Intermediate 3b, 420 mg, 0.774 mmol), PdCl$_2$(dppf) (23.6 mg, 0.032 mmol) and 2N aq. NaOH (0.645 mL, 1.29 mmol) under a nitrogen atmosphere at RT. The reaction mixture was stirred at 80° C. for 2 h, then diluted with EtOAc and water. After two extractions with EtOAc the organic layers were washed with a sat. aq. solution of NaHCO$_3$ and brine, respectively, dried over MgSO$_4$, filtered, and concentrated under reduced pressure. The crude product was dissolved in MeOH and passed through a silica-thiol cartridge (500 mg loading; pre-conditioned with MeOH) to remove palladium. The filtrate was concentrated under reduced pressure. The residue was purified by normal-phase chromatography (Method 2b) to give the title compound as a brownish solid. 1H NMR (400 MHz, DMSO-d6) δ 8.37 (d, 1H), 8.27 (d, 1H), 8.09-8.14 (m, 1H), 7.57 (bs, 2H), 7.33 (bs, 2H), 7.12 (bs, 2H), 4.54-4.58 (m, 1H), 4.51-4.66 (m, 3H), 3.55-3.81 (m, 1H), 3.35-3.54 (m, 2H), 3.20-3.24 (m, 1H), 3.20-3.27 (m, 2H), 3.15 (bs, 1H), 1.78-1.91 (m, 4H), 1.14-1.41 (m, 5H), 1.11 (bs, 3H). (UPLC-MS) $t_R$ 0.45 min; ESI-MS 437 [M+H]$^+$.

Intermediate 3a: (6-amino-5-(((1r,4r)-4-hydroxycyclohexyl)carbamoyl)pyridin-3-yl)boronic acid To a solution of 2-amino-5-bromo-N-((1r,4r)-4-hydroxycyclohexyl)nicotinamide (Intermediate 3c, 1.00 g, 2.67 mmol) in dioxane (25 mL) was added bis(pinacolato)diboron (0.815 g, 3.21 mmol), PdCl$_2$(dppf) (0.098 g, 0.134 mmol) and KOAc (0.525 g, 5.35 mmol) under a nitrogen atmosphere at RT. The reaction mixture was stirred at 80° C. for 18 h, cooled, filtered through a pad of celite, and concentrated under reduced pressure to give the title compound (the pinacolate ester had hydrolyzed under the reaction conditions) as a crude brownish solid that was used without further purification. (UPLC-MS) $t_R$ 0.32 min; ESI-MS 280 [M+H]$^+$.

Intermediate 3b: (R)-6-(1-(4-bromophenyl)ethyl)-2-oxa-6-azaspiro[3.3]heptane To a solution of (R)-1-(4-bromophenyl)ethanamine (0.216 mL, 1.499 mmol) in DMF (7 mL) was added DIPEA (0.524 mL, 3.00 mmol) and 3,3-bis(bromomethyl)oxetane (439 mg, 1.80 mmol) under a nitrogen atmosphere at RT. The reaction mixture was stirred at 100° C. for 5 h, cooled, and diluted with water and EtOAc. After phase separation, the aqeuous layer was extracted twice with EtOAc, and the combined organic layers were washed with brine, dried over MgSO$_4$, filtered and concentrated under reduced pressure to give the title compound as a yellow oil that was used without further purification. (UPLC-MS) $t_R$ 0.52 min; ESI-MS 282/284 [M+H]$^+$.

Intermediate 3c: 2-amino-5-bromo-N-((1r,4r)-4-hydroxycyclohexyl)nicotinamide To a solution of 2-amino-5-bromonicotinic acid (2.00 g, 9.22 mmol) in DMF (30 mL) was added trans-4-aminocyclohexanol (1.68 g, 11.1 mmol), HATU (7.01 g, 18.4 mmol) and N-methylmorpholine (4.05 mL, 36.9 mmol) at RT. After stirring for 2 h the reaction mixture was diluted with EtOAc and a sat. aq. solution of NaHCO$_3$. The aq. phase was extracted two times with EtOAc. The combined organic layers were dried over MgSO$_4$, filtered and concentrated under reduced pressure. The residue was purified by normal-phase chromatography (Method 2a) to give the title compound as a yellow solid. (UPLC-MS) $t_R$ 0.62 min; ESI-MS 314/316 [M+H]$^+$.

Example 4: 5-(4-((S)-1-(2-oxa-6-azaspiro[3.3]heptan-6-yl)ethyl)phenyl)-2-amino-N-((1r,4R)-4-hydroxycyclohexyl)nicotinamide

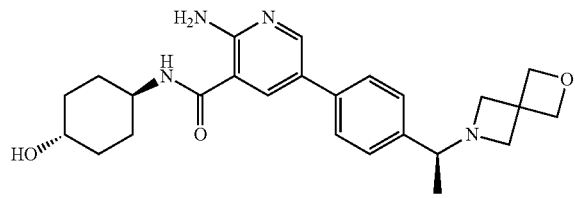 [SMILES: C[C@@H](c1ccc(-c2cnc(N)c(C(=O)N[C@H]3CC[C@H](O)CC3)c2)cc1)N1CC2(COC2)C1]

The title compound was prepared in an analogous manner to 5-(4-((R)-1-(2-oxa-6-azaspiro[3.3]heptan-6-yl)ethyl)phenyl)-2-amino-N-((1r,4R)-4-hydroxycyclohexyl)nicotinamide (Example 3) except (S)-6-(1-(4-bromophenyl)ethyl)-2-oxa-6-azaspiro[3.3]heptane (Intermediate 4a) was used in place of (R)-6-(1-(4-bromophenyl)ethyl)-2-oxa-6-azaspiro[3.3]heptane (Intermediate 3b). 1H NMR (400 MHz, DMSO-d6) δ 8.37 (d, 1H), 8.27 (d, 1H), 8.09-8.14 (m, 1H), 7.57 (bs, 2H), 7.33 (bs, 2H), 7.12 (bs, 2H), 4.54-4.58 (m, 1H), 4.51-4.66 (m, 3H), 3.55-3.81 (m, 1H), 3.35-3.54 (m, 2H), 3.20-3.24 (m, 1H), 3.20-3.27 (m, 2H), 3.15 (bs, 1H), 1.78-1.91 (m, 4H), 1.14-1.41 (m, 5H), 1.11 (bs, 3H). (UPLC-MS) $t_R$ 0.45 min; ESI-MS 437 [M+H]$^+$.

Intermediate 4a: (S)-6-(1-(4-bromophenyl)ethyl)-2-oxa-6-azaspiro[3.3]heptane The title compound was prepared in an analogous manner to (R)-6-(1-(4-bromophenyl)ethyl)-2-oxa-6-azaspiro[3.3]heptane (Intermediate 3b) except (S)-1-(4-bromophenyl)ethanamine was used in place of (R)-1-(4-bromophenyl)ethanamine. (UPLC-MS) $t_R$ 0.55 min; ESI-MS 282/284 [M+H]$^+$.

Example 5: 2-amino-N-((1r,4S)-4-hydroxycyclohexyl)-5-(4-((1S,5R)-3-(3-morpholinopropyl)-3-azabicyclo[3.1.0]hexan-1-yl)phenyl)nicotinamide

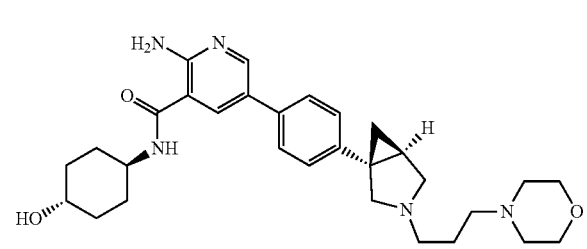 [SMILES: Nc1ncc(-c2ccc([C@]34C[C@H]3CN(CCCN3CCOCC3)C4)cc2)cc1C(=O)N[C@H]1CC[C@H](O)CC1]

To a solution of 5-(4-((1S,5R)-3-azabicyclo[3.1.0]hexan-1-yl)phenyl)-2-amino-N-((1r,4S)-4-hydroxycyclohexyl)nicotinamide TFA salt (Intermediate 5a, 70 mg, 0.138 mmol) in acetonitrile (3 mL) was added K$_2$CO$_3$ (47.7 mg, 0.345 mmol) and 4-(3-bromopropyl)morpholine (47.9 mg, 0.166 mmol) at RT. The reaction mixture was stirred at 65° C. for 2 h. The reaction mixture was then diluted with a sat. aq. solution of NaHCO$_3$ and mixed with EtOAc. After phase separation, the aq. layer was extracted again with EtOAc. The combined organic layers were washed with brine, dried over MgSO$_4$, filtered and concentrated under reduced pressure. The crude product was purified by prepHPLC (Method 1a) to give the title compound as a yellow solid. 1H NMR (400 MHz, DMSO-d6) δ 8.38 (d, 1H), 8.31 (d, 1H), 8.11 (d, 1H), 7.58 (d, 2H), 7.22 (d, 2H), 7.12 (s, 2H), 4.58 (d, 1H), 3.82-3.67 (m, 1H), 3.61-3.50 (m, 4H), 3.41 (s, 2H), 3.05 (d, 1H), 2.48-2.24 (m, 9H), 1.93-1.76 (m, 5H), 1.61 (m, 2H), 1.46-1.17 (m, 6H), 0.76 (dd, 1H). (UPLC-MS) $t_R$ 0.40 min; ESI-MS 520 [M+H]$^+$.

Intermediate 5a: 5-(4-((1S,5R)-3-azabicyclo[3.1.0]hexan-1-yl)phenyl)-2-amino-N-((1r,4R)-4-hydroxycyclohexyl)nicotinamide To a solution of (1S,5R)-tert-butyl 1-(4-(6-amino-5-(((1r,4S)-4-hydroxycyclohexyl)carbamoyl)pyridin-3-yl)phenyl)-3-azabicyclo[3.1.0]hexane-3-carboxylate (Intermediate 5b, 1.18 g, 1.95 mmol) in dioxane (10 mL) was added a 4M solution of HCl in dioxane (1.95 mL, 7.78 mmol) at RT. The reaction mixture was stirred at 65° C. for 5 h and then concentrated under reduced pressure to give the title compound as a hydrochloride salt. Occasionally the product was further purified by prepHPLC (Method 1a) to give the title compound as a TFA salt after evaporation of solvents. (UPLC-MS) $t_R$ 0.45 min; ESI-MS 393 [M+H]$^+$.

Intermediate 5b: (1S,5R)-tert-butyl 1-(4-(6-amino-5-(((1r,4S)-4-hydroxycyclohexyl)carbamoyl)pyridin-3-yl)phenyl)-3-azabicyclo[3.1.0]hexane-3-carboxylate The title compound was prepared in an analogous manner to (1R,5S)-tert-butyl 1-(4-(6-amino-5-(((1r,4R)-4-hydroxycyclohexyl)carbamoyl)pyridin-3-yl)phenyl)-3-azabicyclo[3.1.0]hexane-3-carboxylate (Intermediate 1 b) except 2-amino-5-(4-((1S,5R)-3-(tert-butoxycarbonyl)-3-azabicyclo[3.1.0]hexan-1-yl)phenyl)nicotinic acid (Intermediate 5c) was used in place of 2-amino-5-(4-((1R,5S)-3-(tert-butoxycarbonyl)-3-azabicyclo[3.1.0]hexan-1-yl)phenyl)nicotinic acid (Intermediate 1c). (UPLC-MS) $t_R$ 1.00 min; ESI-MS 493 [M+H]$^+$.

Intermediate 5c: 2-amino-5-(4-((1S,5R)-3-(tert-butoxycarbonyl)-3-azabicyclo[3.1.0]hexan-1-yl)phenyl)nicotinic acid The title compound was prepared in an analogous manner to 2-amino-5-(4-((1R,5S)-3-(tert-butoxycarbonyl)-3-azabicyclo[3.1.0]hexan-1-yl)phenyl)nicotinic acid (Intermediate 1c) except (1S,5R)-tert-butyl 1-(4-(6-amino-5-(methoxycarbonyl)pyridin-3-yl)phenyl)-3-azabicyclo[3.1.0]hexane-3-carboxylate (Intermediate 5d) was used in place of (1R,5S)-tert-butyl 1-(4-(6-amino-5-(methoxycarbonyl)pyridin-3-yl)phenyl)-3-azabicyclo[3.1.0]hexane-3-carboxylate (Intermediate 1d). (UPLC-MS) $t_R$ 0.92 min; ESI-MS 396 [M+H]$^+$.

Intermediate 5d: (1S,5R)-tert-butyl 1-(4-(6-amino-5-(methoxycarbonyl)pyridin-3-yl)phenyl)-3-azabicyclo[3.1.0]hexane-3-carboxylate Racemic tert-butyl 1-(4-(6-amino-5-(methoxycarbonyl)pyridin-3-yl)phenyl)-3-aza-bicyclo[3.1.0]hexane-3-carboxylate (Intermediate 1e, 13.5 g, 33.0 mmol) was resolved by chiral preparative SFC (CHIRALPAK AD-H 5 μm 30*250 mm, mobile phase CO$_2$/i-PrOH 70:30, flow rate 120 g/min; UV detection at 278 nm). The title compound was obtained as an off-white solid after concentration under reduced pressure. Chiral analytical HPLC (CHIRALPAK AD-3 3 μm 2*100 mm, mobile phase CO$_2$/MeOH+0.1% DEA 60:40, flow rate 1 mL/min; UV detection at 274 nm): $t_R$ 2.90 min, ee=98.7%, $[\alpha]_D^{20}=-87°$.

Example 6: 2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide

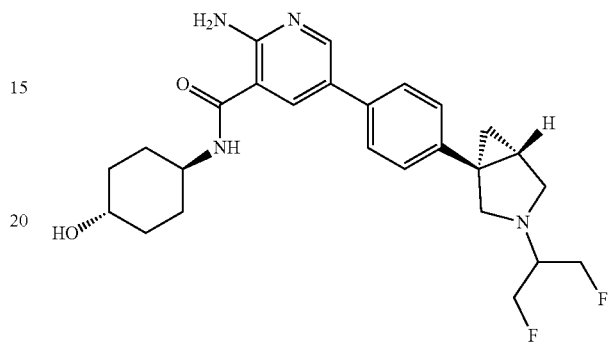

To a solution of 5-(4-((1R,5S)-3-azabicyclo[3.1.0]hexan-1-yl)phenyl)-2-amino-N-((1r,4R)-4-hydroxycyclohexyl)nicotinamide TFA salt (Intermediate 1a, 70 mg, 0.138 mmol) in acetonitrile (3 mL) was added K$_2$CO$_3$ (38.2 mg, 0.276 mmol) and 1,3-difluoropropan-2-yl trifluoromethanesulfonate (Intermediate 6a) (37.8 mg, 0.166 mmol) at RT. The reaction mixture was stirred at RT for 1 h, then diluted with a sat. aq. solution of NaHCO$_3$ and mixed with EtOAc. After phase separation, the aq. layer was extracted again with EtOAc. The combined organic layers were washed with brine, dried over MgSO$_4$, filtered and concentrated under reduced pressure. The crude product was purified by prepHPLC (Method 1a) to give the title compound. 1H NMR (400 MHz, DMSO-d6) δ 8.41 (d, 1H), 8.37 (d, 1H), 8.18 (s, 1H), 7.62 (s, 2H), 7.35 (d, 1H), 7.25 (m, 3H), 4.64 (d, 3H), 3.74 (m, 4H), 2.89 (d, 4H), 1.87 (t, 5H), 1.34 (m, 6H), 0.82 (s, 1H). (UPLC-MS) $t_R$ 0.68 min; ESI-MS 471 [M+H]$^+$.

Intermediate 6a: 1,3-difluoropropan-2-yl trifluoromethanesulfonate

To a solution of 1,3-difluoropropan-2-ol (300 mg, 3.12 mmol) in DCM (8 mL) was added DMAP (26.7 mg, 0.219 mmol) and TEA (0.522 mL, 3.75 mmol) under a nitrogen atmosphere at RT. The reaction mixture was cooled to 0° C. and trifluoromethanesulfonic anhydride (0.630 mL, 3.75 mmol) was added. After stirring at 0° C. for 60 min and at RT for 3 h, the reaction mixture was diluted with DCM. The organic layer was washed with water, twice with an aq. solution of citric acid and twice with a sat. aq. solution of NaHCO$_3$, dried over MgSO$_4$ and concentrated at 500 mbar. The title compound was obtained as a crude oil that was used without further purification.

Example 7: 2-amino-N-(4-hydroxybicyclo[2.2.2]octan-1-yl)-5-(4-((1S,5R)-3-(2-methoxyethyl)-3-azabicyclo[3.1.0]hexan-1-yl)phenyl)nicotinamide

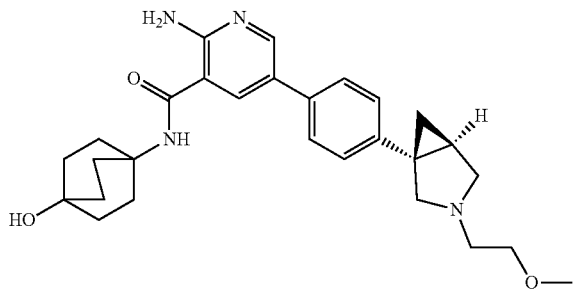 [SMILES: COCCN1C[C@@H]2C[C@]2(c2ccc(-c3cnc(N)c(C(=O)NC45CCC(O)(CC4)CC5)c3)cc2)C1]

The title compound was prepared in an analogous manner to (1R,5S)-tert-butyl 1-(4-(6-amino-5-(((1r,4R)-4-hydroxycyclohexyl)carbamoyl)pyridin-3-yl)phenyl)-3-azabicyclo[3.1.0]hexane-3-carboxylate (Intermediate 1 b) except 2-amino-5-(4-((1S,5R)-3-(2-methoxyethyl)-3-azabicyclo[3.1.0]hexan-1-yl)phenyl)nicotinic acid (Intermediate 7a) was used in place of 2-amino-5-(4-((1R,5S)-3-(tert-butoxycarbonyl)-3-azabicyclo[3.1.0]hexan-1-yl)phenyl)nicotinic acid (Intermediate 1c), and 4-aminobicyclo[2.2.2]octan-1-ol hydrochloride was used in place of trans-4-aminocyclohexanol. The crude product was purified first by prepHPLC (Method 1a) then by reversed-phase flash chromatography (Method 3a) to give the title compound as a colorless solid. 1H NMR (400 MHz, DMSO-d6) δ 8.34 (d, 1H), 7.98 (d, 1H), 7.79 (s, 1H), 7.57 (d, 2H), 7.21 (d, 2H), 6.92 (s, 2H), 4.32 (s, 1H), 3.45 (t, 2H), 3.41-3.29 (m, 2H), 3.27 (s, 3H), 3.08 (d, 1H), 2.68-2.51 (m, 3H), 2.07-2.03 (m, 6H), 1.83-1.79 (m, 1H), 1.65-1.61 (m, 6H), 1.33 (t, 1H), 0.77 (bs, 1H). (UPLC-MS) $t_R$ 0.52 min; ESI-MS 477 [M+H]$^+$.

Intermediate 7a: 2-amino-5-(4-((1S,5R)-3-(2-methoxyethyl)-3-azabicyclo[3.1.0]hexan-1-yl)phenyl)nicotinic acid The title compound was prepared in an analogous manner to 2-amino-5-(4-((1R,5S)-3-(tert-butoxycarbonyl)-3-azabicyclo[3.1.0]hexan-1-yl)phenyl)nicotinic acid (Intermediate 2c) except methyl 2-amino-5-(4-((1S,5R)-3-(2-methoxyethyl)-3-azabicyclo[3.1.0]hexan-1-yl)phenyl)nicotinate (Intermediate 7b) was used in place of (1R,5S)-tert-butyl 1-(4-(6-amino-5-(methoxycarbonyl)pyridin-3-yl)phenyl)-3-azabicyclo[3.1.0]hexane-3-carboxylate (Intermediate 1d). (UPLC-MS) $t_R$ 0.32 min; ESI-MS 354 [M+H]$^+$.

Intermediate 7b: methyl 2-amino-5-(4-((1S,5R)-3-(2-methoxyethyl)-3-azabicyclo[3.1.0]hexan-1-yl)phenyl)nicotinate To a solution of methyl 5-(4-((1S,5R)-3-azabicyclo[3.1.0]hexan-1-yl)phenyl)-2-aminonicotinate hydrochloride (Intermediate 7c, 210 mg, 0.607 mmol) in acetonitrile (6 mL) was added K$_2$CO$_3$ (168 mg, 0.729 mmol) and 1-bromo-2-methoxyethane (0.068 mL, 0.729 mmol) at RT. The reaction mixture was stirred at 65° C. for 3 h. The reaction mixture was then diluted with a sat. aq. solution of NaHCO$_3$ and mixed with EtOAc. After phase separation, the aq. layer was extracted again with EtOAc. The combined organic layers were washed with brine, dried over MgSO$_4$, filtered, and concentrated under reduced pressure to give the title compound which was used without further purification. (UPLC-MS) $t_R$ 0.62 min; ESI-MS 368 [M+H]$^+$.

Intermediate 7c: methyl 5-(4-((1S,5R)-3-azabicyclo[3.1.0]hexan-1-yl)phenyl)-2-aminonicotinate hydrochloride To a solution of (1S,5R)-tert-butyl 1-(4-(6-amino-5-(methoxycarbonyl)pyridin-3-yl)phenyl)-3-azabicyclo[3.1.0]hexane-3-carboxylate (Intermediate 5d, 500 mg, 1.22 mmol) in dioxane (7 mL) was added a 4M solution of HCl in dioxane (1.22 mL, 4.88 mmol) at RT. The reaction mixture was stirred at 60° C. for 3 h and then concentrated under reduced pressure to give the title compound as a hydrochloride salt. (UPLC-MS) $t_R$ 0.58 min; ESI-MS 310 [M+H]$^+$.

Example 8: 2-amino-5-(2-fluoro-4-(4-isopropylpiperazin-1-yl)phenyl)-N-((1r,4r)-4-hydroxycyclohexyl)nicotinamide To a solution of 2-amino-5-bromo-N-((1r,4r)-4-hydroxycyclohexyl)nicotinamide (Intermediate 3c, 230 mg, 0.731 mmol) in dioxane (4 mL) was added 1-(3-fluoro-4-(4,4,5,5-tetramethyl-1,3,2-dioxaborolan-2-yl)phenyl)-4-isopropylpiperazine (Intermediate 8a, 463 mg, 0.731 mmol), 2N aq. K$_2$CO$_3$ (0.73 mL, 1.46 mmol) and PdCl$_2$(dppf)-DCM adduct (29.9 mg, 0.037 mmol) under a nitrogen atmosphere at RT. The reaction mixture was stirred at 80° C. for 60 min, then diluted with EtOAc and aq. NaHCO$_3$. After phase separation, the aq. layer was extracted with EtOAc. The organic layers were washed with a sat. aq. solution of NaHCO$_3$ and brine, respectively, dried over MgSO$_4$, filtered, and concentrated under reduced pressure. The crude product was purified by prepHPLC (Method 1a) to give the title compound as a yellow solid. 1H NMR (400 MHz, DMSO-d6) δ 8.24-8.16 (m, 2H), 7.95 (d, 1H), 7.39 (t, 1H), 7.06 (s, 2H), 6.86 (d, 2H), 4.54 (d, 1H), 3.69 (m, 1H), 3.41-3.33 (m, 2H), 3.15 (s, 3H), 2.66 (q, 3H), 1.82 (m, 4H), 1.42-0.88 (m, 10H). (UPLC-MS) $t_R$ 0.48 min; ESI-MS 456 [M+H]$^+$.

Intermediate 8a: 1-(3-fluoro-4-(4,4,5,5-tetramethyl-1,3,2-dioxaborolan-2-yl)phenyl)-4-isopropylpiperazine To a solution of 1-(4-bromo-3-fluorophenyl)-4-isopropylpiperazine (Intermediate 8b, 212 mg, 0.662 mmol) in dioxane (8 mL) was added bis(pinacolato)diboron (202 mg, 0.794 mmol), KOAc (130 mg, 1.323 mmol) and PdCl$_2$(dppf)-DCM adduct (27 mg, 0.033 mmol) under a nitrogen atmosphere at RT. The reaction mixture was stirred at 90° C. for 2 h, then filtered through a pad of celite, and concentrated under reduced pressure to give the title compound which was used without any further purification. (UPLC-MS) $t_R$ 0.79 min; ESI-MS 349 [M+H]$^+$.

Intermediate 8b: 1-(4-bromo-3-fluorophenyl)-4-isopropylpiperazine

To a solution of 1-(4-bromo-3-fluorophenyl)piperazine (Intermediate 8c, 215 mg, 0.797 mmol) in acetonitrile (7 mL) was added 2-iodopropane (0.095 mL, 0.956 mmol) and K$_2$CO$_3$ (220 mg, 1.593 mmol) at RT. The reaction mixture was stirred at 65° C. for 4 h, then diluted with EtOAc and aq. NaHCO$_3$. After phase separation, the aq. layer was extracted with EtOAc. The organic layers were washed with brine, dried over MgSO$_4$, filtered, and concentrated under reduced pressure to give the title compound as a colorless oil which was used without any further purification. (UPLC-MS) $t_R$ 0.66 min; ESI-MS 302 [M+H]$^+$.

Intermediate 8c: 1-(4-bromo-3-fluorophenyl)piperazine

To a solution of tert-butyl 4-(4-bromo-3-fluorophenyl)piperazine-1-carboxylate (300 mg, 0.835 mmol) in dioxane (8 mL) was added 4N HCl in dioxane (0.84 mL, 3.34 mmol) under a nitrogen atmosphere at RT. The reaction mixture was stirred for 2 h, then diluted with EtOAc and aq. NaHCO$_3$. After phase separation, the aq. layer was extracted with EtOAc. The organic layers were washed with brine, dried over MgSO$_4$, filtered, and concentrated under reduced pressure to give the title compound which was used without any further purification. (UPLC-MS) $t_R$ 0.60 min; ESI-MS 260 [M+H]$^+$.

Example 9: 2-amino-N-((1r,4S)-4-hydroxycyclohexyl)-5-(4-((1S,5R)-3-isopropyl-3-azabicyclo[3.1.0]hexan-1-yl)phenyl)nicotinamide

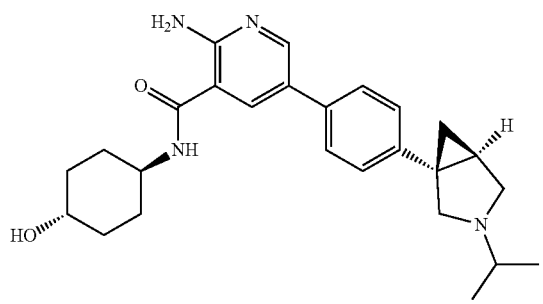 [SMILES: CC(C)N1C[C@@H]2C[C@]2(c2ccc(-c3cnc(N)c(C(=O)N[C@H]4CC[C@H](O)CC4)c3)cc2)C1]

The title compound was prepared in an analogous manner to 2-amino-N-((1r,4R)-4-hydroxycyclohexyl)-5-(4-((1R,5S)-3-isopropyl-3-azabicyclo[3.1.0]hexan-1-yl)phenyl)nicotinamide (Example 2) except 2-amino-5-(4-((1S,5R)-3-isopropyl-3-azabicyclo[3.1.0]hexan-1-yl)phenyl)nicotinic acid TFA salt (Intermediate 9a) was used instead of 2-amino-5-(4-((1R,5S)-3-isopropyl-3-azabicyclo[3.1.0]hexan-1-yl)phenyl)nicotinic acid TFA salt (Intermediate 2a). 1H NMR (400 MHz, DMSO-d6) δ 8.38 (d, 1H), 8.31 (d, 1H), 8.11 (d, 1H), 7.58 (d, 2H), 7.23 (d, 2H), 7.12 (s, 2H), 4.58 (d, 1H), 3.82-3.66 (m, 1H), 3.48-3.34 (m, 3H), 3.07 (d, 1H), 2.64-2.55 (m, 2H), 1.96-1.77 (m, 5H), 1.50-1.19 (m, 5H), 1.04 (dd, 6H), 0.75 (dd, 1H). (UPLC-MS) $t_R$ 0.50 min; ESI-MS 435 [M+H]$^+$.

Intermediate 9a: 2-amino-5-(4-((1S,5R)-3-isopropyl-3-azabicyclo[3.1.0]hexan-1-yl)phenyl)nicotinic acid TFA salt The title compound was prepared in an analogous manner to 2-amino-5-(4-((1R,5S)-3-isopropyl-3-azabicyclo[3.1.0] hexan-1-yl)phenyl)nicotinic acid TFA salt (Intermediate 2a) except methyl 2-amino-5-(4-((1S,5R)-3-isopropyl-3-azabicyclo[3.1.0]hexan-1-yl)phenyl)nicotinate (Intermediate 9b) was used instead of methyl 2-amino-5-(4-((1R,5S)-3-isopropyl-3-azabicyclo[3.1.0]hexan-1-yl)phenyl)nicotinate (Intermediate 2b). (UPLC-MS) $t_R$ 0.37 min; ESI-MS 338 [M+H]$^+$.

Intermediate 9b: methyl 2-amino-5-(4-((1R,5S)-3-isopropyl-3-azabicyclo[3.1.0]hexan-1-yl)phenyl)nicotinate The title compound was prepared in an analogous manner to methyl 2-amino-5-(4-((1R,5S)-3-isopropyl-3-azabicyclo[3.1.0]hexan-1-yl)phenyl)nicotinate (Intermediate 2b) except (1S,5R)-1-(4-bromophenyl)-3-isopropyl-3-azabicyclo[3.1.0]hexane (Intermediate 9c) was used instead of (1R,5S)-1-(4-bromophenyl)-3-isopropyl-3-azabicyclo[3.1.0]hexane (Intermediate 2c). (UPLC-MS) $t_R$ 0.62 min; ESI-MS 352 [M+H]$^+$.

Intermediate 9c: (1S,5R)-1-(4-bromophenyl)-3-isopropyl-3-azabicyclo[3.1.0]hexane The title compound was prepared in an analogous manner to (1R,5S)-1-(4-bromophenyl)-3-isopropyl-3-azabicyclo[3.1.0]hexane (Intermediate 2c) except (1S,5R)-1-(4-bromophenyl)-3-azabicyclo[3.1.0]hexane (prepared analogously to a description in WO2007/022935) was used instead of (1R,5S)-1-(4-bromophenyl)-3-azabicyclo[3.1.0]hexane. (UPLC-MS) $t_R$ 0.70 min; ESI-MS 280/282 [M+H]$^+$.

Example 10: 2-amino-N-((1r,4R)-4-hydroxycyclohexyl)-5-(4-((1R,5S)-3-(2-morpholinoethyl)-3-azabicyclo[3.1.0]hexan-1-yl)phenyl)nicotinamide

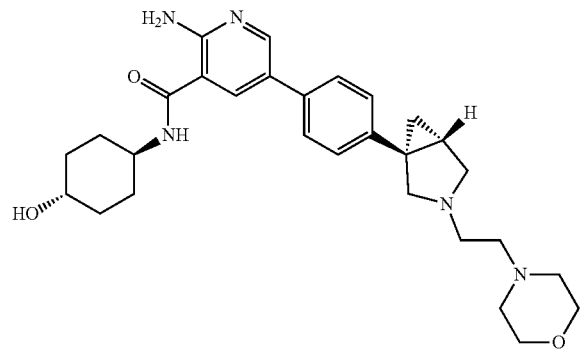 [SMILES: Nc1ncc(-c2ccc([C@@]34C[C@@H]3CN(CCN3CCOCC3)C4)cc2)cc1C(=O)N[C@H]1CC[C@H](O)CC1]

The title compound was prepared in an analogous manner to 2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide (Example 6) except 4-(2-bromoethyl)morpholine was used instead of 1,3-difluoropropan-2-yl trifluoromethanesulfonate (Intermediate 6a), and the reaction mixture was stirred at 65° C. for 1 h. 1H NMR (400 MHz, DMSO-d6) δ 8.38 (d, 1H), 8.31 (d, 1H), 8.11 (d, 1H), 7.59 (d, 2H), 7.22 (d, 2H), 7.12 (s, 2H), 4.59 (d, 1H), 3.84-3.67 (m, 1H), 3.63-3.51 (m, 4H), 3.46-3.39 (m, 2H), 3.09 (d, 1H), 2.71-2.57 (m, 3H), 2.42 (s, 6H), 1.95-1.75 (m, 5H), 1.53-1.15 (m, 5H), 0.77 (d, 1H). (UPLC-MS) $t_R$ 0.49 min; ESI-MS 506 [M+H]$^+$.

Example 11: 2-amino-5-(4-((1S,5R)-3-(2-fluoro-ethyl)-3-azabicyclo[3.1.0]hexan-1-yl)phenyl)-N-((1r,4S)-4-hydroxycyclohexyl)nicotinamide

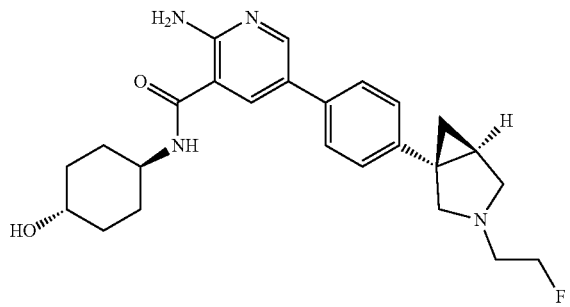 [SMILES: Nc1ncc(-c2ccc([C@]34C[C@H]3CN(CCF)C4)cc2)cc1C(=O)N[C@H]1CC[C@H](O)CC1]

The title compound was prepared in an analogous manner to 2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide (Example 5) except 1-bromo-2-fluoroethane was used instead of 4-(3-bromopropyl)morpholine, and the reaction mixture was stirred at 60° C. for 5 h. 1H NMR (400 MHz, DMSO-d6) δ 8.38 (d, 1H), 8.31 (d, 1H), 8.11 (d, 1H), 7.59 (d, 2H), 7.22 (d, 2H), 7.13 (s, 2H), 4.59 (d, 2H), 4.50 (s, 1H), 3.73 (d, 1H), 3.41 (d, 3H), 2.83-2.78 (m, 3H), 1.85 (t, 5H), 1.47-1.16 (m, 6H), 0.78 (s, 1H). (UPLC-MS) $t_R$ 0.47 min; ESI-MS 439 [M+H]$^+$.

Example 12: 2-amino-N-((1r,4r)-4-hydroxycyclohexyl)-5-(4-(1-isopropylpyrrolidin-3-yl)phenyl)nicotinamide

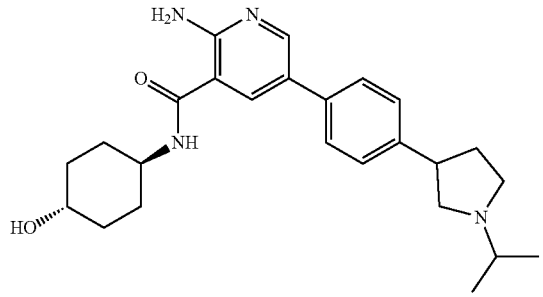 [SMILES: CC(C)N1CCC(c2ccc(-c3cnc(N)c(C(=O)N[C@H]4CC[C@H](O)CC4)c3)cc2)C1]

The title compound was prepared in an analogous manner to 2-amino-5-(2-fluoro-4-(4-isopropylpiperazin-1-yl)phenyl)-N-((1r,4r)-4-hydroxycyclohexyl)nicotinamide (Example 8) except 1-isopropyl-3-(4-(4,4,5,5-tetramethyl-1,3,2-dioxaborolan-2-yl)phenyl)pyrrolidine (Intermediate 12a) was used in place of 1-(3-fluoro-4-(4,4,5,5-tetramethyl-1,3,2-dioxaborolan-2-yl)phenyl)-4-isopropylpiperazine (Intermediate 8a). 1H NMR (400 MHz, DMSO-d6) δ 8.36 (d, 1H), 8.26 (d, 1H), 8.09 (d, 1H), 7.62-7.51 (m, 2H), 7.37-7.28 (m, 2H), 7.09 (s, 2H), 4.55 (d, 1H), 3.70 (dq, 1H), 3.44-3.34 (m, 2H), 3.03 (d, 1H), 2.75 (s, 2H), 2.29-2.06 (m, 2H), 1.87-1.68 (m, 5H), 1.42-1.17 (m, 5H), 1.06 (t, 6H). (UPLC-MS) $t_R$ 0.48 min; ESI-MS 423 [M+H]$^+$.

Intermediate 12a: 1-isopropyl-3-(4-(4,4,5,5-tetramethyl-1,3,2-dioxaborolan-2-yl)phenyl)pyrrolidine The title compound was prepared in an analogous manner to 1-(3-fluoro-4-(4,4,5,5-tetramethyl-1,3,2-dioxaborolan-2-yl)phenyl)-4-isopropylpiperazine (Intermediate 8a) except 3-(4-bromophenyl)-1-isopropylpyrrolidine (Intermediate 12b) was used in place of 1-(4-bromo-3-fluorophenyl)-4-isopropylpiperazine (Intermediate 8b). (UPLC-MS) $t_R$ 0.79 min; ESI-MS 316 [M+H]$^+$.

Intermediate 12b: 3-(4-bromophenyl)-1-isopropylpyrrolidine

The title compound was prepared in an analogous manner to 1-(4-bromo-3-fluorophenyl)-4-isopropylpiperazine (Intermediate 8b) except 3-(4-bromophenyl)pyrrolidine hydrochloride was used in place of 1-(4-bromo-3-fluorophenyl)piperazine (Intermediate 8c). (UPLC-MS) $t_R$ 0.62 min; ESI-MS 269 [M+H]$^+$.

Example 13: 2-amino-N-((1r,4S)-4-hydroxycyclohexyl)-5-(4-((1S,5R)-3-(2-morpholinoethyl)-3-azabicyclo[3.1.0]hexan-1-yl)phenyl)nicotinamide

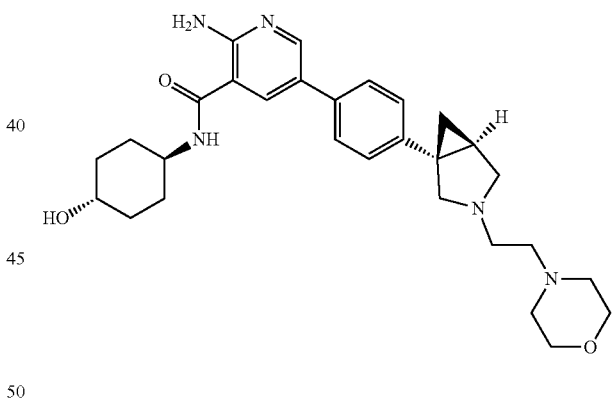

The title compound was prepared in an analogous manner to 2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide (Example 5) except 4-(2-bromoethyl)morpholine was used instead of 4-(3-bromopropyl)morpholine. 1H NMR (400 MHz, DMSO-d6) δ 8.38 (d, 1H), 8.31 (d, 1H), 8.11 (d, 1H), 7.59 (d, 2H), 7.22 (d, 2H), 7.12 (s, 2H), 4.59 (d, 1H), 3.84-3.67 (m, 1H), 3.63-3.51 (m, 4H), 3.46-3.39 (m, 2H), 3.09 (d, 1H), 2.71-2.57 (m, 3H), 2.42 (s, 6H), 1.95-1.75 (m, 5H), 1.53-1.15 (m, 5H), 0.77 (d, 1H). (UPLC-MS) $t_R$ 0.49 min; ESI-MS 506 [M+H]$^+$.

Example 14: 2-amino-N-((1r,4R)-4-hydroxy-4-methylcyclohexyl)-5-(4-((1R,5S)-3-(tetrahydro-2H-pyran-4-yl)-3-azabicyclo[3.1.0]hexan-1-yl)phenyl)nicotinamide

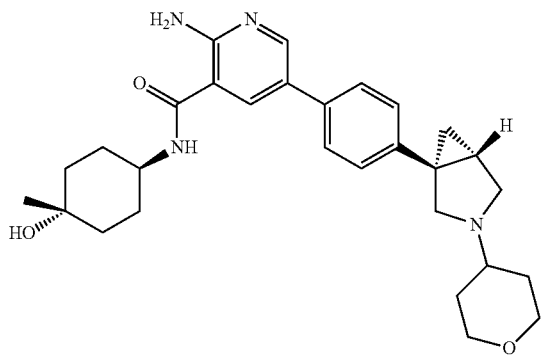 [SMILES: C[C@]1(O)CC[C@H](NC(=O)c2cc(-c3ccc([C@@]45C[C@@H]4CN(C4CCOCC4)C5)cc3)cnc2N)CC1]

The title compound was prepared in an analogous manner to (1R,5S)-tert-butyl 1-(4-(6-amino-5-(((1r,4R)-4-hydroxycyclohexyl)carbamoyl)pyridin-3-yl)phenyl)-3-azabicyclo[3.1.0]hexane-3-carboxylate (Intermediate 1 b) except 2-amino-5-(4-((1R,5S)-3-(tetrahydro-2H-pyran-4-yl)-3-azabicyclo[3.1.0]hexan-1-yl)phenyl)nicotinic acid (Intermediate 14a) was used in place of 2-amino-5-(4-((1R,5S)-3-(tert-butoxycarbonyl)-3-azabicyclo[3.1.0]hexan-1-yl)phenyl)nicotinic acid (Intermediate 1c), and trans-4-amino-1-methylcyclohexanol was used in place of trans-4-aminocyclohexanol. The crude product was purified by prepHPLC (Method 1a) to give the title compound as a TFA salt. 1H NMR (400 MHz, DMSO-d6) δ 8.53 (d, 1H), 8.46 (d, 1H), 8.35 (s, 1H), 7.72 (d, 2H), 7.71 (bs, 2H), 7.41 (d, 2H), 4.06 (dd, 1H), 3.98 (dd, 2H), 3.85-3.43 (m, 5H), 3.27 (t, 2H), 2.26 (dd, 1H), 1.99 (d, 2H), 1.83-1.76 (m, 4H), 1.68-1.56 (m, 3H), 1.51-1.45 (m, 5H), 1.21-1.13 (m, 5H). (UPLC-MS) $t_R$ 0.51 min; ESI-MS 491 [M+H]$^+$.

Intermediate 14a: 2-amino-5-(4-((1R,5S)-3-(tetrahydro-2H-pyran-4-yl)-3-azabicyclo[3.1.0]hexan-1-yl)phenyl)nicotinic acid (TFA salt)

To a solution of methyl 2-amino-5-(4-((1R,5S)-3-(tetrahydro-2H-pyran-4-yl)-3-azabicyclo[3.1.0]hexan-1-yl)phenyl)nicotinate (Intermediate 14b, 1.30 g, 2.97 mmol) in anhydrous THF (16 mL) was added a 2M aq. solution of LiOH (4.46 mL, 8.92 mmol) at RT. The reaction mixture was stirred at 65° C. for 140 min and then concentrated under reduced pressure. The residue was purified by reversed-phase chromatography (Method 3b). Pure fractions were concentrated and lyophilized to give the title compound as an off-white TFA salt. (UPLC-MS) $t_R$ 0.40 min; ESI-MS 380 [M+H]$^+$.

Intermediate 14b: methyl 2-amino-5-(4-((1R,5S)-3-(tetrahydro-2H-pyran-4-yl)-3-azabicyclo[3.1.0]hexan-1-yl)phenyl)nicotinate To a solution of methyl 5-(4-((1R,5S)-3-azabicyclo[3.1.0]hexan-1-yl)phenyl)-2-aminonicotinate hydrochloride (Intermediate 14c, 1.18 g, 3.28 mmol) in DCM (16 mL) was added dihydro-2H-pyran-4(3H)-one (0.33 mL, 3.60 mmol) and AcOH (0.38 mL, 6.55 mmol) at RT. The reaction mixture was stirred at 45° C. for 30 min. Sodium triacetoxyborohydride (1.74 g, 8.19 mmol) was added at RT and the reaction mixture was stirred at 45° C. for 1 h. The reaction mixture was then diluted with a sat. solution of NaHCO$_3$ and mixed with EtOAc. After phase separation, the aq. layer was extracted again with EtOAc. The combined organic layers were washed with brine, dried over MgSO$_4$, filtered and concentrated under reduced pressure to give the title compound which was used without further purification. (UPLC-MS) $t_R$ 0.67 min; ESI-MS 394 [M+H]$^+$.

Intermediate 14c: methyl 5-(4-((1R,5S)-3-azabicyclo[3.1.0]hexan-1-yl)phenyl)-2-aminonicotinate hydrochloride To a solution of (1R,5S)-tert-butyl-1-(4-(6-amino-5-(methoxycarbonyl)pyridin-3-yl)phenyl)-3-azabicyclo[3.1.0]hexane-3-carboxylate (Intermediate 1d, 1.50 g, 3.66 mmol) in dioxane (25 mL) was added a 4M solution of HCl in dioxane (3.66 mL, 14.7 mmol) at RT. The reaction mixture was stirred at 60° C. for 3 h and then concentrated under reduced pressure to give the title compound as a hydrochloride salt. (UPLC-MS) $t_R$ 0.58 min; ESI-MS 310 [M+H]$^+$.

Example 15: 2-amino-N-(4-hydroxybicyclo[2.2.2]oct-1-yl)-5-(4-((1R,5S)-3-(2-morpholinoethyl)-3-azabicyclo[3.1.0]hexan-1-yl)phenyl)nicotinamide

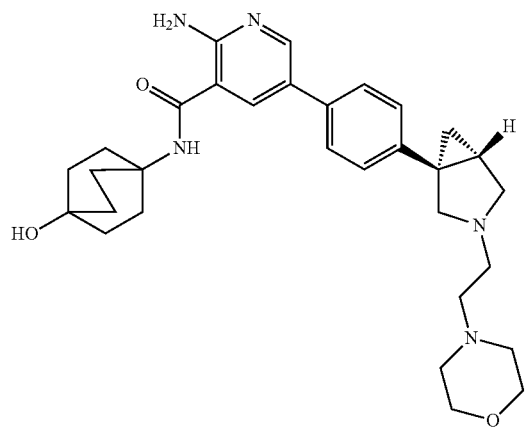 [SMILES: Nc1ncc(-c2ccc([C@@]34C[C@@H]3CN(CCN3CCOCC3)C4)cc2)cc1C(=O)NC12CCC(O)(CC1)CC2]

The title compound was prepared in an analogous manner to (1R,5S)-tert-butyl 1-(4-(6-amino-5-(((1r,4R)-4-hydroxycyclohexyl)carbamoyl)pyridin-3-yl)phenyl)-3-azabicyclo[3.1.0]hexane-3-carboxylate (Intermediate 1 b) except 2-amino-5-(4-((1R,5S)-3-(2-morpholinoethyl)-3-azabicyclo[3.1.0]hexan-1-yl)phenyl)nicotinic acid (Intermediate 15a) was used in place of 2-amino-5-(4-((1R,5S)-3-(tert-butoxycarbonyl)-3-azabicyclo[3.1.0]hexan-1-yl)phenyl)nicotinic acid (Intermediate 1c), and 4-aminobicyclo[2.2.2]octan-1-ol hydrochloride was used in place of trans-4-aminocyclohexanol. The crude product was purified first by prepHPLC (Method 1a) then by reversed-phase flash chromatography (Method 3a) to give the title compound as a colorless solid. 1H NMR (400 MHz, DMSO-d6) δ 8.34 (d, 1H), 7.98 (d, 1H), 7.79 (s, 1H), 7.56 (d, 2H), 7.21 (d, 2H), 6.92 (s, 2H), 4.31 (s, 1H), 3.58-3.56 (m, 4H), 3.09 (d, 1H), 2.64-2.62 (m, 2H), 2.59-2.41 (m, 9H), 2.07-2.04 (m, 6H), 1.82-1.79 (m, 1H), 1.65-1.61 (m, 6H), 1.31 (t, 1H), 0.75 (dd, 1H). (UPLC-MS) $t_R$ 0.53 min; ESI-MS 532 [M+H]$^+$.

Intermediate 15a: 2-amino-5-(4-((1R,5S)-3-(2-morpholinoethyl)-3-azabicyclo[3.1.0]hexan-1-yl)phenyl)nicotinic acid The title compound was prepared in an analogous manner to 2-amino-5-(4-((1R,5S)-3-(tert-butoxycarbonyl)-3-azabicyclo[3.1.0]hexan-1-yl)phenyl)nicotinic acid (Intermediate 2c) except methyl 2-amino-5-(4-((1R,5S)-3-(2-morpholinoethyl)-3-azabicyclo[3.1.0]hexan-1-yl)phenyl)nicotinate (Intermediate 15b) was used in place of (1R,5S)-tert-butyl 1-(4-(6-amino-5-(methoxycarbonyl)pyridin-3-yl)phenyl)-3-azabicyclo[3.1.0]hexane-3-carboxylate (Intermediate 1d). (UPLC-MS) $t_R$ 0.39 min; ESI-MS 409 [M+H]$^+$.

Intermediate 15b: methyl 2-amino-5-(4-((1R,5S)-3-(2-morpholinoethyl)-3-azabicyclo[3.1.0]hexan-1-yl)phenyl)nicotinate The title compound was prepared in an analogous manner to methyl 2-amino-5-(4-((1S,5R)-3-(2-methoxyethyl)-3-azabicyclo[3.1.0]hexan-1-yl)phenyl)nicotinate (Intermediate 7b) except methyl 5-(4-((1R,5S)-3-azabicyclo[3.1.0]hexan-1-yl)phenyl)-2-aminonicotinate hydrochloride (Intermediate 14c) was used in place of methyl 5-(4-((1S,5R)-3-azabicyclo[3.1.0]hexan-1-yl)phenyl)-2-aminonicotinate hydrochloride (Intermediate 7c), and 4-(2-bromoethyl)morpholine was used in place of 1-bromo-2-methoxyethane. (UPLC-MS) $t_R$ 0.62 min; ESI-MS 423 [M+H]$^+$.

Example 16: 2-amino-N-(3-(hydroxymethyl)bicyclo[1.1.1]pentan-1-yl)-5-(4-((1S,5R)-3-isopropyl-3-azabicyclo[3.1.0]hexan-1-yl)phenyl)nicotinamide

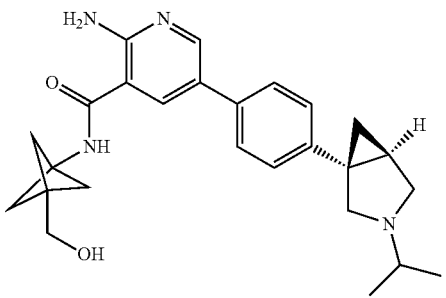 [SMILES: CC(C)N1C[C@@H]2C[C@]2(c2ccc(-c3cnc(N)c(C(=O)NC45CC(CO)(C4)C5)c3)cc2)C1]

The title compound was prepared in an analogous manner to 2-amino-N-((1r,4R)-4-hydroxycyclohexyl)-5-(4-((1R,5S)-3-isopropyl-3-azabicyclo[3.1.0]hexan-1-yl)phenyl)nicotinamide (Example 2) except 2-amino-5-(4-((1S,5R)-3-isopropyl-3-azabicyclo[3.1.0]hexan-1-yl)phenyl)nicotinic acid (Intermediate 9a) was used instead of 2-amino-5-(4-((1R,5S)-3-isopropyl-3-azabicyclo[3.1.0]hexan-1-yl)phenyl)nicotinic acid TFA salt (Intermediate 2a), and (3-aminobicyclo[1.1.1]pentan-1-yl)methanol (Intermediate 16a) was used in place of trans-4-aminocyclohexanol hydrochloride. 1H NMR (400 MHz, DMSO-d6) δ 9.05 (s, 1H), 8.41 (d, 1H), 8.18 (d, 1H), 7.61 (d, 2H), 7.48 (dd, 1H), 7.33-7.17 (m, 4H), 4.55 (t, 1H), 3.51 (d, 3H), 3.31 (s, 2H), 3.08 (s, 2H), 2.07-1.99 (m, 1H), 1.41-1.22 (m, 3H), 1.17-0.98 (m, 9H), 0.79 (d, 1H). (UPLC-MS) $t_R$ 0.54 min; ESI-MS 433 [M+H]$^+$.

Intermediate 16a: (3-aminobicyclo[1.1.1]pentan-1-yl)methanol

To a solution of methyl 3-aminobicyclo[1.1.1]pentane-1-carboxylate HCl salt (218 mg, 1.23 mmol) in THF (7 mL) was added LiAlH$_4$ (140 mg, 3.68 mmol) in small portions at 0° C. The reaction mixture was stirred at RT for 2 h and quenched at 0° C. with a mixture of THF and water, then filtered through a pad of celite, and concentrated under reduced pressure to give the title compound as a yellow oil that was used without further purification. FIA-MS 114 [M+H]$^+$.

Example 17: 2-amino-N-((1r,4S)-4-hydroxycyclohexyl)-5-(4-((1S,5R)-3-(3,3,3-trifluoropropyl)-3-azabicyclo[3.1.0]hexan-1-yl)phenyl)nicotinamide

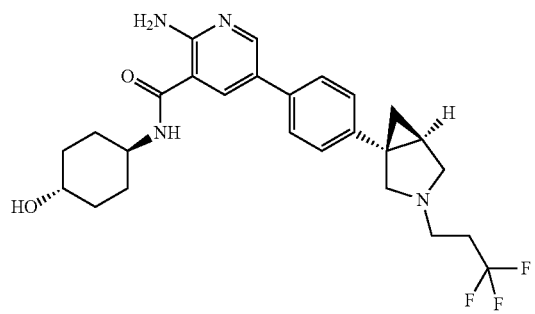 [SMILES: Nc1ncc(-c2ccc([C@]34C[C@H]3CN(CCC(F)(F)F)C4)cc2)cc1C(=O)N[C@H]1CC[C@H](O)CC1]

The title compound was prepared in an analogous manner to 2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide (Example 5) except 3,3,3-trifluoropropyl trifluoromethanesulfonate was used instead of 4-(3-bromopropyl)morpholine, and the reaction mixture was stirred at RT for 60 min. 1H NMR (400 MHz, DMSO-d6) δ 8.39 (d, 1H), 8.31 (d, 1H), 8.12 (d, 1H), 7.60 (d, 2H), 7.23 (d, 2H), 7.12 (s, 2H), 4.59 (d, 1H), 3.79-3.66 (m, 1H), 3.39 (m, 3H), 3.09 (s, 1H), 2.72-2.59 (m, 4H), 1.86 (m, 5H), 1.52-1.18 (m, 6H), 0.79 (s, 1H). (UPLC-MS) $t_R$ 0.59 min; ESI-MS 489 [M+H]$^+$.

Example 18: 2-amino-N-((1r,4r)-4-hydroxycyclohexyl)-5-(4-(pyrrolidin-3-yl)phenyl)nicotinamide

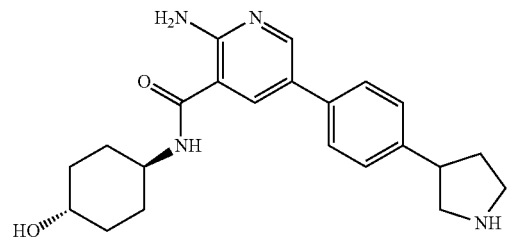 [SMILES: Nc1ncc(-c2ccc(C3CCNC3)cc2)cc1C(=O)N[C@H]1CC[C@H](O)CC1]

To a solution of tert-butyl 3-(4-(6-amino-5-(((1r,4r)-4-hydroxycyclohexyl)carbamoyl)pyridin-3-yl)phenyl)pyrrolidine-1-carboxylate (Intermediate 18a, 120 mg, 0.140 mmol) in dioxane (3 mL) was added 4N HCl in dioxane (0.210 mL, 0.839 mmol) under a nitrogen atmosphere at RT and the resulting mixture was stirred for 4 h. After concentration under reduced pressure the crude product was purified by reversed-phase chromatography (Method 3a). Pure fractions were partitioned between a sat. aq. solution of NaHCO$_3$ and EtOAc. The combined organic layers were washed with brine, dried over MgSO$_4$, filtered and concentrated under reduced pressure to give the title compound as a mixture of diastereomers. 1H NMR (400 MHz, DMSO-d6) δ 8.26 (d, 1H), 8.09 (d, 1H), 7.57 (d, 2H), 7.35-7.29 (m, 2H), 7.09 (s, 2H), 4.55 (d, 1H), 3.77-3.69 (m, 2H), 3.22-3.15 (m, 2H), 3.12-2.91 (m, 2H), 2.74-2.62 (m, 2H), 2.24-2.07 (m, 1H), 1.83 (dd, 4H), 1.42-1.16 (m, 5H). (UPLC-MS) $t_R$ 0.42 min; ESI-MS 381 [M+H]+.

Intermediate 18a: tert-butyl 3-(4-(6-amino-5-(((1r,4r)-4-hydroxycyclohexyl)carbamoyl)pyridin-3-yl)phenyl)pyrrolidine-1-carboxylate The title compound was prepared in an analogous manner to 2-amino-5-(2-fluoro-4-(4-isopropylpiperazin-1-yl)phenyl)-N-((1r,4r)-4-hydroxycyclohexyl)nicotinamide (Example 8) except tert-butyl 3-(4-(4,4,5,5-tetramethyl-1,3,2-dioxaborolan-2-yl)phenyl)pyrrolidine-1-carboxylate (Intermediate 18b) was used in place of 1-(3-fluoro-4-(4,4,5,5-tetramethyl-1,3,2-dioxaborolan-2-yl)phenyl)-4-isopropylpiperazine (Intermediate 8a). (UPLC-MS) $t_R$ 0.95 min; ESI-MS 481 [M+H]+.

Intermediate 18b: tert-butyl 3-(4-(4,4,5,5-tetramethyl-1,3,2-dioxaborolan-2-yl)phenyl)pyrrolidine-1-carboxylate The title compound was prepared in an analogous manner to 1-(3-fluoro-4-(4,4,5,5-tetramethyl-1,3,2-dioxaborolan-2-yl)phenyl)-4-isopropylpiperazine (Intermediate 8a) except tert-butyl 3-(4-bromophenyl)pyrrolidine-1-carboxylate (Intermediate 18c) was used in place of 1-(4-bromo-3-fluorophenyl)-4-isopropylpiperazine (Intermediate 8b). (UPLC-MS) $t_R$ 1.43 min; ESI-MS 374 [M+H]+.

Intermediate 18c: tert-butyl 3-(4-bromophenyl)pyrrolidine-1-carboxylate

To a solution of 3-(4-bromophenyl)pyrrolidine (200 mg, 0.885 mmol) in DCM (7 mL) was added di-tert-butyl dicarbonate (0.308 mL, 1.327 mmol) and TEA (0.247 mL, 1.769 mmol) under a nitrogen atmosphere at RT. The reaction mixture was stirred for 2 h. The reaction mixture was then diluted with a sat. aq. solution of NaHCO3 and mixed with DCM. After phase separation, the aq. layer was extracted again with DCM. The combined organic layers were washed with brine, dried over MgSO4, filtered and concentrated under reduced pressure to give the title compound as a colorless oil which was used without further purification. (UPLC-MS) $t_R$ 1.33 min; ESI-MS 270 [M+H]+.

Example 19: 2-amino-N-((1r,4R)-4-hydroxycyclohexyl)-5-(4-((1R,5S)-3-(tetrahydro-2H-pyran-4-yl)-3-azabicyclo[3.1.0]hexan-1-yl)phenyl)nicotinamide

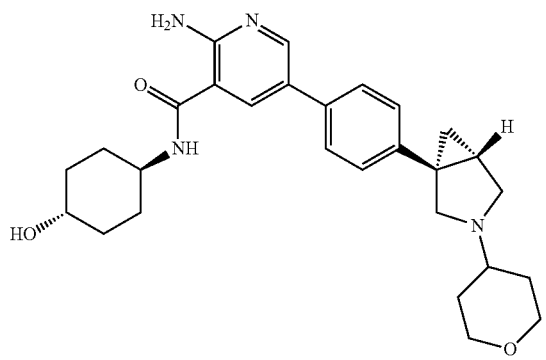 [SMILES: Nc1ncc(-c2ccc([C@@]34C[C@@H]3CN(C3CCOCC3)C4)cc2)cc1C(=O)N[C@H]1CC[C@H](O)CC1]

The title compound was prepared in an analogous manner to 2-amino-N-((1r,4R)-4-hydroxycyclohexyl)-5-(4-((1R,5S)-3-(1-(methylsulfonyl)piperidin-4-yl)-3-azabicyclo[3.1.0]hexan-1-yl)phenyl)nicotinamide (Example 1) except dihydro-2H-pyran-4(3H)-one was used instead of 1-(methylsulfonyl)piperidin-4-one. 1H NMR (400 MHz, DMSO-d6) δ 8.39 (s, 1H), 8.31 (d, 1H), 8.12 (d, 1H), 7.62 (dd, 2H), 7.25 (s, 2H), 7.12 (s, 2H), 4.59 (d, 1H), 3.97-3.63 (m, 4H), 3.40 (m, 2H), 3.31 (m, 2H), 3.19-3.03 (m, 2H), 1.99-1.65 (m, 8H), 1.51-1.16 (m, 8H). (UPLC-MS) $t_R$ 0.48 min; ESI-MS 477 [M+H]+.

Example 20: 2-amino-N-((1r,4S)-4-hydroxycyclohexyl)-5-(4-((1S,5R)-3-(2-methoxyethyl)-3-azabicyclo[3.1.0]hexan-1-yl)phenyl)nicotinamide

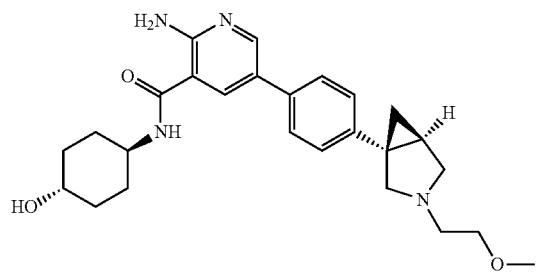 [SMILES: COCCN1C[C@@H]2C[C@]2(c2ccc(-c3cnc(N)c(C(=O)N[C@H]4CC[C@H](O)CC4)c3)cc2)C1]

The title compound was prepared in an analogous manner to 2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide (Example 5) except 1-bromo-2-methoxyethane was used instead of 4-(3-bromopropyl)morpholine, and the reaction mixture was stirred at 60° C. for 4 h. 1H NMR (400 MHz, DMSO-d6) δ 8.38 (s, 1H), 8.11 (s, 1H), 7.59 (d, 2H), 7.22 (d, 2H), 7.13 (s, 2H), 4.60 (d, 1H), 3.73 (d, 1H), 3.54-3.36 (m, 4H), 3.27 (s, 3H), 2.64 (m, 4H), 1.87 (m, 6H), 1.40-1.27 (m, 6H), 0.76 (s, 1H). (UPLC-MS) $t_R$ 0.49 min; ESI-MS 451 [M+H]+.

Example 21: 2-amino-N-((1R,3S,4R)-3-fluoro-4-hydroxycyclohexyl)-5-(4-((1R,5S)-3-(tetrahydro-2H-pyran-4-yl)-3-azabicyclo[3.1.0]hexan-1-yl)phenyl)nicotinamide

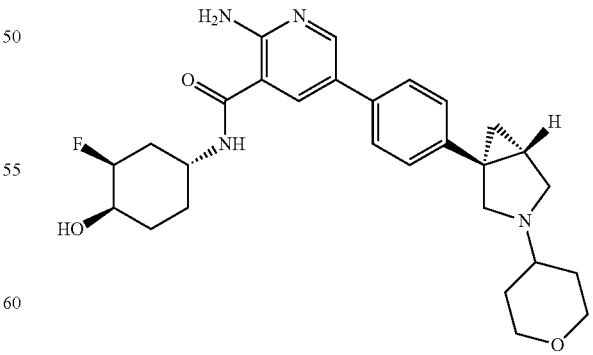

The title compound was prepared in an analogous manner to (1R,5S)-tert-butyl 1-(4-(6-amino-5-(((1r,4R)-4-hydroxycyclohexyl)carbamoyl)pyridin-3-yl)phenyl)-3-azabicyclo[3.1.0]hexane-3-carboxylate (Intermediate 1 b) except 2-amino-5-(4-((1R,5S)-3-(tetrahydro-2H-pyran-4-yl)-3-azabicyclo[3.1.0]hexan-1-yl)phenyl)nicotinic acid (Intermediate 14a) was used in place of 2-amino-5-(4-((1R,5S)-3-(tert-butoxycarbonyl)-3-azabicyclo[3.1.0]hexan-1-yl)phenyl)nicotinic acid (Intermediate 1c), and (1R,2S,4R)-4-amino-2-fluorocyclohexanol hydrochloride (Intermediate 21a) was used in place of trans-4-aminocyclohexanol. The crude product was purified by prepHPLC (Method 1a) to give the title compound as a TFA salt. 1H NMR (400 MHz, DMSO-d6) δ 9.60 (bs, 1H), 8.42 (s, 1H), 8.35 (d, 1H), 8.12 (s, 1H), 7.64 (bs, 2H), 7.36 (bs, 2H), 7.14 (s, 2H), 4.94 (t, 1H), 4.80 (d, 1H), 4.16-3.82 (m, 4H), 3.81-3.45 (m, 4H), 3.30-3.25 (m, 4H), 2.15 (bs, 1H), 1.88-1.85 (m, 2H), 1.65-1.59 (m, 5H), 1.76-1.27 (m, 3H), 1.18 (bs, 1H). (UPLC-MS) $t_R$ 0.48 min; ESI-MS 495 [M+H]$^+$.

Intermediate 21a: (1R,2S,4R)-4-amino-2-fluorocyclohexanol hydrochloride

To a solution of benzyl ((1R,3S,4R)-3-fluoro-4-hydroxycyclohexyl)carbamate (Intermediate 21b, 376 mg, 1.41 mmol) in EtOH (20 mL) was added palladium on charcoal (10%) (80 mg, 0.075 mmol) under a nitrogen atmosphere. The reaction vessel was purged three times with nitrogen, then purged twice with hydrogen. After stirring at RT for 17 h, the reaction mixture was passed through a pad of celite and the filter cake was washed with EtOH to afford a colorless solution. Hydrochloric acid (1.25M in EtOH, 14 mL, 17.5 mmol) was slowly added and the mixture was stirred at RT for 5 h. Concentration under reduced pressure yielded the title compound as an off-white hygroscopic solid. FIA ESI-MS 134 [M+H]$^+$.

Intermediate 21 b: benzyl ((1R,3S,4R)-3-fluoro-4-hydroxycyclohexyl)carbamate To a solution of benzyl ((1R,3S)-3-fluoro-4-oxocyclohexyl)carbamate (Intermediate 21c, 768 mg, 2.90 mmol) in MeOH (15 mL) was added portionwise NaBH$_4$ (274 mg, 7.24 mmol) at 0° C. After stirring for 30 min at 0° C. the reaction mixture was diluted with a sat. aq. NH$_4$Cl solution and allowed to reach RT. The solvent was removed under reduced pressure, and DCM and water were added. After phase separation the aq. layer was extracted three times with DCM. The combined organic layers were washed with brine, dried over anhydrous MgSO$_4$, filtered and concentrated under reduced pressure to afford a white solid. The crude product was purified by normal-phase chromatography (Method 2b) to give the title compound as a colorless solid. (UPLC-MS) $t_R$ 0.76 min; ESI-MS 268 [M+H]$^+$. The absolute configuration as depicted was confirmed by X-ray crystallography.

Intermediate 21c: benzyl ((1R,3S)-3-fluoro-4-oxocyclohexyl)carbamate

To a solution of benzyl ((1R,3S,4S)-3-fluoro-4-hydroxycyclohexyl)carbamate (Intermediate 21d, 710 mg, 2.66 mmol) in DCM (26 mL) was added pyridinium chlorochromate (859 mg, 3.98 mmol). The reaction mixture was stirred for 6 h at RT. Another portion of pyridinium chlorochromate (573 mg, 2.66 mmol) was added and the reaction mixture was stirred for another 18 h. After addition of DCM and a sat. aq. NaHCO$_3$ solution, both phases were separated, the aq. layer was extracted twice with DCM, and the combined organic layers were washed with brine, dried over anhydrous MgSO$_4$, filtered and concentrated under reduced pressure. The residue was purified by normal-phase chromatography (Method 2b) to give the title compound as a colorless oil. (UPLC-MS) $t_R$ 0.82 min; ESI-MS 266 [M+H]$^+$.

Intermediate 21d: benzyl ((1R,3S,4S)-3-fluoro-4-hydroxycyclohexyl)carbamate

A vial was charged with benzyl (1R,3R,6S)-7-oxabicyclo[4.1.0]heptan-3-ylcarbamate (Intermediate 21e, 1.50 g, 6.07 mmol) and TEA trihydrofluoride (4.94 mL, 30.3 mmol) was added. The vial was sealed and stirred at 100° C. for 2 h. After cooling, the reaction mixture was slowly poured into a stirred solution of K$_2$CO$_3$ (5.87 g, 42.5 mmol) in water (400 mL) and extracted three times with DCM. The combined organic layers were washed with water and brine, dried over anhydrous MgSO$_4$, filtered and concentrated under reduced pressure. The crude material was purified by normal-phase chromatography (Method 2b) to afford a mixture of regioisomers, which was resolved by preparative chiral HPLC (column: ChiralPak AD, 20 µm, 50×5 cm, flow rate: 90 mL/min, detection wavelength: 220 nm, mobile phase: n-heptane:EtOH 90:10 until t=52 min, 85:15 until t=69 min, then 80:20). The title compound was isolated as a colorless oil and characterized by UPLC-MS (SQ13, column: Acquity HSS T3 1.8 µm 2.1×50 mm at 60° C., eluent A: water+0.05% formic acid+3.75 mM NH$_4$OAc, eluent B: acetonitrile+0.04% formic acid, gradient: from 5 to 98% B in 1.4 min, flow 1.0 mL/min, $t_R$ 0.81 min; ESI-MS 268 [M+H]$^+$).

Intermediate 21e: (1R,3R,6S)-7-oxabicyclo[4.1.0]heptan-3-ylcarbamate syn-Benzyl (7-oxabicyclo[4.1.0]heptan-3-yl)carbamate (prepared as described by Gómez-Sánchez et al, Tetrahedron 2005, 61(5), 1207-1219) was resolved by preparative chiral HPLC (column: ChiralPak AY, 10 um, 25×5 cm, flow rate: 30 mL/min, detection wavelength: 214 nm, mobile phase: n-heptane:isopropanol 80:20). The title compound was isolated as a colorless oil and characterized by chiral HPLC (ChiralPak AY-H, 5 um, 15×0.46 cm, flow rate: 1 mL/min, detection wavelength: 214 nm, mobile phase: hexane:isopropanol 70:30, $t_R$ 2.24 min, 99.2% ee). (UPLC-MS) $t_R$ 0.90 min; ESI-MS 248 [M+H]$^+$.

Example 22: 2-amino-N-((1s,4S)-4-hydroxycyclohexyl)-5-(4-((1R,5S)-3-(tetrahydro-2H-pyran-4-yl)-3-azabicyclo[3.1.0]hexan-1-yl)phenyl)nicotinamide

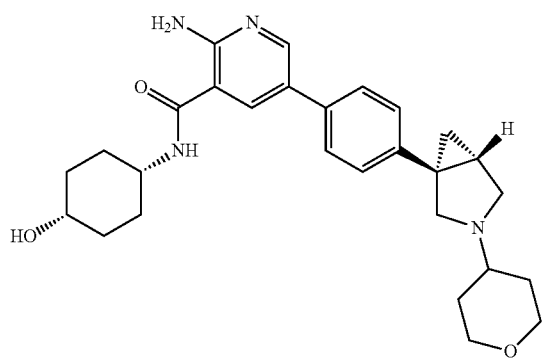 [SMILES: Nc1ncc(-c2ccc([C@@]34C[C@@H]3CN(C3CCOCC3)C4)cc2)cc1C(=O)N[C@H]1CC[C@@H](O)CC1]

The title compound was prepared in an analogous manner to (1R,5S)-tert-butyl 1-(4-(6-amino-5-(((1r,4R)-4-hydroxycyclohexyl)carbamoyl)pyridin-3-yl)phenyl)-3-azabicyclo[3.1.0]hexane-3-carboxylate (Intermediate 1b) except 2-amino-5-(4-((1R,5S)-3-(tetrahydro-2H-pyran-4-yl)-3-azabicyclo[3.1.0]hexan-1-yl)phenyl)nicotinic acid (Intermediate 14a) was used in place of 2-amino-5-(4-((1R,5S)-3-(tert-butoxycarbonyl)-3-azabicyclo[3.1.0]hexan-1-yl)phenyl)nicotinic acid (Intermediate 1c), and cis-4-aminocyclohexanol was used in place of trans-4-aminocyclohexanol. The crude product was purified by prepHPLC (Method 1a) to give the title compound as a TFA salt. 1H NMR (400 MHz, DMSO-d6) δ 9.50 (bs, 1H), 8.41-8.33 (m, 2H), 8.17 (d, 1H), 7.62 (bs, 2H), 7.26 (bs, 2H), 7.14 (s, 1H), 4.42 (d, 1H), 4.05-3.79 (m, 5H), 3.34-3.24 (m, 4H), 3.11 (bs, 1H), 2.70-2.50 (m, 1H), 1.83-1.71 (m, 7H), 1.62-1.47 (m, 7H), 1.35-1.29 (m, 1H). (UPLC-MS) $t_R$ 0.52 min; ESI-MS 477 [M+H]$^+$.

Example 23: 5-(4-(2-azaspiro[3.3]heptan-2-ylmethyl)phenyl)-2-amino-N-((1r,4r)-4-hydroxycyclohexyl)nicotinamide

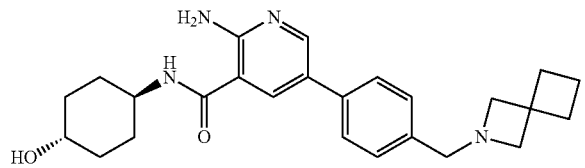 [SMILES: Nc1ncc(-c2ccc(CN3CC4(CCC4)C3)cc2)cc1C(=O)N[C@H]1CC[C@H](O)CC1]

The title compound was prepared in an analogous manner to 2-amino-5-(2-fluoro-4-(4-isopropylpiperazin-1-yl)phenyl)-N-((1r,4r)-4-hydroxycyclohexyl)nicotinamide (Example 8) except 2-(4-(4,4,5,5-tetramethyl-1,3,2-dioxaborolan-2-yl)benzyl)-2-azaspiro[3.3]heptane (Intermediate 23a) was used in place of 1-(3-fluoro-4-(4,4,5,5-tetramethyl-1,3,2-dioxaborolan-2-yl)phenyl)-4-isopropylpiperazine (Intermediate 8a). 1H NMR (400 MHz, DMSO-d6) δ 8.40 (d, 1H), 8.30 (d, 1H), 8.14 (d, 1H), 7.61 (d, 2H), 7.33 (d, 2H), 7.14 (s, 2H), 4.58 (d, 1H), 3.79-3.66 (m, 1H), 3.55 (s, 2H), 3.41 (dt, 1H), 3.14 (s, 3H), 2.07 (t, 4H), 1.94-1.72 (m, 6H), 1.47-1.20 (m, 5H) (UPLC-MS) $t_R$ 0.51 min; ESI-MS 421 [M+H]$^+$.

Intermediate 23a: 2-(4-(4,4,5,5-tetramethyl-1,3,2-dioxaborolan-2-yl)benzyl)-2-azaspiro[3.3]heptane To a solution of 2-(4-(bromomethyl)phenyl)-4,4,5,5-tetramethyl-1,3,2-dioxaborolane (300 mg, 1.01 mmol) in acetonitrile (8 mL) was added 2-azaspiro[3.3]heptane (148 mg, 1.11 mmol) and cesium carbonate (428 mg, 1.31 mmol) under a nitrogen atmosphere at RT. The reaction mixture was stirred for 60 min, then diluted with a sat. aq. solution of NaHCO$_3$ and EtOAc. After phase separation, the aq. layer was extracted with EtOAc and the combined organic layers were washed with brine, dried over MgSO$_4$, filtered and concentrated under reduced pressure to give the title compound which was used without further purification (UPLC-MS) $t_R$ 0.82 min; ESI-MS 314 [M+H]$^+$.

Example 24: 2-amino-N-((1r,4R)-4-hydroxy-4-methylcyclohexyl)-5-(4-((1R,5S)-3-isopropyl-3-azabicyclo[3.1.0]hexan-1-yl)phenyl)nicotinamide

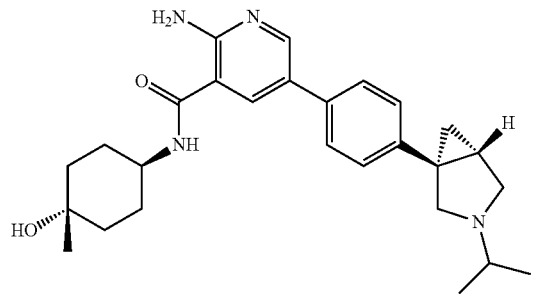 [SMILES: CC(C)N1C[C@H]2C[C@@]2(c2ccc(-c3cnc(N)c(C(=O)N[C@H]4CC[C@](C)(O)CC4)c3)cc2)C1]

The title compound was prepared in an analogous manner to 2-amino-N-((1r,4R)-4-hydroxycyclohexyl)-5-(4-((1R,5S)-3-isopropyl-3-azabicyclo[3.1.0]hexan-1-yl)phenyl)nicotinamide (Example 2) except trans-4-amino-1-methylcyclohexanol was used in place of trans-4-aminocyclohexanol hydrochloride. 1H NMR (400 MHz, DMSO-d6) δ 8.43 (d, 1H), 8.34 (d, 1H), 8.16 (d, 1H), 7.68 (d, 2H), 7.39 (d, 2H), 4.06 (dd, 1H), 3.86-3.41 (m, 9H), 2.26 (dt, 1H), 1.78 (d, 2H), 1.68-1.55 (m, 2H), 1.47 (t, 4H), 1.33 (dd, 6H), 1.18 (s, 4H). (UPLC-MS) $t_R$ 0.53 min; ESI-MS 449 [M+H]$^+$.

Example 25: 2-amino-5-(4-((1R,5S)-3-(4,4-difluorocyclohexyl)-3-azabicyclo[3.1.0]hexan-1-yl)phenyl)-N-((1r,4R)-4-hydroxycyclohexyl)nicotinamide

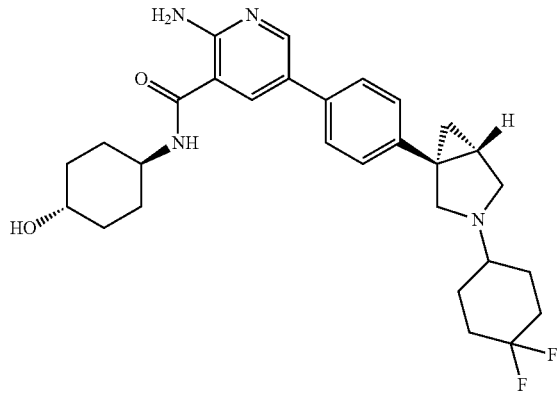 [SMILES: Nc1ncc(-c2ccc([C@@]34C[C@@H]3CN(C3CCC(F)(F)CC3)C4)cc2)cc1C(=O)N[C@H]1CC[C@H](O)CC1]

The title compound was prepared in an analogous manner to 2-amino-N-((1r,4R)-4-hydroxycyclohexyl)-5-(4-((1R,5S)-3-(1-(methylsulfonyl)piperidin-4-yl)-3-azabicyclo[3.1.0]hexan-1-yl)phenyl)nicotinamide (Example 1) except 4,4-difluorocyclohexanone was used instead of 1-(methylsulfonyl)piperidin-4-one. 1H NMR (400 MHz, DMSO-d6) δ 8.38 (d, 1H), 8.32 (d, 1H), 8.11 (d, 1H), 7.59 (d, 2H), 7.23 (d, 2H), 7.13 (s, 2H), 4.59 (d, 1H), 3.73 (d, 1H), 3.39 (d, 2H), 3.09 (d, 1H), 2.68-2.55 (m, 2H), 2.37 (d, 2H), 2.00 (s, 2H), 1.84 (d, 8H), 1.64 (d, 2H), 1.46-1.16 (m, 5H), 0.78 (s, 1H). (UPLC-MS) $t_R$ 0.56 min; ESI-MS 511 [M+H]$^+$.

Example 26: 2-amino-N-((1r,4S)-4-hydroxycyclohexyl)-5-(4-((1S,5R)-3-(oxetan-3-yl)-3-azabicyclo[3.1.0]hexan-1-yl)phenyl)nicotinamide

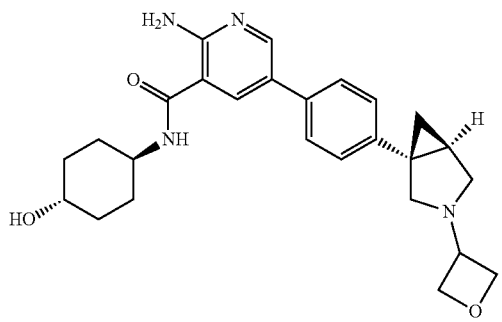 [SMILES: Nc1ncc(-c2ccc([C@]34C[C@H]3CN(C3COC3)C4)cc2)cc1C(=O)N[C@H]1CC[C@H](O)CC1]

To a solution of 5-(4-((1S,5R)-3-azabicyclo[3.1.0]hexan-1-yl)phenyl)-2-amino-N-((1r,4S)-4-hydroxycyclohexyl)nicotinamide TFA salt (Intermediate 5a, 70 mg, 0.138 mmol) in DCM (4 mL) was added oxetan-3-one (12.0 mg, 0.166 mmol) and AcOH (0.012 mL, 0.207 mmol) under a nitrogen atmosphere at RT. The reaction mixture was stirred at 45° C. for 30 min. Sodium triacetoxyborohydride (58.6 mg, 0.276 mmol) was added at RT and the reaction mixture was stirred at 45° C. for 3 h. The reaction mixture was then diluted with a sat. aq. solution of NaHCO$_3$ and mixed with EtOAc. After phase separation, the aq. layer was extracted again with EtOAc. The combined organic layers were washed with brine, dried over MgSO$_4$, filtered and concentrated under reduced pressure. The crude product was purified first by prepHPLC (Method 1a) then by reversed-phase flash chromatography (Method 3a) to give the title compound as a colorless solid. (UPLC-MS) $t_R$ 0.48 min; ESI-MS 449 [M+H]$^+$.

Example 27: 2-amino-5-(4-((1S,5R)-3-(4,4-difluorocyclohexyl)-3-azabicyclo[3.1.0]hexan-1-yl)phenyl)-N-((1r,4S)-4-hydroxycyclohexyl)nicotinamide

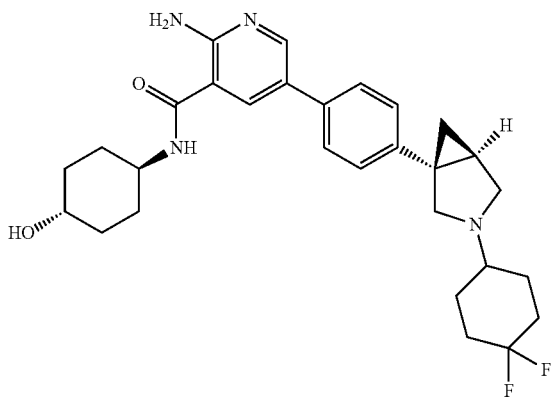 [SMILES: Nc1ncc(-c2ccc([C@]34C[C@H]3CN(C3CCC(F)(F)CC3)C4)cc2)cc1C(=O)N[C@H]1CC[C@H](O)CC1]

The title compound was prepared in an analogous manner to 2-amino-N-((1r,4S)-4-hydroxycyclohexyl)-5-(4-((1S,5R)-3-(oxetan-3-yl)-3-azabicyclo[3.1.0]hexan-1-yl)phenyl)nicotinamide (Example 26) except 4,4-difluorocyclohexanone was used instead of oxetan-3-one. After purification the title compound was obtained as a TFA salt. 1H NMR (400 MHz, DMSO-d6) δ 9.50 (bs, 1H), 8.38 (d, 1H), 8.32 (d, 1H), 8.11 (d, 1H), 7.59 (d, 2H), 7.23 (d, 2H), 7.13 (s, 2H), 4.59 (d, 1H), 4.12 (bs, 1H), 3.73 (d, 1H), 3.39 (d, 2H), 3.09 (d, 1H), 2.68-2.55 (m, 2H), 2.37 (d, 2H), 2.00 (s, 2H), 1.84 (d, 8H), 1.64 (d, 2H), 1.46-1.16 (m, 5H). (UPLC-MS) $t_R$ 0.56 min; ESI-MS 511 [M+H]$^+$.

Example 28: 2-amino-N-(3-(hydroxymethyl)bicyclo[1.1.1]pentan-1-yl)-5-(4-((1S,5R)-3-(tetrahydro-2H-pyran-4-yl)-3-azabicyclo[3.1.0]hexan-1-yl)phenyl)nicotinamide

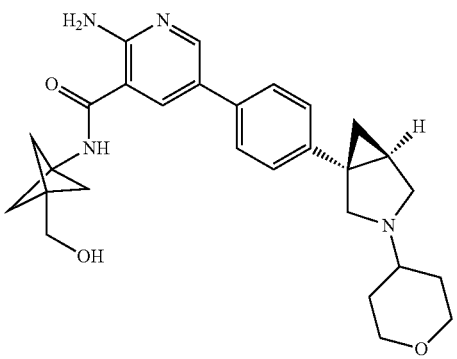 [SMILES: Nc1ncc(-c2ccc([C@]34C[C@H]3CN(C3CCOCC3)C4)cc2)cc1C(=O)NC12CC(CO)(C1)C2]

The title compound was prepared in an analogous manner to (1R,5S)-tert-butyl 1-(4-(6-amino-5-(((1r,4R)-4-hydroxycyclohexyl)carbamoyl)pyridin-3-yl)phenyl)-3-azabicyclo[3.1.0]hexane-3-carboxylate (Intermediate 1b) except 2-amino-5-(4-((1S,5R)-3-(tetrahydro-2H-pyran-4-yl)-3-azabicyclo[3.1.0]hexan-1-yl)phenyl)nicotinic acid (Intermediate 28a) was used in place of 2-amino-5-(4-((1R,5S)-3-(tert-butoxycarbonyl)-3-azabicyclo[3.1.0]hexan-1-yl)phenyl)nicotinic acid (Intermediate 1c), and (3-aminobicyclo[1.1.1]pentan-1-yl)methanol (Intermediate 16a) was used in place of trans-4-aminocyclohexanol. The crude product was purified first by prepHPLC (Method 1a) then by reversed-phase flash chromatography (Method 3a) to give the title compound as a colorless solid. 1H NMR (400 MHz, DMSO-d6) δ 9.35 (bs, 1H), 9.06 (s, 1H), 8.44 (s, 1H), 8.19 (s, 1H), 7.68 (d, 2H), 7.37 (d, 2H), 7.26 (bs, 2H), 4.57 (t, 1H), 4.12 (d, 1H), 3.97 (bs, 1H), 3.80-3.56 (m, 2H), 3.51 (d, 2H), 3.35-3.20 (m, 6H), 2.29-2.23 (m, 1H), 2.11-2.05 (m, 1H), 1.99 (bs, 1H), 1.97 (s, 6H), 1.67-1.61 (m, 1H), 1.19-1.14 (bs, 1H). (UPLC-MS) $t_R$ 0.50 min; ESI-MS 475 [M+H]$^+$.

Intermediate 28a: 2-amino-5-(4-((1S,5R)-3-(tetrahydro-2H-pyran-4-yl)-3-azabicyclo[3.1.0]hexan-1-yl)phenyl)nicotinic acid The title compound was prepared in an analogous manner to 2-amino-5-(4-((1R,5S)-3-(tert-butoxycarbonyl)-3-azabicyclo[3.1.0]hexan-1-yl)phenyl)nicotinic acid (Intermediate 2c) except methyl 2-amino-5-(4-((1S,5R)-3-(tetrahydro-2H-pyran-4-yl)-3-azabicyclo[3.1.0]hexan-1-yl)phenyl) nicotinate (Intermediate 28b) was used in place of (1R,5S)-tert-butyl 1-(4-(6-amino-5-(methoxycarbonyl)pyridin-3-yl)phenyl)-3-azabicyclo[3.1.0]hexane-3-carboxylate (Intermediate 1d). (UPLC-MS) $t_R$ 0.37 min; ESI-MS 380 [M+H]$^+$.

Intermediate 28b: methyl 2-amino-5-(4-((1S,5R)-3-(tetrahydro-2H-pyran-4-yl)-3-azabicyclo[3.1.0]hexan-1-yl)phenyl)nicotinate The title compound was prepared in an analogous manner to methyl 2-amino-5-(4-((1R,5S)-3-(tetrahydro-2H-pyran-4-yl)-3-azabicyclo[3.1.0]hexan-1-yl)phenyl)nicotinate (Intermediate 14b) except methyl 5-(4-((1S,5R)-3-azabicyclo[3.1.0]hexan-1-yl)phenyl)-2-aminonicotinate hydrochloride (Intermediate 7c) was used in place of methyl 5-(4-((1R,5S)-3-azabicyclo[3.1.0]hexan-1-yl)phenyl)-2-aminonicotinate hydrochloride (Intermediate 14c). (UPLC-MS) $t_R$ 0.62 min; ESI-MS 394 [M+H]$^+$.

Example 29: 2-amino-5-(2-fluoro-4-(piperazin-1-yl)phenyl)-N-((1r,4r)-4-hydroxycyclohexyl)nicotinamide

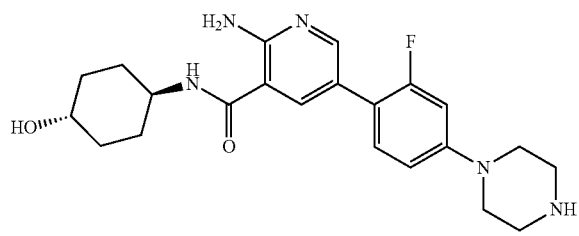 [SMILES: Nc1ncc(-c2ccc(N3CCNCC3)cc2F)cc1C(=O)N[C@H]1CC[C@H](O)CC1]

The title compound was prepared in an analogous manner to 2-amino-N-((1r,4r)-4-hydroxycyclohexyl)-5-(4-(pyrrolidin-3-yl)phenyl)nicotinamide (Example 18) except tert-butyl 4-(4-(6-amino-5-(((1r,4r)-4-hydroxycyclohexyl)carbamoyl)pyridin-3-yl)-3-fluorophenyl)piperazine-1-carboxylate (Intermediate 29a) was used in place of 3-(4-(6-amino-5-(((1r,4r)-4-hydroxycyclohexyl)carbamoyl)pyridin-3-yl)phenyl)pyrrolidine-1-carboxylate (Intermediate 18a). 1H NMR (400 MHz, DMSO-d6) δ 8.29-8.16 (m, 2H), 7.95 (d, 1H), 7.38 (t, 1H), 7.06 (s, 2H), 6.88-6.75 (m, 2H), 4.54 (d, 1H), 3.69 (m, 1H), 3.42-3.32 (m, 2H), 3.17 (dd, 4H), 2.92 (dt, 4H), 1.88-1.73 (m, 4H), 1.43-1.15 (m, 4H). (UPLC-MS) $t_R$ 0.42 min; ESI-MS 414 [M+H]$^+$.

Intermediate 29a: tert-butyl 4-(4-(6-amino-5-(((1r,4r)-4-hydroxycyclohexyl)carbamoyl)pyridin-3-yl)-3-fluorophenyl)piperazine-1-carboxylate The title compound was prepared in an analogous manner to 1-(3-fluoro-4-(4,4,5,5-tetramethyl-1,3,2-dioxaborolan-2-yl)phenyl)-4-isopropylpiperazine (Example 8) except tert-butyl 4-(3-fluoro-4-(4,4,5,5-tetramethyl-1,3,2-dioxaborolan-2-yl)phenyl)piperazine-1-carboxylate (Intermediate 29b) was used in place of 1-(3-fluoro-4-(4,4,5,5-tetramethyl-1,3,2-dioxaborolan-2-yl)phenyl)-4-isopropylpiperazine (Intermediate 8a). The reaction mixture was stirred at 80° C. for 60 min, and purification was done by normal-phase chromatography (Method 2b) to give the title compound as a brownish solid. (UPLC-MS) $t_R$ 0.96 min; ESI-MS 514 [M+H]$^+$.

Intermediate 29b: tert-butyl 4-(3-fluoro-4-(4,4,5,5-tetramethyl-1,3,2-dioxaborolan-2-yl)phenyl)piperazine-1-carboxylate The title compound was prepared in an analogous manner to tert-butyl 4-(3-fluoro-4-(4,4,5,5-tetramethyl-1,3,2-dioxaborolan-2-yl)phenyl)piperazine-1-carboxylate (Intermediate 8a) except tert-butyl 4-(4-bromo-3-fluorophenyl)piperazine-1-carboxylate was used in place of 1-(4-bromo-3-fluorophenyl)piperazine (Intermediate 8b). (UPLC-MS) $t_R$ 1.38 min; ESI-MS 407 [M+H]$^+$.

Example 30: 2-amino-N-(3-(hydroxymethyl)bicyclo[1.1.1]pentan-1-yl)-5-(4-((1R,5S)-3-(tetrahydro-2H-pyran-4-yl)-3-azabicyclo[3.1.0]hexan-1-yl)phenyl)nicotinamide

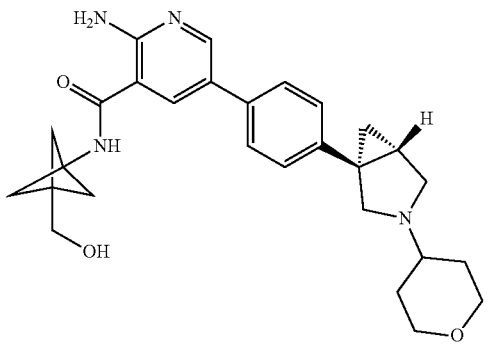 [SMILES: Nc1ncc(-c2ccc([C@@]34C[C@@H]3CN(C3CCOCC3)C4)cc2)cc1C(=O)NC12CC(CO)(C1)C2]

The title compound was prepared in an analogous manner to (1R,5S)-tert-butyl 1-(4-(6-amino-5-(((1r,4R)-4-hydroxycyclohexyl)carbamoyl)pyridin-3-yl)phenyl)-3-azabicyclo[3.1.0]hexane-3-carboxylate (Intermediate 1 b) except 2-amino-5-(4-((1R,5S)-3-(tetrahydro-2H-pyran-4-yl)-3-azabicyclo[3.1.0]hexan-1-yl)phenyl)nicotinic acid (Intermediate 14a) was used in place of 2-amino-5-(4-((1R,5S)-3-(tert-butoxycarbonyl)-3-azabicyclo[3.1.0]hexan-1-yl)phenyl)nicotinic acid (Intermediate 1c), and (3-aminobicyclo[1.1.1]pentan-1-yl)methanol (Intermediate 16a) was used in place of trans-4-aminocyclohexanol. The crude product was purified first by prepHPLC (Method 1a) then by reversed-phase flash chromatography (Method 3a) to give the title compound as a colorless solid. 1H NMR (400 MHz, DMSO-d6) δ 9.05 (s, 1H), 8.41 (d, 1H), 8.18 (d, 1H), 7.61 (d, 2H), 7.24-7.22 (m, 4H), 4.55 (t, 1H), 3.87-3.84 (m, 2H), 3.51 (d, 2H), 3.48-3.25 (m, 2H), 3.10 (bs, 1H), 2.56-2.47 (m, 4H), 1.97 (s, 6H), 1.96-1.74 (m, 3H), 1.39-0.30 (m, 3H), 0.77 (bs, 1H). (UPLC-MS) $t_R$ 0.51 min; ESI-MS 475 [M+H]$^+$.

Example 31: 2-amino-N-((1r,4R)-4-hydroxycyclohexyl)-5-(4-(((R)-2-methylpyrrolidin-1-yl)methyl)phenyl)nicotinamide

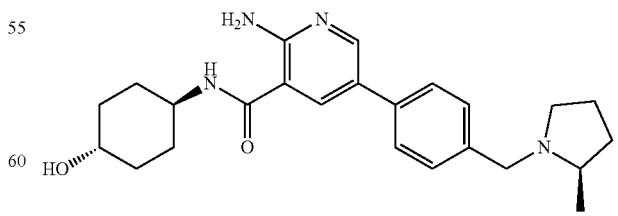

The title compound was prepared in an analogous manner to 2-amino-5-(2-fluoro-4-(4-isopropylpiperazin-1-yl)phenyl)-N-((1r,4r)-4-hydroxycyclohexyl)nicotinamide (Example 8) except (R)-(4-((2-methylpyrrolidin-1-yl)methyl)

phenyl)boronic acid (Intermediate 31a) was used in place of 1-(3-fluoro-4-(4,4,5,5-tetramethyl-1,3,2-dioxaborolan-2-yl)phenyl)-4-isopropylpiperazine (Intermediate 8a). Purification was done by normal-phase chromatography (Method 2b) to give the title compound as a yellow solid. 1H NMR (400 MHz, DMSO-d6) δ 8.75 (d, 1H), 8.65 (d, 1H), 8.48 (d, 1H), 7.81 (dd, 2H), 7.63 (d, 2H), 4.52 (dd, 1H), 4.18 (dd, 1H), 3.69 (ddt, 1H), 3.51-3.31 (m, 2H), 3.25-3.04 (m, 3H), 2.19 (ddt, 1H), 1.82 (td, 6H), 1.64-1.52 (m, 1H), 1.39-1.15 (m, 7H). (UPLC-MS) $t_R$ 0.44 min; ESI-MS 409 [M+H]$^+$.

Intermediate 31a: (R)-(4-((2-methylpyrrolidin-1-yl)methyl)phenyl)boronic acid

To a solution of (4-(bromomethyl)phenyl)boronic acid (125 mg, 0.582 mmol) in acetonitrile (4 mL) was added $K_2CO_3$ (161 mg, 1.164 mmol) and (R)-2-methylpyrrolidine (54.5 mg, 0.640 mmol) under a nitrogen atmosphere at RT. The reaction mixture was stirred for 60 min then filtered through a pad of celite. The filtrate was concentrated under reduced pressure to give the title compound as an off-white solid which was used without further purification. (UPLC-MS) $t_R$ 0.33 min; ESI-MS 220 [M+H]$^+$.

Example 32: 2-amino-N-((1r,4S)-4-hydroxy-4-methylcyclohexyl)-5-(4-((1S,5R)-3-isopropyl-3-azabicyclo[3.1.0]hexan-1-yl)phenyl)nicotinamide

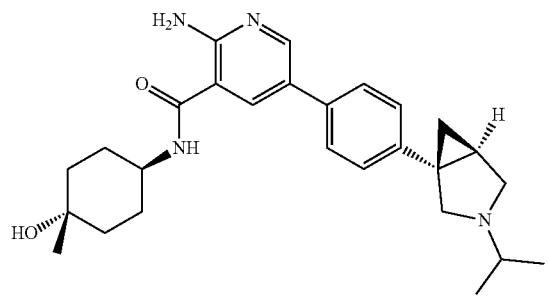 [SMILES: CC(C)N1C[C@@H]2C[C@]2(c2ccc(-c3cnc(N)c(C(=O)N[C@H]4CC[C@](C)(O)CC4)c3)cc2)C1]

The title compound was prepared in an analogous manner to 2-amino-N-((1r,4R)-4-hydroxycyclohexyl)-5-(4-((1R,5S)-3-isopropyl-3-azabicyclo[3.1.0]hexan-1-yl)phenyl)nicotinamide (Example 2) except 2-amino-5-(4-((1S,5R)-3-isopropyl-3-azabicyclo[3.1.0]hexan-1-yl)phenyl)nicotinic acid TFA salt (Intermediate 9a) was used instead of 2-amino-5-(4-((1R,5S)-3-isopropyl-3-azabicyclo[3.1.0]hexan-1-yl)phenyl)nicotinic acid TFA salt (Intermediate 2a), and trans-4-amino-1-methylcyclohexanol was used in place of trans-4-aminocyclohexanol hydrochloride. 1H NMR (400 MHz, DMSO-d6) δ 8.43 (d, 1H), 8.34 (d, 1H), 8.16 (d, 1H), 7.68 (d, 2H), 7.39 (d, 2H), 4.06 (dd, 1H), 3.86-3.41 (m, 9H), 2.26 (dt, 1H), 1.78 (d, 2H), 1.68-1.55 (m, 2H), 1.47 (t, 4H), 1.33 (dd, 6H), 1.18 (s, 4H). (UPLC-MS) $t_R$ 0.50 min; ESI-MS 449 [M+H]$^+$.

Example 33: 2-amino-5-(4-((1S,5R)-3-(4,4-difluorocyclohexyl)-3-azabicyclo[3.1.0]hexan-1-yl)phenyl)-N-((1r,4S)-4-hydroxycyclohexyl)nicotinamide

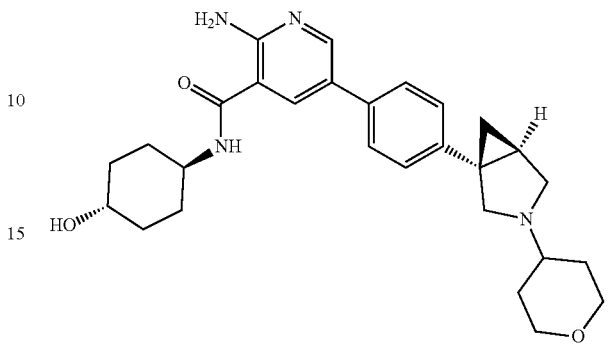

The title compound was prepared in an analogous manner to 2-amino-N-((1r,4S)-4-hydroxycyclohexyl)-5-(4-((1S,5R)-3-(oxetan-3-yl)-3-azabicyclo[3.1.0]hexan-1-yl)phenyl)nicotinamide (Example 26) except dihydro-2H-pyran-4(3H)-one was used instead of oxetan-3-one. 1H NMR (400 MHz, DMSO-d6) δ 8.39 (s, 1H), 8.31 (d, 1H), 8.12 (d, 1H), 7.62 (dd, 2H), 7.25 (s, 2H), 7.12 (s, 2H), 4.59 (d, 1H), 3.97-3.63 (m, 4H), 3.40 (m, 2H), 3.31 (m, 2H), 3.19-3.03 (m, 2H), 1.99-1.65 (m, 8H), 1.51-1.16 (m, 8H). (UPLC-MS) $t_R$ 0.47 min; ESI-MS 477 [M+H]$^+$.

Example 34: 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide (Also Named Compound A Herein)

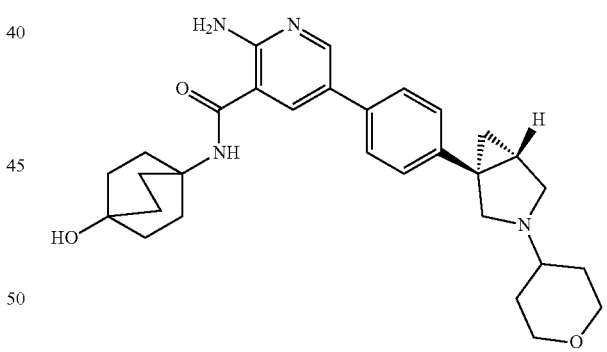

To a solution of 2-amino-5-(4-((1R,5S)-3-(tetrahydro-2H-pyran-4-yl)-3-azabicyclo[3.1.0]hexan-1-yl)phenyl)nicotinic acid TFA salt (Intermediate 14a, 4.10 g, 8.14 mmol) and 4-aminobicyclo[2.2.2]octan-1-ol hydrochloride (2.17 g, 12.2 mmol) in anhydrous DMF (60 mL) was added N-methylmorpholine (2.24 mL, 20.4 mmol) and HATU (4.64 g, 12.2 mmol) under a nitrogen atmosphere at RT. The reaction mixture was stirred for 2 h and then diluted with a sat. aq. solution of $NaHCO_3$ and extracted three times with EtOAc. The combined organic extracts were washed with brine, dried over $MgSO_4$, filtered and concentrated under reduced pressure. The crude product was purified by reversed-phase chromatography (Method 3b). Pure fractions were treated with a sat. aq. $NaHCO_3$ solution and extracted three times with EtOAc. The combined organic extracts were washed with brine, dried over MgSO$_4$, filtered and concentrated under reduced pressure to give the title compound as an off-white solid. The absolute configuration as depicted was confirmed by X-ray crystallography of the title compound in a complex with the ALK-2 kinase domain. 1H NMR (400 MHz, DMSO-d6) δ 8.34 (d, 1H), 7.98 (d, 1H), 7.79 (s, 1H), 7.57 (d, 2H), 7.23 (d, 2H), 6.92 (s, 2H), 4.31 (s, 1H), 3.91-3.78 (m, 2H), 3.40 (bs, 1H), 3.33-3.24 (m, 2H), 3.11 (d, 1H), 2.57 (bs, 1H), 2.50-2.34 (m, 1H), 2.34 (bs, 1H), 2.12-1.94 (m, 6H), 1.90-1.72 (m, 3H), 1.71-1.51 (m, 6H), 1.51-1.34 (m, 2H), 1.31 (t, 1H), 0.82-0.68 (m, 1H). (UPLC-MS) t$_R$ 0.54 min; ESI-MS 503 [M+H]$^+$. Chiral HPLC (ChiralPak Id, 5 µm, flow rate: 1 mL/min, detection wavelength: 270 nm, mobile phase: heptane:isopropanol 60:40 (+0.1% diethylamine)): t$_R$ 18.7 min, 92.3% ee.

Alternative Example 34A

To a solution of 2-amino-5-(4-((1R,5S)-3-(tetrahydro-2H-pyran-4-yl)-3-azabicyclo[3.1.0]hexan-1-yl)phenyl)nicotinic acid hydrochloride (1 kg, 1.683 mol) and 4-aminobicyclo[2.2.2]octan-1-ol hydrochloride (343.9 g, 1.935 mol) in DMF (3500 mL) was added Et$_3$N (681.2 g, 6.732 mol) and HATU (767.9 g, 2.019 mol) at RT. The reaction mixture was stirred at RT for 1 h. The mixture was heated to IT=45° C., 5% NH$_3$.H$_2$O solution (5200 g) was added. Stirred for about 30 min, another 5% NH$_3$.H$_2$O solution (1800 g) was added. The mixture was heated to IT=45° C. for 2 h. The mixture was cooled to IT=22° C. Filtered, the wet cake was washed with H$_2$O (1500 mL×3). The wet cake was dried under vacuum at 45° C. for 24 h. The crude product was dissolved in acetone (3000 mL), then filtered to remove some undissolved solid. The filtrate was heated to IT=50° C. H$_2$O (2000 mL) was added. The mixture was stirred at IT=50° C. for 30 min until a white precipitate formed. H$_2$O (4000 mL) was added slowly. The mixture was stirred at IT=50° C. for 2 h. The mixture was cooled to IT=22° C. in 2 h, Filtered, the wet cake was washed with acetone:H$_2$O=1:2 (v/v, 1000 mL×2). The wet cake was dried under vacuum at 45° C. for 24 h. total 760 g white solid was obtained (89% yield, 99.4% ee).

$^1$H NMR (DMSO-d6) δ: 8.32 (d, J=2.3 Hz, 1H), 7.97 (d, J=2.3 Hz, 1H), 7.77 (s, 1H), 7.54 (d, J=8.3 Hz, 2H), 7.20 (d, J=8.4 Hz, 2H), 6.90 (s, 2H), 4.31 (s, 1H), 3.82 (m, 2H), 3.29 (m, 2H), 3.07 (d, J=8.5 Hz, 1H), 2.54 (d, J=8.3 Hz, 1H), 2.44 (dd, J=8.5, 3.5 Hz, 1H), 2.37 (m, 1H), 2.31 (td, J=10.2, 5.0 Hz, 1H), 2.04 (m, 6H), 1.80 (dt, J=7.9, 3.8 Hz, 1H), 1.71 (d, J=12.3 Hz, 1H), 1.65 (d, J=11.5 Hz, 1H), 1.62 (m, 6H), 1.38 (m, 1H), 1.34 (m, 1H), 1.29 (t, J=3.9 Hz, 1H), 0.73 (dd, J=7.9, 3.6 Hz, 1H).

$^{13}$C NMR (DMSO-d6) δ: 167.80, 157.69, 148.28, 141.27, 134.91, 134.79, 126.40, 125.66, 123.53, 111.01, 66.22, 65.59, 59.10, 55.46, 52.04, 33.72, 31.92, 31.77, 30.59, 29.61, 24.14, 17.20.

MS(ESI-TOF): 503.3018 [M+H]$^+$.

The starting material (hydrochloride salt) was obtained as follows:

Methyl 2-amino-5-(4-((1R,5S)-3-(tetrahydro-2H-pyran-4-yl)-3-azabicyclo[3.1.0]hexan-1-yl)phenyl)nicotinate dihydrochloride (10 g, 19.5 mmol, 1.0 eq) was suspended in MeOH (31.7 g). A solution of NaOH (2.9 g, 72.2 mmol, 3.7 eq) in H$_2$O (10 g) was then added. The reaction mixture was heated to 45±5° C. and stirred for more than 3 h, yielding a suspension.

To another flask containing acetone (200 g), 5-6 N HCl in i-PrOH (14.8 g, 97.6 mmol, 5 eq) was added. The solution was heated to 47±3° C. Then the above MeOH suspension was added to the mixture dropwise and stirred at 47±3° C. for 3 h. The mixture was cooled down to 23±3° C. and stirred for 3 h. After filtration, the wet cake was washed with acetone (40 g). The wet cake was dried under vacuum at 55° C. for 8 h. 2-Amino-5-(4-((1R,5S)-3-(tetrahydro-2H-pyran-4-yl)-3-azabicyclo[3.1.0]hexan-1-yl)phenyl)nicotinic acid hydrochloride (12.3 g, 99.3% HPLC purity, 62.1% assay yield) was obtained as an off-white solid.

$^1$H NMR (DMSO-d6) δ: 11.53 (br s, 1H), 8.64 (br s, 1H), 8.54 (br s, 1H), 7.72-8.42 (m, 2H), 7.64 (br d, J=7.9 Hz, 2H), 7.38 (br d, J=7.8 Hz, 2H), 3.85-4.04 (m, 3H), 3.40-3.73 (m, 4H), 3.15-3.33 (m, 2H), 2.18 (br d, J=3.9 Hz, 1H), 1.95-2.12 (m, 4H), 1.88 (br d, J=10.0 Hz, 1H), 1.05 (br t, J=6.4 Hz, 1H).

$^{13}$C NMR (DMSO-d6) δ: 167.2, 155.8, 144.3, 142.0, 139.6, 133.8, 127.7, 126.3, 124.1, 110.0, 65.8, 62.5, 55.7, 53.2, 29.9, 28.8, 28.7, 23.5, 16.6.

MS(ESI-TOF): 380.1974 [M+H]$^+$.

The starting material, 2-Amino-5-(4-((1R,5S)-3-(tetrahydro-2H-pyran-4-yl)-3-azabicyclo[3.1.0]hexan-1-yl)phenyl)nicotinate dihydrochloride, was obtained as follows:

To a 500 mL round bottom flask were charged 1R,5S)-1-(4-bromophenyl)-3-(tetrahydro-2H-pyran-4-yl)-3-azabicyclo[3.1.0]hexan-3-ium chloride (20 g, 1 eq), EA (200 mL), and 25% K$_2$CO$_3$ (62 g). The mixture was stirred for 30 min until all solids were dissolved. After phase separation, the organic layer was concentrated. 2-Methyl-2-butanol (48 g, 60 mL) was added. The organic layer was concentrated. 2-Methyl-2-butanol (144 g, 180 mL) was added.

The mixture was transferred to a 500 mL Redlay. K$_2$CO$_3$ (18.8 g, 2.5 eq) and methyl 2-amino-5-(4,4,5,5-tetramethyl-1,3,2-dioxaborolan-2-yl)nicotinate (16.8 g, 1.04 eq; see Intermediate 1e) were added. The mixture was degassed with N$_2$ for three times. The mixture was heated to IT=50±5 15° C. within 1 h. Pd(dppf)Cl$_2$ (1.2 g, 0.03 eq) was added. The mixture was heated to IT=70±3° C. and stirred for 2 h. After cooling to 22° C., H$_2$O (120 g) and EA (180 g) were added and stirred for 30 min. MCC (6 g) was added and the mixture was filtered through MCC. The cake was washed with EA (54 g). After phase separation, the organic layer was washed with 5% NaCl (124 g). Quadrasil MP (Heavy metal scavenger from Johnson Matthey, 6 g) was then added to the organic layer. The mixture was heated to IT=55° C. for 8 h, filtered through MCC and washed with EA (54 g). Quadrasil MP (2 g) was added to the organic layer. The mixture was heated to IT=55° C. for 6 h, filtered through CMC and washed with EA (54 g). The organic layer was concentrated. Acetone (158 g, 200 mL) was added. After stirring at IT=22±3° C. for 30 min, the mixture was heated to IT=40±3° C. 15.5% HCl (38.4 g) was added dropwise with IT<50° C. The mixture was stirred at IT=45±3° C. for 1 h. The mixture was cooled to 22±3° C. The mixture was stirred at 22±3° C. for 1 h and filtered. The cake was washed with acetone (32 g×2). The wet cake was dried under vacuum at 50° C. for at least 8 h. The starting material was obtained, 22.5 g white solid (97.1% HPLC purity, 5.2% water content, 87% assay yield) was obtained.

$^1$H NMR (DMSO-d6) δ: 11.43 (br d, J=5.7 Hz, 1H), 8.62-8.80 (m, 2H), 7.85-8.58 (m, 2H), 7.67 (d, J=8.3 Hz, 2H), 7.39 (d, J=8.4 Hz, 2H), 3.85-4.06 (m, 6H), 3.60-3.69 (m, 2H), 3.50-3.59 (m, 1H), 3.44 (br d, J=7.7 Hz, 1H), 3.14-3.31 (m, 2H), 2.21 (dt, J=8.4, 4.2 Hz, 1H), 1.94-2.12 (m, 4H), 1.76-1.93 (m, 1H), 1.07 (br t, J=7.1 Hz, 1H).

$^{13}$C NMR (DMSO-d6) δ: 165.0, 154.0, 143.5, 142.0, 140.1, 132.8, 127.7, 126.5, 124.2, 110.7, 65.8, 62.5, 55.6, 53.3, 53.3, 29.9, 28.9, 28.8, 23.6, 16.8.

MS(ESI-TOF): 394.2071 [M+H]$^+$.

The starting material, 1R,5S)-1-(4-bromophenyl)-3-(tetrahydro-2H-pyran-4-yl)-3-azabicyclo[3.1.0]hexan-3-ium chloride, was obtained as follows:

To a 1 L Redlay were charged (1R,5S)-1-(4-bromophenyl)-3-azabicyclo[3.1.0]hexan-3-ium chloride (30 g, 1 eq), dihydro-2H-pyran-4(3H)-one (13.13 g, 1.2 eq) and THF (300 mL). The mixture was stirred at IT=22±5° C. for 1 h. NaBH(OAc)$_3$ (30.1 g, 1.3 eq) was added portion wise while keeping IT<30° C. The mixture was stirred at IT=22±5° C. for 2 h. 6.2% HCl (93 g, 90 ml, 1.5 eq) was added while maintaining IT<30° C. and pH<2. The mixture was stirred for 10 min. 25% K$_2$CO$_3$ (259 g, 210 mL) was added to adjust pH=8-9. IPAc (300 mL) was added. The mixture was stirred for 10 min. After phase separation, H$_2$O (150 g) was added to the organic layer. The mixture was stirred for 10 min. After phase separation, the organic layer was concentrated under vacuum (50-100 mbar, 50° C. water bath). IPA (120 g, 150 mL) was added. The organic layer was concentrated under vacuum (50-100 mbar, 50° C. water bath). IPA (144 g, 180 mL) was added. The mixture was filtered through CMC. The cake was washed with IPA (24 g×2). H$_2$O (5 g) was added to the organic layer. 31% HCl (19.3 g) was added dropwise with IT<35 OC. The mixture was stirred at IT=22±5° C. for 2 h and filtered. The cake was washed with IPA (48 g×2). The wet cake was dried under vacuum at 50° C. for at least 6 h. The desired product (31.4 g, 98% HPLC purity, 78% yield) was obtained as a white solid.

$^1$H NMR (DMSO-d6 and D$_2$O) δ: 7.46 (br d, J=8.4 Hz, 2H), 7.15 (br d, J=8.4 Hz, 2H), 3.90 (br d, J=7.8 Hz, 3H), 3.62 (br s, 1H), 3.51 (br s, 2H), 3.16-3.38 (m, 3H), 2.05-2.21 (m, 1H), 1.93 (br s, 2H), 1.49-1.71 (m, 2H), 1.05-1.30 (m, 1H).

$^{13}$C NMR (DMSO-d6) δ: 138.3, 131.9, 129.2, 120.4, 65.5, 62.3, 56.2, 53.9, 29.1, 28.9, 24.8, 23.0.

MS(ESI-TOF): 322.0761 [M+H]+

The complete way of manufacture of Alternative Example 34 A is depicted in the following Reaction

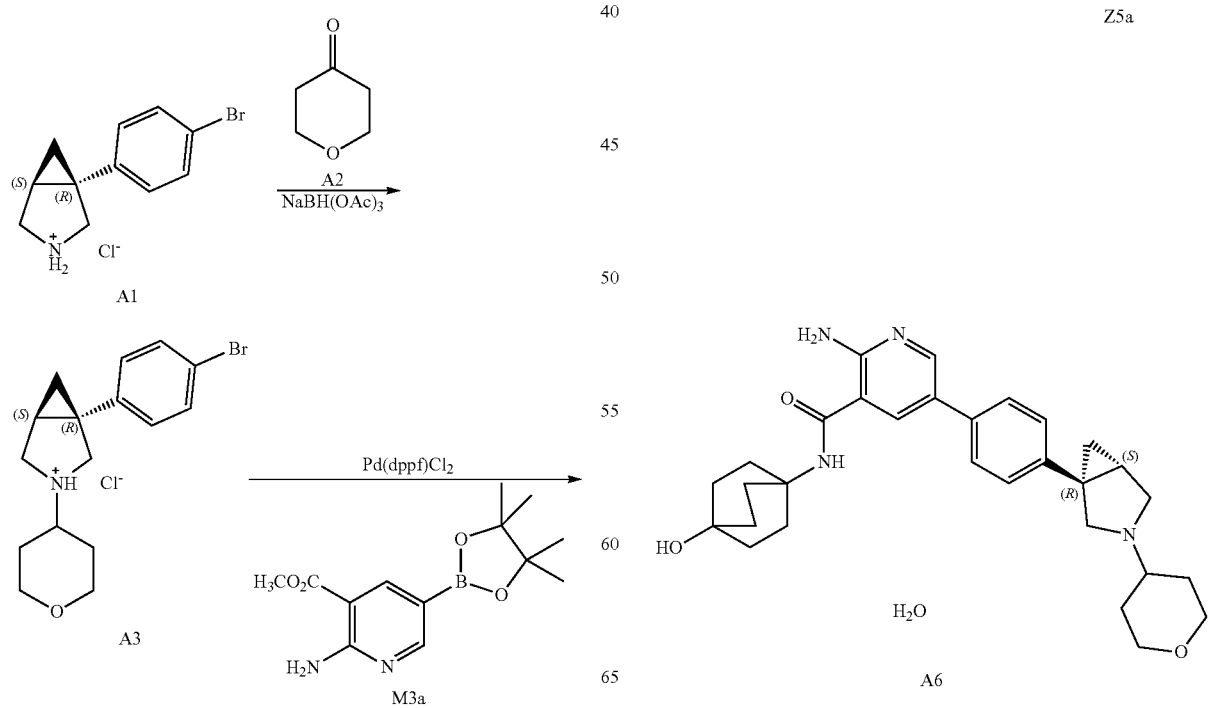

The first compound in this scheme, A1, can be obtained as follows:

Step 1-2 Synthesis of 1c and 1d

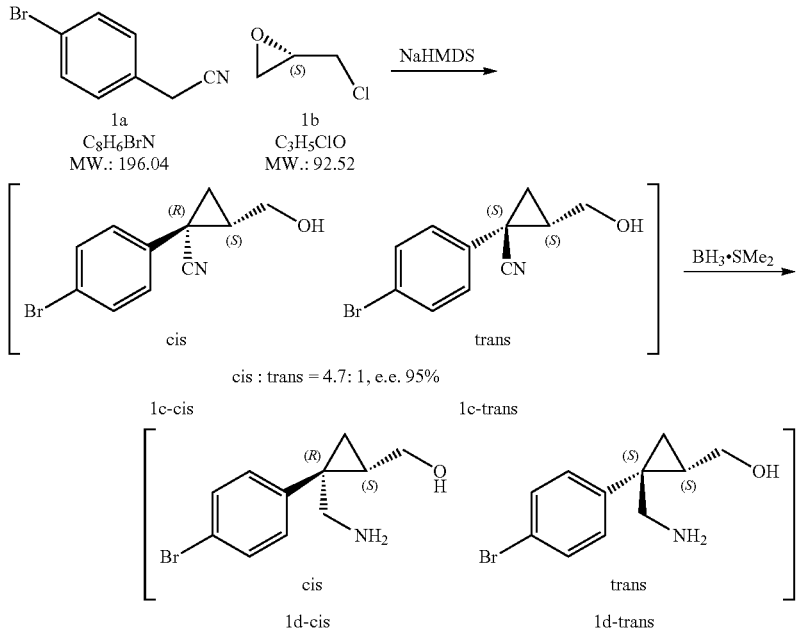

Reaction procedure (see also Xu, Feng et al., Org. Lett. Vol 8, No. 17, 2006, pages 3885-3888):

NaHMDS (2.0 M in THF, 19.2 L, 38.4 mol, 2.5 eq) was added dropwise to a solution of 1a (3.00 kg, 15.3 mol, 1.0 eq, obtainable e.g. from Sigma-Aldrich) and 1b (1.80 kg, 19.47 mmol, 1.27 eq; obtainable e.g. from Sigma-Aldrich) in THF (30 L) at −15-20° C. under $N_2$ over 5h. The reaction mixture was stirred for additional 3h at −15° C., then warmed to r.t. gradually and stirred for 16h. HPLC showed the 4-bromophenylacetonitrile was consumed completely.

$BF_3.Et_2O$ (4.74 kg, 15.3 mol, 1.0 eq) was added slowly at 2040° C. After addition, $BH_3$. DMS (19.2 L, 38.4 mol, 2.5 eq) was added slowly at 2040° C. After addition, the mixture was stirred at 50-55° C. for 16h. HPLC showed the intermediate was consumed completely.

The mixture was cooled to −5-0° C., AcOH (4.5 kg, 74.4 mol, 4.86 eq) was added slowly. After addition, 3 N HCl (36 kg) was added slowly. The mixture was stirred for 1 hour and most of THF was removed under vacuum at 40-45° C. Then the residue was extracted with MTBE (3×10 L). The MTBE phase was washed with 3N HCl (4×5 L). The combined aqueous layer was cooled to 0° C. Then the aqueous layer was neutralized with 30% NaOH to pH >10, extracted with IPAc (3×15 kg), washed with brine (5 L), evaporated under vacuum to offer crude compound 1d (3.71 kg) which was used for next step directly.

Step 3-4 Synthesis of 1e and 1f

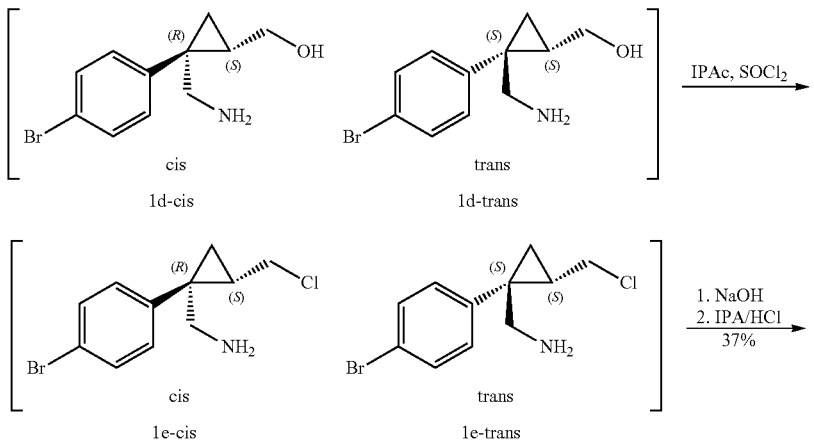

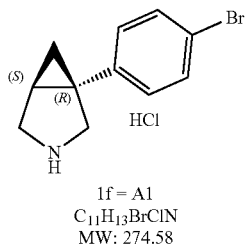

1f = A1
C₁₁H₁₃BrClN
MW: 274.58

Reaction Procedure:

IPAc (12 L) was cooled to 00° C., and SOCl$_2$(5.46 kg, 45.9 mol, 1.5 eq) was added, keeping the temperature at 0-4° C. After addition, a solution of crude compound id (7.46 kg, two batches combined from 6 kg 1a) in IPAc (24 L) was added slowly. After addition, the mixture was stirred for 1h at 00° C., then warmed to RT and stirred for 4h. HPLC showed the intermediate was consumed completely.

The mixture was cooled to −5-0° C. and quenched with water (30 L), then 30% NaOH aq solution was added slowly to adjust the pH to 8.5-9 and stirred for overnight at 0-5° C. HPLC showed the intermediate was consumed completely.

30% NaOH aq solution was added slowly to adjust the pH to 11-12 at 0-10° C. and stirred at rt for 30 min. Phases separation, the aqueous layer was extracted with IPAc (10 kg), the combined organic phase was washes with brine (5 L), dired over Na$_2$SO$_4$ and filtered. The filtrate was then cooled to 0-5° C.4M HCl\IPA (8.0 kg, 151 mol) was added slowly at 0-5° C. After the addition, the reaction mixture was stirred for 4h at 0-5° C. The mixture was filtered, the solid was collected, washed MTBE (6 L) and dried under vacuum to give compound 1f (3.10 kg, assay 98%, yield 37%)

Alternative Example 34B

The starting material A5 in Scheme 34A can, by way of an alternative, also be obtained as follows (Reaction Scheme 34B), and then be used as shown in Alternative Example 34A above:

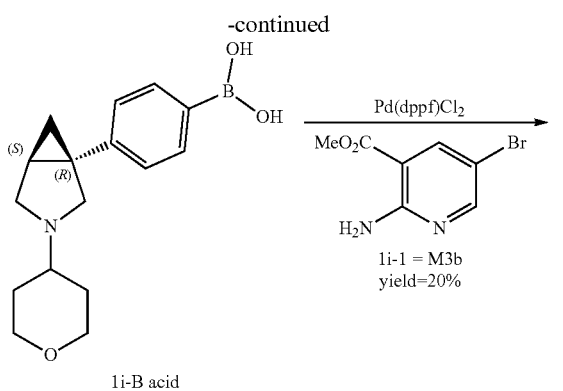

1i-B acid 1i-1 = M3b
yield=20%

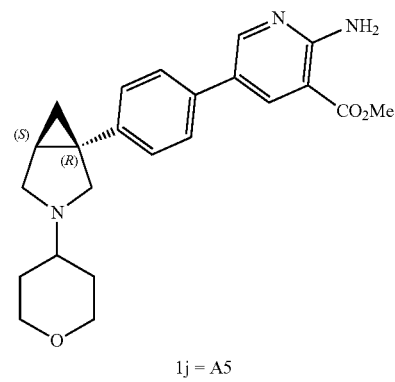

1j = A5

In detail, the procedure is as follows:

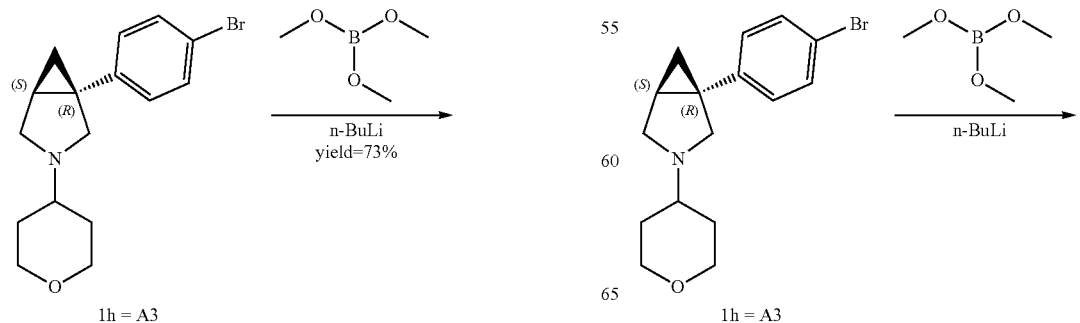

1h = A3

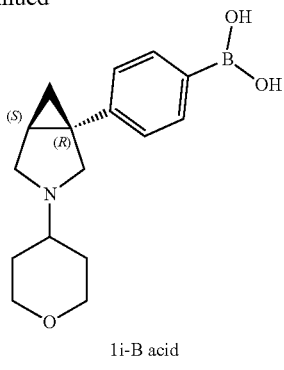

1i-B acid

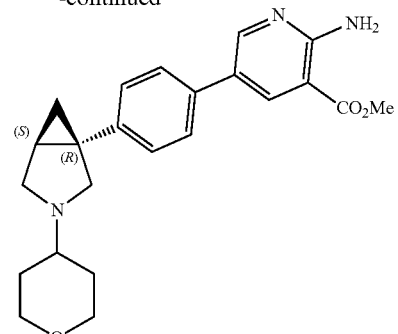

1j = A5

In a 100 mL three-necked flask, a solution of (1R,5S)-1-(4-bromophenyl)-3-tetrahydropyran-4-yl-3-azabicyclo[3.1.0]hexane (5.00 g, 15.52 mmol, 1.00 eq) in anhydrous THF (50.00 mL) was cooled to −78° C. under $N_2$. n-BuLi (2.5 M in hexane, 7.45 mL, 1.20 eq) was added dropwise at −78° C. and stirred for 1 h at −78° C. A solution of trimethyl borate (4.84 g, 46.56 mmol, 5.26 mL, 3.00 eq) in anhydrous THF (10.00 mL) was added dropwise at −78° C. After addition, the reaction mixture was allowed to warm to 25° C. and stirred at 25° C. for 16 h. After the starting material was completely consumed, monitoring by LC-MS followed and 74.23% of the target compound was observed. The reaction mixture was cooled to 0° C. under ice bath and quenched with a saturated $NH_4Cl$ solution (50 mL). The pH of the mixture was adjusted to 12-13 with NaOH solution (1 M) and extracted with EtOAc (30 mL×3). The aqueous layer was concentrated under reduced pressure to give the residue (18 g). The residue was purified by prep-HPLC (TFA condition) to afford [4-[(1R,5S)-3-tetrahydropyran-4-yl-3-azabicyclo[3.1.0]hexan-1-yl]phenyl]boronic acid (4.60 g, 11.47 mmol, 73.88% yield, TFA salt) as a white solid.

$^1$H NMR (400 MHz, DMSO-d6) δ: 7.72 (d, 2H), 7.24 (d, 2H), 4.13 (d, 1H), 4.06-4.03 (m, 2H), 3.86 (d, 1H), 3.70-3.67 (m, 2H), 3.45-3.32 (m, 3H), 2.26-2.23 (m, 1H), 2.11-2.05 (m, 2H), 1.81-1.77 (m, 2H), 1.34-1.20 (m, 2H). ESI-MS 288 [M+H]$^+$.

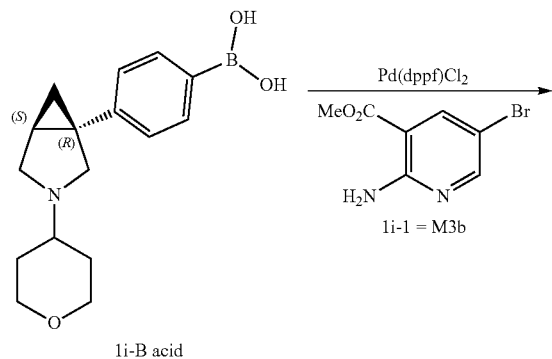

1i-B acid

A mixture of [4-[(1R,5S)-3-tetrahydropyran-4-yl-3-azabicyclo[3.1.0]hexan-1-yl]phenyl]boronic acid (500.00 mg, 1.25 mmol, 1.00 eq, TFA salt), methyl 2-amino-5-bromopyridine-3-carboxylate (433.22 mg, 1.88 mmol, 1.50 eq), Pd(dppf)Cl$_2$ (91.46 mg, 0.125 mmol, 0.10 eq) and $K_2CO_3$ (518.29 mg, 3.75 mmol, 3.00 eq) in dioxane (5.00 mL) and $H_2O$ (1.00 mL) was heated to 100° C. and stirred for 16 h at 100° C. under $N_2$. The reaction mixture was cooled to 30° C. and concentrated under reduced pressure. The residue was purified by prep-HPLC (neutral condition) to give methyl 2-amino-5-[4-[(1R,5S)-3-tetrahydropyran-4-yl-3-azabicyclo[3.1.0]hexan-1-yl]phenyl]pyridine-3-carboxylate (100.00 mg, 20.02% yield, 98.47% HPLC purity) as a brown solid $^1$H NMR (400 MHz, DMSO-d6) δ: 8.49 (d, 1H), 8.35 (d, 1H), 7.46 (d, 2H), 7.24 (d, 2H), 4.01-3.98 (m, 2H), 3.94 (s, 3H), 3.47-3.41 (m, 3H), 3.19 (d, 1H), 2.65 (d, 1H), 2.50-2.55 (m, 1H), 2.45-2.35 (m, 1H), 1.81-1.76 (m, 3H), 1.64-1.46 (m, 2H), 1.45-1.40 (m, 1H), 0.86-0.83 (m, 1H). ESI-MS 394 [M+H]$^+$.

Example 35: 2-amino-5-(4-(((1S,5R)-3-(4,4-difluorocyclohexyl)-3-azabicyclo[3.1.0]hexan-1-yl)phenyl)-N-(4-hydroxybicyclo[2.2.2]octan-1-yl)nicotinamide

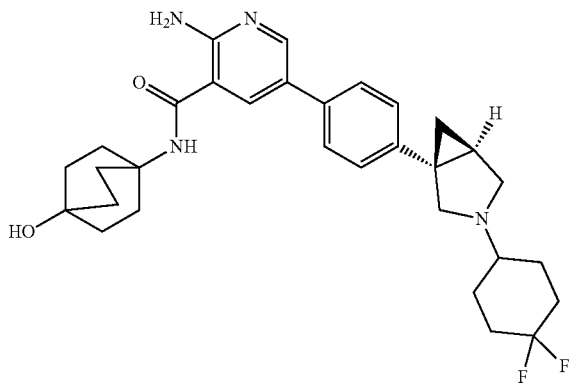 [SMILES: Nc1ncc(-c2ccc([C@]34C[C@H]3CN(C3CCC(F)(F)CC3)C4)cc2)cc1C(=O)NC12CCC(O)(CC1)CC2]

The title compound was prepared in an analogous manner to (1R,5S)-tert-butyl 1-(4-(6-amino-5-(((1r,4R)-4-hydroxycyclohexyl)carbamoyl)pyridin-3-yl)phenyl)-3-azabicyclo[3.1.0]hexane-3-carboxylate (Intermediate 1b) except 2-amino-5-(4-(((1S,5R)-3-(4,4-difluorocyclohexyl)-3-azabicyclo[3.1.0]hexan-1-yl)phenyl)nicotinic acid (Intermediate 35a) was used in place of 2-amino-5-(4-((1R,5S)-3-(tert-butoxycarbonyl)-3-azabicyclo[3.1.0]hexan-1-yl)phenyl) nicotinic acid (Intermediate 1c), and 4-aminobicyclo[2.2.2]octan-1-ol hydrochloride was used in place of trans-4-aminocyclohexanol. The crude product was purified by prepHPLC (Method 1a) to give the title compound as a TFA salt. 1H NMR (400 MHz, DMSO-d6) δ 9.05 (bs, 1H), 8.42 (d, 1H), 8.22 (s, 1H), 8.02 (s, 1H), 7.69 (d, 2H), 7.50 (bs, 2H), 7.39 (d, 2H), 4.83 (bs, 1H), 4.08 (dd, 1H), 3.80-3.25 (m, 6H), 2.31-2.09 (m, 4H), 2.09-1.99 (m, 6H), 1.98-1.71 (m, 4H), 1.70-1.56 (m, 6H), 1.42-1.40 (m, 1H), 1.10 (t, 1H). (UPLC-MS) t$_R$ 0.62 min; ESI-MS 537 [M+H]$^+$.

Intermediate 35a: 2-amino-5-(4-((1S,5R)-3-(4,4-difluorocyclohexyl)-3-azabicyclo[3.1.0]hexan-1-yl)phenyl)nicotinic acid The title compound was prepared in an analogous manner to 2-amino-5-(4-((1R,5S)-3-(tert-butoxycarbonyl)-3-azabicyclo[3.1.0]hexan-1-yl)phenyl)nicotinic acid (Intermediate 2c) except methyl 2-amino-5-(4-((1S,5R)-3-(4,4-difluorocyclohexyl)-3-azabicyclo[3.1.0]hexan-1-yl)phenyl)nicotinate (Intermediate 35b) was used in place of (1R,5S)-tert-butyl 1-(4-(6-amino-5-(methoxycarbonyl)pyridin-3-yl)phenyl)-3-azabicyclo[3.1.0]hexane-3-carboxylate (Intermediate 1d). (UPLC-MS) t$_R$ 0.46 min; ESI-MS 414 [M+H]$^+$.

Intermediate 35b: methyl 2-amino-5-(4-((1S,5R)-3-(4,4-difluorocyclohexyl)-3-azabicyclo[3.1.0]hexan-1-yl)phenyl)nicotinate The title compound was prepared in an analogous manner to methyl 2-amino-5-(4-((1R,5S)-3-(tetrahydro-2H-pyran-4-yl)-3-azabicyclo[3.1.0]hexan-1-yl)phenyl)nicotinate (Intermediate 14b) except methyl 5-(4-((1S,5R)-3-azabicyclo[3.1.0]hexan-1-yl)phenyl)-2-aminonicotinate hydrochloride (Intermediate 7c) was used in place of methyl 5-(4-((1R,5S)-3-azabicyclo[3.1.0]hexan-1-yl)phenyl)-2-aminonicotinate hydrochloride (Intermediate 14c), and 4,4-difluorocyclohexanone was used in place of dihydro-2H-pyran-4(3H)-one. (UPLC-MS) t$_R$ 0.73 min; ESI-MS 428 [M+H]$^+$.

Example 36: 2-amino-N-(3-(hydroxymethyl)bicyclo[1.1.1]pentan-1-yl)-5-(4-((1R,5S)-3-isopropyl-3-azabicyclo[3.1.0]hexan-1-yl)phenyl)nicotinamide

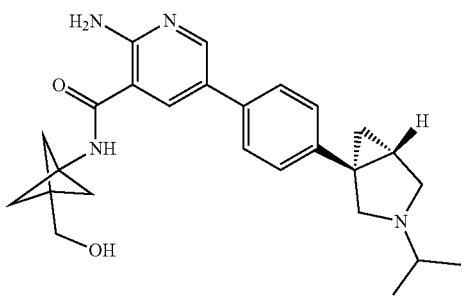 [SMILES: CC(C)N1C[C@H]2C[C@@]2(c2ccc(-c3cnc(N)c(C(=O)NC45CC(CO)(C4)C5)c3)cc2)C1]

The title compound was prepared in an analogous manner to 2-amino-N-((1r,4R)-4-hydroxycyclohexyl)-5-(4-((1R,5S)-3-isopropyl-3-azabicyclo[3.1.0]hexan-1-yl)phenyl) nicotinamide (Example 2) except (3-aminobicyclo[1.1.1]pentan-1-yl)methanol (Intermediate 16a) was used in place of trans-4-aminocyclohexanol hydrochloride. 1H NMR (400 MHz, DMSO-d6) δ 9.05 (s, 1H), 8.41 (d, 1H), 8.18 (d, 1H), 7.61 (d, 2H), 7.48 (dd, 1H), 7.33-7.17 (m, 4H), 4.55 (t, 1H), 3.51 (d, 3H), 3.31 (s, 2H), 3.08 (s, 2H), 2.07-1.99 (m, 1H), 1.41-1.22 (m, 3H), 1.17-0.98 (m, 9H), 0.79 (d, 1H). (UPLC-MS) t$_R$ 0.54 min; ESI-MS 433 [M+H]$^+$.

Example 37: 2-amino-5-(4-((1S,5R)-3-(but-2-yn-1-yl)-3-azabicyclo[3.1.0]hexan-1-yl)phenyl)-N-((1r,4S)-4-hydroxycyclohexyl)nicotinamide

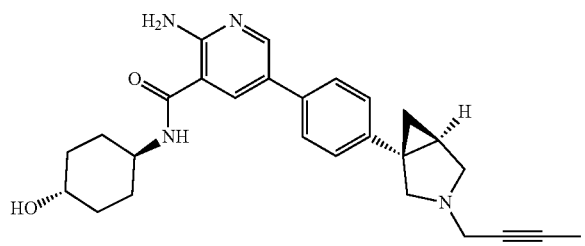 [SMILES: CC#CCN1C[C@@H]2C[C@]2(c2ccc(-c3cnc(N)c(C(=O)N[C@H]4CC[C@H](O)CC4)c3)cc2)C1]

The title compound was prepared in an analogous manner to 2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide (Example 5) except 1-bromobut-2-yne was used instead of 4-(3-bromopropyl)morpholine, and the reaction mixture was stirred at RT for 30 min. 1H NMR (400 MHz, DMSO-d6) δ 8.38 (s, 1H), 8.31 (d, 1H), 8.12 (d, 1H), 7.59 (d, 2H), 7.21 (s, 2H), 7.13 (s, 2H), 4.60 (d1H), 3.72 (s, 1H), 3.39 (s, 3H), 3.21 (s, 1H), 2.98-2.58 (m, 3H), 1.84 (dd, 8H), 1.49-1.17 (m, 5H), 0.78 (s, 1H). (UPLC-MS) t$_R$ 0.54 min; ESI-MS 445 [M+H]$^+$.

Example 38: 2-amino-N-((1r,4S)-4-hydroxycyclohexyl)-5-(4-((1S,5R)-3-(oxetan-3-ylmethyl)-3-azabicyclo[3.1.0]hexan-1-yl)phenyl)nicotinamide

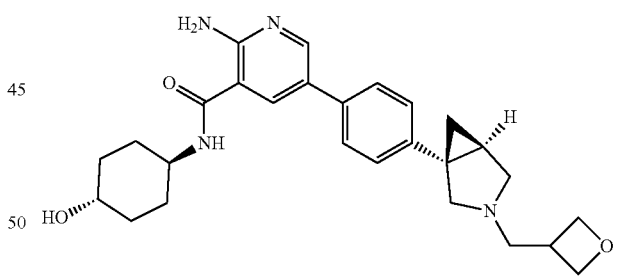

The title compound was prepared in an analogous manner to 2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide (Example 5) except 3-(iodomethyl)oxetane was used instead of 4-(3-bromopropyl)morpholine, and the reaction mixture was stirred at 60° C. for 60 min. 1H NMR (400 MHz, DMSO-d6) δ 8.39 (d, 1H), 8.30 (d, 1H), 8.11 (d, 1H), 7.59 (d, 2H), 7.22 (d, 2H), 7.12 (s, 2H), 4.73-4.61 (m, 2H), 4.58 (d, 1H), 4.29 (s, 2H), 3.84-3.67 (m, 1H), 3.52-3.38 (m, 2H), 3.27-3.12 (m, 2H), 2.94 (d, 1H), 2.80 (s, 2H), 1.95-1.76 (m, 5H), 1.54-1.14 (m, 6H), 0.76 (s, 1H). (UPLC-MS) t$_R$ 0.49 min; ESI-MS 463 [M+H]$^+$.

Example 39: 2-amino-N-((1r,4R)-4-hydroxycyclo-hexyl)-5-(4-((1R,5S)-3-(1-(2,2,2-trifluoroethyl)piperidin-4-yl)-3-azabicyclo[3.1.0]hexan-1-yl)phenyl)nicotinamide

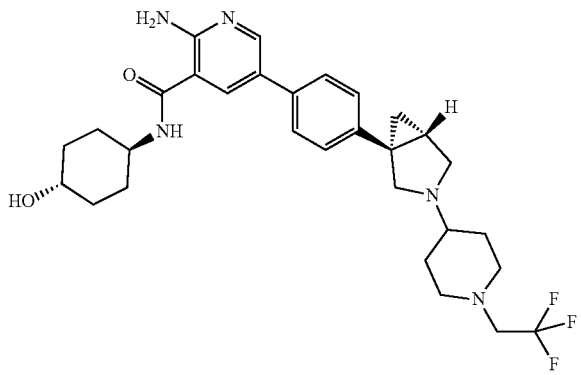 [SMILES: Nc1ncc(-c2ccc([C@@]34C[C@@H]3CN(C3CCN(CC(F)(F)F)CC3)C4)cc2)cc1C(=O)N[C@H]1CC[C@H](O)CC1]

The title compound was prepared in an analogous manner to 2-amino-N-((1r,4R)-4-hydroxycyclohexyl)-5-(4-((1R,5S)-3-(1-(methylsulfonyl)piperidin-4-yl)-3-azabicyclo[3.1.0]hexan-1-yl)phenyl)nicotinamide (Example 1) except 1-(2,2,2-trifluoroethyl)piperidin-4-one was used instead of 1-(methylsulfonyl)piperidin-4-one. 1H NMR (400 MHz, DMSO-d6) δ 8.38 (d, 1H), 8.31 (d, 1H), 8.11 (d, 1H), 7.58 (d, 2H), 7.23 (d, 2H), 7.12 (s, 2H), 4.55 (bs, 1H), 3.80-3.62 (m, 1H), 3.20-3.04 (m, 3H), 2.88 (d, 2H), 2.57 (d, 1H), 2.46 (dd, 1H), 2.41-2.29 (m, 2H), 2.15 (t, 1H), 1.99-1.69 (m, 8H), 1.49-1.17 (m, 7H), 1.15 (t, 1H), 0.75 (dd, 1H). (UPLC-MS) $t_R$ 0.62 min; ESI-MS 558 [M+H]$^+$.

Example 40: 2-amino-N-(4-hydroxybicyclo[2.2.2]octan-1-yl)-5-(4-((1S,5R)-3-(2-morpholinoethyl)-3-azabicyclo[3.1.0]hexan-1-yl)phenyl)nicotinamide

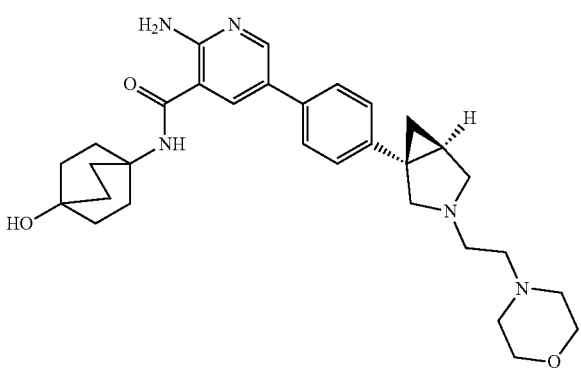 [SMILES: Nc1ncc(-c2ccc([C@]34C[C@H]3CN(CCN3CCOCC3)C4)cc2)cc1C(=O)NC12CCC(O)(CC1)CC2]

The title compound was prepared in an analogous manner to 2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide (Example 5) except 5-(4-((1S,5R)-3-azabicyclo[3.1.0]hexan-1-yl)phenyl)-2-amino-N-(4-hydroxybicyclo[2.2.2]octan-1-yl)nicotinamide HCl salt (Intermediate 40a) was used instead of 5-(4-((1S,5R)-3-azabicyclo[3.1.0]hexan-1-yl)phenyl)-2-amino-N-((1r,4R)-4-hydroxycyclohexyl)nicotinamide (Intermediate 5a), and 4-(2-bromoethyl)morpholine was used instead of 4-(3-bromopropyl)morpholine, and the reaction mixture was stirred at 60° C. for 3 h. 1H NMR (400 MHz, DMSO-d6) δ 8.34 (d, 1H), 7.98 (d, 1H), 7.79 (s, 1H), 7.57 (d, 2H), 7.21 (d, 2H), 6.92 (s, 2H), 4.32 (s, 1H), 3.65-3.49 (m, 4H), 3.08 (d, 1H), 2.61 (t, 2H), 2.59-2.39 (m, 9H), 2.15-1.98 (m, 6H), 1.85-1.73 (m, 1H), 1.70-1.54 (m, 6H), 1.31 (t, 1H), 0.75 (dd, 1H). (UPLC-MS) $t_R$ 0.52 min; ESI-MS 532 [M+H]$^+$.

Intermediate 40a: 5-(4-((1S,5R)-3-azabicyclo[3.1.0]hexan-1-yl)phenyl)-2-amino-N-(4-hydroxybicyclo[2.2.2]octan-1-yl)nicotinamide The title compound was prepared in an analogous manner to 5-(4-((1S,5R)-3-azabicyclo[3.1.0]hexan-1-yl)phenyl)-2-amino-N-((1r,4R)-4-hydroxycyclohexyl)nicotinamide (Intermediate 5a) except (1S,5R)-tert-butyl 1-(4-(6-amino-5-((4-hydroxybicyclo[2.2.2]octan-1-yl)carbamoyl)pyridin-3-yl)phenyl)-3-azabicyclo[3.1.0]hexane-3-carboxylate (Intermediate 40b) was used in place of (1S,5R)-tert-butyl 1-(4-(6-amino-5-(((1r,4S)-4-hydroxycyclohexyl)carbamoyl)pyridin-3-yl)phenyl)-3-azabicyclo[3.1.0]hexane-3-carboxylate (Intermediate 5b). One fraction of the title compound was obtained as a hydrochloride salt after evaporation of dioxane; another fraction was obtained as a TFA salt after additional purification by prepHPLC (Method 1a). (UPLC-MS) $t_R$ 0.48 min; ESI-MS 419 [M+H]$^+$.

Intermediate 40b: (1S,5R)-tert-butyl 1-(4-(6-amino-5-((4-hydroxybicyclo[2.2.2]octan-1-yl)carbamoyl)pyridin-3-yl)phenyl)-3-azabicyclo[3.1.0]hexane-3-carboxylate The title compound was prepared in an analogous manner to (1R,5S)-tert-butyl 1-(4-(6-amino-5-(((1r,4R)-4-hydroxycyclohexyl)carbamoyl)pyridin-3-yl)phenyl)-3-azabicyclo[3.1.0]hexane-3-carboxylate (Intermediate 1b) except 2-amino-5-(4-((1S,5R)-3-(tert-butoxycarbonyl)-3-azabicyclo[3.1.0]hexan-1-yl)phenyl)nicotinic acid (Intermediate 5c) was used in place of 2-amino-5-(4-((1R,5S)-3-(tert-butoxycarbonyl)-3-azabicyclo[3.1.0]hexan-1-yl)phenyl)nicotinic acid (Intermediate 1c), and 4-aminobicyclo[2.2.2]octan-1-ol hydrochloride was used in place of trans-4-aminocyclohexanol. (UPLC-MS) $t_R$ 1.05 min; ESI-MS 519 [M+H]$^+$.

Example 41: 2-amino-N-((1r,4R)-4-hydroxycyclo-hexyl)-5-(4-((1R,5S)-3-(2-(2,2,2-trifluoroethoxy)ethyl)-3-azabicyclo[3.1.0]hexan-1-yl)phenyl)nicotinamide

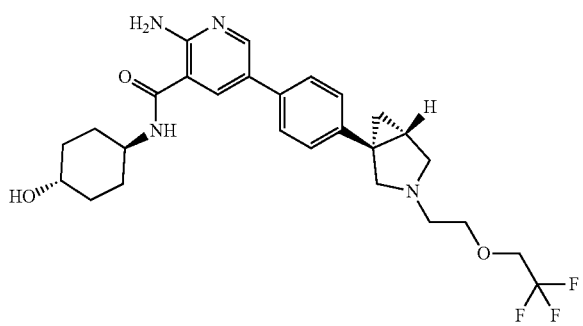 [SMILES: Nc1ncc(-c2ccc([C@@]34C[C@@H]3CN(CCOCC(F)(F)F)C4)cc2)cc1C(=O)N[C@H]1CC[C@H](O)CC1]

The title compound was prepared in an analogous manner to 2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide (Example 6) except 2-(2,2,2-trifluoroethoxy)ethyl trifluoromethanesulfonate (Intermediate 41a) was used instead of 1,3-difluoropropan-2-yl trifluoromethanesulfonate (Intermediate 6a). After purification the title compound was obtained as a TFA salt. 1H NMR (400 MHz, DMSO-d6) δ 9.15 (bs, 1H), 8.40 (s, 1H), 8.31 (d, 1H), 8.12 (d, 1H), 7.63 (d, 2H), 7.23 (s, 2H), 7.13 (s, 2H), 4.59 (d, 1H), 4.11 (s, 2H), 3.80-3.63 (m, 3H), 3.40 (m, 4H), 2.75-2.60 (m, 3H), 1.86 (m, 5H), 1.51-1.15 (m, 6H). (UPLC-MS) $t_R$ 0.60 min; ESI-MS 519 [M+H]$^+$.

Intermediate 41a: 2-(2,2,2-trifluoroethoxy)ethyl trifluoromethanesulfonate

The title compound was prepared in an analogous manner to 1,3-difluoropropan-2-yl trifluoromethanesulfonate (Intermediate 6a) except 2-(2,2,2-trifluoroethoxy)ethanol was used in place of 1,3-difluoropropan-2-ol, and obtained as a crude oil that was used without further purification.

Example 42: 2-amino-N-(4-hydroxybicyclo[2.2.2]octan-1-yl)-5-(4-((1S,5R)-3-(tetrahydro-2H-pyran-4-yl)-3-azabicyclo[3.1.0]hexan-1-yl)phenyl)nicotinamide

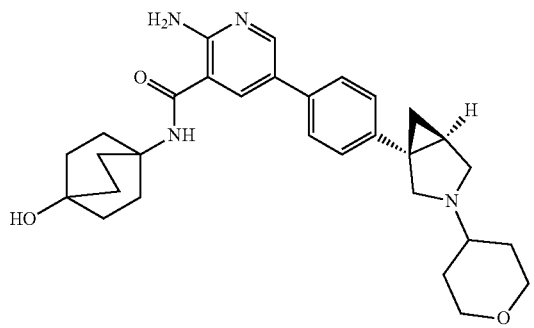 [SMILES: Nc1ncc(-c2ccc([C@]34C[C@H]3CN(C3CCOCC3)C4)cc2)cc1C(=O)NC12CCC(O)(CC1)CC2]

The title compound was prepared in an analogous manner to 2-amino-N-((1r,4R)-4-hydroxycyclohexyl)-5-(4-((1R,5S)-3-(1-(methylsulfonyl)piperidin-4-yl)-3-azabicyclo[3.1.0]hexan-1-yl)phenyl)nicotinamide (Example 1) except 5-(4-((1S,5R)-3-azabicyclo[3.1.0]hexan-1-yl)phenyl)-2-amino-N-(4-hydroxybicyclo[2.2.2]octan-1-yl)nicotinamide HCl salt (Intermediate 40a) was used instead of 5-(4-((1R,5S)-3-azabicyclo[3.1.0]hexan-1-yl)phenyl)-2-amino-N-((1r,4R)-4-hydroxycyclohexyl)nicotinamide (Intermediate 1a), and dihydro-2H-pyran-4(3H)-one was used instead of 1-(methylsulfonyl)piperidin-4-one. After purification the title compound was obtained as a TFA salt. 1H NMR (400 MHz, DMSO-d6) δ 9.62 (bs, 1H), 8.38 (d, 1H), 7.98 (d, 1H), 7.81 (s, 1H), 7.65 (d, 2H), 7.37 (d, 2H), 6.95 (s, 2H), 4.33 (s, 1H), 4.06-3.97 (m, 3H), 3.75-3.43 (m, 4H), 3.29-3.26 (m, 2H), 2.28-2.19 (m, 1H), 2.07-2.03 (m, 6H), 2.03-1.96 (m, 2H), 1.75-1.63 (m, 1H), 1.63-1.61 (m, 6H), 1.63-1.61 (m, 1H), 1.25-1.17 (m, 1H). (UPLC-MS) $t_R$ 0.52 min; ESI-MS 503 [M+H]$^+$.

Example 43: 2-amino-N-cyclohexyl-5-(4-(3-(piperidin-1-yl)propoxy)phenyl)nicotinamide

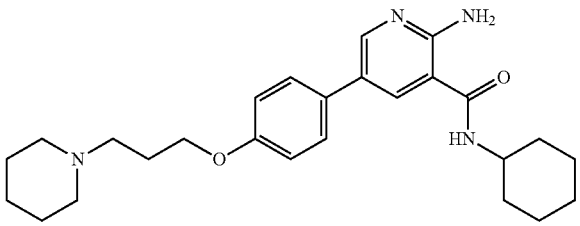 [SMILES: Nc1ncc(-c2ccc(OCCCN3CCCCC3)cc2)cc1C(=O)NC1CCCCC1]

To a solution of 2-amino-5-bromo-N-cyclohexylnicotinamide (Intermediate 43a, 50 mg, 0.168 mmol) in 2 mL of DMF/EtOH/water (2:1:1) was added 1-(3-(4-(4,4,5,5-tetramethyl-1,3,2-dioxaborolan-2-yl)phenoxy)propyl)piperidine (60.9 mg, 0.168 mmol), $K_2CO_3$ (69.5 mg, 0.503 mmol) and $PdCl_2(PPh_3)_2$ (11.8 mg, 0.017 mmol). The reaction mixture was stirred for 15 min at 80° C. then cooled and diluted with 5 mL of EtOAc and filtered over a pad of $Na_2SO_4$. After concentration under reduced pressure, the crude product was purified by prepHPLC (Method 1a) to give the title compound as a colorless solid. 1H NMR (400 MHz, DMSO-d6) δ 8.34 (d, 1H), 8.33 (d, 1H), 8.09 (d, 1H), 7.59 (d, 2H), 7.06 (s, 2H), 7.01 (d, 2H), 4.03 (t, 2H), 3.75 (s, 1H), 2.50-2.22 (m, 6H), 1.95-1.65 (m, 6H), 1.62 (d, 1H), 1.52-1.48 (m, 4H), 1.46-1.34 (m, 6H), 1.32-1.15 (m, 1H). (HPLC-MS) $t_R$ 1.46 min; APCI-MS 437.3 [M+H]$^+$.

Intermediate 43a: 2-amino-5-bromo-N-cyclohexylnicotinamide

The title compound was prepared in an analogous manner to (1R,5S)-tert-butyl 1-(4-(6-amino-5-(((1r,4R)-4-hydroxycyclohexyl)carbamoyl)pyridin-3-yl)phenyl)-3-azabicyclo[3.1.0]hexane-3-carboxylate (Intermediate ib) except 2-amino-5-bromonicotinic acid was used in place of 2-amino-5-(4-((1R,5S)-3-(tert-butoxycarbonyl)-3-azabicyclo[3.1.0]hexan-1-yl)phenyl)nicotinic acid (Intermediate 1c), and cyclohexanamine was used in place of trans-4-aminocyclohexanol. The crude product was used without further purification. (HPLC-MS) $t_R$ 0.98 min; ESI-MS 208/300 [M+H]$^+$.

Example 44: 2-amino-5-(4-((1R,5S)-3-(1,1-dioxido-tetrahydro-2H-thiopyran-4-yl)-3-azabicyclo[3.1.0]hexan-1-yl)phenyl)-N-((1r,4R)-4-hydroxycyclohexyl)nicotinamide

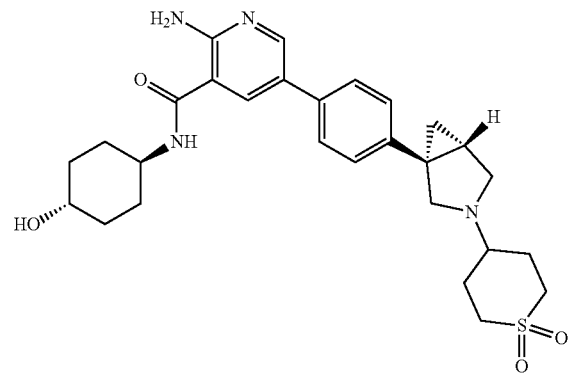 [SMILES: Nc1ncc(-c2ccc([C@@]34C[C@@H]3CN(C3CCS(=O)(=O)CC3)C4)cc2)cc1C(=O)N[C@H]1CC[C@H](O)CC1]

The title compound was prepared in an analogous manner to 2-amino-N-((1r,4R)-4-hydroxycyclohexyl)-5-(4-((1R,5S)-3-(1-(methylsulfonyl)piperidin-4-yl)-3-azabicyclo[3.1.0]hexan-1-yl)phenyl)nicotinamide (Example 1) except dihydro-2H-thiopyran-4(3H)-one 1,1-dioxide was used instead of 1-(methylsulfonyl)piperidin-4-one. 1H NMR (400 MHz, DMSO-d6) δ 8.39 (d, 1H), 8.31 (d, 1H), 8.12 (d, 1H), 7.59 (d, 2H), 7.24 (d, 2H), 7.12 (s, 2H), 4.58 (d, 1H), 3.82-3.65 (m, 1H), 3.48-3.35 (m, 2H), 3.19-2.91 (m, 5H), 2.62-2.51 (m, 2H), 2.17-1.97 (m, 4H), 1.89-1.83 (m, 5H), 1.45-1.19 (m, 6H), 0.81 (dd, 1H). (UPLC-MS) $t_R$ 0.48 min; ESI-MS 525 [M+H]⁺.

Example 45: 2-amino-N-cyclohexyl-5-(4-(4-methylpiperazine-1-carbonyl)phenyl)nicotinamide

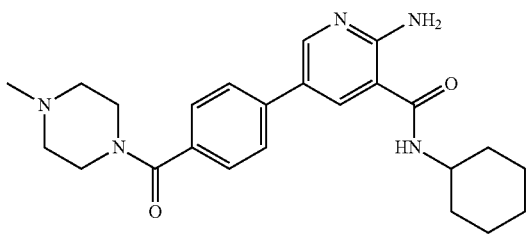 [SMILES: CN1CCN(C(=O)c2ccc(-c3cnc(N)c(C(=O)NC4CCCCC4)c3)cc2)CC1]

The title compound was prepared in an analogous manner to 2-amino-N-cyclohexyl-5-(4-(3-(piperidin-1-yl)propoxy)phenyl)nicotinamide (Example 43) except (4-methylpiperazin-1-yl)(4-(4,4,5,5-tetramethyl-1,3,2-dioxaborolan-2-yl)phenyl)methanone was used in place of 1-(3-(4-(4,4,5,5-tetramethyl-1,3,2-dioxaborolan-2-yl)phenoxy)propyl)piperidine. 1H NMR (400 MHz, DMSO-d6) δ 8.46 (d, 1H), 8.37 (s, 1H), 8.21 (d, 1H), 7.76 (d, 2H), 7.47 (d, 2H), 7.22 (s, 2H), 3.82-3.55 (m, 1H), 3.35 (t, 4H), 2.31-2.22 (t, 4H), 2.21 (s, 3H), 1.90-1.80 (m, 2H), 1.80-1.70 (m, 2H), 1.70-1.55 (m, 1H), 1.35-1.29 (m, 4H), 1.28-1.05 (m, 1H). (HPLC-MS) $t_R$ 1.29 min; APCI-MS 422 [M+H]⁺.

Example 46: 2-amino-5-(3-fluoro-4-(((R)-2-methylpyrrolidin-1-yl)methyl)phenyl)-N-((1r,4R)-4-hydroxy-4-methylcyclohexyl)nicotinamide

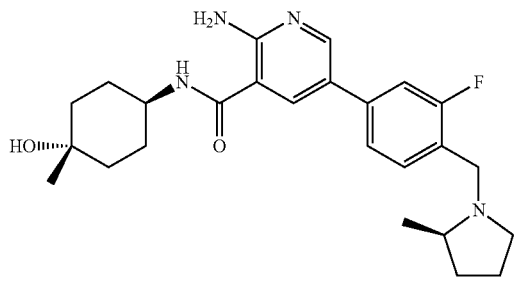 [SMILES: C[C@@H]1CCCN1Cc1ccc(-c2cnc(N)c(C(=O)N[C@H]3CC[C@](C)(O)CC3)c2)cc1F]

A microwave vial was charged with 2-amino-5-bromo-N-((1r,4r)-4-hydroxy-4-methylcyclohexyl)nicotinamide (Intermediate 59b, 33 mg, 0.10 mmol), (R)-2-(3-fluoro-4-((2-methylpyrrolidin-1-yl)methyl)phenyl)-6-methyl-1,3,6,2-dioxazaborocane-4,8-dione (Intermediate 46a, 38.3 mg, 0.11 mmol) and XPhos Pd (7.39 mg, 0.01 mmol). Dioxane (1 mL) was added followed by a 3N aq. solution of K₃PO₄ (0.10 ml, 0.30 mmol). The reaction mixture was purged with a stream of nitrogen for 5 min and then irradiated in a microwave reactor at 120° C. for 30 min. After cooling, the reaction mixture was concentrated under reduced pressure and purified by prepHPLC (Method 1b) to give the title compound. UPLC-HRMS $t_R$ 3.21 min; ESI 441.26 [M+H]⁺.

Intermediate 46a: (R)-2-(3-fluoro-4-((2-methylpyrrolidin-1-yl)methyl)phenyl)-6-methyl-1,3,6,2-dioxazaborocane-4,8-dione A solution of 2-fluoro-4-(6-methyl-4,8-dioxo-1,3,6,2-dioxazaborocan-2-yl)benzaldehyde (Intermediate 46b, 112 mg, 0.40 mmol), (R)-(2)-methylpyrrolidine (37.5 mg, 0.44 mmol) and acetic acid (2.4 mg, 0.040 mmol) in THF (2 mL) was shaken for 2 h at RT, and sodium triacetoxyborohydride (110 mg, 0.52 mmol) was added. The resulting reaction mixture was shaken for 18 h and then filtered through a SPE carbonate cartridge followed by washing with THF. The filtrate and the wash solutions were concentrated under reduced pressure to give the title compound which was used without further purification. ESI-MS 349 [M+H]⁺.

Intermediate 46b: 2-fluoro-4-(6-methyl-4,8-dioxo-1,3,6,2-dioxazaborocan-2-yl)benzaldehyde A solution of (3-fluoro-4-formylphenyl)boronic acid (67 mg, 0.40 mmol) and N-methyl iminodiacetic acid (65 mg, 0.44 mmol) in DMF (2 mL) was stirred at 90° C. for 18 h. The reaction mixture was cooled and filtered through a SPE carbonate cartridge followed by washing three times with acetonitrile. The filtrate and the wash solutions were concentrated under reduced pressure to give the title compound which was used without further purification. ESI-MS 558 [2M+H]⁺.

Example 47: 2-amino-N-((1r,4R)-4-hydroxycyclohexyl)-5-(4-((1R,5S)-3-(3,3,3-trifluoropropyl)-3-azabicyclo[3.1.0]hexan-1-yl)phenyl)nicotinamide

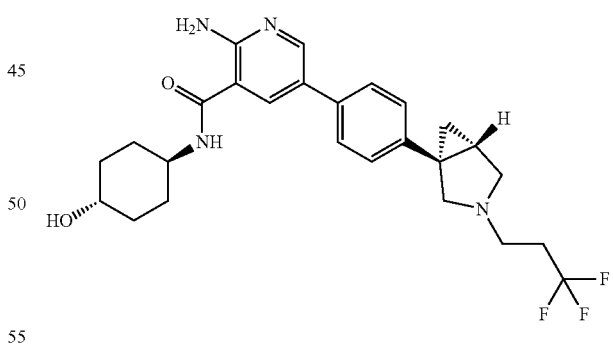

The title compound was prepared in an analogous manner to 2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide (Example 6) except 3,3,3-trifluoropropyl trifluoromethanesulfonate was used instead of 1,3-difluoropropan-2-yl trifluoromethanesulfonate (Intermediate 6a). 1H NMR (400 MHz, DMSO-d6) δ 8.39 (s, 1H), 8.31 (d, 1H), 8.12 (d, 1H), 7.60 (d, 2H), 7.23 (d, 2H), 7.13 (s, 2H), 4.59 (d, 1H), 3.74 (m, 1H), 3.40 (m, 3H), 3.09 (m, 1H), 2.72-2.64 (m, 4H), 1.86 (m, 5H), 1.49-1.14 (m, 6H), 0.78 (s, 1H). (UPLC-MS) $t_R$ 0.60 min; ESI-MS 489 [M+H]⁺.

Example 48: 2-amino-5-(4-((1R,5S)-3-(2-fluoro-ethyl)-3-azabicyclo[3.1.0]hexan-1-yl)phenyl)-N-((1r,4R)-4-hydroxycyclohexyl)nicotinamide

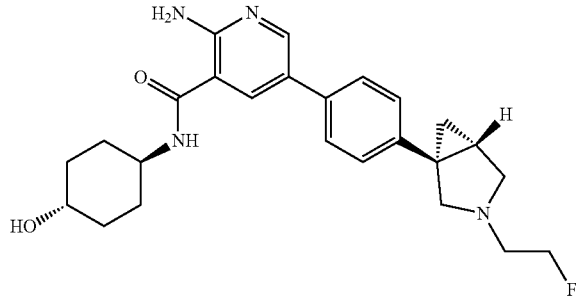 [SMILES: Nc1ncc(-c2ccc([C@@]34C[C@@H]3CN(CCF)C4)cc2)cc1C(=O)N[C@H]1CC[C@H](O)CC1]

The title compound was prepared in an analogous manner to 2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide (Example 6) except 1-bromo-2-fluoroethane was used instead of 1,3-difluoropropan-2-yl trifluoromethanesulfonate (Intermediate 6a), and the reaction mixture was stirred at 60° C. for 3 h. After purification the title compound was obtained as a TFA salt. 1H NMR (400 MHz, DMSO-d6) δ 9.95 (bs, 1H), 8.41 (s, 1H), 8.32 (d, 1H), 8.13 (d, 1H), 7.70-7.57 (m, 2H), 7.36 (bs, 2H), 7.16 (s, 2H), 4.80-4.62 (m, 2H), 4.59 (d, 1H), 4.08 (bs, 1H), 3.77-3.52 (m, 4H), 3.51-3.35 (m, 3H), 2.24 (bs, 1H), 1.87 (t, 4H), 1.59-1.13 (m, 6H). (UPLC-MS) $t_R$ 0.46 min; ESI-MS 439 [M+H]$^+$.

Example 49: 2-amino-N-cyclohexyl-5-(4-(morpholinophenyl)nicotinamide

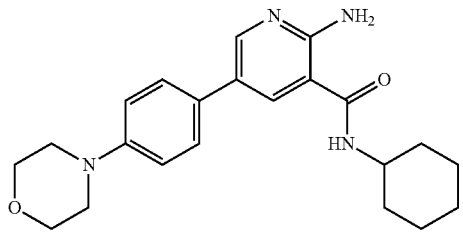 [SMILES: Nc1ncc(-c2ccc(N3CCOCC3)cc2)cc1C(=O)NC1CCCCC1]

The title compound was prepared in an analogous manner to 2-amino-N-cyclohexyl-5-(4-(3-(piperidin-1-yl)propoxy)phenyl)nicotinamide (Example 43) except 4-(4-(4,4,5,5-tetramethyl-1,3,2-dioxaborolan-2-yl)phenyl)morpholine was used in place of 1-(3-(4-(4,4,5,5-tetramethyl-1,3,2-dioxaborolan-2-yl)phenoxy)propyl)piperidine. 1H NMR (400 MHz, DMSO-d6) δ 8.35 (d, 1H), 8.34 (s, 1H), 8.08 (d, 1H), 7.55 (d, 2H), 7.03 (d, 2H), 7.03 (s, 2H), 3.85-3.65 (m, 1H), 3.77 (t, 4H), 3.14 (t, 4H), 1.90-1.80 (m, 2H), 1.80-1.70 (m, 2H), 1.80 (dd, 1H), 1.38-1.20 (m, 4H), 1.19-1.05 (m, 1H). (HPLC-MS) $t_R$ 1.60 min; APCI-MS 381 [M+H]$^+$.

Example 50: 2-amino-5-(4-((1R,5S)-3-(2,2-difluoropropyl)-3-azabicyclo[3.1.0]hexan-1-yl)phenyl)-N-((1r,4R)-4-hydroxycyclohexyl)nicotinamide

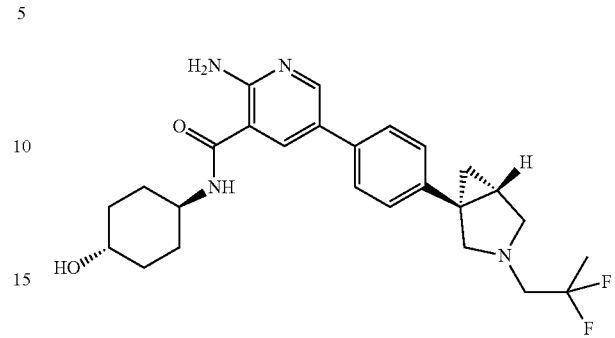

The title compound was prepared in an analogous manner to 2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide (Example 6) except 2,2-difluoropropyl trifluoromethanesulfonate was used instead of 1,3-difluoropropan-2-yl trifluoromethanesulfonate (Intermediate 6a), and the reaction mixture was stirred at RT for 60 min. 1H NMR (400 MHz, DMSO-d6) δ 8.39 (s, 1H), 8.33 (s, 1H), 8.14 (s, 1H), 7.59 (d, 2H), 7.32-7.11 (m, 4H), 4.58 (bs, 1H), 3.74 (bs, 1H), 3.11 (bs, 1H), 3.00-2.66 (m, 5H), 1.86 (bs, 5H), 1.63 (t, 3H), 1.48-1.18 (m, 6H), 0.81 (bs, 1H). (UPLC-MS) $t_R$ 0.81 min; ESI-MS 471 [M+H]$^+$.

Example 51: 2-amino-5-(4-((1S,5R)-3-(2-cyano-ethyl)-3-azabicyclo[3.1.0]hexan-1-yl)phenyl)-N-((1r,4S)-4-hydroxycyclohexyl)nicotinamide

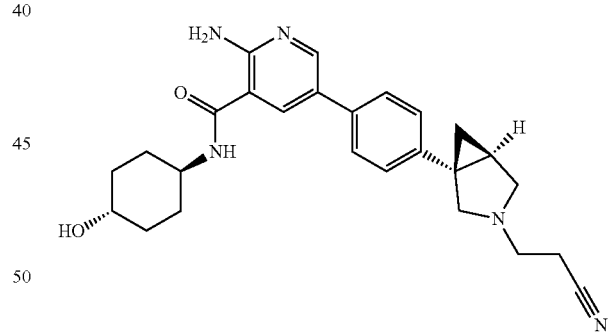

The title compound was prepared in an analogous manner to 2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide (Example 5) except 3-bromopropanenitrile was used instead of 4-(3-bromopropyl)morpholine, and the reaction mixture was stirred at 60° C. for 24 h. 1H NMR (400 MHz, DMSO-d6) δ 8.39 (d, 1H), 8.30 (d, 1H), 8.12 (d, 1H), 7.60 (d, 2H), 7.23 (d, 2H), 7.12 (s, 2H), 4.59 (d, 1H), 3.73 (d, 1H), 3.18 (d, 1H), 3.09 (d, 1H), 2.81-2.62 (m, 6H), 1.99-1.78 (m, 5H), 1.48-1.18 (m, 6H), 0.80 (dd, 1H). (UPLC-MS) $t_R$ 0.50 min; ESI-MS 446 [M+H]$^+$.

Example 52: 2-amino-N-cyclohexyl-5-(4-(3-morpholinopropoxy)phenyl)nicotinamide

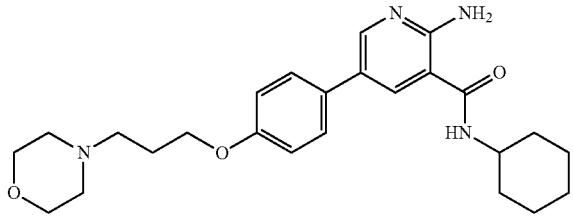 [SMILES: Nc1ncc(-c2ccc(OCCCN3CCOCC3)cc2)cc1C(=O)NC1CCCCC1]

The title compound was prepared in an analogous manner to 2-amino-N-cyclohexyl-5-(4-(3-(piperidin-1-yl)propoxy)phenyl)nicotinamide (Example 43) except 4-(3-(4-(4,4,5,5-tetramethyl-1,3,2-dioxaborolan-2-yl)phenoxy)propyl)morpholine was used in place of 1-(3-(4-(4,4,5,5-tetramethyl-1,3,2-dioxaborolan-2-yl)phenoxy)propyl)piperidine. 1H NMR (400 MHz, DMSO-d6) δ 8.35 (d, 1H), 8.34 (s, 1H), 8.10 (d, 1H), 7.59 (d, 2H), 7.06 (s, 2H), 7.01 (d, 2H), 4.04 (t, 2H), 3.82-3.68 (m, 1H), 3.58 (t, 4H), 2.50-2.22 (m, 6H), 1.90-1.78 (m, 4H), 1.78-1.69 (m, 2H), 1.63 (dd, 1H), 1.38-1.20 (m, 4H), 1.19-1.05 (m, 1H). (HPLC-MS) $t_R$ 1.40 min; APCI-MS 439 [M+H]$^+$.

Example 53: 2-amino-N-((1r,4S)-4-hydroxycyclohexyl)-5-(4-((1S,5R)-3-(prop-2-yn-1-yl)-3-azabicyclo[3.1.0]hexan-1-yl)phenyl)nicotinamide

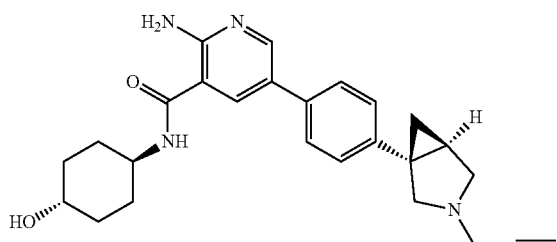

The title compound was prepared in an analogous manner to 2-amino-N-((1r,4S)-4-hydroxycyclohexyl)-5-(4-((1S,5R)-3-(3-morpholinopropyl)-3-azabicyclo[3.1.0]hexan-1-yl)phenyl)nicotinamide (Example 5) except 3-bromoprop-1-yne was used instead of 4-(3-bromopropyl)morpholine. 1H NMR (400 MHz, DMSO-d6) δ 8.38 (d, 1H), 8.31 (d, 1H), 8.12 (d, 1H), 7.59 (d, 2H), 7.21 (d, 2H), 7.13 (s, 2H), 4.59 (d, 1H), 3.73 (d, 1H), 3.52-3.38 (m, 2H), 3.21 (d, 1H), 2.93 (d, 1H), 2.83 (d, 1H), 2.72 (d, 1H), 2.40 (s, 3H), 1.95-1.75 (m, 4H), 1.44-1.19 (m, 5H), 0.80 (dd, 1H). (UPLC-MS) $t_R$ 0.49 min; ESI-MS 431 [M+H]$^+$.

Example 54: 2-amino-N-((1r,4R)-4-hydroxycyclohexyl)-5-(4-((1R,5S)-3-(prop-2-yn-1-yl)-3-azabicyclo[3.1.0]hexan-1-yl)phenyl)nicotinamide

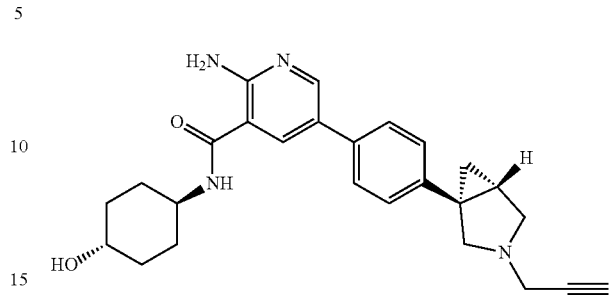

The title compound was prepared in an analogous manner to 2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide (Example 6) except 3-bromoprop-1-yne was used instead of 1,3-difluoropropan-2-yl trifluoromethanesulfonate (Intermediate 6a). 1H NMR (400 MHz, DMSO-d6) δ 8.39 (d, 1H), 8.31 (d, 1H), 8.12 (d, 1H), 7.59 (d, 2H), 7.21 (d, 2H), 7.12 (s, 2H), 4.59 (d, 1H), 3.76-3.70 (m, 1H), 3.46 (s, 2H), 3.45-3.37 (m, 1H), 3.22 (d, 1H), 2.83 (d, 1H), 2.72 (d, 1H), 2.71-2.69 (m, 2H), 1.92-1.77 (m, 5H), 1.51-1.17 (m, 5H), 0.80 (dd, 1H). (UPLC-MS) $t_R$ 0.52 min; ESI-MS 431 [M+H]$^+$.

Example 55: 5-(4-((R)-1-(2-oxa-6-azaspiro[3.3]heptan-6-yl)ethyl)-2-chlorophenyl)-2-amino-N-((1r,4R)-4-hydroxycyclohexyl)nicotinamide

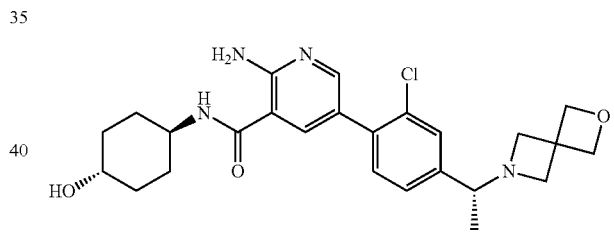

The title compound was prepared in an analogous manner to 5-(4-((R)-1-(2-oxa-6-azaspiro[3.3]heptan-6-yl)ethyl)phenyl)-2-amino-N-((1r,4R)-4-hydroxycyclohexyl)nicotinamide (Example 3) except (R)-6-(1-(4-bromo-3-chlorophenyl)ethyl)-2-oxa-6-azaspiro[3.3]heptane (Intermediate 55a) was used in place of (R)-6-(1-(4-bromophenyl)ethyl)-2-oxa-6-azaspiro[3.3]heptane (Intermediate 3b). 1H NMR (400 MHz, DMSO-d6) δ 8.17 (m, 2H), 8.00 (s, 1H), 7.42-7.44 (m, 2H), 7.40 (m, 1H), 7.34 (bs, 2H), 4.62 (s, 3H), 4.55-4.57 (m, 1H), 3.72 (m, 1H), 3.35-3.54 (m, 4H), 3.20-3.24 (m, 2H), 3.15 (bs, 1H), 1.78-1.88 (m, 4H), 1.20-1.41 (m, 4H), 1.11 (bs, 3H). (UPLC-MS) $t_R$ 0.47 min; ESI-MS 471/473 [M+H]$^+$.

Intermediate 55a: (R)-6-(1-(4-bromo-3-chlorophenyl)ethyl)-2-oxa-6-azaspiro[3.3]heptane The title compound was prepared in an analogous manner to (R)-6-(1-(4-bromophenyl)ethyl)-2-oxa-6-azaspiro[3.3]heptane (Intermediate 3b) except (R)-1-(4-bromo-3-chlorophenyl)ethanamine was used in place of (R)-1-(4-bromophenyl)ethanamine. (UPLC-MS) $t_R$ 0.63 min; ESI-MS 316/318 [M+H]$^+$.

Example 56: 2-amino-5-(2-fluoro-4-(((R)-2-methylpyrrolidin-1-yl)methyl)phenyl)-N-((1r,4R)-4-hydroxy-4-methylcyclohexyl)nicotinamide

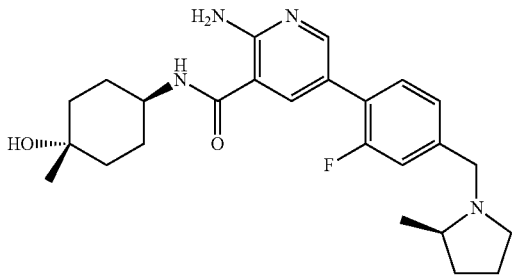 [SMILES: C[C@@H]1CCCN1Cc1ccc(-c2cnc(N)c(C(=O)N[C@H]3CC[C@](C)(O)CC3)c2)c(F)c1]

The title compound was prepared in an analogous manner to 2-amino-5-(3-fluoro-4-(((R)-2-methylpyrrolidin-1-yl)methyl)phenyl)-N-((1r,4R)-4-hydroxy-4-methylcyclohexyl)nicotinamide (Example 46) except (R)-2-(2-fluoro-4-((2-methylpyrrolidin-1-yl)methyl)phenyl)-6-methyl-1,3,6,2-dioxazaborocane-4,8-dione (Intermediate 56a) was used in place of (R)-2-(3-fluoro-4-((2-methylpyrrolidin-1-yl)methyl)phenyl)-6-methyl-1,3,6,2-dioxazaborocane-4,8-dione (Intermediate 46a). UPLC-HRMS $t_R$ 3.22 min; ESI 441.26 [M+H]$^+$.

Intermediate 56a: (R)-2-(2-fluoro-4-((2-methylpyrrolidin-1-yl)methyl)phenyl)-6-methyl-1,3,6,2-dioxazaborocane-4,8-dione The title compound was prepared in an analogous manner to (R)-2-(3-fluoro-4-((2-methylpyrrolidin-1-yl)methyl)phenyl)-6-methyl-1,3,6,2-dioxazaborocane-4,8-dione (Intermediate 46a) except 3-fluoro-4-(6-methyl-4,8-dioxo-1,3,6,2-dioxazaborocan-2-yl)benzaldehyde (Intermediate 56b) was used in place of 2-fluoro-4-(6-methyl-4,8-dioxo-1,3,6,2-dioxazaborocan-2-yl)benzaldehyde (Intermediate 46b). ESI-MS 349 [M+H]$^+$.

Intermediate 56b: 3-fluoro-4-(6-methyl-4,8-dioxo-1,3,6,2-dioxazaborocan-2-yl)benzaldehyde The title compound was prepared in an analogous manner to 2-fluoro-4-(6-methyl-4,8-dioxo-1,3,6,2-dioxazaborocan-2-yl)benzaldehyde (Intermediate 46b) except (2-fluoro-4-formylphenyl)boronic acid was used in place of (3-fluoro-4-formylphenyl)boronic acid. ESI-MS 576 [2M+H$_2$O+H]$^+$.

Example 57: 2-amino-5-(4-((1R,5S)-3-(2-fluoroethyl)-3-azabicyclo[3.1.0]hexan-1-yl)phenyl)-N-(4-hydroxybicyclo[2.2.2]octan-1-yl)nicotinamide

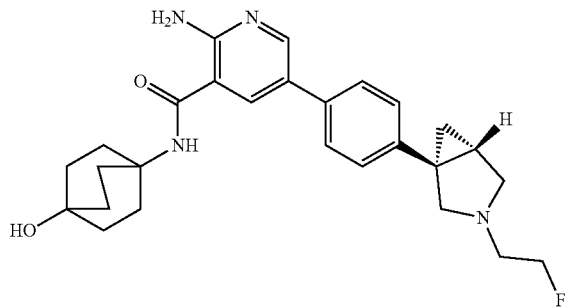 [SMILES: Nc1ncc(-c2ccc([C@@]34C[C@@H]3CN(CCF)C4)cc2)cc1C(=O)NC12CCC(O)(CC1)CC2]

The title compound was prepared in an analogous manner to 2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide (Example 6) except 5-(4-((1R,5S)-3-azabicyclo[3.1.0]hexan-1-yl)phenyl)-2-amino-N-(4-hydroxybicyclo[2.2.2]octan-1-yl)nicotinamide HCl salt (Intermediate 34a) was used instead of 5-(4-((1R,5S)-3-azabicyclo[3.1.0]hexan-1-yl)phenyl)-2-amino-N-((1r,4R)-4-hydroxycyclohexyl)nicotinamide (Intermediate 1a), and 1-bromo-2-fluoroethane was used instead of 1,3-difluoropropan-2-yl trifluoromethanesulfonate (Intermediate 6a). After purification the title compound was obtained as a TFA salt. 1H NMR (400 MHz, DMSO-d6) 3 10.00 (bs, 1H), 8.38 (d, 1H), 8.04 (d, 1H), 7.85 (s, 1H), 7.77 (d, 2H), 7.35 (d, 2H), 7.08 (s, 2H), 4.83 (td, 2H), 4.74 (bs, 1H), 4.08 (bs, 1H), 3.89-3.57 (m, 4H), 3.18 (d, 1H), 2.24 (bs, 1H), 2.13-1.97 (m, 6H), 1.74-1.53 (m, 6H), 1.48 (bs, 1H), 1.17 (bs, 1H). (UPLC-MS) $t_R$ 0.53 min; ESI-MS 465 [M+H]$^+$.

Example 58: 2-amino-5-(4-((1S,5R)-3-(4,4-difluorocyclohexyl)-3-azabicyclo[3.1.0]hexan-1-yl)phenyl)-N-((1r,4S)-4-hydroxy-4-methylcyclohexyl)nicotinamide

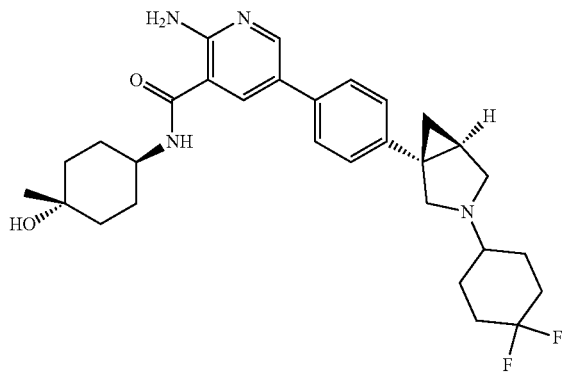 [SMILES: C[C@]1(O)CC[C@H](NC(=O)c2cc(-c3ccc([C@]45C[C@H]4CN(C4CCC(F)(F)CC4)C5)cc3)cnc2N)CC1]

The title compound was prepared in an analogous manner to (1R,5S)-tert-butyl 1-(4-(6-amino-5-(((1r,4R)-4-hydroxycyclohexyl)carbamoyl)pyridin-3-yl)phenyl)-3-azabicyclo[3.1.0]hexane-3-carboxylate (Intermediate 1b) except 2-amino-5-(4-((1S,5R)-3-(4,4-difluorocyclohexyl)-3-azabicyclo[3.1.0]hexan-1-yl)phenyl)nicotinic acid (Intermediate 35a) was used in place of 2-amino-5-(4-((1R,5S)-3-(tert-butoxycarbonyl)-3-azabicyclo[3.1.0]hexan-1-yl)phenyl)nicotinic acid (Intermediate 1c), and trans-4-amino-1-methylcyclohexanol was used in place of trans-4-aminocyclohexanol. The crude product was purified by prepHPLC (Method 1a) and passed through an ion exchange cartridge (PL-HCO$_3$) for desalting to give the title compound. 1H NMR (400 MHz, DMSO-d6) δ 8.39 (d, 1H), 8.29 (d, 1H), 8.10 (d, 1H), 7.59 (d, 2H), 7.25 (d, 2H), 7.10 (s, 2H), 4.33 (s, 1H), 3.81 (bs, 1H), 3.39 (d, 2H), 2.62-2.56 (m, 1H), 2.00 (bs, 2H), 1.88-1.76 (m, 8H), 1.67-1.53 (m, 4H), 1.50-1.43 (m, 4H), 1.30 (t, 1H), 1.17 (s, 3H), 0.86-0.68 (m, 1H). (UPLC-MS) $t_R$ 0.61 min; ESI-MS 525 [M+H]$^+$.

Example 59: 5-(4-((R)-1-(2-oxa-6-azaspiro[3.3]heptan-6-yl)ethyl)phenyl)-2-amino-N-((1r,4R)-4-hydroxy-4-methylcyclohexyl)nicotinamide

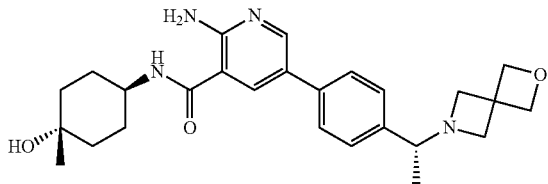 [SMILES: C[C@H](c1ccc(-c2cnc(N)c(C(=O)N[C@H]3CC[C@](C)(O)CC3)c2)cc1)N1CC2(COC2)C1]

The title compound was prepared in an analogous manner to 5-(4-((R)-1-(2-oxa-6-azaspiro[3.3]heptan-6-yl)ethyl)phenyl)-2-amino-N-((1r,4R)-4-hydroxycyclohexyl)nicotinamide (Example 3) except (6-amino-5-(((1r,4r)-4-hydroxy-4-methylcyclohexyl)carbamoyl)pyridin-3-yl)boronic acid (Intermediate 59a) was used in place of (6-amino-5-(((1r,4r)-4-hydroxycyclohexyl)carbamoyl)pyridin-3-yl)boronic acid (Intermediate 3a). 1H NMR (400 MHz, DMSO-d6) δ 8.38 (s, 1H), 8.25 (bs, 1H), 8.11 (d, 1H) 7.71-7.54 (m, 2H), 7.49-7.28 (m, 2H), 7.12 (bs, 2H), 4.61 (bs, 4H), 4.31 (s, 1H), 3.89-3.68 (m, 2H), 3.31 (s, 15H), 3.27-2.99 (m, 2H), 1.86-1.69 (m, 2H), 1.66-1.52 (m, 2H), 1.51-1.35 (m, 5H), 1.16 (s, 1H), 1.30-0.95 (m, 2H). (UPLC-MS) $t_R$ 0.47 min; ESI-MS 451 [M+H]$^+$.

Intermediate 59a: (6-amino-5-(((1r,4r)-4-hydroxy-4-methylcyclohexyl)carbamoyl)pyridin-3-yl)boronic acid The title compound was prepared in an analogous manner to (6-amino-5-(((1r,4r)-4-hydroxycyclohexyl)carbamoyl)pyridin-3-yl)boronic acid (Intermediate 3a) except 2-amino-5-bromo-N-((1r,4r)-4-hydroxy-4-methylcyclohexyl)nicotinamide (Intermediate 59b) was used in place of 2-amino-5-bromo-N-((1r,4r)-4-hydroxycyclohexyl)nicotinamide (Intermediate 3c). (UPLC-MS) $t_R$ 0.33 min; ESI-MS 394 [M+H]$^+$.

Intermediate 59b: 2-amino-5-bromo-N-((1r,4r)-4-hydroxy-4-methylcyclohexyl)nicotinamide The title compound was prepared in an analogous manner to 2-amino-5-bromo-N-((1r,4r)-4-hydroxycyclohexyl)nicotinamide (Intermediate 3c) except trans-4-amino-1-methylcyclohexanol was used in place of trans-4-aminocyclohexanol. (UPLC-MS) $t_R$ 0.68 min; ESI-MS 328/330 [M+H]$^+$.

Example 60: 2-amino-5-(4-((1R,5S)-3-(but-2-yn-1-yl)-3-azabicyclo[3.1.0]hexan-1-yl)phenyl)-N-((1r,4R)-4-hydroxycyclohexyl)nicotinamide

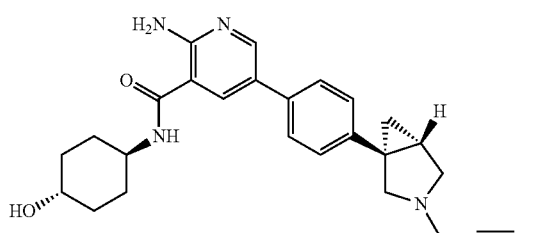

The title compound was prepared in an analogous manner to 2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide (Example 6) except 1-bromobut-2-yne was used instead of 1,3-difluoropropan-2-yl trifluoromethanesulfonate (Intermediate 6a). 1H NMR (400 MHz, DMSO-d6) δ 8.39 (d, 1H), 8.31 (d, 1H), 8.12 (d, 1H), 7.59 (d, 2H), 7.21 (d, 2H), 7.12 (s, 2H), 4.58 (d, 1H), 3.77-3.71 (m, 1H), 3.43-3.37 (m, 3H), 3.22 (d, 1H), 2.92 (d, 1H), 2.80 (d, 1H), 1.93-1.78 (m, 8H), 1.44-1.19 (m, 6H), 0.79 (dd, 1H). (UPLC-MS) $t_R$ 0.54 min; ESI-MS 445 [M+H]$^+$.

Example 61: 2-amino-N-cyclohexyl-5-(4-(piperidin-1-yl)phenyl)nicotinamide

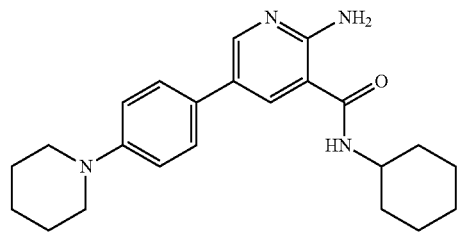 [SMILES: Nc1ncc(-c2ccc(N3CCCCC3)cc2)cc1C(=O)NC1CCCCC1]

The title compound was prepared in an analogous manner to 2-amino-N-cyclohexyl-5-(4-(3-(piperidin-1-yl)propoxy)phenyl)nicotinamide (Example 43) except 4-(piperidin-1-yl)phenylboronic acid was used in place of 1-(3-(4-(4,4,5,5-tetramethyl-1,3,2-dioxaborolan-2-yl)phenoxy)propyl)piperidine. 1H NMR (400 MHz, DMSO-d6) δ 8.33 (d, 1H), 8.33 (s, 1H), 8.08 (d, 1H), 7.51 (d, 2H), 7.01 (s, 2H), 7.00 (d, 2H), 3.82-3.68 (m, 1H), 3.17 (t, 4H), 1.90-1.78 (m, 2H), 1.78-1.69 (m, 2H), 1.68-1.49 (m, 7H), 1.38-1.20 (m, 4H), 1.19-1.05 (m, 1H). (HPLC-MS) $t_R$ 1.40 min; APCI-MS 379 [M+H]$^+$.

Example 62: 2-amino-N-(3-(hydroxymethyl)bicyclo[1.1.1]pentan-1-yl)-5-(4-((1S,5R)-3-(tetrahydro-2H-pyran-4-yl)-3-azabicyclo[3.1.0]hexan-1-yl)phenyl)nicotinamide

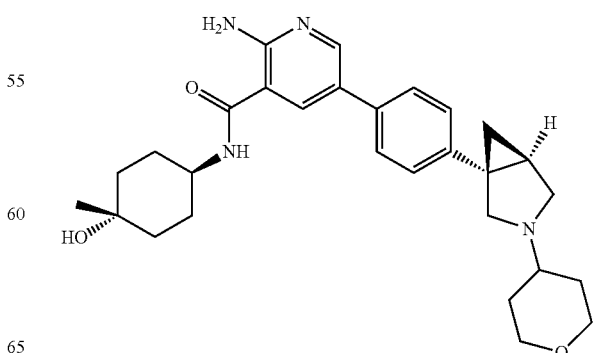

The title compound was prepared in an analogous manner to (1R,5S)-tert-butyl 1-(4-(6-amino-5-(((1r,4R)-4-hydroxycyclohexyl)carbamoyl)pyridin-3-yl)phenyl)-3-azabicyclo[3.1.0]hexane-3-carboxylate (Intermediate 1 b) except 2-amino-5-(4-((1S,5R)-3-(tetrahydro-2H-pyran-4-yl)-3-azabicyclo[3.1.0]hexan-1-yl)phenyl)nicotinic acid (Intermediate 28a) was used in place of 2-amino-5-(4-((1R,5S)-3-(tert-butoxycarbonyl)-3-azabicyclo[3.1.0]hexan-1-yl)phenyl)nicotinic acid (Intermediate 1c), and trans-4-amino-1-methylcyclohexanol was used in place of trans-4-aminocyclohexanol. The crude product was purified first by prepHPLC (Method 1a) then by reversed-phase flash chromatography (Method 3a) to give the title compound as a colorless solid. 1H NMR (400 MHz, DMSO-d6) δ 8.92 (d, 1H), 8.46 (s, 1H), 8.22 (s, 1H), 7.61 (d, 2H), 7.25 (d, 2H), 7.18 (s, 2H), 4.15-4.09 (m, 1H), 3.88-3.82 (m, 2H), 3.42-3.36 (m, 3H), 3.10 (bs, 1H), 2.65-2.34 (m, 12H), 1.85-1.75 (m, 3H), 1.45-1.31 (m, 6H), 0.77 (bs, 1H). (UPLC-MS) $t_R$ 0.49 min; ESI-MS 491 [M+H]$^+$.

Example 63: 2-amino-N-(4-hydroxybicyclo[2.2.2]octan-1-yl)-5-(4-((1S,5R)-3-(oxetan-3-yl)-3-azabicyclo[3.1.0]hexan-1-yl)phenyl)nicotinamide

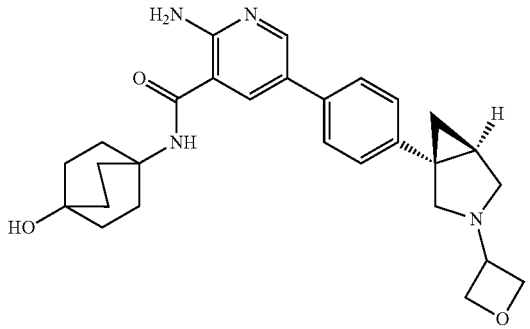 [SMILES: Nc1ncc(-c2ccc([C@]34C[C@H]3CN(C3COC3)C4)cc2)cc1C(=O)NC12CCC(O)(CC1)CC2]

The title compound was prepared in an analogous manner to 2-amino-N-((1r,4R)-4-hydroxycyclohexyl)-5-(4-((1R,5S)-3-(1-(methylsulfonyl)piperidin-4-yl)-3-azabicyclo[3.1.0]hexan-1-yl)phenyl)nicotinamide (Example 1) except 5-(4-((1S,5R)-3-azabicyclo[3.1.0]hexan-1-yl)phenyl)-2-amino-N-(4-hydroxybicyclo[2.2.2]octan-1-yl)nicotinamide HCl salt (Intermediate 40a) was used instead of 5-(4-((1R,5S)-3-azabicyclo[3.1.0]hexan-1-yl)phenyl)-2-amino-N-((1r,4R)-4-hydroxycyclohexyl)nicotinamide (Intermediate 1a), and oxetan-3-one was used instead of 1-(methylsulfonyl)piperidin-4-one. 1H NMR (400 MHz, DMSO-d6) δ 8.34 (d, 1H), 7.98 (d, 1H), 7.80 (s, 1H), 7.57 (d, 2H), 7.22 (d, 2H), 6.92 (s, 2H), 4.61-4.56 (m, 2H), 4.52-4.48 (m, 2H), 4.32 (s, 1H), 3.80-3.74 (m, 1H), 3.03 (d, 1H), 2.57-2.51 (m, 3H), 2.14-1.98 (m, 6H), 1.88-1.85 (m, 1H), 1.71-1.55 (m, 6H), 1.45-1.35 (m, 1H), 0.83-0.80 (m, 1H). (UPLC-MS) $t_R$ 0.51 min; ESI-MS 475 [M+H]$^+$.

Example 64: 2-amino-N-(4-hydroxybicyclo[2.2.2]octan-1-yl)-5-(4-((1R,5S)-3-(oxetan-3-yl)-3-azabicyclo[3.1.0]hexan-1-yl)phenyl)nicotinamide

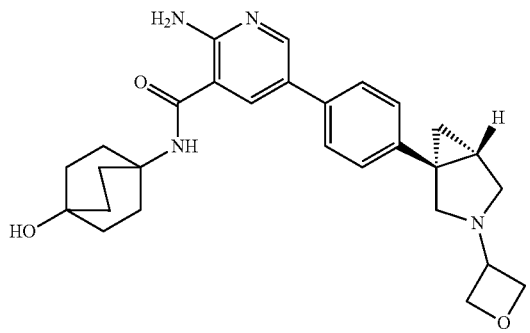 [SMILES: Nc1ncc(-c2ccc([C@@]34C[C@@H]3CN(C3COC3)C4)cc2)cc1C(=O)NC12CCC(O)(CC1)CC2]

The title compound was prepared in an analogous manner to 2-amino-N-((1r,4R)-4-hydroxycyclohexyl)-5-(4-((1R,5S)-3-(1-(methylsulfonyl)piperidin-4-yl)-3-azabicyclo[3.1.0]hexan-1-yl)phenyl)nicotinamide (Example 1) except 5-(4-((1R,5S)-3-azabicyclo[3.1.0]hexan-1-yl)phenyl)-2-amino-N-(4-hydroxybicyclo[2.2.2]octan-1-yl)nicotinamide HCl salt (Intermediate 34a) was used instead of 5-(4-((1R,5S)-3-azabicyclo[3.1.0]hexan-1-yl)phenyl)-2-amino-N-((1r,4R)-4-hydroxycyclohexyl)nicotinamide (Intermediate 1a), and oxetan-3-one was used instead of 1-(methylsulfonyl)piperidin-4-one. 1H NMR (400 MHz, DMSO-d6) δ 8.34 (d, 1H), 7.98 (d, 1H), 7.80 (s, 1H), 7.57 (d, 2H), 7.22 (d, 2H), 6.92 (s, 2H), 4.61-4.56 (m, 2H), 4.52-4.48 (m, 2H), 4.31 (s, 1H), 3.81-3.76 (m, 1H), 3.03 (d, 1H), 2.57-2.51 (m, 3H), 2.07-2.03 (m, 6H), 1.88-1.85 (m, 1H), 1.65-1.61 (m, 6H), 1.45-1.35 (m, 1H), 0.83-0.80 (m, 1H). (UPLC-MS) $t_R$ 0.55 min; ESI-MS 475 [M+H]$^+$.

Example 65: 2-amino-N-cyclohexyl-5-(4-((2-(4-methylpiperazin-1-yl)ethyl)carbamoyl)phenyl)nicotinamide

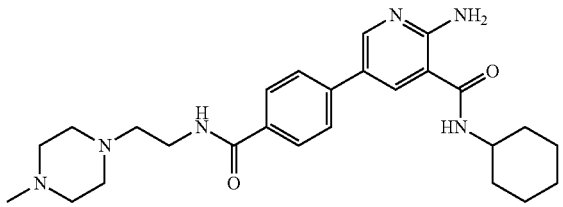 [SMILES: CN1CCN(CCNC(=O)c2ccc(-c3cnc(N)c(C(=O)NC4CCCCC4)c3)cc2)CC1]

The title compound was prepared in an analogous manner to (1R,5S)-tert-butyl 1-(4-(6-amino-5-(((1r,4R)-4-hydroxycyclohexyl)carbamoyl)pyridin-3-yl)phenyl)-3-azabicyclo[3.1.0]hexane-3-carboxylate (Intermediate 1b) except 4-(6-amino-5-(cyclohexylcarbamoyl)pyridin-3-yl)benzoic acid (Intermediate 65a) was used in place of 2-amino-5-(4-((1R,5S)-3-(tert-butoxycarbonyl)-3-azabicyclo[3.1.0]hexan-1-yl)phenyl)nicotinic acid (Intermediate 1c), and 2-(4-methylpiperazin-1-yl)ethanamine was used in place of trans-4-aminocyclohexanol. The crude product was purified by normal-phase chromatography (Method 2c) to give the title compound as an off-white solid. 1H NMR (400 MHz, DMSO-d6) δ 8.50 (d, 1H), 8.42 (t, 1H), 8.37 (d, 1H), 8.23 (d, 1H), 7.91 (d, 2H), 7.80 (d, 2H), 7.25 (s, 2H), 3.82-3.65 (m, 1H), 3.40 (q, 2H), 3.32-3.13 (m, 3H), 2.99-2.83 (m, 1H), 2.43-2.31 (m, 6H), 2.17 (s, 3H), 1.90-1.80 (m, 2H), 1.80-1.70 (m, 2H), 1.70-1.55 (m, 1H), 1.40-1.25 (m, 4H), 1.20-1.10 (m, 1H). (HPLC-MS) $t_R$ 1.28 min; APCI-MS 465 [M+H]$^+$.

Intermediate 65a: 4-(6-amino-5-(cyclohexylcarbamoyl)pyridin-3-yl)benzoic acid

The title compound was prepared in an analogous manner to 2-amino-N-cyclohexyl-5-(4-(3-(piperidin-1-yl)propoxy)phenyl)nicotinamide (Example 43) except 4-(4,4,5,5-tetramethyl-1,3,2-dioxaborolan-2-yl)benzoic acid was used in place of 1-(3-(4-(4,4,5,5-tetramethyl-1,3,2-dioxaborolan-2-yl)phenoxy)propyl)piperidine. The crude product was triturated with 2-propanol to give a brownish solid that was purified by prepHPLC (Method 1a). Pure fractions were collected and concentrated under reduced pressure, then basified with Na$_2$CO$_3$ upon which the title compound precipitated as a colorless solid which was filtered off and dried under reduced pressure. (HPLC-MS) $t_R$ 1.52 min; ESI-MS 340 [M+H]$^+$.

Example 66: 2-amino-5-(4-((1S,5R)-3-(1,3-difluoropropan-2-yl)-3-azabicyclo[3.1.0]hexan-1-yl)phenyl)-N-((1r,4S)-4-hydroxycyclohexyl)nicotinamide

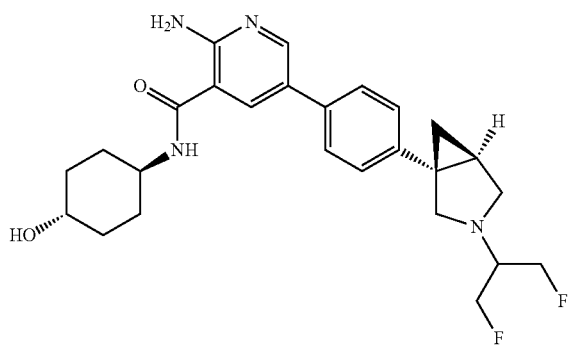 [SMILES: Nc1ncc(-c2ccc([C@]34C[C@H]3CN(C(CF)CF)C4)cc2)cc1C(=O)N[C@H]1CC[C@H](O)CC1]

The title compound was prepared in an analogous manner to 2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide (Example 5) except 1,3-difluoropropan-2-yl trifluoromethanesulfonate (Intermediate 6a) was used instead of 4-(3-bromopropyl)morpholine. 1H NMR (400 MHz, DMSO-d6) δ 8.39 (d, 1H), 8.31 (d, 1H), 8.12 (d, 1H), 7.59 (d, 2H), 7.24 (d, 2H), 7.12 (s, 2H), 4.68 (t, 2H), 4.57 (dd, 3H), 3.81-3.65 (m, 1H), 3.46-3.35 (m, 2H), 3.08 (d, 1H), 2.93 (d, 1H), 2.83 (dd, 1H), 2.05-1.76 (m, 5H), 1.53-1.16 (m, 6H), 0.78 (dd, 1H). (UPLC-MS) $t_R$ 0.68 min; ESI-MS 471 [M+H]$^+$.

Example 67: 2-amino-N-((1r,4S)-4-hydroxycyclohexyl)-5-(4-((1S,5R)-3-(2,2,2-trifluoroethyl)-3-azabicyclo[3.1.0]hexan-1-yl)phenyl)nicotinamide

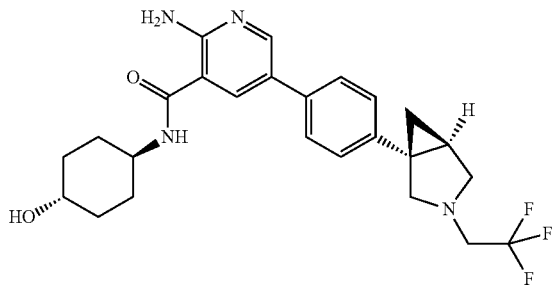 [SMILES: Nc1ncc(-c2ccc([C@]34C[C@H]3CN(CC(F)(F)F)C4)cc2)cc1C(=O)N[C@H]1CC[C@H](O)CC1]

The title compound was prepared in an analogous manner to 2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide (Example 5) except 2,2,2-trifluoroethyl trifluoromethanesulfonate was used instead of 4-(3-bromopropyl)morpholine. 1H NMR (400 MHz, DMSO-d6) δ 8.46-8.31 (m, 2H), 8.18 (bs, 1H), 7.59 (d, 2H), 7.29 (bs, 1H), 7.23 (d, 2H), 3.83-3.54 (m, 1H), 3.51-3.24 (m, 5H), 3.11 (d, 1H), 2.92 (d, 1H), 2.86 (m, 1H), 1.92-1.77 (m, 5H), 1.29-1.21 (m, 1H), 1.42-1.18 (m, 4H), 1.14 (bs, 1H), 0.85-0.79 (m, 1H). (UPLC-MS) $t_R$ 1.04 min; ESI-MS 475 [M+H]$^+$.

Example 68: 5-(4-((R)-1-(2-oxa-6-azaspiro[3.3]heptan-6-yl)ethyl)phenyl)-2-amino-N-((1r,3R)-3-hydroxyadamantan-1-yl)nicotinamide

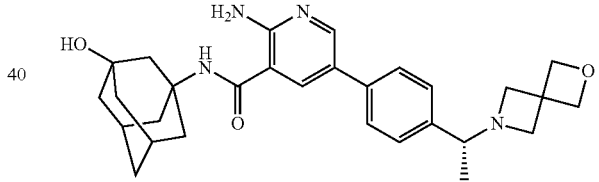

The title compound was prepared in an analogous manner to 5-(4-((R)-1-(2-oxa-6-azaspiro[3.3]heptan-6-yl)ethyl)phenyl)-2-amino-N-((1r,4R)-4-hydroxycyclohexyl)nicotinamide (Example 3) except (6-amino-5-(((1r,3r)-3-hydroxyadamantan-1-yl)carbamoyl)pyridin-3-yl)boronic acid (Intermediate 68a) was used in place of (6-amino-5-(((1r,4r)-4-hydroxycyclohexyl)carbamoyl)pyridin-3-yl)boronic acid (Intermediate 3a). 1H NMR (400 MHz, DMSO-d6) δ 8.65 (bs, 1H), 8.49 (s, 1H), 8.35 (s, 1H), 7.87 (d, 2H), 7.59 (d, 2H), 4.73 (dd, 2H), 4.65-4.54 (m, 4H), 4.45-4.39 (m, 1H), 4.16-4.10 (m, 1H), 3.98 (s, 1H), 3.90 (bs, 1H), 2.21 (s, 2H), 2.04-1.94 (m, 6H), 1.60 (bs, 2H), 1.49-1.43 (m, 3H). (UPLC-MS) $t_R$ 0.56 min; ESI-MS 489 [M+H]$^+$.

Intermediate 68a: 6-amino-5-(((1r,3r)-3-hydroxyadamantan-1-yl)carbamoyl)pyridin-3-yl)boronic acid The title compound was prepared in an analogous manner to (6-amino-5-(((1r,4r)-4-hydroxycyclohexyl)carbamoyl)pyridin-3-yl)boronic acid (Intermediate 3a) except 2-amino-5-bromo-N-((1r,3r)-3-hydroxyadamantan-1-yl)nicotinamide (Intermediate 68b) was used in place of 2-amino-5-bromo-N-((1r,4r)-4-hydroxycyclohexyl)nicotinamide (Intermediate 3c). (UPLC-MS) $t_R$ 0.47 min; ESI-MS 332 [M+H]$^+$.

Intermediate 68b: 2-amino-5-bromo-N-((1r,3r)-3-hydroxyadamantan-1-yl)nicotinamide The title compound was prepared in an analogous manner to 2-amino-5-bromo-N-((1r,4r)-4-hydroxycyclohexyl)nicotinamide Intermediate 3c except 3-amino-1-adamantanol was used in place of trans-4-aminocyclohexanol. (UPLC-MS) $t_R$ 0.82 min; ESI-MS 366/368 [M+H]$^+$.

Example 69: 2-amino-N-cyclohexyl-5-(4-(morpholine-4-carbonyl)phenyl)nicotinamide

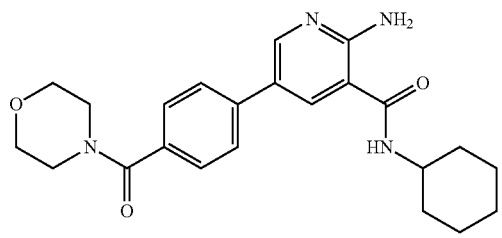 [SMILES: Nc1ncc(-c2ccc(C(=O)N3CCOCC3)cc2)cc1C(=O)NC1CCCCC1]

The title compound was prepared in an analogous manner to 2-amino-N-cyclohexyl-5-(4-(3-(piperidin-1-yl)propoxy)phenyl)nicotinamide (Example 43) except 4-(morpholine-4-carbonyl)phenylboronic acid was used in place of 1-(3-(4-(4,4,5,5-tetramethyl-1,3,2-dioxaborolan-2-yl)phenoxy)propyl)piperidine. 1H NMR (400 MHz, DMSO-d6) δ 8.47 (d, 1H), 8.42 (s, 1H), 8.30 (d, 1H), 7.78 (d, 2H), 7.51 (d, 2H), 7.49 (s, 2H), 3.85-3.70 (m, 1H), 3.70-3.50 (m, 8H), 1.90-1.80 (m, 2H), 1.80-1.70 (m, 2H), 1.70-1.55 (m, 1H), 1.35-1.29 (m, 4H), 1.28-1.05 (m, 1H). (HPLC-MS) $t_R$ 1.51 min; APCI-MS 409 [M+H]$^+$.

Example 70: 2-amino-N-((1r,4R)-4-hydroxycyclohexyl)-5-(4-((1R,5S)-3-(oxetan-3-ylmethyl)-3-azabicyclo[3.1.0]hexan-1-yl)phenyl)nicotinamide

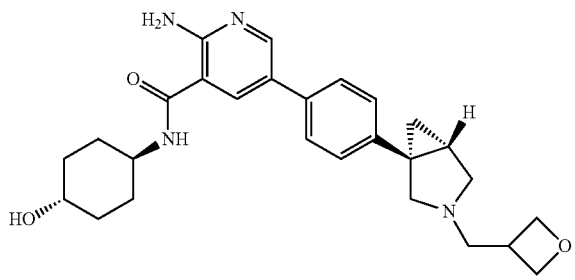 [SMILES: Nc1ncc(-c2ccc([C@@]34C[C@@H]3CN(CC3COC3)C4)cc2)cc1C(=O)N[C@H]1CC[C@H](O)CC1]

The title compound was prepared in an analogous manner to 2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide (Example 6) except oxetan-3-ylmethyl trifluoromethanesulfonate (Intermediate 70a) was used instead of 1,3-difluoropropan-2-yl trifluoromethanesulfonate (Intermediate 6a), and the reaction mixture was stirred at 60° C. for 3 h. 1H NMR (400 MHz, DMSO-d6) δ 8.38 (d, 1H), 8.30 (d, 1H), 8.11 (d, 1H), 7.58 (d, 2H), 7.21 (d, 2H), 7.12 (s, 2H), 4.66 (dt, 2H), 4.58 (d, 1H), 4.28 (t, 2H), 3.90-3.66 (m, 1H), 3.43-3.35 (m, 1H), 3.25 (dd, 1H), 3.19-3.09 (m, 1H), 2.97 (d, 1H), 2.79 (d, 2H), 2.62-2.51 (m, 2H), 1.98-1.75 (m, 5H), 1.48-1.13 (m, 5H), 0.75 (dd, 1H). (UPLC-MS) $t_R$ 0.46 min; ESI-MS 463 [M+H]$^+$.

Intermediate 70a: oxetan-3-ylmethyl trifluoromethanesulfonate

The title compound was prepared in an analogous manner to 1,3-difluoropropan-2-yl trifluoromethanesulfonate (Intermediate 6a), except oxetan-3-ylmethanol was used in place of 1,3-difluoropropan-2-ol, and was obtained as a crude oil that was used without further purification.

Example 71: 2-amino-N-((1s,4R)-4-hydroxycyclohexyl)-5-(4-((1S,5R)-3-isopropyl-3-azabicyclo[3.1.0]hexan-1-yl)phenyl)nicotinamide

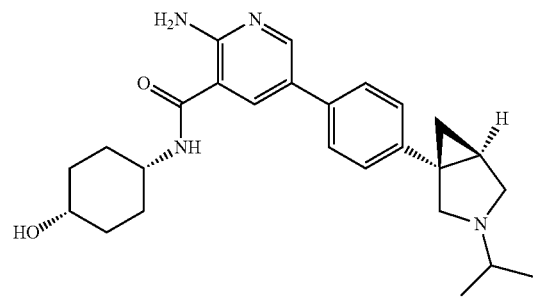 [SMILES: CC(C)N1C[C@@H]2C[C@]2(c2ccc(-c3cnc(N)c(C(=O)N[C@H]4CC[C@@H](O)CC4)c3)cc2)C1]

The title compound was prepared in an analogous manner to (1R,5S)-tert-butyl 1-(4-(6-amino-5-(((1r,4R)-4-hydroxycyclohexyl)carbamoyl)pyridin-3-yl)phenyl)-3-azabicyclo[3.1.0]hexane-3-carboxylate (Intermediate 1b) except 2-amino-5-(4-((1S,5R)-3-isopropyl-3-azabicyclo[3.1.0]hexan-1-yl)phenyl)nicotinic acid (Intermediate 71a) was used in place of 2-amino-5-(4-((1R,5S)-3-(tert-butoxycarbonyl)-3-azabicyclo[3.1.0]hexan-1-yl)phenyl)nicotinic acid (Intermediate 1c), and cis-4-aminocyclohexanol hydrochloride was used in place of trans-4-aminocyclohexanol. The crude product was purified by prepHPLC (Method 1a) to give the title compound as a yellow solid. 1H NMR (400 MHz, DMSO-d6) δ 8.49-8.34 (m, 2H), 8.17 (s, 1H), 7.67 (s, 2H), 7.36 (s, 2H), 7.16 (s, 2H), 4.43 (d, 1H), 3.81 (s, 2H), 3.81-3.59 (m, 4H), 1.88-1.62 (m, 5H), 1.61-1.44 (m, 5H), 1.35 (s, 6H), 1.16 (s, 2H). (UPLC-MS) $t_R$ 0.52 min; ESI-MS 435 [M+H]$^+$.

Intermediate 71a: 2-amino-5-(4-((1S,5R)-3-isopropyl-3-azabicyclo[3.1.0]hexan-1-yl)phenyl)nicotinic acid The title compound was prepared in an analogous manner to 2-amino-5-(4-((1R,5S)-3-(tert-butoxycarbonyl)-3-azabicyclo[3.1.0]hexan-1-yl)phenyl)nicotinic acid (Intermediate 1c) except methyl 2-amino-5-(4-((1S,5R)-3-isopropyl-3-azabicyclo[3.1.0]hexan-1-yl)phenyl)nicotinate (Intermediate 71b) was used in place of (1R,5S)-tert-butyl 1-(4-(6-amino-5-(methoxycarbonyl)pyridin-3-yl)phenyl)-3-azabicyclo[3.1.0]hexane-3-carboxylate (Intermediate 1d). (UPLC-MS) $t_R$ 0.40 min; ESI-MS 338 [M+H]$^+$.

Intermediate 71b: methyl 2-amino-5-(4-((1S,5R)-3-isopropyl-3-azabicyclo[3.1.0]hexan-1-yl)phenyl)nicotinate The title compound was prepared in an analogous manner to methyl 2-amino-5-(4-((1S,5R)-3-(2-methoxyethyl)-3-azabicyclo[3.1.0]hexan-1-yl)phenyl)nicotinate (Intermediate 7b) except 2-iodopropane was used in place of 1-bromo-2-methoxyethane. (UPLC-MS) $t_R$ 0.65 min; ESI-MS 352 [M+H]$^+$.

Example 72: 2-amino-N-((1r,4R)-4-hydroxy-4-methylcyclohexyl)-5-(4-(((R)-2-methylpyrrolidin-1-yl)methyl)phenyl)nicotinamide

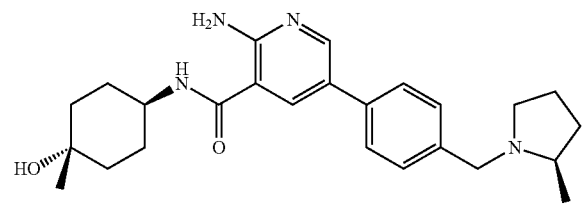 [SMILES: C[C@@H]1CCCN1Cc1ccc(-c2cnc(N)c(C(=O)N[C@H]3CC[C@](C)(O)CC3)c2)cc1]

To a solution of (4-(bromomethyl)phenyl)boronic acid (73.1 mg, 0.340 mmol) in acetonitrile (2 mL) was added (R)-2-methylpyrrolidine (29.0 mg, 0.340 mmol) and K$_2$CO$_3$ (78 mg, 0.567 mmol) at RT under a nitrogen atmosphere and the resulting white suspension was stirred at 60° C. for 2 h. Water (1 mL) was added at RT, followed by addition of 2-amino-5-bromo-N-((1r,4r)-4-hydroxy-4-methylcyclohexyl)nicotinamide (Intermediate 59b, 150 mg, 0.283 mmol) in acetonitrile (2 mL). Then PdCl$_2$(dppf) (10.37 mg, 0.014 mmol) was added and the reaction mixture was stirred at 90° C. for 60 min. After filtering through a pad of celite and concentration under reduced pressure, the crude product was diluted with a sat. aq. solution of NaHCO$_3$ and EtOAc. After phase separation, the aq. layer was extracted with EtOAc and the combined organic layers were washed with brine, dried over MgSO$_4$, filtered and concentrated under reduced pressure. The crude product obtained was purified first by prepHPLC (Method 1a) then by normal-phase chromatography (Method 2b) to give the title compound as a colorless solid. 1H NMR (400 MHz, DMSO-d6) δ 9.75 (d, 1H), 8.52 (t, 1H), 8.41 (d, 1H), 8.27 (d, 1H), 7.85 (d, 2H), 7.66 (d, 2H), 7.38 (bs, 2H), 4.67-4.53 (m, 1H), 4.25 (dd, 1H), 3.85 (s, 1H), 3.58-3.49 (m, 1H), 3.37-3.18 (m, 3H), 2.29 (m, 1H), 2.06-1.88 (m, 2H), 1.83 (s, 1H), 1.65 (dd, 2H), 1.51 (d, 4H), 1.39 (dd, 3H), 1.22 (d, 3H). (UPLC-MS) $t_R$ 0.47 min; ESI-MS 423 [M+H]$^+$.

Example 73: 2-amino-5-(4-((1S,5R)-3-(2-fluoroethyl)-3-azabicyclo[3.1.0]hexan-1-yl)phenyl)-N-(4-hydroxybicyclo[2.2.2]octan-1-yl)nicotinamide

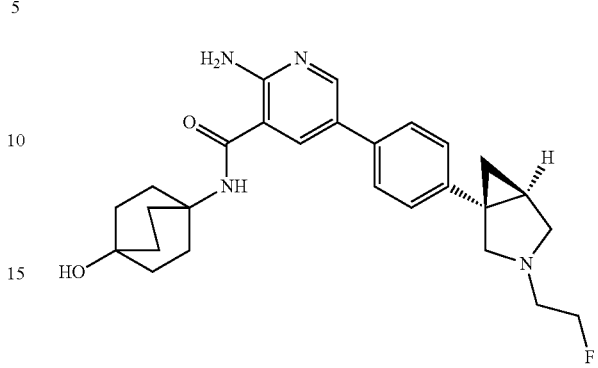

The title compound was prepared in an analogous manner to 2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide (Example 5) except 5-(4-((1S,5R)-3-azabicyclo[3.1.0]hexan-1-yl)phenyl)-2-amino-N-(4-hydroxybicyclo[2.2.2]octan-1-yl)nicotinamide HCl salt (Intermediate 40a) was used instead of 5-(4-((1S,5R)-3-azabicyclo[3.1.0]hexan-1-yl)phenyl)-2-amino-N-((1r,4R)-4-hydroxycyclohexyl)nicotinamide (Intermediate 5a), and 1-bromo-2-fluoroethane was used instead of 4-(3-bromopropyl)morpholine, and the reaction mixture was stirred at 60° C. for 3 h. 1H NMR (400 MHz, DMSO-d6) δ 8.35 (d, 1H), 7.98 (d, 1H), 7.79 (s, 1H), 7.57 (d, 2H), 7.22 (d, 2H), 6.92 (s, 2H), 4.55 (td, 2H), 4.31 (s, 1H), 3.38 (d, 1H), 3.10 (d, 1H), 2.84 (t, 1H), 2.76 (t, 1H), 2.64 (d, 1H), 2.54-2.51 (m, 1H), 2.13-1.96 (m, 6H), 1.83 (dd, 1H), 1.73-1.54 (m, 6H), 1.34 (t, 1H), 0.78 (dd, 1H). (UPLC-MS) $t_R$ 0.51 min; ESI-MS 465 [M+H]$^+$.

Example 74: 2-amino-5-(2,3-difluoro-4-(((R)-2-methylpyrrolidin-1-yl)methyl)phenyl)-N-((1r,4R)-4-hydroxy-4-methylcyclohexyl)nicotinamide

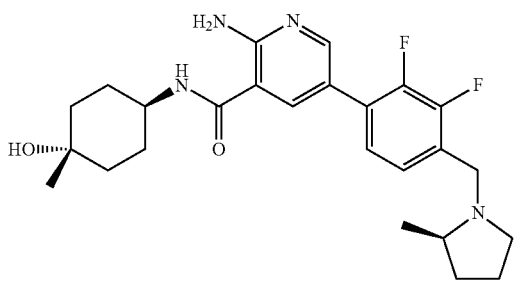 [SMILES: C[C@@H]1CCCN1Cc1ccc(-c2cnc(N)c(C(=O)N[C@H]3CC[C@](C)(O)CC3)c2)c(F)c1F]

The title compound was prepared in an analogous manner to 2-amino-5-(3-fluoro-4-(((R)-2-methylpyrrolidin-1-yl)methyl)phenyl)-N-((1r,4R)-4-hydroxy-4-methylcyclohexyl)nicotinamide (Example 46) except (R)-2-(2,3-difluoro-4-((2-methylpyrrolidin-1-yl)methyl)phenyl)-6-methyl-1,3,6,2-dioxazaborocane-4,8-dione (Intermediate 74a) was used in place of (R)-2-(3-fluoro-4-((2-methylpyrrolidin-1-yl)methyl)phenyl)-6-methyl-1,3,6,2-dioxazaborocane-4,8-dione (Intermediate 46a). (UPLC-MS) $t_R$ 0.76 min; ESI-MS 459 [M+H]$^+$.

Intermediate 74a: (R)-2-(2,3-difluoro-4-((2-methylpyrrolidin-1-yl)methyl)phenyl)-6-methyl-1,3,6,2-dioxazaborocane-4,8-dione The title compound was prepared in an analogous manner to (R)-2-(3-fluoro-4-((2-methylpyrrolidin-1-yl)methyl)phenyl)-6-methyl-1,3,6,2-dioxazaborocane-4,8-dione (Intermediate 46a) except 2,3-difluoro-4-(6-methyl-4,8-dioxo-1,3,6,2-dioxazaborocan-2-yl)benzaldehyde (Intermediate 74b) was used in place of 2-fluoro-4-(6-methyl-4,8-dioxo-1,3,6,2-dioxazaborocan-2-yl)benzaldehyde (Intermediate 46b). ESI-MS 367 [M+H]$^+$.

Intermediate 74b: 2,3-difluoro-4-(6-methyl-4,8-dioxo-1,3,6,2-dioxazaborocan-2-yl)benzaldehyde The title compound was prepared in an analogous manner to 2-fluoro-4-(6-methyl-4,8-dioxo-1,3,6,2-dioxazaborocan-2-yl)benzaldehyde (Intermediate 46b) except (2,3-difluoro-4-formylphenyl)boronic acid was used in place of (3-fluoro-4-formylphenyl)boronic acid. ESI-MS 595 [2M+H]$^+$.

Example 75: 2-amino-N-((1r,4R)-4-hydroxycyclohexyl)-5-(4-((1R,5S)-3-(2-methoxyethyl)-3-azabicyclo[3.1.0]hexan-1-yl)phenyl)nicotinamide

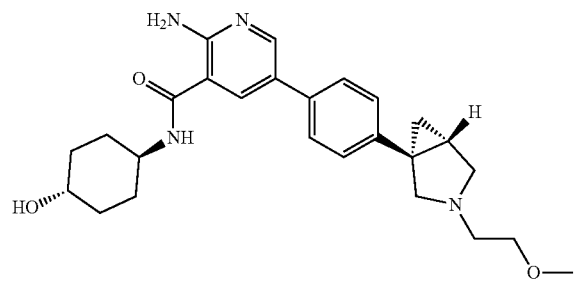 [SMILES: COCCN1C[C@H]2C[C@@]2(c2ccc(-c3cnc(N)c(C(=O)N[C@H]4CC[C@H](O)CC4)c3)cc2)C1]

The title compound was prepared in an analogous manner to 2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide (Example 6) except 1-bromo-2-methoxyethane was used instead of 1,3-difluoropropan-2-yl trifluoromethanesulfonate (Intermediate 6a), and the reaction mixture was stirred at 60° C. for 3 h. After purification the title compound was obtained as a TFA salt. 1H NMR (400 MHz, DMSO-d6) δ 9.70 (bs, 1H), 8.41 (s, 1H), 8.31 (d, 1H), 8.12 (d, 1H), 7.66-7.60 (m, 2H), 7.30 (bs, 2H), 7.14 (s, 2H), 4.59 (d, 1H), 3.81-3.38 (m, 8H), 3.31 (s, 3H), 2.75-2.25 (m, 4H), 1.86 (t, 4H), 1.50-1.21 (m, 6H). (UPLC-MS) $t_R$ 0.48 min; ESI-MS 451 [M+H]$^+$.

Example 76: 2-amino-5-(4-((1S,5R)-3-(2,2-difluoropropyl)-3-azabicyclo[3.1.0]hexan-1-yl)phenyl)-N-((1r,4S)-4-hydroxycyclohexyl)nicotinamide

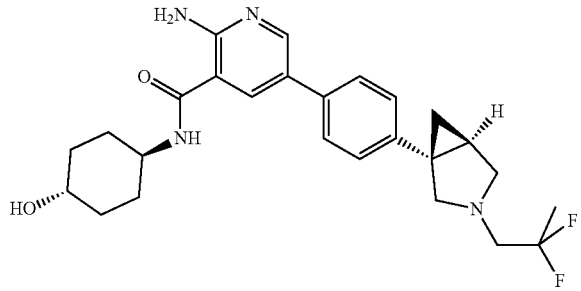 [SMILES: CC(F)(F)CN1C[C@@H]2C[C@]2(c2ccc(-c3cnc(N)c(C(=O)N[C@H]4CC[C@H](O)CC4)c3)cc2)C1]

The title compound was prepared in an analogous manner to 2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide (Example 5) except 2,2-difluoropropyl trifluoromethanesulfonate was used instead of 4-(3-bromopropyl)morpholine. 1H NMR (400 MHz, DMSO-d6) δ 8.39 (d, 1H), 8.33 (d, 1H), 8.14 (d, 1H), 7.60 (d, 2H), 7.32-7.09 (m, 4H), 4.59 (bs, 1H), 3.74 (bs, 1H), 3.11 (d, 1H), 2.98-2.63 (m, 5H), 1.89-1.83 (m, 5H), 1.63 (t, 3H), 1.42-1.25 (m, 6H), 0.81 (bs, 1H). (UPLC-MS) $t_R$ 0.82 min; ESI-MS 471 [M+H]$^+$.

Example 77: 2-amino-N-((1r,4R)-4-hydroxycyclohexyl)-5-(4-((1R,5S)-3-(2,2,2-trifluoroethyl)-3-azabicyclo[3.1.0]hexan-1-yl)phenyl)nicotinamide

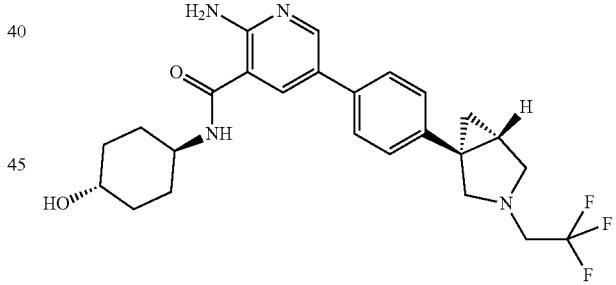

The title compound was prepared in an analogous manner to 2-amino-5-(4-((1R,5S)-3-(1,3-difluoropropan-2-yl)-3-azabicyclo[3.1.0]hexan-1-yl)phenyl)-N-((1r,4R)-4-hydroxycyclohexyl)nicotinamide (Example 6) except 2,2,2-trifluoroethyl trifluoromethanesulfonate was used instead of 1,3-difluoropropan-2-yl trifluoromethanesulfonate (Intermediate 6a), and the reaction mixture was stirred at 60° C. for 1 h. 1H NMR (400 MHz, DMSO-d6) δ 8.39 (d, 1H), 8.32 (d, 1H), 8.13 (d, 1H), 7.60 (d, 2H), 7.24 (d, 2H), 7.16 (s, 2H), 4.58 (s, 1H), 3.73 (dt, 1H), 3.41 (m, 4H), 3.13 (d, 1H), 2.93 (d, 1H), 2.84 (dd, 1H), 1.92-1.77 (m, 5H), 1.51-1.15 (m, 5H), 0.84 (dd, 1H). (UPLC-MS) $t_R$ 1.03 min; ESI-MS 475 [M+H]$^+$.

Example 78: 2-amino-N-((1r,4S)-4-hydroxycyclohexyl-4-d)-5-(4-((1S,5R)-3-isopropyl-3-azabicyclo[3.1.0]hexan-1-yl)phenyl)nicotinamide

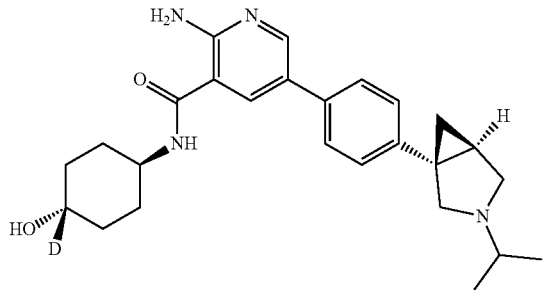 [SMILES: [2H][C@]1(O)CC[C@H](NC(=O)c2cc(-c3ccc([C@]45C[C@H]4CN(C(C)C)C5)cc3)cnc2N)CC1]

The title compound was prepared in an analogous manner to (1R,5S)-tert-butyl 1-(4-(6-amino-5-(((1r,4R)-4-hydroxycyclohexyl)carbamoyl)pyridin-3-yl)phenyl)-3-azabicyclo[3.1.0]hexane-3-carboxylate (Intermediate 1b) except 2-amino-5-(4-((1S,5R)-3-isopropyl-3-azabicyclo[3.1.0]hexan-1-yl)phenyl)nicotinic acid (Intermediate 71a) was used in place of 2-amino-5-(4-((1R,5S)-3-(tert-butoxycarbonyl)-3-azabicyclo[3.1.0]hexan-1-yl)phenyl)nicotinic acid (Intermediate 1c), and trans-4-aminocyclohexan-1-d-1-ol hydrochloride (Intermediate 78a) was used in place of trans-4-aminocyclohexanol. The crude product was purified first by prepHPLC (Method 1a) then by reversed-phase flash chromatography (Method 3a) to give the title compound as a colorless solid. 1H NMR (400 MHz, DMSO-d6) δ 8.38 (d, 1H), 8.31 (d, 1H), 8.11 (d, 1H), 7.58 (d, 2H), 7.22 (d, 2H), 7.12 (s, 2H), 4.56 (s, 1H), 3.73 (dt, 1H), 3.37 (s, 1H), 3.06 (d, 1H), 2.57 (d, 1H), 2.49-2.41 (m, 2H), 1.93-1.73 (m, 5H), 1.31 (m, 5H), 1.04 (dd, 6H), 0.74 (dd, 1H). (UPLC-MS) $t_R$ 0.50 min; ESI-MS 436 [M+H]$^+$.

Intermediate 78a: trans-4-aminocyclohexan-1-d-1-ol hydrochloride

Deuterated aminocyclohexyl starting materials can be prepared using methods similar to those known in the art (e.g. Quirante, J. et al, J. Org. Chem. 67(7): 2323-2328 (2002)). For example, tert-butyl benzyl(4-oxocyclohexyl)carbamate can be reduced with NaBD$_4$ to provide deuterated tert-butyl benzyl((1r,4r)-4-hydroxy-cyclohexyl)carbamate which, after deprotection of the tert-butyloxycarbonyl and benzyl protecting groups, can be incorporated by the synthesis methods described herein.

Example 79: 2-amino-N-((1s,4s)-4-hydroxycyclohexyl)-5-(4-(4-methylpiperazine-1-carbonyl)phenyl)nicotinamide TFA salt

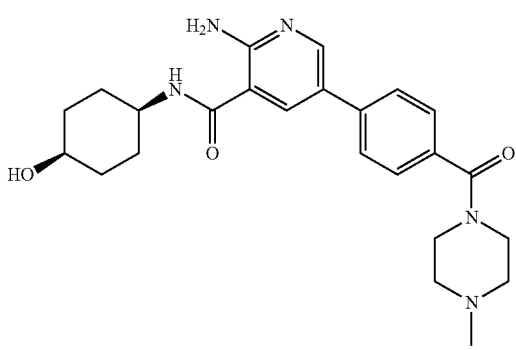

The title compound was prepared in an analogous manner to 2-amino-N-cyclohexyl-5-(4-(3-(piperidin-1-yl)propoxy)phenyl)nicotinamide (Example 43) except 2-amino-5-bromo-N-((1s,4s)-4-hydroxycyclohexyl)nicotinamide (Intermediate 79a) was used in place of 2-amino-5-bromo-N-cyclohexylnicotinamide (Intermediate 43a) and (4-methylpiperazin-1-yl)(4-(4,4,5,5-tetramethyl-1,3,2-dioxaborolan-2-yl)phenyl)methanone was used in place of 1-(3-(4-(4,4,5,5-tetramethyl-1,3,2-dioxaborolan-2-yl)phenoxy)propyl)piperidine. The reaction was carried out in a microwave reactor (15 min irradiation time at 80° C.). The title compound was obtained as a TFA salt. 1H NMR (400 MHz, DMSO-d6) δ 10.01 (s, 2H), 8.56 (d, 1H), 8.51 (d, 1H), 8.43 (d, 1H), 7.85 (d, 2H), 7.57 (d, 2H), 3.86-3.55 (m, 3H), 3.55-3.20 (m, 4H), 3.40-3.15 (m, 3H), 2.85 (s, 3H), 1.85-1.70 (m, 2H), 1.70-1.65 (m, 2H), 1.65-1.40 (m, 4H). (HPLC-MS) $t_R$ 0.35 min; ESI-MS 438 [M+H]$^+$.

Intermediate 79a: 2-amino-5-bromo-N-((1s,4s)-4-hydroxycyclohexyl)nicotinamide

The title compound was prepared in an analogous manner to 2-amino-5-bromo-N-((1r,4r)-4-hydroxycyclohexyl)nicotinamide (Intermediate 3c) except cis-4-aminocyclohexanol was used in place of trans-4-aminocyclohexanol. (UPLC-MS) $t_R$ 0.53 min; ESI-MS 314/316 [M+H]$^+$.

Example 80: 2-amino-5-(4-((1R,5S)-3-(4,4-difluorocyclohexyl)-3-azabicyclo[3.1.0]hexan-1-yl)phenyl)-N-(4-hydroxybicyclo[2.2.2]octan-1-yl)nicotinamide

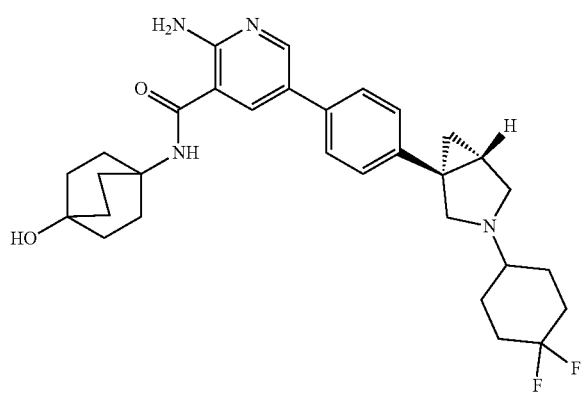 [SMILES: Nc1ncc(-c2ccc([C@@]34C[C@@H]3CN(C3CCC(F)(F)CC3)C4)cc2)cc1C(=O)NC12CCC(O)(CC1)CC2]

The title compound was prepared in an analogous manner to 2-amino-N-((1r,4R)-4-hydroxycyclohexyl)-5-(4-((1R,5S)-3-(1-(methylsulfonyl)piperidin-4-yl)-3-azabicyclo[3.1.0]hexan-1-yl)phenyl)nicotinamide (Example 1) except 5-(4-((1R,5S)-3-azabicyclo[3.1.0]hexan-1-yl)phenyl)-2-amino-N-(4-hydroxybicyclo[2.2.2]octan-1-yl)nicotinamide HCl salt (Intermediate 34a) was used instead of 5-(4-((1R,5S)-3-azabicyclo[3.1.0]hexan-1-yl)phenyl)-2-amino-N-((1r,4R)-4-hydroxycyclohexyl)nicotinamide (Intermediate 1a), and 4,4-difluorocyclohexanone was used instead of 1-(methylsulfonyl)piperidin-4-one. 1H NMR (400 MHz, DMSO-d6) δ 8.32 (d, 1H), 7.95 (d, 1H), 7.76 (s, 1H), 7.55 (d, 2H), 7.21 (d, 2H), 6.88 (s, 2H), 4.28 (s, 1H), 3.36 (s, 1H), 3.07 (s, 1H), 2.55 (s, 1H), 2.45 (s, 1H), 2.32 (d, 1H), 2.30-1.95 (m, 8H), 1.77 (d, 5H), 1.70-1.32 (m, 8H), 1.27 (t, 1H), 0.75 (s, 1H). (UPLC-MS) $t_R$ 0.63 min; ESI-MS 537 [M+H]$^+$.

Example 81: 2-amino-5-(2-chloro-4-(((R)-2-methylpyrrolidin-1-yl)methyl)phenyl)-N-((1r,4R)-4-hydroxy-4-methylcyclohexyl)nicotinamide TFA salt

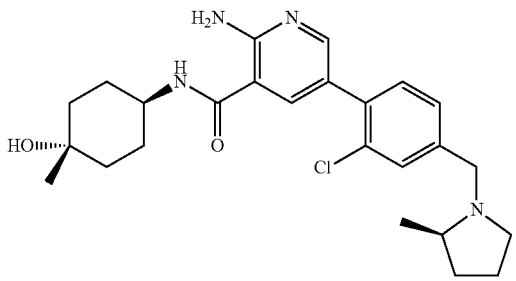 [SMILES: C[C@@H]1CCCN1Cc1ccc(-c2cnc(N)c(C(=O)N[C@H]3CC[C@](C)(O)CC3)c2)c(Cl)c1]

The title compound was prepared in an analogous manner to 2-amino-5-(3-fluoro-4-(((R)-2-methylpyrrolidin-1-yl)methyl)phenyl)-N-((1r,4R)-4-hydroxy-4-methylcyclohexyl)nicotinamide (Example 46) except (R)-2-(2-chloro-4-((2-methylpyrrolidin-1-yl)methyl)phenyl)-6-methyl-1,3,6,2-dioxazaborocane-4,8-dione (Intermediate 81a) was used in place of (R)-2-(3-fluoro-4-((2-methylpyrrolidin-1-yl)methyl)phenyl)-6-methyl-1,3,6,2-dioxazaborocane-4,8-dione (Intermediate 46a). UPLC-HRMS $t_R$ 3.45 min 457.24/459.24 [M+H]$^+$.

Intermediate 81a: (R)-2-(2-chloro-4-((2-methylpyrrolidin-1-yl)methyl)phenyl)-6-methyl-1,3,6,2-dioxazaborocane-4,8-dione The title compound was prepared in an analogous manner to (R)-2-(3-fluoro-4-((2-methylpyrrolidin-1-yl)methyl)phenyl)-6-methyl-1,3,6,2-dioxazaborocane-4,8-dione (Intermediate 46a) except 3-chloro-4-(6-methyl-4,8-dioxo-1,3,6,2-dioxazaborocan-2-yl)benzaldehyde (Intermediate 81b) was used in place of 2-fluoro-4-(6-methyl-4,8-dioxo-1,3,6,2-dioxazaborocan-2-yl)benzaldehyde (Intermediate 46b). ESI-MS 365/367 [M+H]$^+$.

Intermediate 81b: 3-chloro-4-(6-methyl-4,8-dioxo-1,3,6,2-dioxazaborocan-2-yl)benzaldehyde The title compound was prepared in an analogous manner to 2-fluoro-4-(6-methyl-4,8-dioxo-1,3,6,2-dioxazaborocan-2-yl)benzaldehyde (Intermediate 46b) except (2-chloro-4-formylphenyl)boronic acid was used in place of (3-fluoro-4-formylphenyl)boronic acid. ESI-MS 313/315 [M+H$_2$O+H]$^+$.

Example 82: 2-amino-5-(4-((1R,5S)-3-(4,4-difluorocyclohexyl)-3-azabicyclo[3.1.0]hexan-1-yl)phenyl)-N-((1r,4R)-4-hydroxy-4-methylcyclohexyl)nicotinamide

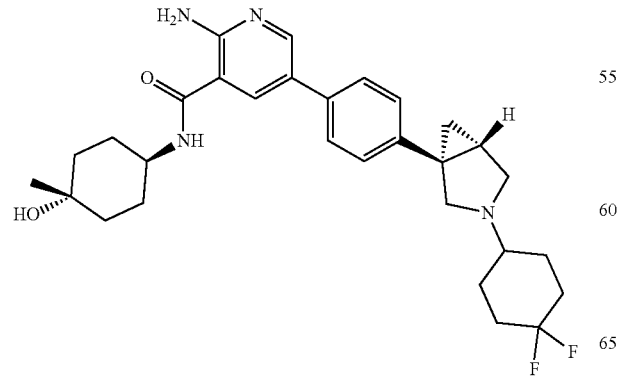

The title compound was prepared in an analogous manner to (1R,5S)-tert-butyl 1-(4-(6-amino-5-(((1r,4R)-4-hydroxycyclohexyl)carbamoyl)pyridin-3-yl)phenyl)-3-azabicyclo[3.1.0]hexane-3-carboxylate (Intermediate 1 b) except 2-amino-5-(4-((1R,5S)-3-(4,4-difluorocyclohexyl)-3-azabicyclo[3.1.0]hexan-1-yl)phenyl)nicotinic acid (Intermediate 82a) was used in place of 2-amino-5-(4-((1R,5S)-3-(tert-butoxycarbonyl)-3-azabicyclo[3.1.0]hexan-1-yl)phenyl)nicotinic acid (Intermediate 1c), and trans-4-amino-1-methylcyclohexanol was used in place of trans-4-aminocyclohexanol. The crude product was purified by prepHPLC (Method 1a) to give the title compound which was obtained as a TFA salt. 1H NMR (400 MHz, DMSO-d6) δ 8.37 (s, 1H), 8.26 (d, 1H), 8.09 (d, 1H), 7.57 (d, 2H), 7.23 (d, 2H), 7.08 (s, 2H), 4.33 (s, 1H), 3.81 (bs, 1H), 3.39 (d, 2H), 2.62-2.56 (m, 2H), 2.00 (bs, 2H), 1.88-1.76 (m, 8H), 1.67-1.53 (m, 4H), 1.50-1.43 (m, 4H), 1.30 (t, 1H), 1.17 (s, 3H), 0.76 (bs, 1H). (UPLC-MS) $t_R$ 0.61 min; ESI-MS 525 [M+H]$^+$.

Intermediate 82a: 2-amino-5-(4-((1R,5S)-3-(4,4-difluorocyclohexyl)-3-azabicyclo[3.1.0]hexan-1-yl)phenyl)nicotinic acid The title compound was prepared in an analogous manner to 2-amino-5-(4-((1R,5S)-3-(tert-butoxycarbonyl)-3-azabicyclo[3.1.0]hexan-1-yl)phenyl)nicotinic acid (Intermediate 2c) except methyl 2-amino-5-(4-((1R,5S)-3-(4,4-difluorocyclohexyl)-3-azabicyclo[3.1.0]hexan-1-yl)phenyl)nicotinate (Intermediate 82b) was used in place of (1R,5S)-tert-butyl 1-(4-(6-amino-5-(methoxycarbonyl)pyridin-3-yl)phenyl)-3-azabicyclo[3.1.0]hexane-3-carboxylate (Intermediate 1d). (UPLC-MS) $t_R$ 0.46 min; ESI-MS 414 [M+H]$^+$.

Intermediate 82b: methyl 2-amino-5-(4-((1R,5S)-3-(4,4-difluorocyclohexyl)-3-azabicyclo[3.1.0]hexan-1-yl)phenyl)nicotinate The title compound was prepared in an analogous manner to methyl 2-amino-5-(4-((1R,5S)-3-(tetrahydro-2H-pyran-4-yl)-3-azabicyclo[3.1.0]hexan-1-yl)phenyl)nicotinate (Intermediate 14b) except 4,4-difluorocyclohexanone was used in place of dihydro-2H-pyran-4(3H)-one. (UPLC-MS) $t_R$ 0.72 min; ESI-MS 428 [M+H]$^+$.

Example 83: 2-amino-N-(3-(2-hydroxypropan-2-yl)bicyclo[1.1.1]pentan-1-yl)-5-(4-((1R,5S)-3-(tetrahydro-2H-pyran-4-yl)-3-azabicyclo[3.1.0]hexan-1-yl)phenyl)nicotinamide

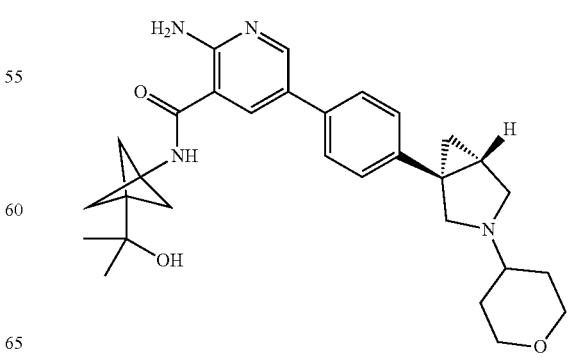

The title compound was prepared in an analogous manner to (1R,5S)-tert-butyl 1-(4-(6-amino-5-(((1r,4R)-4-hydroxycyclohexyl)carbamoyl)pyridin-3-yl)phenyl)-3-azabicyclo[3.1.0]hexane-3-carboxylate (Intermediate 1 b) except 2-amino-5-(4-((1R,5S)-3-(tetrahydro-2H-pyran-4-yl)-3-azabicyclo[3.1.0]hexan-1-yl)phenyl)nicotinic acid (Intermediate 14a) was used in place of 2-amino-5-(4-((1R,5S)-3-(tert-butoxycarbonyl)-3-azabicyclo[3.1.0]hexan-1-yl)phenyl)nicotinic acid (Intermediate 1c), and 2-(3-aminobicyclo[1.1.1]pentan-1-yl)propan-2-ol hydrochloride (Intermediate 83a) was used in place of trans-4-aminocyclohexanol. The crude product was purified by prepHPLC (Method 1a) to give the title compound. 1H NMR (400 MHz, DMSO-d6) δ 8.98 (s, 1H), 8.37 (s, 1H), 8.15 (s, 1H), 7.57 (d, 2H), 7.20 (d, 2H), 7.18 (s, 2H), 4.15 (s, 1H), 3.85-3.79 (m, 2H), 3.38 (bs, 1H), 3.08 (bs, 1H), 2.55-2.25 (m, 5H), 1.90 (s, 6H), 1.89-1.71 (m, 3H), 1.39-1.22 (m, 3H), 1.06 (s, 6H), 0.75 (bs, 1H). (UPLC-MS) $t_R$ 0.59 min; ESI-MS 503 [M+H]$^+$.

Intermediate 83a: 2-(3-aminobicyclo[1.1.1]pentan-1-yl)propan-2-ol hydrochloride tert-Butyl (3-(2-hydroxypropan-2-yl)bicyclo[1.1.1]pentan-1-yl)carbamate (Intermediate 83b, 298 mg, 1.235 mmol) was stirred in an ethanolic solution saturated with HCl (3.8 mL) for 29 h at RT. The reaction mixture was concentrated under reduced pressure to obtain the title compound as a crude hydrochloride salt which was used without further purification. 1H-NMR (400 MHz, DMSO-d6) b 8.51 (s, 3H), 1.78 (s, 6H), 1.03 (s, 6H).

Intermediate 83b: tert-butyl (3-(2-hydroxypropan-2-yl)bicyclo[1.1.1]pentan-1-yl)carbamate To a solution of methyl 3-((tert-butoxycarbonyl)amino)bicyclo[1.1.1]pentane-1-carboxylate (679 mg, 2.81 mmol) in anhydrous THF was added dropwise 3M methyl magnesium bromide in THF (4.13 mL, 12.4 mmol) at −78° C. under an argon atmosphere. The reaction mixture was allowed to reach RT and was stirred for 4 h, then slowly diluted with 2 mL of MeOH under temperature control. The mixture was concentrated under reduced pressure and the crude product was purified by normal-phase chromatography (Method 2a) to give the title compound. (UPLC-MS) $t_R$ 0.22 min; ESI-MS 142 [M+H]$^+$ indicating loss of the BOC group under ionization conditions.

Example 84: 2-amino-N-cyclohexyl-5-(3-(morpholine-4-carbonyl)phenyl)nicotinamide

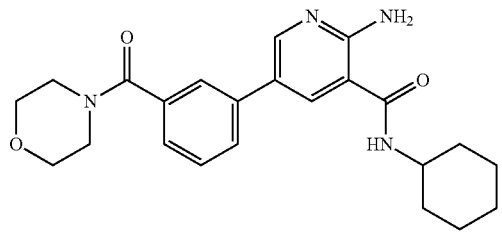 [SMILES: Nc1ncc(-c2cccc(C(=O)N3CCOCC3)c2)cc1C(=O)NC1CCCCC1]

The title compound was prepared in an analogous manner to 2-amino-N-cyclohexyl-5-(4-(3-(piperidin-1-yl)propoxy)phenyl)nicotinamide (Example 43) except 3-(morpholine-4-carbonyl)phenylboronic acid was used in place of 1-(3-(4-(4,4,5,5-tetramethyl-1,3,2-dioxaborolan-2-yl)phenoxy)propyl)piperidine. 1H NMR (400 MHz, DMSO-d6) δ 8.45 (s, 1H), 8.38 (d, 1H), 8.18 (s, 1H), 7.78 (d, 1H), 7.71 (s, 1H), 7.52 (t, 1H), 7.34 (d, 1H), 7.20 (s, 2H), 3.85-3.70 (m, 1H), 3.70-3.50 (m, 8H), 1.90-1.80 (m, 2H), 1.80-1.70 (m, 2H), 1.70-1.55 (m, 1H), 1.35-1.29 (m, 4H), 1.28-1.05 (m, 1H). (HPLC-MS) $t_R$ 1.52 min; APCI-MS 409 [M+H]$^+$.

Example 85: 2-amino-5-(3-chloro-4-(((R)-2-methylpyrrolidin-1-yl)methyl)phenyl)-N-((1r,4R)-4-hydroxy-4-methylcyclohexyl)nicotinamide

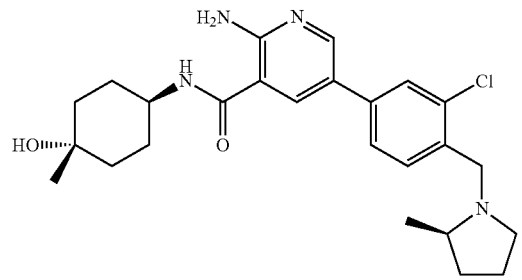 [SMILES: C[C@@H]1CCCN1Cc1ccc(-c2cnc(N)c(C(=O)N[C@H]3CC[C@](C)(O)CC3)c2)cc1Cl]

The title compound was prepared in an analogous manner to 2-amino-5-(3-fluoro-4-(((R)-2-methylpyrrolidin-1-yl)methyl)phenyl)-N-((1r,4R)-4-hydroxy-4-methylcyclohexyl)nicotinamide (Example 46) except (R)-2-(3-chloro-4-((2-methylpyrrolidin-1-yl)methyl)phenyl)-6-methyl-1,3,6,2-dioxazaborocane-4,8-dione (Intermediate 85a) was used in place of (R)-2-(3-fluoro-4-((2-methylpyrrolidin-1-yl)methyl)phenyl)-6-methyl-1,3,6,2-dioxazaborocane-4,8-dione (Intermediate 46a). (UPLC-MS) $t_R$ 0.79 min; ESI-MS 457/459 [M+H]$^+$.

Intermediate 85a: (R)-2-(3-chloro-4-((2-methylpyrrolidin-1-yl)methyl)phenyl)-6-methyl-1,3,6,2-dioxazaborocane-4,8-dione The title compound was prepared in an analogous manner to (R)-2-(3-fluoro-4-((2-methylpyrrolidin-1-yl)methyl)phenyl)-6-methyl-1,3,6,2-dioxazaborocane-4,8-dione (Intermediate 46a) except 2-chloro-4-(6-methyl-4,8-dioxo-1,3,6,2-dioxazaborocan-2-yl)benzaldehyde (Intermediate 85b) was used in place of 2-fluoro-4-(6-methyl-4,8-dioxo-1,3,6,2-dioxazaborocan-2-yl)benzaldehyde (Intermediate 46b). ESI-MS 365/367 [M+H]$^+$.

Intermediate 85b: 2-chloro-4-(6-methyl-4,8-dioxo-1,3,6,2-dioxazaborocan-2-yl)benzaldehyde The title compound was prepared in an analogous manner to 2-fluoro-4-(6-methyl-4,8-dioxo-1,3,6,2-dioxazaborocan-2-yl)benzaldehyde (Intermediate 46b) except (3-chloro-4-formylphenyl)boronic acid was used in place of (3-fluoro-4-formylphenyl)boronic acid. ESI-MS 591 [2M+H]$^+$.

Example 86: 5-(4-((R)-1-(2-oxa-6-azaspiro[3.3]heptan-6-yl)ethyl)phenyl)-2-amino-N-((1r,4R)-4-hydroxy-1-methylcyclohexyl)nicotinamide

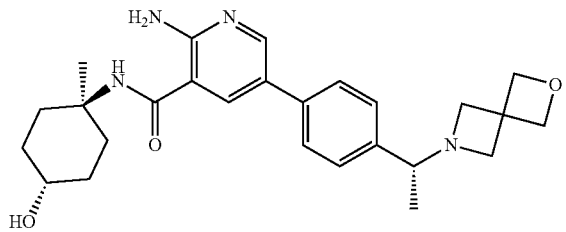 [SMILES: C[C@H](c1ccc(-c2cnc(N)c(C(=O)N[C@]3(C)CC[C@@H](O)CC3)c2)cc1)N1CC2(COC2)C1]

To a solution of 2-amino-5-bromo-N-((1r,4r)-4-hydroxy-1-methylcyclohexyl)nicotinamide (Intermediate 86a, 100 mg, 0.152 mmol) in dioxane (3 mL) was added (R)-6-(1-(4-(4,4,5,5-tetramethyl-1,3,2-dioxaborolan-2-yl)phenyl)ethyl)-2-oxa-6-azaspiro[3.3]heptane (Intermediate 86b, 100 mg, 0.152 mmol), PdCl$_2$(dppf) (5.57 mg, 7.62 μmol) and 2N aq. NaOH (0.152 mL, 0.305 mmol) under a nitrogen atmosphere at RT. The reaction mixture was stirred at 80° C. for 2 h then diluted with EtOAc and water. After two extractions with EtOAc the combined organic layers were washed with a sat. aq. solution of NaHCO$_3$ and brine, respectively. After drying over MgSO$_4$, filtering and concentration under reduced pressure, the crude product was purified by normal-phase chromatography (Method 2b) to give the title compound. 1H NMR (400 MHz, DMSO-d6) δ 8.37 (s, 1H), 8.05 (bs, 1H), 7.70 (s, 1H), 7.62 (bs, 2H), 7.38 (bs, 2H), 6.92 (bs, 2H), 4.62 (s, 4H), 4.47 (s, 1H), 3.48-3.42 (m, 1H), 3.40-3.35 (m, 4H), 3.27-3.20 (m, 2H), 3.15 (bs, 1H), 1.60 (m, 2H), 1.65-1.16 (m, 13H). (UPLC-MS) $t_R$ 0.52 min; ESI-MS 451 [M+H]$^+$.

Intermediate 86a: 2-amino-5-bromo-N-((1r,4r)-4-hydroxy-1-methylcyclohexyl)nicotinamide The title compound was prepared in an analogous manner to 2-amino-5-bromo-N-((1r,4r)-4-hydroxycyclohexyl)nicotinamide Intermediate 3c) except trans-4-amino-4-methylcyclohexanol was used in place of trans-4-aminocyclohexanol. (UPLC-MS) $t_R$ 0.70 min; ESI-MS 328/330 [M+H]$^+$.

Intermediate 86b: (R)-6-(1-(4-(4,4,5,5-tetramethyl-1,3,2-dioxaborolan-2-yl)phenyl)ethyl)-2-oxa-6-azaspiro[3.3]heptane The title compound was prepared in an analogous manner to 1-(3-fluoro-4-(4,4,5,5-tetramethyl-1,3,2-dioxaborolan-2-yl)phenyl)-4-isopropylpiperazine (Intermediate 8a) except (R)-6-(1-(4-bromophenyl)ethyl)-2-oxa-6-azaspiro[3.3]heptane (Intermediate 3b) was used in place of 1-(4-bromo-3-fluorophenyl)-4-isopropylpiperazine (Intermediate 8b). (UPLC-MS) $t_R$ 0.70 min; ESI-MS 330 [M+H]$^+$.

Example 87: 2-amino-N-((1r,4R)-4-hydroxy-4-methylcyclohexyl)-5-(2-methyl-4-(((R)-2-methylpyrrolidin-1-yl)methyl)phenyl)nicotinamide

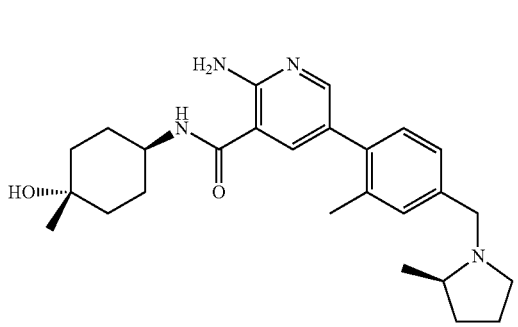

The title compound was prepared in an analogous manner to 2-amino-5-(3-fluoro-4-(((R)-2-methylpyrrolidin-1-yl)methyl)phenyl)-N-((1r,4R)-4-hydroxy-4-methylcyclohexyl)nicotinamide (Example 46) except (R)-6-methyl-2-(2-methyl-4-((2-methylpyrrolidin-1-yl)methyl)phenyl)-1,3,6,2-dioxazaborocane-4,8-dione (Intermediate 87a) was used in place of (R)-2-(3-fluoro-4-((2-methylpyrrolidin-1-yl)methyl)phenyl)-6-methyl-1,3,6,2-dioxazaborocane-4,8-dione (Intermediate 46a). (UPLC-MS) $t_R$ 0.65 min; ESI-MS 437 [M+H]$^+$.

Intermediate 87a: (R)-6-methyl-2-(2-methyl-4-((2-methylpyrrolidin-1-yl)methyl)phenyl)-1,3,6,2-dioxazaborocane-4,8-dione The title compound was prepared in an analogous manner to (R)-2-(3-fluoro-4-((2-methylpyrrolidin-1-yl)methyl)phenyl)-6-methyl-1,3,6,2-dioxazaborocane-4,8-dione (Intermediate 46a) except 3-methyl-4-(6-methyl-4,8-dioxo-1,3,6,2-dioxazaborocan-2-yl)benzaldehyde (Intermediate 87b) was used in place of 2-fluoro-4-(6-methyl-4,8-dioxo-1,3,6,2-dioxazaborocan-2-yl)benzaldehyde (Intermediate 46b). ESI-MS 345 [M+H]$^+$.

Intermediate 87b: 3-methyl-4-(6-methyl-4,8-dioxo-1,3,6,2-dioxazaborocan-2-yl)benzaldehyde The title compound was prepared in an analogous manner to 2-fluoro-4-(6-methyl-4,8-dioxo-1,3,6,2-dioxazaborocan-2-yl)benzaldehyde (Intermediate 46b) except (4-formyl-2-methylphenyl)boronic acid was used in place of (3-fluoro-4-formylphenyl)boronic acid. ESI-MS 568 [2M+H$_2$O+H]$^+$.

Example 88: 2-amino-N-cyclohexyl-5-(3-(4-(2-hydroxyethyl)piperazine-1-carbonyl)phenyl)nicotinamide

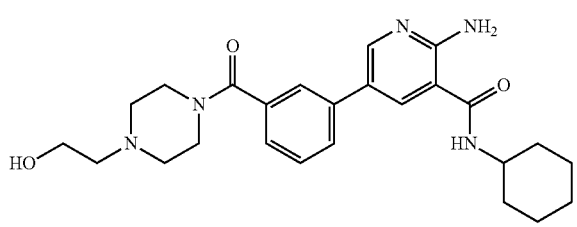 [SMILES: Nc1ncc(-c2cccc(C(=O)N3CCN(CCO)CC3)c2)cc1C(=O)NC1CCCCC1]

The title compound was prepared in an analogous manner to 2-amino-N-cyclohexyl-5-(4-(3-(piperidin-1-yl)propoxy)phenyl)nicotinamide (Example 43) except 3-(4-(2-hydroxyethyl)piperazine-1-carbonyl)phenylboronic acid was used in place of 1-(3-(4-(4,4,5,5-tetramethyl-1,3,2-dioxaborolan-2-yl)phenoxy)propyl)piperidine. 1H NMR (400 MHz, DMSO-d6) δ 8.44 (s, 1H), 8.38 (d, 1H), 8.17 (s, 1H), 7.77 (d, 1H), 7.68 (s, 1H), 7.51 (t, 1H), 7.31 (d, 1H), 7.19 (s, 2H), 4.44 (t, 1H), 3.85-3.70 (m, 1H), 3.70-3.58 (m, 2H), 3.58-3.48 (m, 2H), 3.48-3.35 (m, 2H), 2.50-2.32 (m, 6H), 1.90-1.80 (m, 2H), 1.80-1.70 (m, 2H), 1.70-1.55 (m, 1H), 1.35-1.29 (m, 4H), 1.28-1.05 (m, 1H). (HPLC-MS) $t_R$ 1.31 min; APCI-MS 452 [M+H]$^+$.

Example 89

Salts, amorphous forms and Crystal Polymorphs and Pdeudopolymorphs of the compound of Example 34:
A) Free form Modification $H_A$: 800 g of 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide free form was dissolved in 3 liters of acetone. The resulting solution was stirred at 50° C. and 2 liters of water was added gradually. The mixture was stirred at 50° C. for 30 min, then 4 liters of water was added gradually. The mixture was stirred at 50° C. for 2 hours and was cooled to 22° C. over a period of 2 hours. Solid was separated by suction filtration, washed twice with 1 liter of 1:2 acetone:water, and dried at 45° C. for 24 hours without vacuum. About 660 g of 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide free form Modification $H_A$ was obtained as a white solid. Free form Modification $H_A$ is a monohydrate.
FIG. 3 shows the XRPD diagram for free form Modification $H_A$.
In the following Table A, the corresponding peaks and their 2Theta values ("Angle") are given in detail, together with their relative intensities (all 2Theta values are +/−0.2):

TABLE A

| Angle | Rel. Intensity |
|---|---|
| 15.5 | 100.0% |
| 17.5 | 87.6% |
| 17.8 | 74.4% |
| 7.4 | 68.7% |
| 14.3 | 41.9% |
| 18.6 | 35.8% |
| 17.2 | 33.6% |
| 12.4 | 32.7% |
| 14.8 | 28.9% |
| 16.8 | 27.7% |
| 15.9 | 15.5% |
| 9.4 | 14.4% |
| 19.8 | 11.7% |
| 24.0 | 11.7% |
| 12.2 | 11.7% |
| 20.7 | 10.9% |
| 19.6 | 10.6% |
| 24.7 | 10.5% |
| 10.8 | 10.7% |

FIG. 4 shows an open pan Differencial Scanning Calorimetry (DSC) diagram of free form Modification $H_A$. The first endothermic peak in the DSC diagram corresponds to dehydration of free form Modification $H_A$.

The second endothermic peak corresponds to melting of the anhydrous form resulting from the dehydration.
FIG. 5 shows a Thermogavimetric Analysis (TGA) Diagram of free form Modification $H_A$. The TGA result shows that the free form Modification $H_A$ contains about 3.5% water by weight, which corresponds to about 1 water molecule.
FIG. 6 is the FT-IR diagram of free form Modification $H_A$. The peaks found are: Wave number (in cm$^{-1}$): 3481(w), 3328(m), 2931(m), 2886(w), 2863(w), 2787(w), 1632 (s), 1617(m), 1584(w), 1524(s), 1459 (s), 1242(m), 1090(m), 885(m), 769(m). (s=strong, m=medium, w=weak)
B) Free form Modification A: 0.5 g of 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide free form Modification $H_A$ was added into 3.5 mL of acetone. The mixture was stirred at 40° C. for 1 hour and cooled to 22° C. Solid was filtered and dried at 40° C. for 12 hours. About 0.4 g of free form Modification A was obtained as a white solid.
FIG. 7 shows the XRPD diagram of free form Modification A.
The following Table B defines the corresponding peaks and their 2Theta values ("Angle") in detail, together with their relative intensities (all 2Theta values are +/−0.2):

TABLE B

| | Rel. Intensity |
|---|---|
| 16.2 | 100.0% |
| 17.8 | 85.3% |
| 18.6 | 57.1% |
| 20.5 | 50.2% |
| 20.7 | 48.0% |
| 20.3 | 47.4% |
| 17.2 | 42.9% |
| 16.9 | 41.6% |
| 17.0 | 36.5% |
| 12.4 | 31.9% |
| 19.1 | 25.6% |
| 19.6 | 21.0% |
| 26.4 | 18.6% |
| 24.7 | 16.6% |
| 21.3 | 10.9% |
| 22.4 | 10.6% |
| 15.1 | 10.0% |
| 25.5 | 9.8% |
| 28.1 | 9.1% |
| 10.2 | 8.9% |

FIG. 8 shows an open pan Differencial Scanning Calorimetry (DSC) diagram of free form Modification A.
FIG. 9 shows a Thermogavimetric Analysis (TGA) Diagram of free form Modification A. The TGA result suggests free form Modification A is an anhydrate.
FIG. 10 is the FT-IR diagram of free form Modification A. The peaks found are: Wave number (in cm$^{-1}$): 3480(w), 3436(w), 3401(w), 3301(m), 2944(w), 2864(w), 2805 (w), 1644(s), 1615(m), 1583(w), 1520(s), 1459(m), 1247(m), 1098(m), 883(m), 801(m). (s=strong, m=medium, w=weak)
C) Free form anhydrate: 100 mg 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide free form Modification $H_A$ was exposed to N$_2$ atmosphere at 25° C. for 6 hours. Resulting solid was characterized by XRPD under protection of N$_2$. The solid is the free form anhydrate of 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide.

FIG. 18 shows the XRPD diagram of this anhydrate form.

D) Free form trihydrate: 100 mg 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide free form Modification $H_A$ was exposed to 80% relative humidity at 25° C. overnight. The solid was characterized by XRPD under 80% relative humidity at 25° C. The solid is the free form trihydrate of 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide.

FIG. 19 shows the XRPD diagram of the trihydrate form.

E) Fumarate salt Modification $H_A$: To 3.03 g of 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide free form was added 30 mL of acetone:water (80:20, v/v). The mixture was stirred at 50° C. for 0.5 hour and a clear solution was obtained. To the solution was slowly added a solution of 708.4 mg of fumaric acid in 15 mL of acetone:water (80:20, v/v). Resulting suspension was gradually cooled to 25° C. and kept stirring for 12 hours. Solid was separated by suction filtration, washed with 10 mL acetone once, and exposed to an ambient environment (about 25° C., 50% RH) overnight. 3.3 g of 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide fumarate salt Modification $H_A$ was obtained as a white solid. Fumarate salt Modification $H_A$ is a dihydrate.

FIG. 11 shows the XRPD diagram of fumarate salt Modification $H_A$.

The following Table C defines the corresponding peaks and their 2Theta values ("Angle") in detail, together with their relative intensities (all 2Theta values are +/−0.2):

TABLE C

| Angle | Rel. Intensity |
|---|---|
| 15.6 | 100.0% |
| 18.0 | 91.6% |
| 14.2 | 89.4% |
| 16.2 | 65.0% |
| 7.0 | 65.1% |
| 25.1 | 55.9% |
| 19.2 | 56.0% |
| 14.7 | 38.6% |
| 18.2 | 37.3% |
| 14.9 | 33.9% |
| 22.2 | 31.4% |
| 18.7 | 30.5% |
| 19.4 | 29.4% |
| 20.2 | 28.5% |
| 21.0 | 28.3% |
| 13.2 | 29.4% |
| 25.5 | 26.1% |
| 16.6 | 26.3% |
| 20.8 | 25.7% |
| 25.8 | 22.0% |
| 5.2 | 10.9% |

FIG. 12 shows the DSC diagram of fumarate salt Modification $H_A$. The broad endothermic peak before 150° C. corresponds to dehydration of fumarate salt Modification $H_A$.

FIG. 13 shows a Thermogavimetric Analysis (TGA) Diagram for fumarate salt Modification $H_A$. The TGA result shows that the fumarate salt Modification $H_A$ contains about 5.9% water by weight, which corresponds to about 2 water molecules.

FIG. 14 is the FT-IR diagram of fumarate salt Modification $H_A$. The peaks found are: Wave number (in cm$^{-1}$): 3241(m), 2951(w), 2867(w), 1669(m), 1538(m), 1456 (w), 1355(m), 1249(m), 1087(w), 979(w), 885(w), 797 (w). (s=strong, m=medium, w=weak)

FIG. 15 shows the DVS diagram of fumarate salt Modification $H_A$ at 25° C. From this it can be deduced that fumarate salt Modification $H_A$ is physically stable at least from 0% to 90% RH at 25° C.

FIG. 16 shows the DVS diagram of fumarate salt Modification $H_A$ at 40° C. From this it can be deduced that fumarate salt Modification $H_A$ is physically stable at least from 10% to 90% RH at 40° C.

It is to be noted that Fumarate salt Modification $H_A$ is stable over a wider humidity range than free form polymorphs (data not shown).

F) Fumarate salt amorphous form (variant 1): Added were 500 mg of 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide fumarate salt Modification $H_A$ into 10 mL of ethanol at 25° C. to form a clear solution. Then 3 mL of heptane were added into the solution. White solid precipitated out. The solid was separated by suction filtration and dried at 40° C. under vacuum overnight. 380 mg of a fumarate salt amorphous form of 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide was obtained as a white solid. The amorphous form shows a glass transition at about 143° C. when analyzed by modulated DSC at a heating rate of 2K/min, amplitude temperature of 1K, period 60 seconds.

G) Fumarate salt amorphous form (variant 2): 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)-nicotinamide fumarate salt Modification $H_A$ was heated by DSC to 150° C. at 10K/min then cooled to −20° C. at 20K/min. Resulting material was a 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide fumarate salt amorphous form that is a white solid and shows a glass transition at about 78° C. when analyzed by DSC at a heating rate of 10K/min.

H) Phosphate salt: To 3.01 g of 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide free form was added 30 mL acetone:water (75:25, v/v). Resulting mixture was stirred at 50° C. for 0.5 hour and a clear solution was obtained. To the solution was slowly added a solution of 695.2 mg in 10 mL of acetone:water (95:5, v/v). Resulting suspension was gradually cooled to 25° C. and was kept stirring for 24 hours. Add 1.5 mL water to the suspension. The mixture was kept stirring at 50° C. for 12 hours and slowly cooled to 25° C. Solid was separated by suction filtration, washed with 10 mL acetone:water (90:10, v/v) once, and exposed to an ambient environment (about 25° C., 50% RH) overnight. 2.7 g of 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide phosphate salt was obtained as a white solid.

FIG. 17 shows the XRPD diagram of the phosphate salt.

The following Table D defines the corresponding peaks and their 2Theta values ("Angle") in detail, together with their relative intensities (all 2Theta values are +/−0.2):

TABLE D

| Angle | Rel. Intensity |
|---|---|
| 21.7 | 100.0% |
| 20.7 | 84.7% |
| 16.2 | 78.4% |
| 22.7 | 69.9% |
| 11.9 | 69.5% |
| 14.7 | 56.9% |
| 19.2 | 55.2% |
| 16.3 | 50.9% |
| 20.4 | 48.0% |
| 18.4 | 40.3% |
| 19.5 | 36.5% |
| 17.3 | 36.5% |
| 12.4 | 35.3% |
| 15.8 | 31.6% |
| 18.5 | 27.9% |
| 25.2 | 23.9% |
| 24.3 | 21.7% |
| 24.9 | 21.0% |
| 23.6 | 20.1% |
| 23.3 | 19.5% |
| 27.6 | 15.4% |
| 13.5 | 15.2% |
| 6.8 | 15.0% |
| 29.6 | 13.1% |
| 7.4 | 9.8% |

I) Fumarate salt Modification $H_A$ (F) above) shows better solubility than free form Modification $H_A$ in some aqueous buffers

| | Parameter | | | |
|---|---|---|---|---|
| | Free form Modification $H_A$ | | Fumarate salt Modification $H_A$ | |
| Solubility (at 25° C., 24 h equilibration, target concentration = 2 mg/mL) | | | | |
| Media/measured pH | solubility (mg/mL) | pH | solubility (mg/mL) | pH |
| pH 1.0 1N HCl/1.1 | >2 | 1.03 | >2 | 1.00 |
| pH 2.0 HCl buffer 2.1 | >2 | 2.20 | >2 | 2.09 |
| pH 4.7 acetate buffer/4.8 | >2 | 4.87 | >2 | 4.68 |
| pH 6.8 phosphate buffer/6.8 | 0.34 | 6.61 | 1.08 | 6.50 |
| pH 9.0 borate buffer/8.6 | <LOQ | 8.45 | 0.03 | 8.05 |
| Water/7.2 | 0.07 | 9.04 | >2 | 4.57 |
| pH 2.0 SGF/2.0 | >2 | 2.87 | >2 | 2.43 |
| pH 6.5 FaSSIF/6.5 | 0.47 | 6.47 | 1.69 | 6.09 |
| pH 5.8 FeSSIF/5.9 | 1.69 | 5.92 | >2 | 5.67 |

(LOQ = limit of quantification
FaSSIF = Fasted State Simulated Intestinal Fluid
FeSSIF = Fed State Simulated Intestinal Fluid
SGF = Simulated Gastric Fluid FeSSIF

| Excipients | Amount per 100 mL |
|---|---|
| Sodium taurocholate [mg] | 538.7 |
| water [mg] | 3500 |
| Lipoid E PCS [mg] | 155 |
| Glyceryl monooleate Rylo MG 19 PHARMA [mg] | 178.3 |
| Na oleate [mg] | 24.4 |

FaSSIF

| Excipients | Amount per 100 mL |
|---|---|
| Sodium taurocholate [mg] | 161.4 |
| water [mg] | 1000 |
| Lipoid E PCS [mg] | 15.5 |
| FaSSIF buffer | Add until reaching final volume |

FaSSIF Buffer Preparation

| Excipients | Amount per 100 mL |
|---|---|
| NaCl [g] | 0.401 |
| Maleic acid [g] | 0.222 |

SGF

| Excipient | amount/volume per 1 liter |
|---|---|
| NaCl | 2 g |
| Triton X-100 | 1 g |
| HCl 0.1M | 100 ml |

J) Lactate salt, tartaric acid salt and malic acid salt of compound A can be obtained by analogous processes to those provided above.

K) Various solvates can be obtained from many of the salts and salt forms of compound A mentioned above (details not shown).

Where mentioned in the preceding Examples, XRPD, TGA, DSC, FT-IR and DVS data have been obtained using the following methods:

a) TGA method
   Instrument TA Discovery, TA Discovery, New Castle, Del., USA
   Temperature range 30 to 300° C.
   Scan rate 10° C./min
   Nitrogen flow 20 mL/min
   Sample mass ~2-10 mg b) DSC method
   Instrument TA Discovery
   Temperature range 30 to 250 or 300° C.
   Scan rate 10° C./min
   Nitrogen flow 50 mL/min
   Sample mass ~2 mg c) XRPD method: All XRPD diagrams were obtained in the reflection mode.
   (i) XRPD method 1 (FIG. 3, 11, 17)
      Instrument Bruker D8 Advance (Bruker, Bruchsal, Germany))
      Detector LYNXEYE (1D mode), open angle: 1.996°
      Radiation CuKα (0.15406 nm)
      Monochromator Nickel filter
      X-ray generator power 40 kV, 40 mA
      Step size, resolution 0.041 degree
      Scan range 2° to 45° (2 theta value)
      Scan time 36 min Slits primary: fixed illuminated sample size 5 mm, secondary slit: 5 mm, axial soller: 2.5°
(ii) XRPD method 2 (FIG. 7)
Instrument Bruker D8 Advance
Detector LYNXEYE (1D mode), open angle: 1.996°
Radiation CuKα (0.15406 nm)
Monochromator Nickel filter
X-ray generator power 40 kV, 40 mA
Step size, resolution 0.041 degree
Scan range 2° to 45° (2 theta value)
Scan time 330 seconds
Slits primary: fixed illuminated sample size 5 mm, secondary slit: 5 mm, axial soller: 2.5
XRPD method 3 (FIG. 18, 19)
Instrument Bruker D8 Advance XRPD with a Cryo-RH chamber (Bruker, Bruchsal, Germany)
Detector VANTEC-1 (1D detector)
Radiation CuKα (0.15406 nm)
Monochromator Nickel filter
X-ray generator power 40 kV, 40 mA
Step size, resolution 0.0165 degrees
Scan range 2° to 45° (2 theta value)
Scan time 17 min
Slits divergent slit: V12, antiscattering slit: 10.0 mm, detector slit: 17.43 mm,
primary soller slit: 2.5°, secondary soller slit: 2.5°
d) DVS
Instrument Advantage (Surface Measurement Systems, London, UK)
Sample mass ~10 mg
Temperature 25° C.
dm/dt 0.002%/min
e) FT-IR
Thermo Fisher Nicolet 6700 with Attenuated Total Reflectance (ATR), Thermo Fisher Scientific, Waltham, Mass., USA,
Biochemical Assays (Examples 90 and 91)

For all biochemical assays, human recombinant proteins were expressed in and purified from baculo virus transfected insect cells. The constructs comprised the GS-domain and kinase domain of wild-type ALK2 (aa172-499), ALK2 FOP mutant (aa172-499 R206H), ALK3 (aa198-525), ALK5 (aa162-503) and ALK6 (aa168-495).

Example 90: In Vitro Enzyme Inhibition Using a Biochemical Autophosphorylation Assay (Luminescence-Based ADPGlo Kinase Activity Assay)—"ADPGlo Assay"

A kinase selectivity panel which measures autophosphorylation using the ADP-Glo™ Kinase Assay (Promega, V9101) was set-up for wild-type ALK2 (aa172-499) and ALK3 (aa198-525). The assays were performed in 384-well, low volume microtiter assay plates in a final reaction volume of 6 ul. Dose-response curves were generated by incubating 10 nM of each kinase in 50 mM Hepes pH 7.5, 0.02% Tween 20, 0.02% BSA, 1 mM DTT, 10 μm $Na_3VO_4$, 10 mM ß-Glycerolphosphate, 1 mM $MgCl_2$, 12 mM $MnCl_2$ and 15 μm ATP for 60 min at 32° C. in the presence or absence of compound diluted in DMSO. The amount of generated ADP is a measure of kinase activity and is quantified using the ADP-Glo™ Kinase Assay (Promega) according to manufacturer's instructions. ADP is converted to ATP by adding 3 ul of ADP-Glo™ Reagent and incubation at 32° C. for 60 min. ATP is subsequently converted into a bioluminescent signal by adding 6 ul luciferase assay reagents (Kinase detection buffer+Kinase Detection Substrate (Promega)) and further incubation at 32° C. for 60 min. For the measurement of luminescence a PHERAstar™ Multilabel Reader was used at a measurement interval time of 0.1 second (optical module for luminescence measurements in the 230 nm to 750 nm wavelength range). The luminescent signal positively correlates with kinase activity. Specific activities are shown in the table below.

| Ex. | ALK2 ADPGlo $IC_{50}$ [μmol $l^{-1}$] | ALK3 ADPGlo $IC_{50}$ [μmol $l^{-1}$] |
|---|---|---|
| 1 | 0.005 | 0.310 |
| 2 | 0.012 | 1.767 |
| 3 | 0.012 | 1.050 |
| 4 | 0.005 | 0.830 |
| 5 | 0.007 | 1.100 |
| 6 | 0.018 | 0.940 |
| 7 | 0.012 | 0.875 |
| 8 | 0.013 | 1.900 |
| 9 | 0.011 | 1.600 |
| 10 | 0.011 | 1.400 |
| 11 | 0.009 | 1.100 |
| 12 | 0.014 | 3.100 |
| 13 | 0.008 | 1.400 |
| 14 | 0.018 | 4.100 |
| 15 | 0.029 | 0.967 |
| 16 | 0.012 | 1.400 |
| 17 | 0.012 | 2.000 |
| 18 | 0.014 | 2.300 |
| 19 | 0.012 | 1.800 |
| 20 | 0.007 | 1.350 |
| 21 | 0.006 | 0.260 |
| 22 | 0.009 | 1.500 |
| 23 | 0.009 | 1.600 |
| 24 | 0.011 | 6.475 |
| 25 | 0.009 | 1.300 |
| 26 | 0.018 | 1.700 |
| 27 | 0.010 | 1.300 |
| 28 | 0.011 | 0.530 |
| 29 | 0.022 | 2.500 |
| 30 | 0.007 | 0.500 |
| 31 | 0.013 | 1.200 |
| 32 | 0.022 | 12.700 |
| 33 | 0.010 | 2.400 |
| 34 | 0.018 | 0.914 |
| 35 | 0.017 | 0.903 |
| 36 | 0.016 | 1.450 |
| 37 | 0.008 | 0.960 |
| 38 | 0.007 | 1.300 |
| 39 | 0.013 | 0.830 |
| 40 | 0.032 | 0.995 |
| 41 | 0.019 | 1.800 |
| 42 | 0.026 | 1.300 |
| 43 | 0.031 | 2.350 |
| 44 | 0.018 | 0.430 |
| 45 | 0.020 | 1.600 |
| 46 | 0.024 | 14.600 |
| 47 | 0.021 | 1.300 |
| 48 | 0.008 | 0.970 |
| 49 | 0.027 | 1.600 |
| 50 | 0.011 | 2.400 |
| 51 | 0.016 | 0.780 |
| 52 | 0.067 | 2.800 |
| 53 | 0.013 | 1.200 |
| 54 | 0.011 | 0.920 |
| 55 | 0.022 | 2.440 |
| 56 | 0.028 | 9.900 |
| 57 | 0.038 | 1.185 |
| 58 | 0.025 | 3.725 |
| 59 | 0.024 | 2.700 |
| 60 | 0.011 | 0.990 |
| 61 | 0.043 | 2.100 |
| 62 | 0.024 | 4.500 |
| 63 | 0.091 | 1.800 |
| 64 | 0.110 | 2.200 |
| 65 | 0.082 | 2.400 |
| 66 | 0.015 | 1.200 |
| 67 | 0.022 | 1.900 |
| 68 | 0.034 | 8.000 |

-continued

| Ex. | ALK2 ADPGlo IC$_{50}$ [µmol l$^{-1}$] | ALK3 ADPGlo IC$_{50}$ [µmol l$^{-1}$] |
|---|---|---|
| 69 | 0.041 | 3.100 |
| 70 | 0.020 | 2.850 |
| 71 | 0.022 | 2.900 |
| 72 | 0.046 | 9.900 |
| 73 | 0.075 | 1.900 |
| 74 | 0.064 | 13.200 |
| 75 | 0.011 | 1.800 |
| 76 | 0.034 | 3.200 |
| 77 | 0.028 | 3.300 |
| 78 | 0.037 | 8.300 |
| 79 | 0.086 | 6.500 |
| 80 | 0.058 | 1.800 |
| 81 | 0.150 | 15.100 |
| 82 | 0.082 | 9.500 |
| 83 | 0.100 | 15.100 |
| 84 | 2.400 | 21.900 |
| 85 | 0.190 | 15.100 |
| 86 | 0.110 | 8.200 |
| 87 | 0.880 | 15.100 |
| 88 | 0.990 | 22.800 |

Example 91: In Vitro Enzyme Inhibition Using a Biochemical Peptide Phosphorylation Assay—"Caliper Assay"

A kinase selectivity panel which measures substrate peptide phosphorylation was set-up for wild-type ALK2 (aa172-499), ALK2 FOP mutant (aa172-499 R206H), ALK1 (aa166-493), ALK5 (aa162-503) and ALK6 (aa168-495). The technology used for the described assay is based on the separation and quantification of substrate and product in an electrical field. In the course of the kinase reaction the peptide substrate is phosphorylated by a kinase. The transfer of a phosphate residue also causes the introduction of two additional negative charges and hence to a change in the net charge of the phospho-peptide compared to the unphosphorylated peptide. Due to this difference in charge the phosphorylated und unphosphorylated peptides migrate with different velocities in an electrical field.

In the applied method, this separation takes place inside a chip that contains a complex capillary system for simultaneous analysis of 12 samples ("12-sipper chip", Caliper Technologies Corp., Mountain View, USA). In order to allow the detection and quantification of the peptides in the capillary system, the peptides carry a fluorescent label (fluorescein). With this label the peptides can be quantified by fluorescence intensity through the instruments laser and detection system (LC3000, Caliper Life Sciences).

The assays were performed in 384-well, low volume microtiter assay plates in a final reaction volume of 9 ul. Dose-response curves were generated by incubating 10 nM of each kinase together with 2 µm of the fluorescently labeled substrate peptide 5-Fluo-Ahx-KKYQAEEN-T-YDEYENKK-amid (10 mM stock solution in DMSO) in 50 mM Hepes pH 7.5, 0.02% Tween 20, 0.02% BSA, 1 mM DTT, 10 m Na$_3$VO$_4$, 10 mM If-Glycerolphosphate, 1 mM MgCl$_2$, 12 mM MnCl$_2$ (ALK1 and ALK6 7 mM) and 15 µm ATP for 60 min at 30° C. in the presence or absence of compound diluted in DMSO. Kinase reaction were terminated by adding 15 ul STOP buffer (100 mM HEPES pH 7.5, 5% DMSO, 0.1% Caliper coating reagent, 10 mM EDTA, and 0.015% Brij35.

Plates with terminated kinase reactions were transferred to the Caliper LC3000 workstation (Caliper Technologies Corp., Mountain View, USA) for reading. The relative amount of phosphorylated peptide r, was calculated using the heights of the substrate peak, s, and the product peak, p: r=p/(p+s).

Specific activities are shown in the table below.

| Example | ALK2 EPK (IC$_{50}$ [µmol · l$^{-1}$]) | ALK2 FOP EPK (IC$_{50}$ [µmol · l$^{-1}$]) | ALK1 EPK (IC$_{50}$ [µmol · l$^{-1}$]) | ALK5 EPK (IC$_{50}$ [µmol · l$^{-1}$]) | ALK6 EPK (IC$_{50}$ [µmol · l$^{-1}$]) |
|---|---|---|---|---|---|
| 1 | 0.009 | 0.008 | 0.075 | 0.560 | 0.740 |
| 2 | 0.011 | 0.011 | 0.093 | 2.167 | 2.500 |
| 3 | 0.011 | 0.015 | 0.136 | 2.133 | 1.733 |
| 4 | 0.013 | 0.007 | 0.175 | 2.450 | 1.850 |
| 5 | 0.010 | 0.011 | 0.081 | 2.200 | 2.500 |
| 6 | 0.015 | 0.028 | 0.220 | 10.000 | 5.200 |
| 7 | 0.012 | 0.008 | 0.195 | 5.450 | 2.400 |
| 8 | 0.012 | 0.022 | 0.220 | 4.000 | 5.000 |
| 9 | 0.011 | 0.014 | 0.127 | 3.133 | 3.133 |
| 10 | 0.011 | 0.013 | 0.089 | 2.600 | 2.500 |
| 11 | 0.012 | 0.012 | 0.150 | 2.400 | 3.900 |
| 12 | 0.012 | 0.021 | 0.160 | 1.900 | 2.400 |
| 13 | 0.013 | 0.016 | 0.140 | 3.100 | 3.000 |
| 14 | 0.016 | 0.030 | 0.710 | 10.000 | 10.000 |
| 15 | 0.020 | 0.029 | 0.370 | 3.767 | 2.233 |
| 16 | 0.015 | 0.018 | 0.240 | 9.900 | 5.000 |
| 17 | 0.014 | 0.014 | 0.110 | 1.600 | 2.400 |
| 18 | 0.015 | 0.025 | 0.200 | 2.700 | 2.100 |
| 19 | 0.018 | 0.014 | 0.105 | 1.850 | 2.250 |
| 20 | 0.017 | 0.011 | 0.130 | 3.800 | 3.950 |
| 21 | 0.019 | 0.010 | 0.055 | 0.900 | 1.000 |
| 22 | 0.016 | 0.014 | 0.250 | 2.500 | 3.200 |
| 23 | 0.018 | 0.019 | 0.250 | 2.700 | 2.400 |
| 24 | 0.016 | 0.021 | 0.543 | 6.800 | 7.300 |
| 25 | 0.018 | 0.011 | 0.130 | 1.400 | 3.000 |
| 26 | 0.018 | 0.024 | 0.230 | 4.300 | 2.500 |
| 27 | 0.018 | 0.014 | 0.135 | 1.300 | 1.600 |
| 28 | 0.018 | 0.017 | 0.250 | 9.400 | 3.300 |
| 29 | 0.020 | 0.039 | 0.280 | 4.000 | 4.000 |
| 30 | 0.022 | 0.014 | 0.210 | 4.000 | 2.800 |
| 31 | 0.020 | 0.017 | 0.230 | 3.500 | 4.500 |

-continued

| Example | ALK2 EPK (IC$_{50}$ [μmol·l$^{-1}$]) | ALK2 FOP EPK (IC$_{50}$ [μmol·l$^{-1}$]) | ALK1 EPK (IC$_{50}$ [μmol·l$^{-1}$]) | ALK5 EPK (IC$_{50}$ [μmol·l$^{-1}$]) | ALK6 EPK (IC$_{50}$ [μmol·l$^{-1}$]) |
|---|---|---|---|---|---|
| 32 | 0.020 | 0.027 | 0.743 | 3.200 | 3.300 |
| 33 | 0.020 | 0.014 | 0.220 | 1.800 | 2.000 |
| 34 | 0.023 | 0.021 | 0.323 | 6.280 | 3.300 |
| 35 | 0.021 | 0.018 | 0.283 | 5.725 | 4.500 |
| 36 | 0.023 | 0.024 | 0.295 | 10.000 | 7.200 |
| 37 | 0.027 | 0.008 | 0.100 | 1.100 | 1.700 |
| 38 | 0.028 | 0.007 | 0.160 | 1.500 | 2.600 |
| 39 | 0.024 | 0.019 | 0.190 | 1.600 | 2.000 |
| 40 | 0.029 | 0.049 | 0.410 | 3.900 | 2.850 |
| 41 | 0.023 | 0.027 | 0.310 | 6.700 | 6.900 |
| 42 | 0.029 | 0.036 | 0.540 | 4.767 | 4.100 |
| 43 | 0.025 | 0.026 | 0.765 | 3.500 | 11.050 |
| 44 | 0.024 | 0.025 | 0.170 | 3.200 | 2.000 |
| 45 | 0.025 | 0.027 | 0.750 | 2.700 | 4.800 |
| 46 | 0.025 | 0.029 | 1.200 | 10.000 | 10.000 |
| 47 | 0.025 | 0.027 | 0.290 | 4.700 | 3.500 |
| 48 | 0.034 | 0.011 | 0.120 | 5.300 | 4.400 |
| 49 | 0.027 | 0.033 | 0.590 | 3.400 | 8.800 |
| 50 | 0.037 | 0.014 | 0.500 | 6.400 | 5.100 |
| 51 | 0.031 | 0.018 | 0.120 | 1.400 | 1.700 |
| 52 | 0.031 | 0.056 | 0.970 | 8.600 | 20.200 |
| 53 | 0.032 | 0.020 | 0.190 | 2.000 | 2.500 |
| 54 | 0.033 | 0.018 | 0.140 | 5.300 | 3.500 |
| 55 | 0.030 | 0.033 | 0.627 | 5.033 | 2.900 |
| 56 | 0.030 | 0.038 | 0.930 | 5.800 | 10.000 |
| 57 | 0.035 | 0.051 | 0.485 | 4.400 | 3.200 |
| 58 | 0.032 | 0.032 | 0.663 | 7.550 | 8.400 |
| 59 | 0.033 | 0.038 | 0.770 | 9.100 | 7.700 |
| 60 | 0.042 | 0.019 | 0.170 | 6.300 | 6.300 |
| 61 | 0.035 | 0.046 | 0.940 | 7.200 | 20.200 |
| 62 | 0.036 | 0.043 | 0.840 | 8.800 | 10.000 |
| 63 | 0.057 | 0.140 | 0.940 | 6.700 | 3.500 |
| 64 | 0.063 | 0.160 | 1.000 | 7.500 | 3.800 |
| 65 | 0.044 | 0.034 | 0.580 | 1.700 | 10.000 |
| 66 | 0.056 | 0.026 | 0.190 | 10.000 | 6.200 |
| 67 | 0.050 | 0.034 | 0.180 | 10.000 | 8.700 |
| 68 | 0.049 | 0.067 | 2.500 | 10.000 | 10.000 |
| 69 | 0.052 | 0.042 | 1.100 | 5.200 | 9.000 |
| 70 | 0.068 | 0.037 | 0.305 | 9.400 | 8.750 |
| 71 | 0.065 | 0.032 | 0.490 | 3.000 | 5.800 |
| 72 | 0.061 | 0.068 | 2.950 | 10.000 | 10.000 |
| 73 | 0.061 | 0.091 | 0.640 | 6.900 | 4.000 |
| 74 | 0.070 | 0.092 | 2.500 | 10.000 | 10.000 |
| 75 | 0.140 | 0.018 | 0.210 | 4.600 | 7.700 |
| 76 | 0.079 | 0.055 | 0.370 | 9.400 | 8.400 |
| 77 | 0.080 | 0.059 | 0.320 | 10.000 | 8.600 |
| 78 | 0.109 | 0.043 | 0.310 | 7.800 | 10.000 |
| 79 | 0.087 | 0.053 | 0.890 | 4.100 | 10.000 |
| 80 | 0.087 | 0.087 | 0.680 | 6.600 | 4.600 |
| 81 | 0.110 | 0.150 | 3.000 | 10.000 | 10.000 |
| 82 | 0.117 | 0.091 | 1.600 | 10.000 | 10.000 |
| 83 | 0.145 | 0.180 | 5.600 | 10.000 | 10.000 |
| 84 | 0.350 | 1.800 | 20.200 | 20.200 | 20.200 |
| 85 | 0.170 | 0.210 | 9.800 | 10.000 | 10.000 |
| 86 | 0.205 | 0.190 | 2.300 | 10.000 | 10.000 |
| 87 | 0.630 | 0.900 | 10.000 | 10.000 | 10.000 |
| 88 | 0.810 | 0.950 | 20.200 | 20.200 | 20.200 |

Example 92: BMP Signaling Reporter Gene Assay

A human liver hepatocellular carcinoma cell line (HuH7) stably transfected with a reporter plasmid consisting of the BMP response element (BRE) from the Id1 promoter fused to a luciferase reporter gene was generated through lentiviral transduction.

Cells were maintained in DMEM (GIBCO #41965 high glucose plus L-Glutamine), 10% FCS (Amimed #2-01F10-1), 1% Pen/Strp (Amimed #4-01F00) and 5 ug/ml Blastidicin (InvivoGen #ant-bl-1) at 37° C., 5% CO$_2$. Assays were performed in 384-well flat bottom polystyrene microtiter plates (cell culture treated) with sterile lid. The cells were starved through medium exchange in Blasticidine- and FCS-free medium 16h before the assay. Prior to the assay, cells were detached from the stock flask using trypsin/EDTA and counted. A cell suspension in the same medium without Blasticidin and FCS was prepared. $2 \times 10^4$ cells in a total volume of 40 ul were added to each well of a plate already containing serial dilutions of each compound in DMSO (final DMSO concentration 0.5%). Cells and compound are incubated for 1h at 37° C., 5% CO$_2$ before stimulation with 5 ul/well recombinant BMP6 (R&D Systems #507-BP/CF) at a final concentration of 100 ng/ml. Assay plates are incubated for another 5 hours at 37° C., 5% CO$_2$ before luciferase levels are measured.

The amount of expressed luciferase is quantified using the Steady-Glo® Luciferase Assay System (Promega #E2520).

5 ul of the Steady-Glo® Reagent are added to each well, the samples were mixed through vigorous shaking of the plate before measuring the luminesecence in a PHERAstar™ Multilabel Reader for 1 second/well (optical module for luminescence measurements in the 230 nm to 750 nm wavelength range).

Further specific activities of the compounds of the invention are described in the table below.

| Ex. | MSD BMP RGA $IC_{50}$ [µmol $l^{-1}$] |
|---|---|
| 1 | 0.076 |
| 2 | 0.021 |
| 3 | 0.062 |
| 4 | 0.108 |
| 5 | 0.120 |
| 6 | 0.870 |
| 7 | 0.051 |
| 8 | 0.069 |
| 9 | 0.043 |
| 10 | 0.061 |
| 11 | 0.051 |
| 12 | 0.125 |
| 13 | 0.078 |
| 14 | 0.205 |
| 15 | 0.074 |
| 16 | 0.079 |
| 17 | 0.150 |
| 18 | 2.000 |
| 19 | 0.021 |
| 20 | 0.040 |
| 21 | 0.035 |
| 22 | 0.041 |
| 23 | 0.023 |
| 24 | 0.081 |
| 25 | 0.035 |
| 26 | 0.110 |
| 27 | 0.059 |
| 28 | 0.017 |
| 29 | 0.685 |
| 30 | 0.068 |
| 31 | 0.115 |
| 32 | 0.093 |
| 33 | 0.026 |
| 34 | 0.049 |
| 35 | 0.073 |
| 36 | 0.043 |
| 37 | 0.037 |
| 38 | 0.058 |
| 39 | 0.078 |
| 40 | 0.075 |
| 41 | 0.158 |
| 42 | 0.235 |
| 43 | 0.130 |
| 44 | 0.365 |
| 45 | 0.365 |
| 46 | 0.120 |
| 47 | 0.130 |
| 48 | 0.360 |
| 49 | 0.790 |
| 50 | 0.825 |
| 51 | 0.064 |
| 52 | 0.340 |
| 53 | 0.050 |
| 54 | 0.395 |
| 55 | 0.543 |
| 56 | 0.285 |
| 57 | 0.144 |
| 58 | 0.143 |
| 59 | 0.405 |
| 60 | 0.084 |
| 61 | 2.300 |
| 62 | 0.134 |
| 63 | 0.390 |
| 64 | 0.380 |
| 65 | 0.415 |
| 66 | 0.910 |
| 67 | 1.165 |
| 68 | 0.950 |
| 69 | 1.105 |
| 70 | 0.513 |
| 71 | 0.086 |
| 72 | 0.190 |
| 73 | 0.130 |
| 74 | 0.550 |
| 75 | 0.330 |
| 76 | 2.300 |
| 77 | 1.300 |
| 78 | 0.220 |
| 79 | 2.700 |
| 80 | 0.058 |
| 81 | 1.250 |
| 82 | 0.056 |
| 83 | 0.360 |
| 84 | 9.500 |
| 85 | 0.860 |
| 86 | 1.080 |
| 87 | 3.550 |
| 88 | 9.300 |

Example 93: In Vivo Efficacy in a Pediatric FOP (Fibrodysplasia Ossificans Progressiva) Mouse Model Ubiquitous heterozygous expression of the FOP causing BMP type I receptor Alk2 R206H mutant in mice results in perinatal lethality (Chakkalakal et al., 2012).

To study the postnatal role of Alk2(R206H) in the juvenile organism as a pre-clinical mouse model for FOP, an inducible Alk2(R206H) mutant mouse (Prof. D. Goldhamer, UConn, ASBMR abstract, 2013) with an inserted floxed stop cassette upstream of the mutant exon, which renders the mutant allele expression Cre-recombinase dependent, is required. They were crossed with Rosa26-CreERt2 mice, allowing for temporally and spatially defined heterozygous expression of Alk2(R206H).

Here, ubiquitous inducible Alk2(R206H) heterozygous mice were used with the tamoxifen (tam)-inducible CreER-loxP technology. Successful induction of Alk2(R206H) expression is achieved following administration of tamoxifen to 1-week-old male and female Alk2(R206H); Rosa26-CreERt2 mice.

FOP flare-ups are induced through a deep muscle injury by local intramuscular (im.) injection of cardiotoxin (CTX) and concomitant im. injection of an adenovirus to generate an Alk2(R206H) dependent local FOP flare-up. CTX induces injury in skeletal muscle through inhibition of the Ca/Mg-ATPase in the plasma membrane and induction of calcium release from the sarcoplasmic reticulum.

At the beginning of the experiment and daily thereafter the body weight of 1-week-old male and female Alk2 (R206H); Rosa26-CreERt2 was measured. All pups were treated once daily subcutaneously (sc.) with 20 mg/kg tamoxifen (tamoxifen-free base (Sigma T5648), dissolved in 10% ethanol absolute, 90% sunflower oil (Sigma S5007) at 8 mg/ml) starting at 1 week of age for 10 days.

On the 3rd day of tamoxifen injection, all pups were subjected to local muscle injury by a single intramuscular injection of 100 ul Adenovirus+Cardiotoxin (CTX) into the gastrocnemius muscle of the right hind leg taking care not to inject into any blood vessels and not to touch the bones with the needle. To this end, 90 ul of adenovirus (Ad-GFP-2A-iCre, cat. no. 1772, Vector Biolabs; Titer: $1\times10^{10}$ PFU (plaque-forming units)/mL) were mixed with 10 µl of a 100 µm cardiotoxin stock solution (prepared from Cardiotoxin, cat. no. L8102, Latoxan, or Cardiotoxin, cat. No. C9759, Sigma, using sterile saline). The animals were anesthetized by a low dose isoflurane inhalation, the right hind leg was shaved and the skin disinfected with betaseptic before the intramuscular injection, which was done slowly and carefully using an insulin syringe.

Therapeutic b.i.d. oral treatment of Alk2(R206H) heterozygous mice was started 3 days post-muscle injury with 2, 5, 10 and 25 mg/kg of compound A (compound of example 34=2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide) or the corresponding vehicle for 6 weeks. Heterotopic ossification was assessed bi-weekly by whole body and hind leg radiography (Faxitron device) and in vivo micro-computed tomography (μCT) imaging starting 2 weeks after Ad/CTX application in all mice.

At necropsy, the right hind legs were collected for ex vivo micro-CT imaging to determine the full extent of HO. The entire right hind leg with attached muscle was dissected as fast as possible and transferred to 70% ethanol at 4° C. After 24 h the samples were transferred to fresh 70% ethanol for high resolution μCT imaging using the μCT40 device from Scanco Medical (voxel size: 16 μm, integration time: 250 ms, medium resolution, 55 E (kVp), 145 μA, mode: cone beam continuous rotation, threshold 275, Gauss-Filter: Sigma 0.7, Support 1). The total bone volume (mm3) of the ectopic bone in the hind leg was determined. Results are shown in FIG. 1. The figure shows that compound A (compound of example 34) suppresses right hindleg bone volume ex vivo.

To investigate the effect of compound A (compound of example 34) on heterotopic ossification progression after initiation of the process, Alk2(R206H) heterozygous mice were similarly injected with 100 ul Adenovirus+Cardiotoxin (CTX), but allowed to develop heterotopic bone for 2.5 weeks. Upon confirmation of HO formation after 2 weeks, pups were randomized based on HO presence, genetic background and gender. Treatment was started 2.5 weeks post-injury with vehicle or 10 mg/kg b.i.d. of compound A and continued for 6 weeks. Heterotopic ossification was assessed bi-weekly by whole body and hind leg radiography (Faxitron device) and in vivo micro-computed tomography (μCT) imaging starting 2 weeks after Ad/CTX application in all mice.

Figure 2:
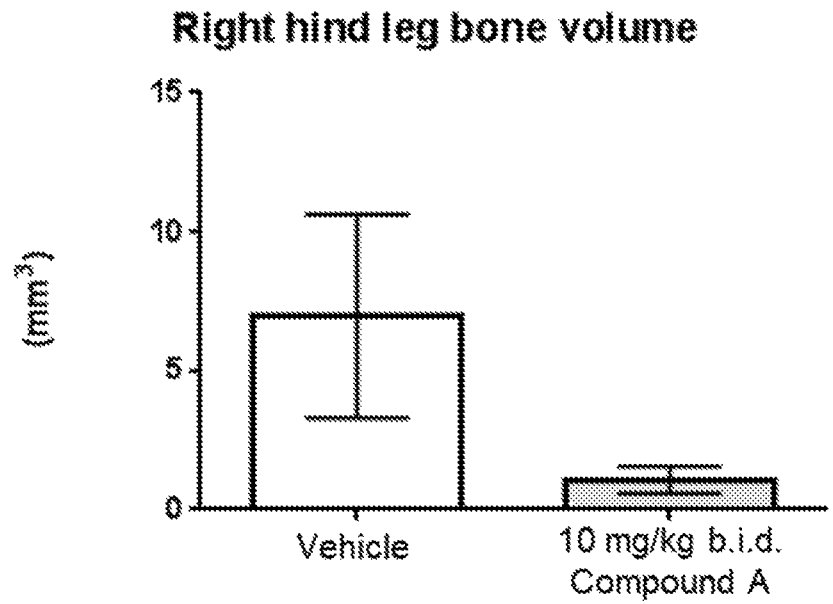

At necropsy, the right hind legs were collected for ex vivo micro-CT imaging to determine the full extent of HO. The entire right hind leg with attached muscle was dissected as fast as possible and transferred to 70% ethanol at 4° C. After 24 h the samples were transferred to fresh 70% ethanol for high resolution μCT imaging using the μCT40 device from Scanco Medical (voxel size: 16 μm, integration time: 250 ms, medium resolution, 55 E (kVp), 145 μA, mode: cone beam continuous rotation, threshold 275, Gauss-Filter: Sigma 0.7, Support 1). The total bone volume (mm$^3$) of the ectopic bone in the hind leg was determined. Results are shown in FIG. 2. The results show that compound A (compound of example 34) prevents progression of right hindleg bone volume ex vivo.

The results shown in FIGS. 1 and 2 show that a compound of the invention (compound A) suppresses heterotopic ossification when dosed early after muscle injury, and prevents further progression of heterotopic ossification in ALK2 (R206H) mouse pups, when dosed after heterotopic ossification has already started.

Example 94: Achilles Midpoint Tenotomy-Induced Heterotopic Ossification in Rats

To test whether the compounds of the invention are able to prevent trauma-induced heterotopic ossification (HO) of soft tissue, the therapeutic efficacy in a rat model of unilateral Achilles midpoint tenotomy can be used (Rooney et al., Matrix 12: 274-281, 1992). To this end, the left Achilles tendon of 8-week-old female Wistar rats (body weight between 190-265 g) is completely transected using a sterile scalpel (blade number 11) under isoflurane inhalation narcosis with concomitant analgesic treatment applying 0.03 mg/kg buprenorphine for 48 hours every 10-12 h subcutaneously. Preventive oral treatment with a compound of the invention (10 mg/kg q.d.) or vehicle (sodium carboxymethyl cellulose:water:Tween 80, 0.5:99:0.5) is given for weeks starting on the day of surgery (n=11-12 rats per group). Rats are housed individual for 3-4 days following surgery and thereafter housed in groups of two animals per cage at 25° C. with a 12:12 h light-dark cycle and were fed a standard rodent diet containing 18.2% protein and 3.0% fat with an energy content of 15.8 MJ/kg (3890, Provimi Kliba SA) with food and water provided ad libitum. Treatment efficacy is assessed longitudinally by taking radiographs of the operated distal leg (Faxitron LX-60 system) at 4 and 10 weeks post-tenotomy. Heterotopic bone volume is quantified in vivo by micro-computed tomography (micro-CT) under isoflurane inhalation narcosis (vivaCT40 instrument, Scanco Medical AG; 17.5 μm resolution) at 6 and 9 weeks post-surgery.

The invention claimed is:
1. A method of inhibiting ALK-2 receptor activity in a subject, wherein the method comprises administering to the subject a therapeutically effective amount of a compound which is 2-amino-N-(4-hydroxybicyclo[2.2.2]octan-1-yl)-5-(4-(3-(tetrahydro-2H-pyran-4-yl)-3-azabicyclo[3.1.0] hexan-1-yl)phenyl)nicotinamide, or a pharmaceutically acceptable salt thereof.

2. A method of treating a disorder or disease selected from heterotopic ossification or fibrodysplasia ossificans progressiva, comprising administering to the subject a therapeutically effective amount of a compound which is 2-amino-N-(4-hydroxybicyclo[2.2.2]octa n-1-yl)-5-(4-(3-(tetrahydro-2H-pyran-4-yl)-3-aza bicyclo[3.1.0]hexan-1-yl)phenyl) nicotinamide, or a pharmaceutically acceptable salt thereof.

3. The method of claim 1, wherein the compound is 2-amino-N-(4-hydroxybicyclo-[2.2.2]octan-1-yl)-5-(4-((1R,5S)-3-(tetrahydro-2H-pyran-4-yl)-3-azabicyclo[3.1.0] hexan-1-yl-phenyl)nicotinamide, or a pharmaceutically acceptable salt thereof.

4. The method of claim 1, wherein the compound is 2-amino-N-(4-hydroxybicyclo-[2.2.2]octan-1-yl)-5-(4-((1S,5R)-3-(tetrahydro-2H-pyran-4-yl)-3-azabicyclo[3.1.0] hexan-1-yl-phenyl)nicotinamide, or a pharmaceutically acceptable salt thereof.

5. The method of claim 2, wherein the compound is 2-amino-N-(4-hydroxybicyclo-[2.2.2]octan-1-yl)-5-(44(1R,5S)-3-(tetrahydro-2H-pyran-4-yl)-3-azabicyclo[3.1.0] hexan-1-yl)-phenyl)nicotinamide, or a pharmaceutically acceptable salt thereof.

6. The method of claim 2, wherein the compound is 2-amino-N-(4 hydroxybicyclo-[2.2.2]octan-1-yl)-5-(4-((1S,5R)-3-(tetrahydro-2H-pyran-4-yl)-3-azabicyclo[3.1.0] hexan-1-yl)-phenyl)nicotinamide, or a pharmaceutically acceptable salt thereof.

7. The method of claim 2, wherein the disorder or disease is heterotopic ossification.

8. The method of claim 2, wherein the disorder or disease fibrodysplasia ossificans progressiva.

9. A method of treating a disorder or disease selected from heterotopic ossification or fibrodysplasia ossificans progressiva, comprising administering to the subject a therapeutically effective amount of a pharmaceutical composition comprising 2-amino-N-(4-hydroxybicyclo[2.2.2]octan-1-yl)-5-(4-(3-(tetrahydro-2H-pyran-4-yl)-3-azabicyclo[3.1.0]hexan-1-yl)phenyl)nicotinamide, or a pharmaceutically acceptable salt thereof, and at least one pharmaceutically acceptable carrier.

10. The method of claim 9, wherein the pharmaceutical composition comprises 2-amino-N-(4-hydroxybicyclo[2.2.2]octan-1-yl)-5-(4-((1S,5R)-3-(tetrahydro-2H-pyran-4-yl)-3-azabicyclo[3.1.0]hexan-1-yl)-phenyl)nicotinamide, or a pharmaceutically acceptable salt thereof.

11. The method of claim 9, wherein the pharmaceutical composition comprises 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)-phenyl)nicotinamide, or a pharmaceutically acceptable salt thereof.

12. The method of claim 9, wherein the disorder or disease is heterotopic ossification.

13. The method of claim 9, wherein the disorder or disease fibrodysplasia ossificans progressiva.

* * * * *

UNITED STATES PATENT AND TRADEMARK OFFICE
CERTIFICATE OF CORRECTION

PATENT NO. : 10,947,218 B2
APPLICATION NO. : 16/884666
DATED : March 16, 2021
INVENTOR(S) : Luca Arista et al.

It is certified that error appears in the above-identified patent and that said Letters Patent is hereby corrected as shown below:

In the Claims

Claim 2, Column 122, Lines 43-44 should read:
(4-hydroxybicyclo[2.2.2]octan-1-yl)-5-(4-(3-(tetrahydro-2H-pyran-4-yl)-3-azabicyclo[3.1.0]hexan-1-yl)phenyl)

Claim 3, Column 122, Lines 47-49 should read:
2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide, or a pharmaceutically Claim 4, Column 122, Lines 52-54 should read:
2-amino-N-(4-hydroxybicyclo[2.2.2]octan-1-yl)-5-(4-((1S,5R)-3-(tetrahydro-2H-pyran-4-yl)-3-azabicyclo[3.1.0]hexan-1-yl)phenyl)nicotinamide, or a pharmaceutically Claim 5, Column 122, Lines 57-59 should read:
2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide, or a pharmaceutically Claim 6, Column 122, Lines 62-64 should read:
2-amino-N-(4-hydroxybicyclo[2.2.2]octan-1-yl)-5-(4-((1S,5R)-3-(tetrahydro-2H-pyran-4-yl)-3-azabicyclo[3.1.0]hexan-1-yl)phenyl)nicotinamide, or a pharmaceutically Claim 8, Column 123, Lines 1-2 should read:
The method of claim 2, wherein the disorder or disease is fibrodysplasia ossificans progressiva Claim 10, Column 123, Line 15 should read:
yl)-3-azabicyclo[3.1.0]hexan-1-yl)phenyl)nicotinamide, or Claim 11, Column 123, Line 20 should read:
yl)-3-azabicyclo[3.1.0]hexan-1-yl)phenyl)nicotinamide, or Signed and Sealed this
Seventeenth Day of August, 2021

Drew Hirshfeld
*Performing the Functions and Duties of the
Under Secretary of Commerce for Intellectual Property and
Director of the United States Patent and Trademark Office*

Claim 13, Column 123, Lines 24-25 should read:
The method of claim 9, wherein the disorder or disease is fibrodysplasia ossificans progressiva.